United States Patent
Zondler et al.

(10) Patent No.: US 6,362,134 B1
(45) Date of Patent: *Mar. 26, 2002

(54) HERBICIDAL 1,2,4,6-THIATRIAZINES

(75) Inventors: Helmut Zondler, Bottmingen (CH); André Stoller, Blotzheim (FR)

(73) Assignee: Syngenta Investment Corporation, Wilmington, DE (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/101,096

(22) PCT Filed: Dec. 20, 1996

(86) PCT No.: PCT/EP96/05770
§ 371 Date: Jul. 1, 1998
§ 102(e) Date: Jul. 1, 1998

(87) PCT Pub. No.: WO97/25318
PCT Pub. Date: Jul. 17, 1997

(30) Foreign Application Priority Data

Jan. 5, 1996 (CH) .................................. 38/96

(51) Int. Cl.$^7$ ........................ C07D 285/16; A01N 43/72
(52) U.S. Cl. ........................ 504/131; 544/7; 514/222.5
(58) Field of Search ............................ 544/7; 514/222, 514/222.5; 504/131

(56) References Cited

U.S. PATENT DOCUMENTS

| | | | |
|---|---|---|---|
| 4,316,015 A | 2/1982 | Hamprecht et al. | 544/7 |
| 4,343,648 A | 8/1982 | Hamprecht et al. | 71/91 |
| 4,426,219 A | 1/1984 | Hamprecht et al. | 71/91 |
| 4,428,766 A | 1/1984 | Hamprecht et al. | 71/91 |
| 4,472,191 A | 9/1984 | Hamprecht et al. | 71/91 |
| 4,585,472 A | 4/1986 | Hamprecht et al. | 71/91 |

FOREIGN PATENT DOCUMENTS

DE 113 006 5/1975

OTHER PUBLICATIONS

Schramm et al. Synthesis of 5-alkylamino-1-dialkylamino-3-chloro-1,2,4,6-thia. Z. Chem. 15(1) 19, 1975.*

Michalik et al. Sterochemical studies of heterocyclic compounds. J. Prakt. Chem 319(5), 739-44, 1977.*

M. Haake et al. Z. Naturforsch., vol. 43b, pp. 763–768, 1988, abstract in English language on front page; Front sheet of the Inaugural–Dissertation of W. Jurgler, Philipps–Universitat Marburg, Marburg/Lahn, 1988.

J. Greeves et al., J. Chem. Soc. (C), pp. 875–878, 1970.

M. Michalik et al., J.f.prakt. Chemie, vol. 319, No. 5, pp. 739–744, 1977, abstract in English language on front page; Wissenschaftliche Zeitschrift der Wilhelm–Pieck–Universitat Rostock, vol. 28(9), p. 855, 1979, summary in English language on p. 859.

R.T. Boere et al., J. Amer. Chem. Soc., vol. 111, pp. 1180–1185, 1989.

W. Reid et al.,Chem. Ber., vol. 121, pp. 383–386, 1988; ibid., E. Fischer, vol. 124, p. 1347, 1991; ibid., S.J. Chen, vol. 126, p. 2601, 1993.

W. Stork et al., Z. Chem. vol. 14(2), p. 471, 1974; ibid. vol.15(1), p. 19, 1975; ibid. (15(2), 57, 1975; ibid. 15(5), p. 193, 1974; ibid., vol. 15(13), 104, 1975, ibid.,16(12), p. 490, 1976; please note that the English language abstracts of the foregoing 6 Z. Chem. references are.

A. Kalman et al., J. Chem. Soc., Perkin Trans II, vol. 10, p. 1322-7, 1977.

A. Kalman et al., Acta Cryst. vol. 35(4), p. 860–6, 1979.

* cited by examiner

Primary Examiner—Mukund J. Shah
Assistant Examiner—Venkataraman Balasubramanian
(74) Attorney, Agent, or Firm—William A. Teoli, Jr.

(57) ABSTRACT

Compounds of formula (I), in which $R_1$, $R_2$ and $R_3$ are as defined in claim 1, are (I)

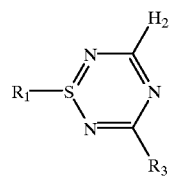

particularly suitable as herbicides.

27 Claims, No Drawings

HERBICIDAL 1,2,4,6-THIATRIAZINES

The present invention relates to novel, herbicidally active thiatriazine derivatives, processes for their preparation, compositions comprising these compounds, and their use for controlling weeds, in particular in crops of useful plants, for example cereals, maize, rice, cotton, soya, oilseed rape, sorghum, sugar cane, sugar beet, sunflower, vegetables and fodder plants, or for inhibiting plant growth.

Thiatriazine compounds are described, for example, in Z. Chem. 15(5), 193–194 (1975), ibid. 15(2), 57–58 (1975), Chem. Ber. 121, 383–386 (1988), Z. Naturforsch. 43, 763–768 (1988), Chem. Ber. 126, 2601–2607 (1993), J. Am. Chem. Soc. 111, 1180–1185 (1989), DD-A-113 006 and in the inaugural dissertation by W. Jürgler, Philipps-University Marburg/Lahn, 1988 ("$1\lambda^4$- and $1\lambda^6$-2,4,6-thiatriazines from sulfodiimides").

Novel and simple synthesis methods for preparing novel diversely substituted thiatriazine derivatives have now been found. In addition to the easy accessibility of diversely substituted thiatriazine derivatives, the low number of synthesis stages is another advantage of the synthesis methods. Herbicidal and growth-inhibiting properties have been found for these thiatriazine derivatives.

The present invention thus relates to compounds of the formula I

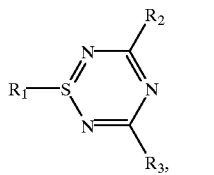

(I)

in which $R_1$ is a group —$OR_7$, —$NR_{90}R_{91}$ or an N-heterocyclic radical, onto which 1 or 2 further carbocyclic, heterocyclic or aromatic rings can be fused and which contains or does not contain further heteroatoms;

$R_7$ is $C_1$–$C_{16}$alkyl, $C_1$–$C_{16}$alkyl substituted by halogen, $NO_2$, CN, $C_1$–$C_5$alkoxy, $C_1$–$C_5$alkylthio, $C_3$–$C_8$cycloalkoxy, $C_3$–$C_8$cycloalkylthio, $C_1$–$C_3$trialkylsilyl, $C_3$–$C_{10}$alkenyloxy, $C_3$–$C_5$alkynyloxy, $C_1$–$C_5$alkylcarbonyloxy, $C_1$–$C_3$alkoxycarbonyl, $C_1$–$C_3$alkylcarbonyl, $C_5$–$C_7$cycloalkenyl or $C_5$–$C_7$cycloalkenyl substituted by $C_1$–$C_4$alkyl, or $R_7$ is $C_1$–$C_{16}$alkyl substituted by $C_3$–$C_8$cycloalkyl, $C_6$–$C_{12}$bicycloalkyl, $C_6$–$C_{12}$chlorobicycloalkyl, $C_6$–$C_{12}$bicycloalkenyl or adamantyl, or $R_7$ $C_1$–$C_{16}$alkyl substituted by substituted or unsubstituted aryl, aryloxy, arylmethyleneoxy, arylcarbonyl, arylcarbonyloxy or a heterocyclic ring, or $R_7$ is $C_3$–$C_{15}$alkenyl, $C_3$–$C_{15}$alkenyl substituted by halogen, $C_1$–$C_3$alkoxy, $C_3$–$C_8$cycloalkyl, $C_1$–$C_3$trialkylsilyl or substituted or unsubstituted aryl or aryloxy, or $R_7$ is $C_3$–$C_5$alkynyl, $C_3$–$C_{12}$cycloalkyl, $C_3$–$C_{12}$cycloalkyl substituted by halogen, CN, $C_1$–$C_3$trialkylsilyl, =O, $C_1$–$C_6$alkyl, cyano-$C_1$–$C_5$alkyl, $C_1$–$C_5$alkyl-CONH—$C_1$–$C_5$alkyl, phenyl-CONH—$C_1$–$C_5$alkyl, $C_1$–$C_5$chloroalkyl, $C_1$–$C_3$alkoxy, $C_1$–$C_3$alkylthio, $C_1$–$C_3$alkoxycarbonyl, $C_1$–$C_3$alkoxycarbonyl-$C_1$–$C_5$alkyl, $C_5$–$C_7$cycloalkyl, $C_2$–$C_4$alkenyl, $C_2$–$C_4$alkynyl, benzyl or $C_1$–$C_3$ halogenoalkyl, or $R_7$ is $C_5$–$C_7$cycloalkenyl, $C_5$–$C_7$cycloalkenyl substituted by $C_1$–$C_3$alkyl, or $R_7$ is $C_6$–$C_{12}$bicycloalkyl, $C_6$–$C_{12}$bicycloalkyl substituted by $C_1$–$C_3$alkyl, cyano or halogen, $C_6$–$C_{12}$bicycloalkenyl, $C_6$–$C_{12}$bicycloalkenyl substituted by $C_1$–$C_3$alkyl, or $R_7$ is a substituted or unsubstituted non-aromatic heterocyclic ring or an alicyclic ring system;

$R_{90}$ and $R_{91}$ independently of one another are hydrogen, $C_1$–$C_{12}$alkyl, $C_1$–$C_{12}$alkyl substituted by halogen, $NO_2$, CN, hydroxyl, $C_1$–$C_3$alkoxy, $C_1$–$C_3$alkoxycarbonyl, $C_1$–$C_3$trialkylsilyl, $C_1$–$C_6$alkylamino, di($C_1$–$C_6$alkyl)amino, $C_3$–$C_7$cycloalkyl,

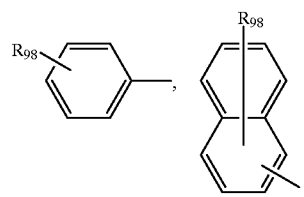

or a heterocyclic ring, or $C_3$–$C_{10}$alkenyl, $C_3$–$C_{10}$alkynyl, $C_6$–$C_{12}$bicycloalkyl, $C_6$–$C_{12}$bicycloalkenyl, $C_3$–$C_{12}$cycloalkyl, $C_3$–$C_{12}$cycloalkyl substituted by $C_1$–$C_4$alkyl, $C_5$–$C_7$cycloalkenyl or $C_5$–$C_7$cycloalkenyl substituted by $C_1$–$C_4$alkyl, with the proviso that $R_{90}$ and $R_{91}$ are not simultaneously hydrogen; or $R_{90}$ and $R_{91}$, together with the nitrogen atom to which they are bonded, form a saturated heterocyclic ring which contains 2–12 carbon atoms and can contain, as further heteroatoms, a nitrogen, an oxygen or a sulfur atom and can be substituted by $C_1$–$C_4$alkyl, $C_1$- or $C_2$halogenoalkyl, $C_1$- or $C_2$hydroxyalkyl, methoxy-$C_1$–$C_4$alkyl, halogen, hydroxyl, CN, $C_1$–$C_4$alkoxy, $C_1$–$C_4$alkylcarbonyl, $C_1$- or $C_2$halogenoalkyl

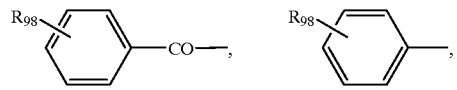

$C_1$–$C_3$alkoxycarbonyl, ($C_1$–$C_3$alkyl)$_2$NCO, di($C_1$–$C_4$alkyl)amino or =O and can additionally be bridged by 1 or 2

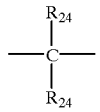

groups and onto which 1 or 2 further carbocyclic, heterocyclic or aromatic rings can be fused, or $R_{90}$ and $R_{91}$, together with the nitrogen atom to which they are bonded, form a mono- or diunsaturated heterocyclic ring which contains 5–7 carbon atoms and is substituted or unsubstituted by $C_1$–$C_4$alkyl, $C_1$- or $C_2$halogenoalkyl, halogen, hydroxyl, CN, amino, $C_1$–$C_4$alkylamino, di($C_1$–$C_4$alkyl)amino, phenyl, $C_1$–$C_4$alkoxy or $C_1$–$C_3$alkoxycarbonyl and additionally bridged by 1 or 2

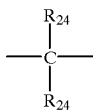

groups and onto which 1 or 2 further carbocyclic, heterocyclic or aromatic rings can be fused;

the radicals $R_{24}$ independently of one another are hydrogen or methyl;

$R_{98}$ is hydrogen, fluorine, chlorine, bromine, CN, $C_1$–$C_3$alkoxy, $C_1$–$C_3$alkoxycarbonyl, $C_1$–$C_3$alkoxy-$C_1$–$C_3$alkyl, $C_1$- or $C_2$halogenoalkyl, $C_1$–$C_5$alkyl, $NO_2$, $C_3$–$C_5$alkenyl, cyclopropyl or $C_1$- or $C_2$halogenoalkoxy;

$R_2$ is halogen, $C_1$–$C_{10}$alkoxy, $C_1$–$C_{10}$alkoxy substituted by halogen, CN, $NO_2$, $C_1$–$C_6$alkoxy, $C_1$–$C_6$alkylthio, $C_3$–$C_6$alkenyloxy, $C_1$–$C_6$alkoxycarbonyl, heterocyclyl or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylthio, $C_1$–$C_{10}$alkylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenylthio or $C_3$–$C_{10}$alkenylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, or $R_2$ is $C_3$–$C_5$alkynyloxy, $C_3$–$C_5$-alkynylthio, $C_3$–$C_8$cycloalkyl-X—, $C_6$–$C_{12}$bicycloalkyl-X—, heterocyclyl-X—, alicyclyl-X—, aryl-X—, phthalidyl-X—, biphenyl-X— or heteroaryl-X—;

X is —O—, —S—, —SO— or —SO$_2$—, or $R_2$ is a group $R_{88}R_{89}N$—,

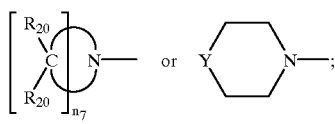

$R_{88}$ and $R_{89}$ independently of one another are hydrogen, $C_1$–$C_6$alkyl, $C_1$–$C_6$alkyl substituted by halogen, CN, $C_1$–$C_3$alkoxy or

$C_3$–$C_{12}$cycloalkyl, $C_3$–$C_{10}$alkenyl, $C_3$–$C_{10}$alkynyl, $C_6$–$C_{12}$bicycloalkyl or $C_6$–$C_{12}$bicycloalkyl substituted by $C_1$–$C_3$alkyl;

the radicals $R_{20}$ independently of one another are hydrogen or $C_1$–$C_4$alkyl;

$n_7$ is 4 or 5;

Y is —O—, —S—, —NH— or —NR$_{101}$—;

$R_{101}$ is $C_1$–$C_4$alkyl, $C_1$–$C_4$alkylcarbonyl or $C_1$–$C_3$alkoxycarbonyl; and $R_{98}$ is as defined above;

$R_3$ is halogen, hydroxyl, $C_1$–$C_{10}$alkoxy, $C_1$–$C_{10}$alkoxy substituted by halogen, CN, $NO_2$, $C_1$–$C_6$alkoxy, $C_1$–$C_6$alkylthio, $C_3$–$C_6$alkenyloxy, $C_1$–$C_6$alkoxycarbonyl, heterocyclyl or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylthio, $C_1$–$C_{10}$alkylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenylthio or $C_3$–$C_{10}$alkenylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, or $R_3$ is $C_3$–$C_5$alkynyloxy, $C_3$–$C_5$alkynylthio, $C_3$–$C_8$cycloalkyl-X—, $C_6$–$C_{12}$bicycloalkyl-X—, heterocyclyl-X—, alicyclyl-X—, aryl-X—, phthalidyl-X—, biphenyl-X— or heteroaryl-X—; and X is as defined above, and stereoisomers of the compounds of the formula I, excluding the compounds of formulae $I_1$ to $I_7$

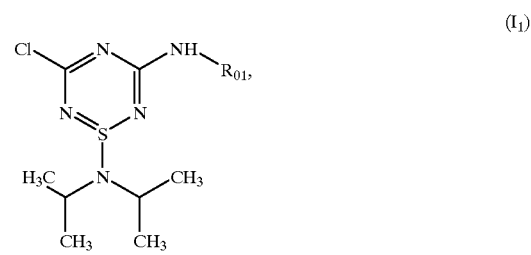

(I$_1$)

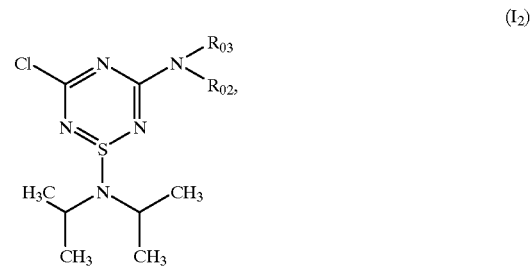

(I$_2$)

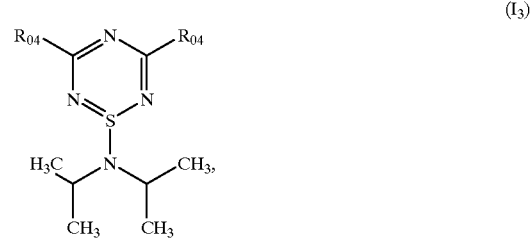

(I$_3$)

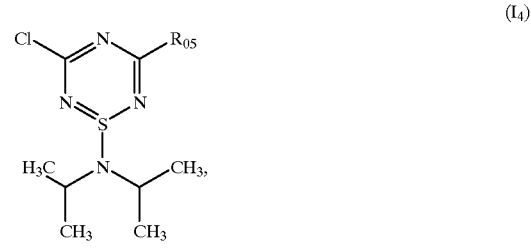

(I$_4$)

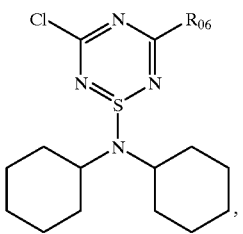
(I₅)

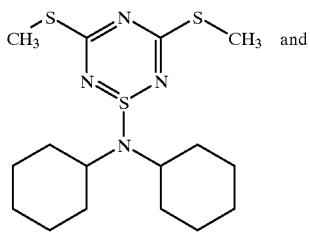
(I₆) and

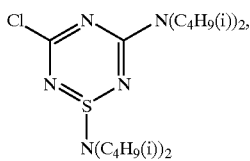
(I₇)

wherein $R_{01}$ is hydrogen, methyl, ethyl, n-propyl, i-butyl, tert-butyl, allyl, cyclohexyl or benzyl;

$R_{02}$ is ethyl or benzyl and $R_{03}$ is ethyl, cyclohexyl or benzyl, or $R_{02}$ and $R_{03}$, together with the nitrogen atom to which they are bonded, form a piperidine ring;

$R_{04}$ is chlorine, methylthio, ethylthio, i-propylthio, n-butylthio, i-butylthio, phenylthio or benzylthio;

$R_{05}$ is ethoxy, methylthio, ethylthio or phenylthio; and $R_{06}$ is chlorine or cyclohexylamino.

The alkyl groups occurring in the substituent definitions can be straight-chain or branched, which also applies to the alkyl, alkenyl and alkynyl moiety of the halogenoalkyl, halogenoalkenyl, alkenyloxy, alkylcarbonyloxy, alkoxyalkyl-, alkoxyalkenyl-, alkoxycarbonyl-, alkoxycarbonylalkyl-, alkylamino-, dialkylamino-, alkoxyalkoxy-, nitroalkyl-, cyanoalkyl-, hydroxyalkyl-, alkylaminoalkyl-, dialkylaminoalkyl-, cycloalkylalkyl-, heterocyclylalkyl-, alkoxyalkenyloxy-, alkoxycarbonylalkenyloxy-, halogenoalkylthio-, alkoxyalkylthio-, alkenylthio, halogenoalkenylthio-, alkoxyalkenylthio-, halogenoalkylcarbonyl- and halogenoalkoxycarbonyl groups.

Examples of alkyl groups are methyl, ethyl, propyl, butyl, pentyl, hexyl, heptyl, octyl, nonyl, decyl, undecyl, dodecyl, tetradecyl or hexadecyl and branched isomers thereof. These alkyl groups can be substituted by halogen, cyano, nitro, hydroxyl, $C_1$–$C_3$alkoxy, $C_1$–$C_6$alkylamino, di($C_1$–$C_6$-alkyl)amino, $C_3$–$C_{10}$alkenyl, $C_3$–$C_{10}$alkynyl, $C_3$–$C_{10}$alkenyloxy, $C_3$–$C_5$alkynyloxy, $C_1$–$C_3$trialkylsilyl, $C_1$–$C_6$alkoxycarbonyl, heterocyclyl, $C_3$–$C_{12}$cycloalkyl, $C_3$–$C_8$cycloalkoxy or $C_6$–$C_{10}$bicycloalkyl. The alkenyl and alkynyl radicals can be mono- or polyunsaturated.

Examples of alkenyls are allyl, methallyl, 1-methylallyl, but-2-en-1-yl, pent-4-en-1-yl, hex-4-en-1-yl and hept-4-en-1-yl, preferably alkenyl radicals having a chain length of 3 to 6 carbon atoms. The alkenyl groups can be substituted on the saturated carbon atoms, for example by $C_1$–$C_6$alkoxy or $C_3$–$C_8$cycloalkyl, and on the saturated or unsaturated carbon atoms by halogen. The alkenyl radicals are preferably bonded to a heteroatom by a saturated carbon atom.

Examples of alkynyls are propargyl, but-3-yn-1-yl, but-2-yn-1-yl, 1-methylpropargyl, 2-methylbutyn-2-yl, pent-4-yn-1-yl or 2-hexynyl, preferably alkynyl radicals having a chain length of 3 to 6 carbon atoms. The alkynyl radicals are preferably bonded to a heteroatom via a saturated carbon atom.

Halogen is fluorine, chlorine, bromine or iodine, preferably fluorine, chlorine or bromine. A corresponding statement also applies to halogen in combination with other definitions, such as halogenoalkyl, halogenoalkenyl, halogenoalkoxy, halogenoalkylcarbonyl, halogenoalkoxycarbonyl, halogenoalkylcarbonyloxy, halogenocycloalkyl or halogenobicycloalkyl.

Halogenoalkyl is alkyl groups which are mono- or polysubstituted, in particular mono- to trisubstituted, by halogen, halogen specifically being iodine and, in particular, fluorine, chlorine and bromine, for example fluoromethyl, difluoromethyl, trifluoromethyl, chloromethyl, dichloromethyl, trichloromethyl, 2,2,2-trifluoroethyl, 1,1-dichloro-2,2,2-trifluoroethyl, pentafluoroethyl, 2-fluoroethyl, 2-chloroethyl and 2,2,2-trichloroethyl.

Alkoxy is, for example, methoxy, ethoxy, n-propoxy, iso-propoxy, n-butoxy, iso-butoxy, sec-butoxy, tert-butoxy, and one of the isomeric pentoxy, hexyloxy, heptyloxy, octyloxy, nonyloxy and decyloxy radicals.

Halogenoalkenyl is alkenyl groups which are mono- or polysubstituted by halogen, halogen being bromine, iodine and, in particular, fluorine and chlorine, for example 2,2-difluoro-1-methylvinyl, 3-fluoropropenyl, 3-chloropropenyl, 3-bromopropenyl, 2,3,3-trifluoropropenyl and 4,4,4-trifluoro-but-2-en-1-yl. Preferred $C_3$–$C_{15}$alkenyl radicals which are mono- di- or trisubstituted by halogen are those which have a chain length of 3 to 6 carbon atoms.

Alkoxycarbonyl is, for example, methoxycarbonyl, ethoxycarbonyl, propoxycarbonyl, butoxycarbonyl, pentoxycarbonyl and hexyloxycarbonyl and branched isomers thereof, preferably methoxycarbonyl, ethoxycarbonyl and propoxycarbonyl.

Alkylamino is, for example, methylamino, ethylamino, propyl-, butyl-, pentyl- and hexylamino and their branched isomers.

Dialkylamino is, for example, dimethylamino, methylethylamino, diethylamino, n-propylmethylamino, dipropyl-, dibutyl-, dipentyl- and dihexylamino and their branched isomers.

In substituents such as dialkylamino or dialkylaminoalkyl, the alkyl radicals can be identical or different. They preferably have the same meaning. Corresponding statements also apply to the alkyl radicals in dialkylaminocarbonyl and trialkylsilyl substituents.

Alkoxyalkoxy is, for example, methoxymethoxy, ethoxymethoxy, ethoxyethoxy, propoxymethoxy, propoxyethoxy, butoxyethoxy and butoxybutoxy.

Halogenoalkoxy is, for example, fluoromethoxy, difluoromethoxy, trifluoromethoxy, 2,2,2-trifluorethoxy, 1,1,2,2-tetrafluorethoxy, 2fluoroethoxy, 2-chloroethoxy and 2,2,2-trichloroethoxy.

Alkylthio is, for example, methylthio, ethylthio, propylthio, butylthio, pentylthio, hexylthio, heptylthio, octylthio, nonylthio or decylthio and branched isomers thereof.

Alkenyloxy is, for example, allyloxy, 1-methylallyloxy, methallyloxy, but-2-en-1-yloxy or hex-2-en-1-yloxy. Alkenyl radicals having a chain length of 3 to 6 carbon atoms are preferred.

Alkynyloxy is, for example, propargyloxy, 1-methylpropargyloxy, but-3-yn-1-yloxy or pent-4-yn-1-yloxy.

Alkenylthio is, for example, allylthio, methallylthio, but-3-en-1-ylthio, pent-4-en-1-ylthio or hex-2-en-1-ylthio.

Alkynylthio is, for example, propargylthio, 1-methylpropargylthio, but-3-yn-1-ylthio, pent-4-yn-1-ylthio or hex-2-yn-1-ylthio.

Suitable cycloalkyl substituents contain 3 to 12 carbon atoms and are, for example, cyclopropyl, cyclobutyl, cyclopentyl, cyclohexyl, cycloheptyl, cyclooctyl, cyclononyl, cyclodecyl or cyclododecyl. Corresponding cycloalkenyl substituents can be mono- or else polyunsaturated, for example cyclopentenyl, cyclopentadienyl, cyclohexenyl, cycloheptenyl or cyclooctatetraenyl.

Cycloalkyl and also cycloalkenyl substituents can, unless stated otherwise, be substituted by $C_1$–$C_4$alkyl and contain fused-on aryl rings.

If alkyl, alkenyl or alkynyl occur as substituents on a cycloalkyl, cycloalkenyl, bicycloalkyl, bicycloalkenyl, phenyl, biphenyl, naphthyl or heterocyclyl, these ring systems can also be polysubstituted by alkyl, alkenyl or alkynyl.

If $R_{20}$, $R_{24}$, $R_{25}$, $R_{97}$, $R_{98}$ or $R_{99}$ occur on phenyl, naphthyl or heteroaryl, these ring systems can also be polysubstituted by $R_{20}$, $R_{24}$, $R_{25}$, $R_{97}$, $R_{98}$ or $R_{99}$.

If $R_{20}$, $R_{24}$, $R_{25}$, $R_{98}$ or $R_{100}$ occur on alicyclic or carbocyclic rings, these ring systems can also be polysubstituted by $R_{20}$, $R_{24}$, $R_{25}$, $R_{98}$ or $R_{100}$.

Carbocyclic radicals are to be understood as meaning saturated and unsaturated, mono- and polycyclic ring systems which consist of cycloalkanes, cycloalkenes, polycycloalkanes and polycycloalkenes. Carbocyclic radicals preferably contain 3 to 12 carbon atoms, for example cyclopropane, cyclobutane, cyclopentane, cyclohexane, cyclohexene, cycloheptane, cyclooctane, cyclononane, cyclodecane, cyclododecane and cis- and trans-decalin, it being possible for these carbocyclic radicals, unless stated otherwise, to be substituted by $C_1$–$C_4$alkyl.

Heterocyclyl is to be understood as meaning mono- and polycyclic ring systems which, in addition to carbon atoms, contain at least one heteroatom, such as nitrogen, oxygen or sulfur. They can be saturated or unsaturated and substituted by $C_1$–$C_3$alkyl, halogen or =O. Such ring systems preferably contain 3 to 12 ring atoms. This also applies to those heterocyclic radicals which, as in the case of groups such as —$NR_{90}R_{91}$, are formed by 2 substituents bonded to a nitrogen atom.

Examples of N-heterocyclic radicals onto which 1 or 2 further carbocyclic, heterocyclic or aromatic rings can be fused or spiro-bonded and which contain or do not contain further heteroatoms, in the definition of $R_1$, are:

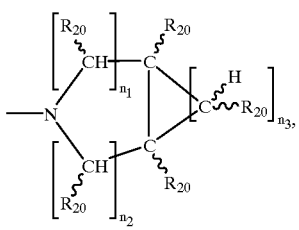

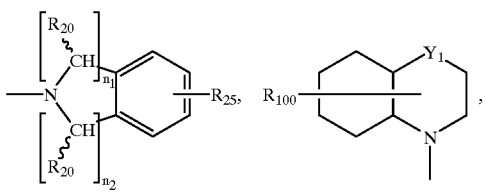

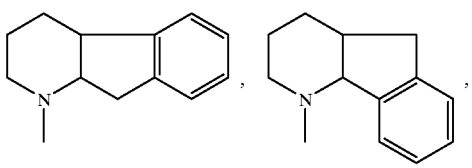

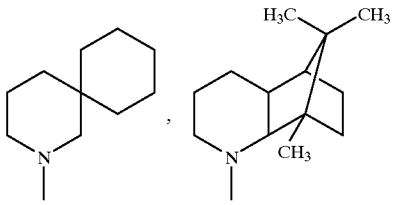

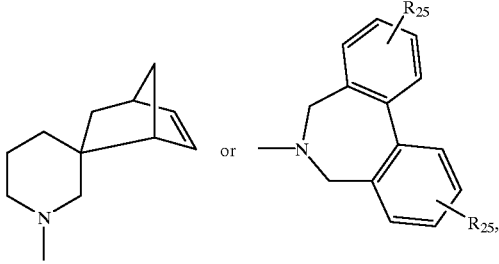

in which the radicals $R_{20}$ independently of one another are hydrogen, $C_1$–$C_4$alkyl or $C_1$–$C_3$alkoxy;

$R_{25}$ is hydrogen, chlorine, methyl or methoxy;

$R_{100}$ is hydrogen or $C_1$–$C_3$alkyl;

$Y_1$ is —O—, —S— or —$NR_{30}$;

$R_{30}$ is hydrogen, methyl, $C_1$–$C_3$alkylcarbonyl or ($C_1$–$C_3$alkyl)$_2$NCO—;

$n_1$ is 1, 2, 3, 4 or 5;

$n_2$ is 0, 1 or 2; and $n_3$ is a number from 3 to 10. The hetererocyclic radical is bonded to the thiatriazine ring via its nitrogen atom.

Examples of aryl, aryloxy, arylmethyleneoxy, arylcarbonyl-, arylcarbonyloxy or aryloxycarbonyl ring systems in the definition of $R_2$, $R_3$, $R_7$, $R_{13}$, $R_{94}$ and $R_{97}$ are:

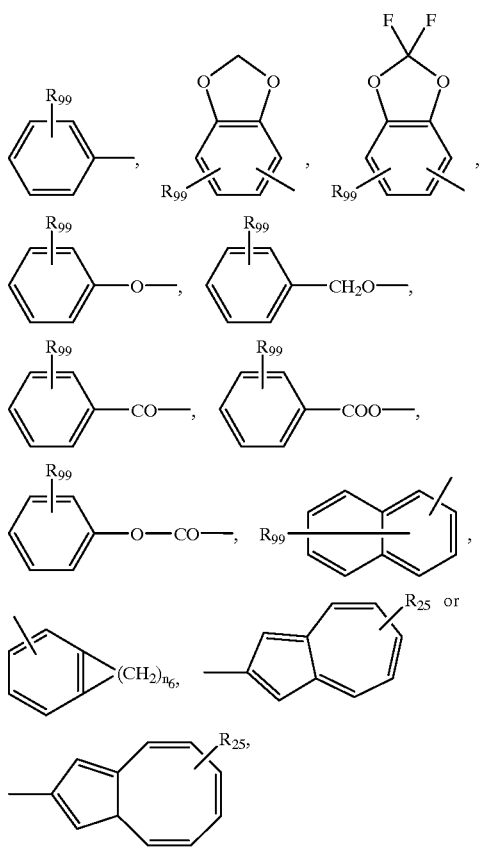

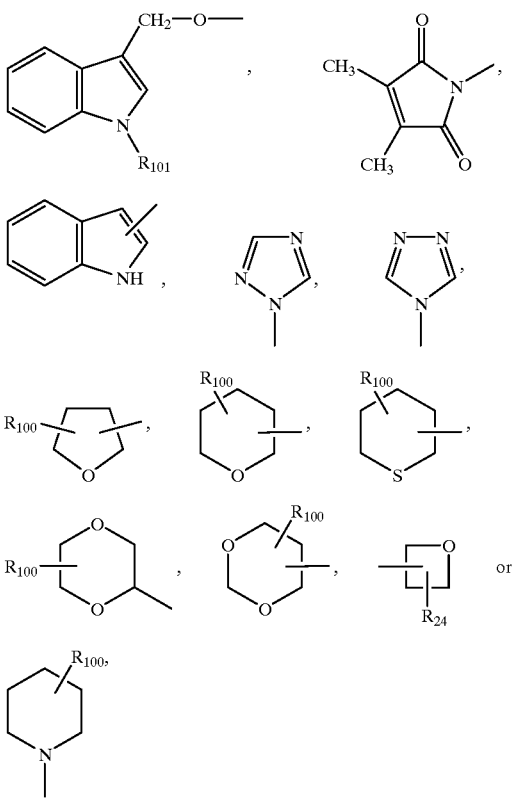

in which $R_{25}$ is as defined above;

$R_{99}$ is hydrogen, halogen, $NO_2$, CN, $C_1$–$C_5$alkyl, $C_1$–$C_6$alkoxy, $C_1$- or $C_2$halogenoalkoxy, $C_1$–$C_6$-alkenyloxycarbonyl, $C_1$–$C_3$alkylthio,

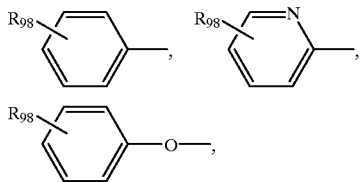

$C_1$–$C_6$alkoxycarbonyl, $NH_2$, $C_1$–$C_3$alkyl-CONH, di($C_1$–$C_6$alkyl)amino or $C_1$–$C_6$alkylamino;

$R_{98}$ is hydrogen, fluorine, chlorine, bromine, CN, $C_1$–$C_3$alkoxy, $C_1$–$C_3$alkoxycarbonyl, $C_1$–$C_3$-alkoxy-$C_1$–$C_3$-alkyl, $C_1$- or $C_2$-halogenoalkyl, $C_1$–$C_5$-alkyl, $NO_2$, $C_3$–$C_5$alkenyl, cyclopropyl or $C_1$- or $C_2$halogenoalkoxy; and $n_6$ is 3, 4, 5 or 6.

Examples of heterocyclic rings $R_7$ and $R_2$ or $R_3$ bonded to alkyl or alkoxy are:

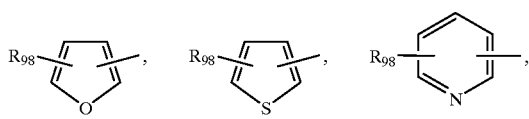

in which $R_{98}$ and $R_{100}$ are as defined above;

$R_{24}$ is hydrogen or methyl; and $R_{101}$ is $C_1$–$C_4$alkyl, $C_1$–$C_4$alkylcarbonyl or $C_1$–$C_3$-alkoxycarbonyl.

Examples of non-aromatic heterocyclic rings in the definition of $R_7$ are:

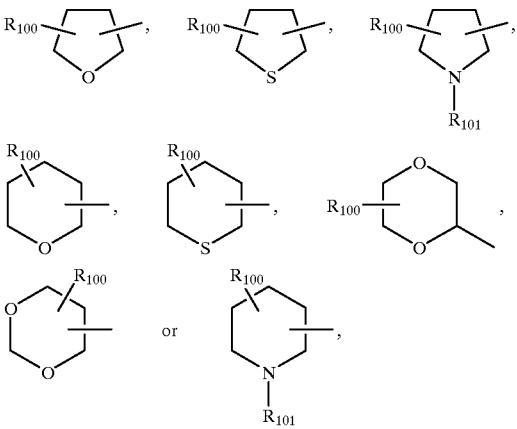

in which $R_{100}$ and $R_{101}$ are as defined above.

Alicyclic ring systems in the definition of $P_7$ are saturated and unsaturated, mono- and polycyclic ring systems containing bridge bonds and heteroatoms, such as nitrogen, oxygen or sulfur. Examples of such alicyclic ring systems are:

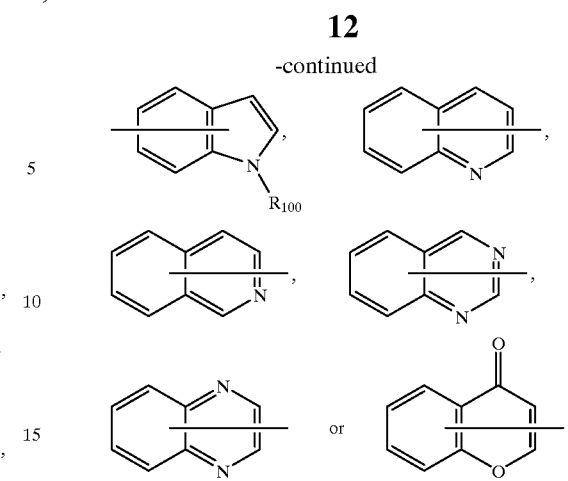

in which $R_{25}$ and $R_{100}$ are as defined above.

Saturated and unsaturated and substituted or unsubstituted mono- or bicyclic heterocyclic radicals formed from —$NR_{90}R_{91}$ include, for example, pyrrolidyl, dimethylpyrrolidyl, piperidyl, morpholinyl, dimethylmorpholinyl, thiomorpholinyl, cis- and trans-decahydro(iso)quinolyl, tetrahydropyridyl, 1,2,3,4-tetrahydro(iso)quinolyl, 1-methylpiperazinyl, perhydroindolyl, 3-pyrrolinyl, hexahydro-azepinyl, aziridyl, azeudyl, 4-piperidonyl and homopiperazinyl, it being possible for these heterocyclic radicals to have 1 or 2 further carbocyclic, heterocyclic or aromatic rings, for example cyclohexane, (nor-)bornane, cyclopentane, cycloheptane, cyclododecane or phenyl, fused-on or spiro-linked carbocyclic rings, for example cyclohexane or (nor-)bornene.

Further examples of saturated, substituted or unsubstituted heterocyclic rings formed from —$NR_{90}R_{91}$ which contain or do not contain heteroatoms or which can additionally be bridged with 1 or 2 groups

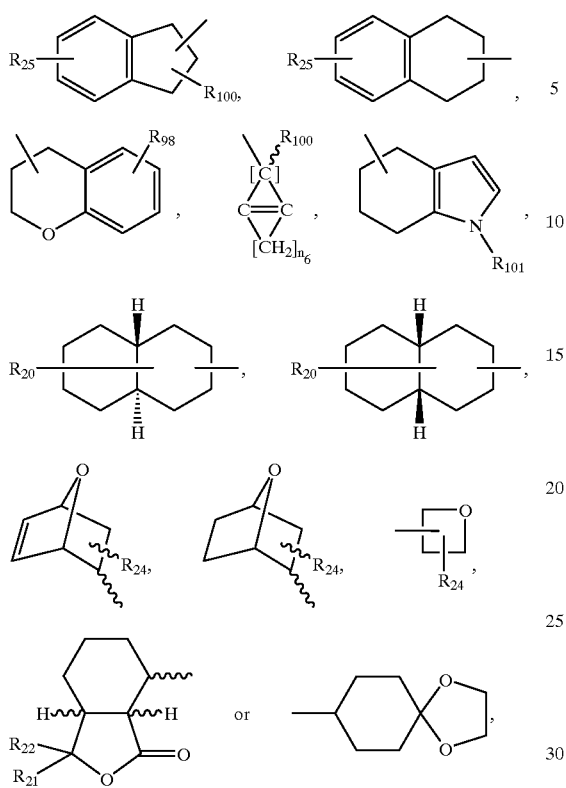

in which $R_{21}$ and $R_{22}$ independently of one another are hydrogen or $C_1$–$C_4$alkyl;

$n_9$ is 3 or 4; and $R_{20}$, $R_{24}$, $R_{25}$, $R_{98}$, $R_{100}$, $R_{101}$ and $n_6$ are as defined above.

Examples of heterocyclic rings $R_{90}$ and $R_{91}$, which are independent of one another, bonded to alkyl are:

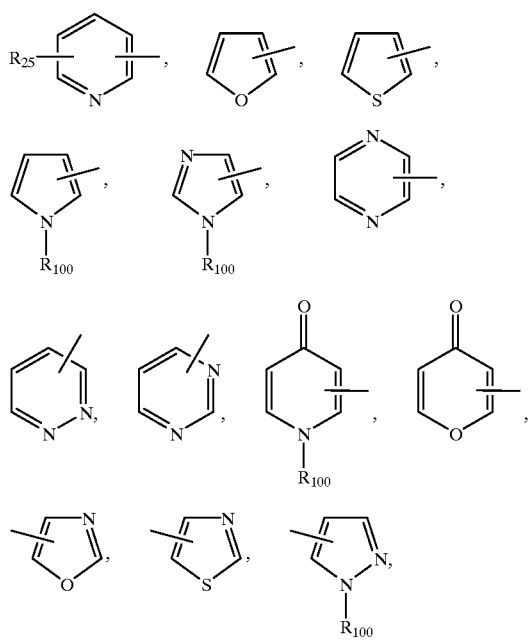

are:

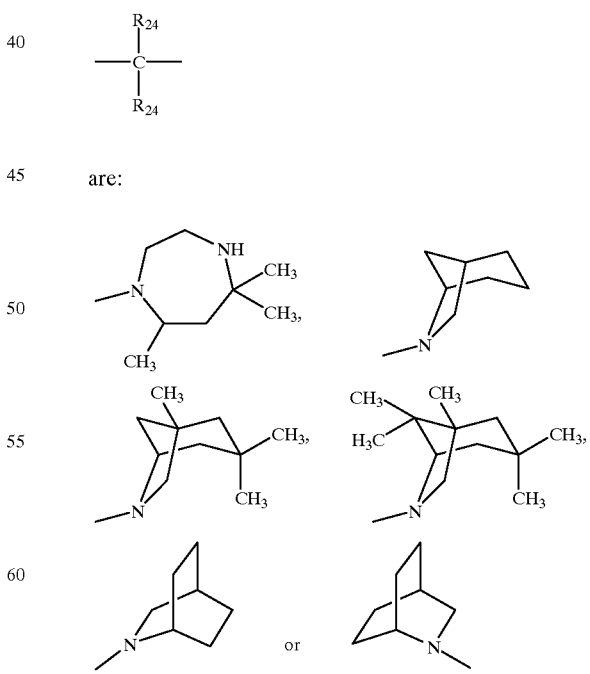

Preferred examples in which $R_{90}$ and $R_{91}$, together with the nitrogen atom, form a ring are pyrrolidyl, piperidyl, dimethylpiperidyl, ethoxycarbonylpiperidyl, morpholinyl, dimethylmorpholinyl, cis- and trans-decahydro(iso)quinolyl and 1,2,3,4-tetrahydro(iso)quinolyl.

Examples of aryl-X—, phthalidyl-X—, biphenyl-X— or heteroaryl-X— $R_2$ and $R_3$ are:

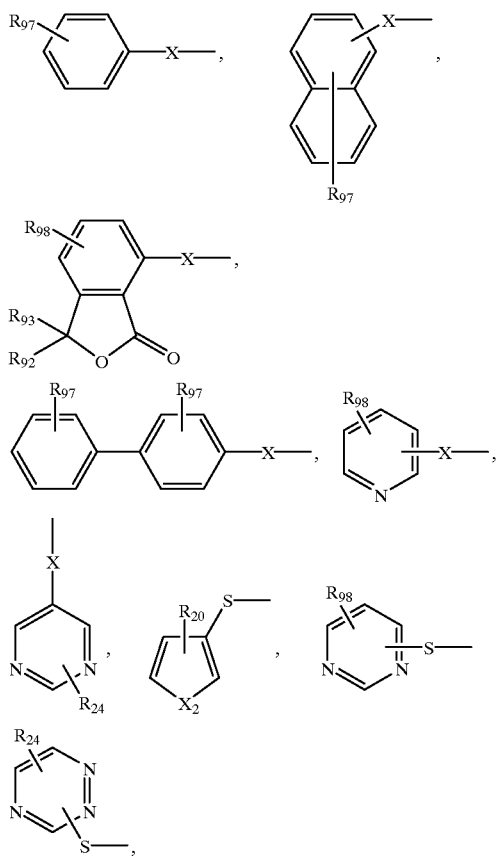

in which X is —O—, —S—, —SO— or —$SO_2$—;
$X_2$ is —O—, —S— or —$NR_{100}$—;
$R_{20}$, $R_{24}$, $R_{98}$ and $R_{100}$ are as defined above;
$R_{92}$ is hydrogen or $C_1$–$C_4$alkyl;
$R_{93}$ is hydrogen, $C_1$–$C_4$alkyl, hydroxyl, $C_1$–$C_4$alkoxy or $C_1$–$C_4$alkylthio; $R_{97}$ is hydrogen, halogen, $NO_2$, CN, $C_3$–$C_6$cycloalkoxy, $C_1$–$C_{10}$alkyl, $C_1$–$C_{10}$alkyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenyl, $C_3$–$C_{10}$alkenyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkoxy, $C_1$–$C_{10}$alkoxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy, $C_3$–$C_6$alkenyloxy, $C_1$–$C_6$-alkoxycarbonyl or substituted or unsubstituted aryl or aryloxy, $C_1$–$C_{10}$alkylcarbonyl, $C_1$–$C_{10}$alkylcarbonyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkoxycarbonyl, $C_1$–$C_{10}$alkoxycarbonyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylcarbonyloxy or $C_1$–$C_{10}$alkylcarbonyloxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, or $R_{97}$ is CHO, $C_3$–$C_8$-cycloalkyl, $C_1$–$C_4$alkylthio, $C_3$- or $C_4$alkenylthio, $(R_{94})_2$N—, $(R_{95})_2$N—CO—, aryl, aryloxy, arylcarbonyl or aryloxycarbonyl, or a group

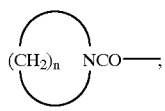

the radicals $R_{94}$ independently of one another are hydrogen, $C_1$–$C_{10}$alkyl, $C_3$–$C_8$cycloalkyl, $C_1$–$C_{10}$alkylcarbonyl or substituted or unsubstituted arylcarbonyl;

the radicals $R_{95}$ independently of one another are hydrogen, $C_1$–$C_5$alkyl or $C_3$–$C_8$cycloalkyl;

and n is a number from 5 to 12.

Examples of alicyclyl-X— $R_2$ and $R_3$ are:

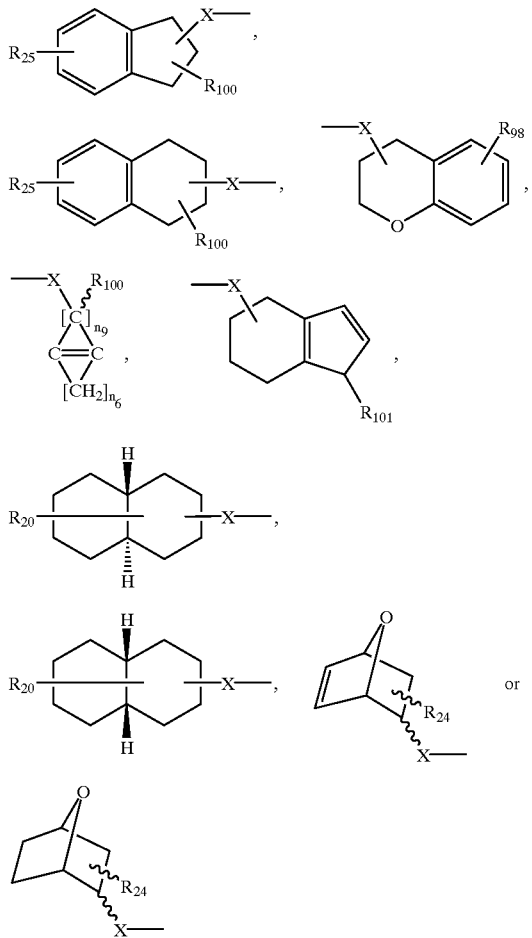

in which $R_{20}$, $R_{24}$, $R_{25}$, $R_{98}$, $R_{100}$, $R_{101}$, X, $n_6$ and $n_9$ are as defined above.

Examples of nonaromatic heterocyclyl-X— $R_2$ and $R_3$ are:

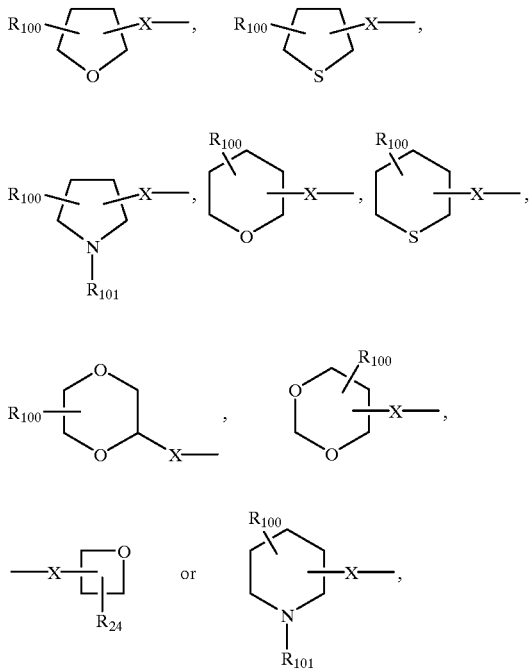

in which $R_{24}$, X, $R_{100}$ and $R_{101}$ are as defined above.

Examples of cyclic radicals $R_{11}$, in the compounds of the formula XII in the preparation process, onto which 1 or 2 further carbocyclic, heterocyclic or aromatic rings can be fused and which contain or do not contain heteroatoms are:

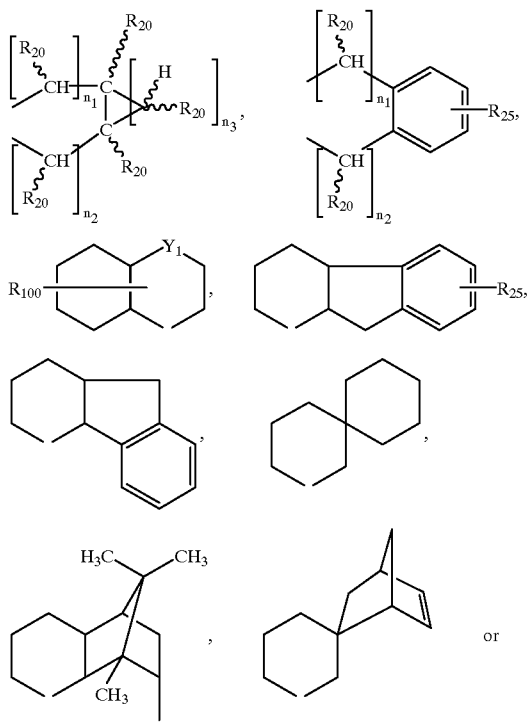

In the definitions cyanoalkyl, alkoxycarbonyl, alkylcarbonyloxy, alkylcarbonyl, alkoxycarbonylalkoxy and alkenyloxycarbonyl, the cyano or carbonyl carbon atom is not included in the particular lower and upper limits stated for the number of carbons.

Unless stated specifically, $^1$H— and $^{13}$C-NMR spectra (Tables 1–6) were recorded with a 300 MHz spectrometer in $CDCl_3$.

The compounds of the formula I in which $R_2$ and $R_3$ differ from one another have a centre of asymmetry in the sulfur atom of the thiatriazine ring.

Furthermore, asymmetric centres can be present in the substituents of the thiatriazine ring, for example in the definition of $R_1$ or $R_7$. This means that diastereomers can be formed, which can sometimes be separated by column chromatography, as shown, for example, in the tabular examples Compound Nos. 5.45/5.46, 6.6, 6.10, 6.55/6.56, 6.92/6.93, 6.120/6.121 and 6.153/6.154.

If substituents are bonded via a wavy line to a ring system in the formulae, for example in the definition of $R_1$, this means that all conformations or geometric isomerisms ('up' and 'down', or 'equatorial' and 'axial') are possible for these substituents.

Unless chiral starting materials are used, the compounds of the formula I are in general obtained as racemates in the process described in this application, and these are separated by customary separation processes, for example chromatographic processes, for example high pressure liquid chromatography (HPLC) over acetylcellulose, on the basis of physico-chemical properties. In the present invention, the active compounds of the formula I are to be understood as meaning both the pure optical antipodes and the racemates. Unless the individual optical antipodes are referred to specifically, those racemic mixtures which are formed in the preparation process described are to be understood under the formula given. If an aliphatic C=C double bond is present or if alicyclic or carbocyclic rings contain substituents, geometric isomerism may also occur.

The formula I is intended to include all these possible isomers, enantiomers and diastereoisomers and mixtures thereof.

Preferred compounds are those of the formula I
in which the radicals $R_{20}$, $R_{25}$, $R_{100}$, $Y_1$, $n_1$, $n_2$ and $n_3$ are as defined above.

Suitable substituted or unsubstituted bicycloalkyl and bicycloalkenyl substituents contain 6 to 12 carbon atoms and are, for example:

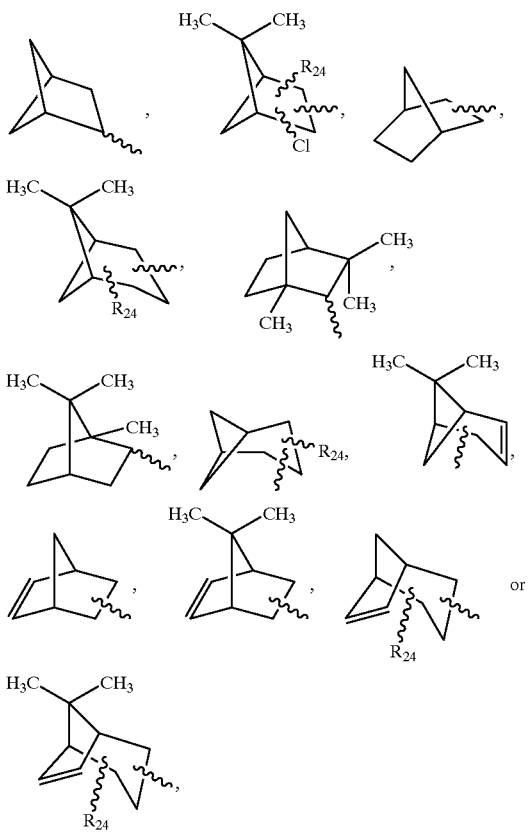

in which R$_{24}$ is as defined above.

The substituents in composite definitions, for example cycloalkoxy, cycloalkylalkyl, cycloalkyl-X—, bicycloalkylalkyl, bicycloalkyl-X—, alkylcarbonyl, alkylcarbonyloxy, cycloalkylalkenyl, cycloalkenylalkyl, alkoxyalkyl, alkoxyalkenyl, halogenobicycloalkyl, alkenyloxycarbonyl, alkenyloxyalkoxy, alkoxycarbonylalkoxy, alkylaminoalkyl, dialkylaminoalkyl, heterocyclylalkyl, heterocyclyl-X—, halogenoalkenyloxy, alkoxyalkenyloxy, alkenyloxyalkenyloxy, alkoxycarbonylalkenyloxy, halogenoalkylthio, alkenyloxyalkylthio, alkoxycarbonylalkylthio, halogenoalkenylthio, alkoxyalkenylthio, alkenyloxyalkenylthio, alkoxycarbonylalkenylthio, halogenoalkylcarbonyl, alkoxyalkylcarbonyl, alkenyloxyalkylcarbonyl, alkoxycarbonylalkylcarbonyl, halogenoalkoxycarbonyl, alkoxyalkoxycarbonyl, alkenyloxyalkoxycarbonyl, alkoxycarbonylalkoxycarbonyl, halogenoalkylcarbonyloxy, alkoxyalkylcarbonyloxy, alkenyloxyalkoxycarbonyloxy and alkoxycarbonylalkylcarbonyloxy can also be assigned corresponding definitions.

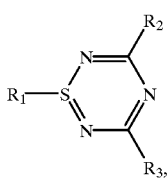

(I)

in which

R$_1$ is a group —OR$_7$, —NR$_{90}$R$_{91}$, or an N-heterocyclic radical, onto which 1 or 2 further carbocyclic, heterocyclic or aromatic rings can be fused and which contains or does not contain further heteroatoms;

R$_7$ is C$_1$–C$_{16}$alkyl, C$_1$–C$_{16}$alkyl substituted by halogen, NO$_2$, CN, C$_1$–C$_5$alkoxy, C$_1$–C$_5$alkylthio, C$_3$–C$_8$cycloalkoxy, C$_1$–C$_3$trialkylsilyl, C$_3$–C$_{10}$alkenyloxy, C$_3$–C$_5$alkynyloxy, C$_1$–C$_5$alkylcarbonyloxy, C$_1$–C$_3$alkoxycarbonyl, C$_1$–C$_3$alkylcarbonyl, C$_5$–C$_7$cycloalkenyl or C$_5$–C$_7$cycloalkenyl substituted by C$_1$–C$_4$alkyl, or R$_7$ is C$_1$–C$_{16}$alkyl substituted by C$_3$–C$_8$cycloalkyl, C$_6$–C$_{12}$bicycloalkyl, C$_6$–C$_{12}$chlorobicycloalkyl, C$_6$–C$_{12}$bicycloalkenyl or adamantyl, or R$_7$ is C$_1$–C$_{16}$alkyl substituted by substituted or unsubstituted aryl, aryloxy, arylmethyleneoxy, arylcarbonyl, arylcarbonyloxy or a heterocyclic ring, or R$_7$ is C$_3$–C$_{15}$alkenyl, C$_3$–C$_{15}$alkenyl substituted by halogen, C$_1$–C$_3$alkoxy, C$_3$–C$_8$cycloalkyl or substituted or unsubstituted aryl or aryloxy, or R$_7$ is C$_3$–C$_5$alkynyl, C$_3$–C$_{12}$cycloalkyl, C$_3$–C$_{12}$cycloalkyl substituted by halogen, CN, C$_1$–C$_3$-trialkylsilyl, =O, C$_1$–C$_6$alkyl, cyano-C$_1$–C$_5$alkyl, C$_1$–C$_5$alkyl-CONH—C$_1$–C$_5$alkyl, phenyl-CONH—C$_1$–C$_5$alkyl, C$_1$–C$_5$chloroalkyl, C$_1$–C$_3$alkoxy, C$_1$–C$_3$alkylthio, C$_1$–C$_3$alkoxycarbonyl, C$_1$–C$_3$alkoxycarbonyl-C$_1$–C$_5$alkyl, C$_5$–C$_7$cycloalkyl, C$_2$–C$_4$alkenyl, C$_2$–C$_4$alkynyl, benzyl or C$_1$–C$_3$halogenoalkyl, or R$_7$ is C$_5$–C$_7$cycloalkenyl, C$_5$–C$_7$cycloalkenyl substituted by C$_1$–C$_3$alkyl, or R$_7$ is C$_6$–C$_{12}$bicycloalkyl, C$_6$–C$_{12}$bicycloalkyl substituted by C$_1$–C$_3$alkyl or halogen, C$_6$–C$_{12}$bicycloalkenyl, C$_6$–C$_{12}$bicycloalkenyl substituted by C$_1$–C$_3$alkyl, or R$_7$ is a substituted or unsubstituted nonaromatic heterocyclic ring or an alicyclic ring system;

R$_{90}$ and R$_{91}$ independently of one another are hydrogen, C$_1$–C$_{12}$alkyl, C$_1$–C$_{12}$alkyl substituted by halogen, NO$_2$, CN, hydroxyl, C$_1$–C$_3$alkoxy, C$_1$–C$_3$trialkylsilyl, C$_1$–C$_6$alkylamino, di(C$_1$–C$_6$-alkyl)amino, C$_3$–C$_7$cycloalkyl,

or a heterocyclic ring, or C$_3$–C$_{10}$alkenyl, C$_3$–C$_{10}$alkynyl, C$_6$–C$_{12}$bicycloalkyl, C$_6$–C$_{12}$bicycloalkenyl, C$_3$–C$_{12}$cycloalkyl, C$_3$–C$_{12}$cycloalkyl substituted by C$_1$–C$_4$alkyl, C$_5$–C$_7$cycloalkenyl or C$_5$–C$_7$cycloalkenyl substituted by C$_1$–C$_4$alkyl, with the proviso that R$_{90}$ and R$_{91}$ are not simultaneously hydrogen; or R$_{90}$ and R$_{91}$, together with the nitrogen atom to which they are bonded, form a saturated heterocyclic ring which contains 2–12 carbon atoms and can contain, as further heteroatoms, a nitrogen, an oxygen or a sulfur atom and can be substituted by C$_1$–C$_4$alkyl, C$_1$- or C$_2$-halogenoalkyl, methoxy-C$_1$–C$_4$alkyl, halogen, hydroxyl, CN, C$_1$–C$_4$alkoxy, C$_1$–C$_4$-alkylcarbonyl, C$_1$- or C$_2$halogenoalkyl,

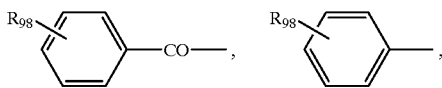

$C_1$–$C_3$alkoxycarbonyl, $(C_1$–$C_3$alkyl$)_2$NCO, di($C_1$–$C_4$alkyl)amino or =O and can additionally be bridged by 1 or 2

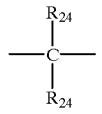

groups and onto which 1 or 2 further carbocyclic, heterocyclic or aromatic rings can be fused, or $R_{90}$ and $R_{91}$, together with the nitrogen atom to which they are bonded, form a monounsaturated heterocyclic ring which contains 5–7 carbon atoms and is substituted or unsubstituted by $C_1$–$C_4$alkyl, $C_1$- or $C_2$halogenoalkyl, halogen, hydroxyl, CN, amino, $C_1$–$C_4$alkylamino, di($C_1$–$C_4$alkyl)amino, phenyl, $C_1$–$C_4$alkoxy or $C_1$–$C_3$alkoxycarbonyl and is additionally bridged by 1 or 2

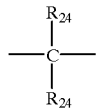

groups and onto which 1 or 2 further carbocyclic, heterocyclic or aromatic rings can be fused;

the radicals $R_{24}$ independently of one another are hydrogen or methyl;

$R_{98}$ is hydrogen, fluorine, chlorine, bromine, CN, $C_1$–$C_3$alkoxy, $C_1$–$C_3$alkoxycarbonyl, $C_1$–$C_3$-alkoxy-$C_1$–$C_3$alkyl, $C_1$- or $C_2$halogenoalkyl, $C_1$–$C_5$alkyl, $NO_2$, $C_3$–$C_5$alkenyl, cyclopropyl or $C_1$- or $C_2$halogenoalkoxy;

$R_2$ is halogen, $C_1$–$C_{10}$alkoxy, $C_1$–$C_{10}$alkoxy substituted by halogen, CN, $NO_2$, $C_1$–$C_6$alkoxy, $C_1$–$C_6$alkylthio, $C_3$–$C_6$alkenyloxy, $C_1$–$C_6$alkoxycarbonyl, heterocyclyl or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylthio, $C_1$–$C_{10}$alkylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenylthio or $C_3$–$C_{10}$alkenylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, or $R_2$ is $C_3$–$C_5$alkynyloxy, $C_3$–$C_5$alkynylthio, $C_3$–$C_8$cycloalkyl-X—, $C_6$–$C_{12}$bicycloalkyl-X—, heterocyclyl-X—, alicyclyl-X—, aryl-X—, phthalidyl-X—, biphenyl-X— or heteroaryl-X—; X is —O—, —S—, —SO— or —$SO_2$—, or $R_2$ is a group $R_{88}R_{89}$N—,

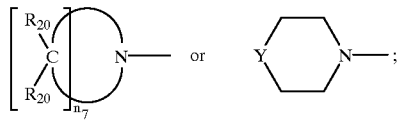

$R_{88}$ and $R_{89}$ independently of one another are hydrogen, $C_1$–$C_6$alkyl, $C_1$–$C_6$alkyl substituted by halogen, CN, $C_1$–$C_3$alkoxy or

$C_3$–$C_{12}$cycloalkyl, $C_3$–$C_{10}$alkenyl, $C_3$–$C_{10}$alkynyl, $C_6$–$C_{12}$bicycloalkyl or $C_6$–$C_{12}$bicycloalkyl substituted by $C_1$–$C_3$alkyl;

the radicals $R_{20}$ independently of one another are hydrogen or $C_1$–$C_4$alkyl;

$n_7$ is 4 or 5;

Y is —O—, —S—, —NH— or —$NR_{101}$—;

$R_{101}$ is $C_1$–$C_4$alkyl, $C_1$–$C_4$alkylcarbonyl or $C_1$–$C_3$alkoxycarbonyl and $R_{98}$ is as defined above; and $R_3$ is halogen, $C_1$–$C_{10}$alkoxy, $C_1$–$C_{10}$alkoxy substituted by halogen, CN, $NO_2$, $C_1$–$C_6$alkoxy, $C_1$–$C_6$alkylthio, $C_3$–$C_6$alkenyloxy, $C_1$–$C_6$alkoxycarbonyl, heterocyclyl or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylthio, $C_1$–$C_{10}$alkylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenylthio or $C_3$–$C_{10}$alkenylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, or $R_3$ is $C_3$–$C_5$alkynyloxy, $C_3$–$C_5$alkynylthio, $C_3$–$C_8$cycloalkyl-X—, $C_6$–$C_{12}$bicycloalkyl-X—, heterocyclyl-X—, alicyclyl-X—, aryl-X—, phthalidyl-X—, biphenyl-X— or heteroaryl-X—; and X is as defined above.

Preferred compounds of the formula I are also those in which $R_1$ is 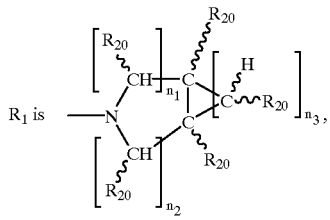

-continued

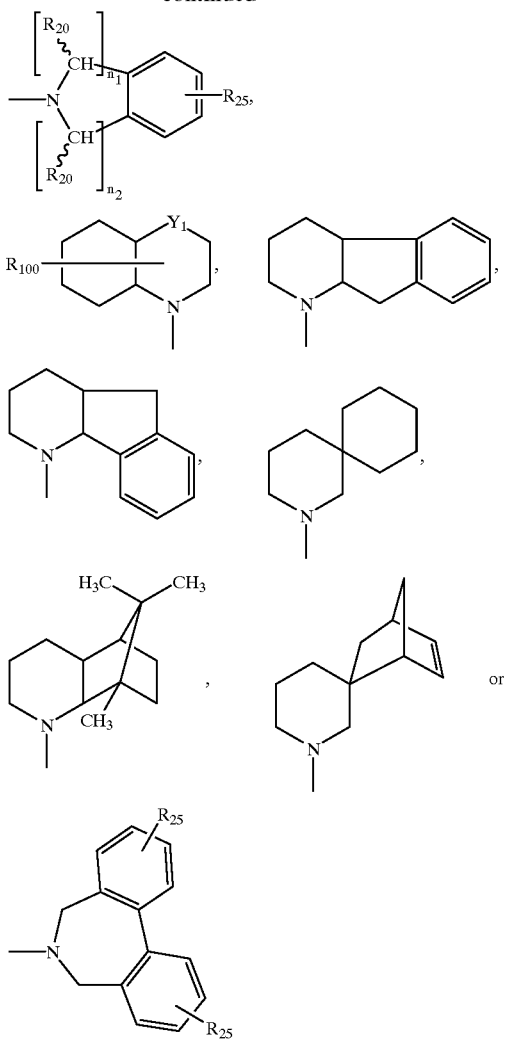

in which the radicals $R_{20}$ independently of one another are hydrogen or $C_1$–$C_4$alkyl;

$R_{25}$ is hydrogen, chlorine, methyl or methoxy;

$R_{100}$ is hydrogen or $C_1$–$C_3$alkyl;

$Y_1$ is —O—, —S— or —$NR_{30}$;

$R_{30}$ is hydrogen, methyl, $C_1$–$C_3$alkylcarbonyl or $(C_1$–$C_3$alkyl$)_2$NCO;

$n_1$ is 1, 2, 3, 4 or 5;

$n_2$ is 0, 1 or 2; and $n_3$ is a number from 3 to 10.

Preferred compounds of the formula I are also those in which $R_1$ is the group —$OR_7$, in which $R_7$ is as defined under formula I and $R_2$ and $R_3$ independently of one another are chlorine, $C_1$–$C_{10}$alkoxy, $C_1$–$C_{10}$alkoxy substituted by halogen, CN, NO$_2$, $C_1$–$C_6$alkoxy, $C_1$–$C_6$alkylthio, $C_3$–$C_6$alkenyloxy, $C_1$–$C_6$alkoxycarbonyl, heterocyclyl or substituted or unsubstituted aryl or aryloxy, $C_3$–$C_{10}$alkenyloxy, $C_3$–$C_{10}$alkenyloxy substituted by halogen, CN, NO$_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylthio, $C_1$–$C_{10}$alkylthio substituted by halogen, CN, NO$_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenylthio or $C_3$–$C_{10}$alkenylthio substituted by halogen, CN, NO$_2$, $C_1$–$C_6$alkoxy, $C_3$–$C_6$alkenyloxy, $C_1$–$C_6$alkoxycarbonyl or substituted or unsubstituted aryl or aryloxy, or $R_2$ and $R_3$ independently of one another are $C_3$–$C_5$alkynyloxy, $C_3$–$C_5$alkynylthio, $C_3$–$C_8$cycloalkyl-X—, $C_6$–$C_{12}$bicycloalkyl-X—, heterocyclyl-X—, alicyclyl-X—, aryl-X—, phthalidyl-X—, biphenyl-X— or heteroaryl-X—.

Compounds of the formula I which are likewise preferred are those in which $R_1$ is the group —$OR_7$;

$R_2$ is a group $R_{88}R_{89}$N—,

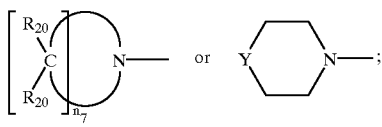

and $R_3$ is aryl-X—, phthalidyl-X—, biphenyl-X—, or heteroaryl-X—, in which $R_7$, $R_{20}$, $R_{88}$, $R_{89}$, Y, $n_7$ and X are as defined under formula I.

Thiatriazine derivatives of the formula I which are furthermore preferred are those in which $R_1$ is a group —$NR_{90}R_{91}$ or an N-heterocyclic radical, onto which 1 or 2 further carbocyclic, heterocyclic or aromatic rings can be fused and which contains or does not contain further heteroatoms.

$R_2$ is a group $R_{88}R_{89}$N—,

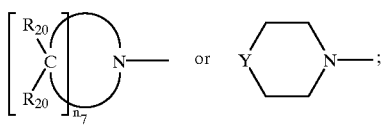

and $R_3$ is aryl-X—, phthalidyl-X—, biphenyl-X— or heteroaryl-X—, in which $R_{20}$, $R_{88}$, $R_{89}$, Y, $n_7$ and X are as defined under formula I.

Particularly preferred thiatriazine derivatives of the formula I are those in which $R_1$ is a group —$OR_7$;

$R_7$ $C_1$–$C_{16}$alkyl, $C_1$–$C_{16}$alkyl substituted by halogen, NO$_2$, CN, $C_1$–$C_5$alkoxy, $C_1$–$C_5$alkylthio, $C_3$–$C_8$cycloalkoxy, $C_1$–$C_3$trialkylsilyl, $C_3$–$C_{10}$alkenyloxy, $C_3$–$C_5$alkynyloxy, $C_1$–$C_5$alkylcarbonyloxy, $C_1$–$C_3$alkoxycarbonyl, $C_1$–$C_3$alkylcarbonyl, $C_5$–$C_7$cycloalkenyl or $C_5$–$C_7$cycloalkenyl substituted by $C_1$–$C_4$alkyl, or $R_7$ is $C_1$–$C_{16}$alkyl substituted by $C_6$–$C_{12}$bicycloalkyl, $C_6$–$C_{12}$chlorobicycloalkyl, $C_6$–$C_{12}$bicycloalkenyl or adamantyl, or $R_7$ is $C_1$–$C_{16}$alkyl substituted by

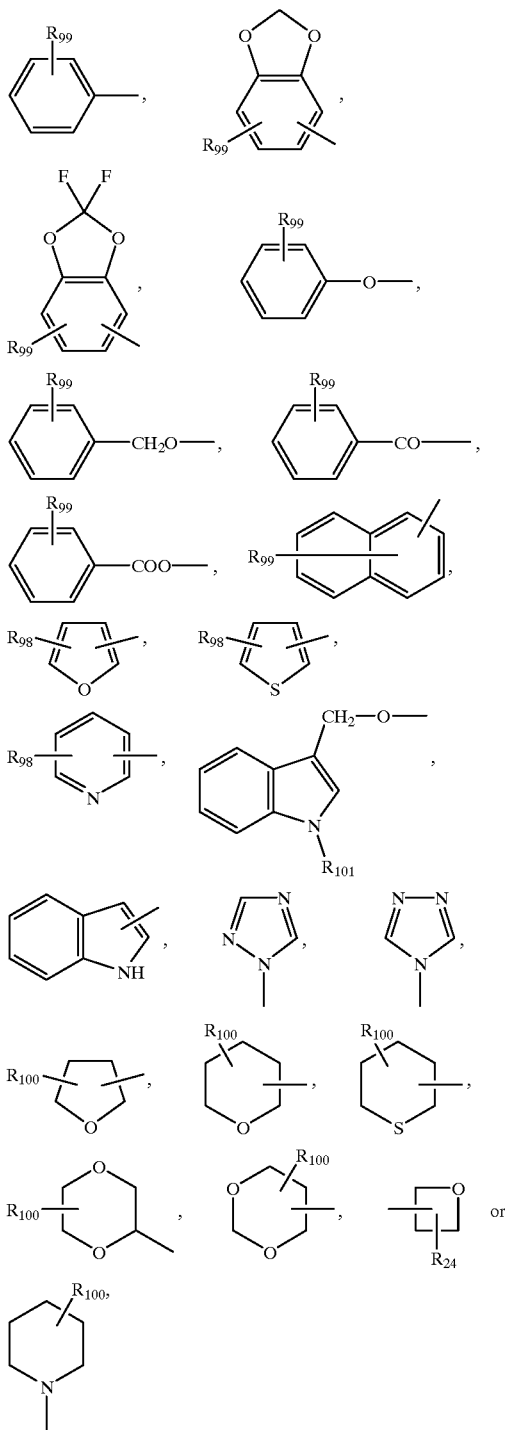

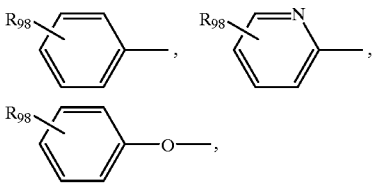

in which $R_{24}$ is hydrogen or methyl;

$R_{98}$ is hydrogen, fluorine, chlorine, bromine, CN, $C_1$–$C_3$alkoxy, $C_1$–$C_3$alkoxycarbonyl, $C_1$–$C_3$alkoxy-$C_1$–$C_3$alkyl, $C_1$- or $C_2$halogenoalkyl, $C_1$–$C_5$alkyl, $NO_2$, $C_3$–$C_5$alkenyl, cyclopropyl or $C_1$- or $C_2$halogenoalkoxy;

$R_{99}$ is hydrogen, halogen, $NO_2$, CN, $C_1$–$C_5$alkyl, $C_1$–$C_6$alkoxy, $C_1$–$C_6$alkenyloxycarbonyl, $C_1$–$C_3$alkylthio, $C_1$–$C_6$alkoxycarbonyl, $NH_2$, $C_1$–$C_3$alkyl-CONH, di($C_1$–$C_6$alkyl)amino or $C_1$–$C_6$alkylamino;

$R_{100}$ is hydrogen or $C_1$–$C_3$alkyl; and $R_{101}$ is $C_1$–$C_4$alkyl, $C_1$–$C_4$alkylcarbonyl or $C_1$–$C_3$alkoxycarbonyl; or $R_7$ is $C_3$–$C_{12}$cycloalkyl, $C_3$–$C_{12}$cycloalkyl substituted by halogen, CN, $C_1$–$C_3$trialkylsilyl, =O, $C_1$–$C_6$alkyl, cyano-$C_1$–$C_5$alkyl, $C_1$–$C_5$alkyl-CONH—$C_1$–$C_5$alkyl, phenyl-CONH—$C_1$–$C_5$alkyl, $C_1$–$C_5$chloroalkyl, $C_1$–$C_3$alkoxy, $C_1$–$C_3$alkylthio, $C_1$–$C_3$alkoxycarbonyl, $C_1$–$C_3$alkoxycarbonyl-$C_1$–$C_5$alkyl, $C_5$–$C_7$cycloalkyl, $C_2$–$C_4$alkenyl, $C_2$–$C_4$alkynyl, benzyl or $C_1$–$C_3$halogenoalkyl, $C_5$–$C_7$-cycloalkenyl or $C_5$–$C_7$cycloalkenyl substituted by $C_1$–$C_3$alkyl, or $R_7$ is $C_6$–$C_{12}$bicycloalkyl, $C_6$–$C_{12}$bicycloalkyl substituted by $C_1$–$C_3$alkyl or halogen, $C_6$–$C_{12}$bicycloalkenyl or $C_6$–$C_{12}$bicycloalkenyl substituted by $C_1$–$C_3$alkyl, or $R_7$ is a substituted or unsubstituted nonaromatic heterocyclic ring or an alicyclic ring system;

$R_2$ is a group $R_{88}R_{89}N$—;

$R_{88}$ and $R_{89}$ independently of one another are hydrogen, $C_1$–$C_6$alkyl, $C_1$–$C_6$alkyl substituted by halogen, CN, $C_1$–$C_3$alkoxy or

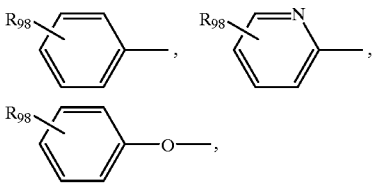

$C_3$–$C_{12}$cycloalkyl, $C_3$–$C_{10}$alkenyl, $C_3$–$C_{10}$alkynyl, $C_6$–$C_{12}$bicycloalkyl or $C_6$–$C_{12}$bicycloalkyl substituted by $C_1$–$C_3$alkyl; and $R_3$ is aryl-X—, phthalidyl-X—, biphenyl-X— or heteroaryl-X—.

Of these, especially preferred thiatriazine derivatives of the formula I are those in which $R_7$ is $C_3$–$C_{12}$cycloalkyl, $C_3$–$C_{12}$cycloalkyl substituted by halogen, CN, $C_1$–$C_6$alkyl, cyano-$C_1$–$C_5$alkyl, $C_1$–$C_3$alkoxy or $C_1$–$C_3$halogenoalkyl, or $R_7$ is $C_5$–$C_7$cycloalkenyl or $C_5$–$C_7$cyclo-alkenyl substituted by methyl, or $R_7$ is $C_6$–$C_{12}$bicycloalkyl, $C_6$–$C_{12}$bicycloalkyl substituted by methyl or chlorine, $C_6$–$C_{12}$bicycloalkenyl or $C_6$–$C_{12}$bicycloalkenyl substituted by methyl, or

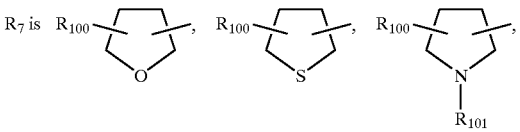

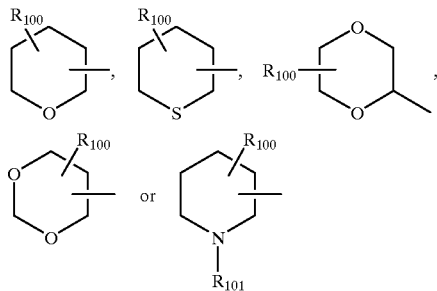

in which
R$_{100}$ is hydrogen or C$_1$–C$_3$alkyl; and
R$_{101}$ is C$_1$–C$_4$alkyl, C$_1$–C$_4$alkylcarbonyl or C$_1$–C$_3$alkoxycarbonyl; or

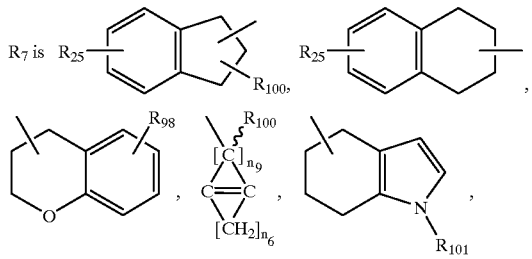

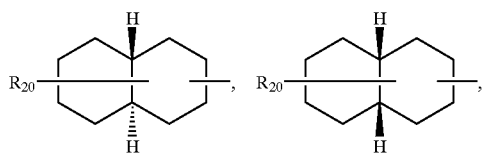

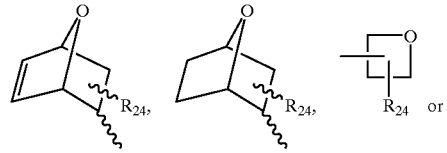

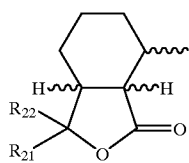

in which R$_{20}$ is hydrogen or C$_1$–C$_4$alkyl;
R$_{21}$ and R$_{22}$ independently of one another are hydrogen or C$_1$–C$_4$alkyl;
R$_{24}$ is hydrogen or methyl;
R$_{25}$ is hydrogen, chlorine, methyl or methoxy;
R$_{98}$ is hydrogen, fluorine, chlorine, bromine, CN, C$_1$–C$_3$alkoxy, C$_1$–C$_3$alkoxycarbonyl, C$_1$–C$_3$alkoxy-C$_1$–C$_3$alkyl, C$_1$- or C$_2$halogenoalkyl, C$_1$–C$_5$alkyl, NO$_2$, C$_3$–C$_5$alkenyl, cyclopropyl or C$_1$- or C$_2$-halogenoalkoxy;
n$_6$ is 3, 4, 5 or 6;
n$_9$ is 3 or 4; and
R$_{100}$ and R$_{101}$ are as defined above;
R$_2$ is a group R$_{88}$R$_{89}$N—;
R$_{88}$ and R$_{89}$ independently of one another are hydrogen or C$_1$–C$_6$alkyl and R$_3$ is

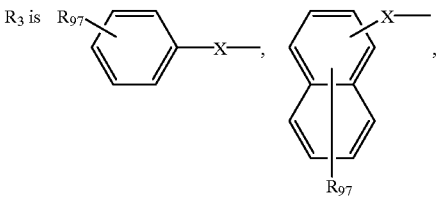

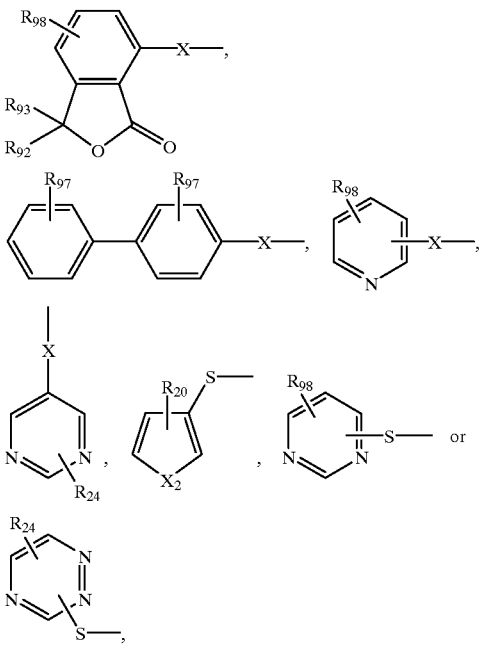

in which X is —O— or —S—;
X$_2$ is —O—, —S— or —NR$_{100}$—;
R$_{20}$, R$_{24}$ and R$_{100}$ are as defined above;
R$_{92}$ is hydrogen or C$_1$–C$_4$alkyl;
R$_{93}$ is hydrogen, C$_1$–C$_4$alkyl, hydroxyl, C$_1$–C$_4$alkoxy or C$_1$–C$_4$alkylthio;
R$_{97}$ is hydrogen, halogen, NO$_2$, CN, C$_3$–C$_6$cycloalkoxy, C$_1$–C$_{10}$alkyl, C$_1$–C$_{10}$calkyl substituted by halogen, CN, NO$_2$, C$_1$–C$_6$alkoxy, C$_3$–C$_6$alkenyloxy, C$_1$–C$_6$alkoxycarbonyl or substituted or unsubstituted aryl or aryloxy, C$_3$–C$_{10}$alkenyl, C$_3$–C$_{10}$alkenyl substituted by halogen, CN, NO$_2$, C$_1$–C$_6$alkoxy, C$_3$–C$_6$alkenyloxy, C$_1$–C$_6$alkoxycarbonyl or substituted or unsubstituted aryl or aryloxy, C$_1$–C$_{10}$alkoxy, C$_1$–C$_{10}$alkoxy substituted by halogen, CN, NO$_2$, C$_1$–C$_6$alkoxy, C$_3$–C$_6$alkenyloxy, C$_1$–C$_6$alkoxycarbonyl or substituted or unsubstituted aryl or aryloxy, C$_3$–C$_{10}$alkenyloxy, C$_3$–C$_{10}$alkenyloxy substituted by halogen, CN, NO$_2$, C$_1$–C$_6$alkoxy, C$_3$–C$_6$alkenyloxy, C$_1$–C$_6$alkoxycarbonyl or substituted or unsubstituted aryl or aryloxy, C$_1$–C$_{10}$alkylcarbonyl, C$_1$–C$_{10}$alkylcarbonyl substituted by halogen, CN, NO$_2$, C$_1$–C$_6$alkoxy, C$_3$–C$_6$alkenyloxy, C$_1$–C$_6$alkoxycarbonyl or substituted or unsubstituted aryl or aryloxy, C$_1$–C$_{10}$alkoxycarbonyl, C$_1$–C$_{10}$alkoxycarbonyl substituted by halogen, CN, NO$_2$, C$_1$–C$_6$alkoxy, C$_3$–C$_6$alkenyloxy, C$_1$–C$_6$alkoxycarbonyl or substituted or unsubstituted aryl or aryloxy, C$_1$–C$_{10}$alkylcarbonyloxy or C$_1$–C$_{10}$alkylcarbonyloxy substituted by halogen, CN, NO$_2$, C$_1$–C$_6$-alkoxy, C$_3$–C$_6$alkenyloxy, C$_1$–C$_6$alkoxycarbonyl or substituted or unsubstituted aryl or aryloxy, or $R_{97}$ is CHO, $C_3$–$C_8$cycloalkyl, $C_1$–$C_4$alkylthio, $C_3$- or $C_4$alkenylthio, $(R_{94})_2$N—, $(R_{95})_2$N—CO—, aryl, aryloxy, arylcarbonyl or aryloxycarbonyl, or a group

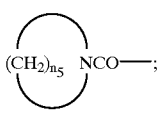

the radicals $R_{94}$ independently of one another are hydrogen, $C_1$–$C_{10}$alkyl, $C_3$–$C_8$cycloalkyl, $C_1$–$C_{10}$alkylcarbonyl or substituted or unsubstituted arylcarbonyl; the radicals $R_{95}$ independently of one another are hydrogen, $C_1$–$C_5$alkyl or $C_3$–$C_8$cycloalkyl;

$n_5$ is a number from 5 to 12; and $R_{98}$ is as defined above.

Of these, those compounds in which X and $X_2$ are —O— are especially important.

Particularly preferred compounds of the formula I are also those in which $R_1$ is a group —$NR_{90}R_{91}$ or

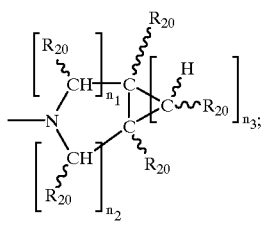

$R_{90}$ and $R_{91}$ independently of one another are $C_1$–$C_{12}$alkyl, $C_1$–$C_{12}$alkyl substituted by halogen, CN or $C_1$–$C_3$alkoxy, $C_6$–$C_{12}$bicycloalkyl, $C_6$–$C_{12}$bicycloalkenyl, $C_3$–$C_{12}$cycloalkyl, $C_3$–$C_{12}$cycloalkyl substituted by $C_1$–$C_4$alkyl, $C_5$–$C_7$cycloalkenyl or $C_5$–$C_7$cycloalkenyl substituted by $C_1$–$C_4$alkyl;

the radicals $R_{20}$ independently of one another are hydrogen or $C_1$–$C_4$alkyl;

$n_1$ is 1, 2, 3, 4 or 5;

$n_2$ is 0, 1 or 2; and $n_3$ is a number from 3 to 10;

$R_2$ is a group $R_{88}R_{89}$N—;

$R_{88}$ and $R_{89}$ independently of one another are hydrogen or $C_1$–$C_6$alkyl and

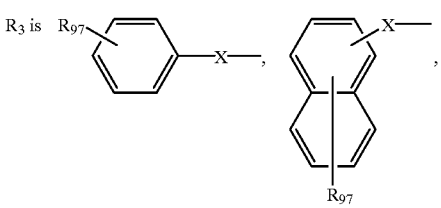

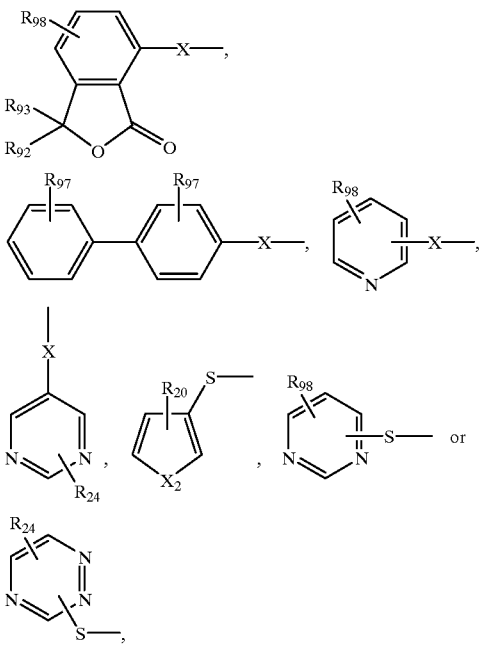

in which X is —O—, —S—, —SO— or —$SO_2$—;

$X_2$ is —O—, —S— or —$NR_{100}$—;

$R_{100}$ is hydrogen or $C_1$–$C_3$alkyl;

$R_{20}$ is as defined above;

$R_{24}$ is hydrogen or methyl;

$R_{92}$ is hydrogen or $C_1$–$C_4$alkyl;

$R_{93}$ is hydrogen, $C_1$–$C_4$alkyl, $C_1$–$C_4$alkoxy or $C_1$–$C_4$alkylthio;

$R_{97}$ is hydrogen, halogen, $NO_2$, CN, $C_3$–$C_6$cycloalkoxy, $C_1$–$C_{10}$alkyl, $C_1$–$C_{10}$alkyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenyl, $C_3$–$C_{10}$alkenyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkoxy, $C_1$–$C_{10}$alkoxy substituted by halogen, CN, $NO_2$, $C_1$–$C_6$alkoxy, $C_3$–$C_6$-alkenyloxy, $C_1$–$C_6$alkoxycarbonyl or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylcarbonyl, $C_1$–$C_{10}$alkylcarbonyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkoxycarbonyl, $C_1$–$C_{10}$alkoxycarbonyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylcarbonyloxy or $C_1$–$C_{10}$alkylcarbonyloxy substituted by halogen, CN, $NO_2$, $C_1$–$C_6$-alkoxy, $C_3$–$C_6$alkenyloxy, $C_1$–$C_6$alkoxycarbonyl or substituted or unsubstituted aryl or aryloxy, or $R_{97}$ is CHO, $C_3$–$C_8$cycloalkyl, $C_1$–$C_4$alkylthio, $C_3$- or $C_4$alkenylthio, $(R_{94})_2$N—, $(R_{95})_2$N—CO—, aryl, aryloxy, arylcarbonyl or aryloxycarbonyl, or a group

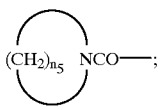

the radicals $R_{94}$ independently of one another are hydrogen, $C_1$–$C_{10}$alkyl, $C_3$–$C_8$cycloalkyl, $C_1$–$C_{10}$alkylcarbonyl or substituted or unsubstituted arylcarbonyl;

the radicals $R_{95}$ independently of one another are hydrogen, $C_1$–$C_5$alkyl or $C_3$–$C_8$cycloalkyl;

$n_5$ is a number from 5 to 12; and $R_{98}$ is hydrogen, fluorine, chlorine, bromine, CN, $C_1$–$C_3$alkoxy, $C_1$–$C_3$alkoxycarbonyl, $C_1$–$C_3$-alkoxy-$C_1$–$C_3$alkyl, $C_1$- or $C_2$halogenoalkyl, $C_1$–$C_5$alkyl, $NO_2$, $C_3$–$C_5$alkenyl, cyclopropyl or $C_1$- or $C_2$halogenoalkoxy.

Especially preferred compounds of these are those in which $R_1$ is a group

—$NR_{90}R_{91}$ or

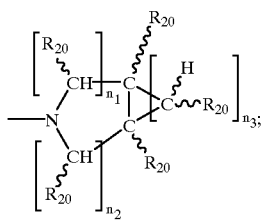

$R_{90}$ and $R_{91}$ independently of one another are $C_1$–$C_{12}$alkyl, $C_1$–$C_{12}$alkyl substituted by halogen, CN or $C_1$–$C_3$alkoxy, $C_3$–$C_8$cycloalkyl, $C_3$–$C_8$cycloalkyl substituted by methyl, $C_5$–$C_7$cycloalkenyl or $C_5$–$C_7$cycloalkenyl substituted by methyl;

the radicals $R_{20}$ independently of one another are hydrogen or methyl;

$n_1$ is 2, 3 or 4;

$n_2$ 0 or 1; and $n_3$ is 3, 4 or 5;

$R_2$ is a group $R_{88}R_{89}N$—;

$R_{88}$ and $R_{89}$ independently of one another are hydrogen or $C_1$–$C_3$alkyl; and

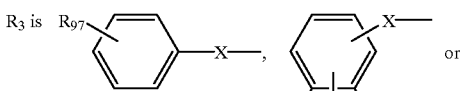

in which X is —O— or —S—;

$R_{97}$ is hydrogen, halogen, $NO_2$, CN, $C_1$–$C_{10}$alkyl, $C_1$–$C_{10}$alkyl substituted by halogen, CN, $NO_2$, $C_1$–$C_6$alkoxy or substituted or unsubstituted aryl or aryloxy, $C_3$–$C_{10}$alkenyl, $C_3$–$C_{10}$alkenyl substituted by halogen, CN, $NO_2$, $C_1$–$C_6$alkoxy or substituted or unsubstituted aryl or aryloxy, $C_1$–$C_{10}$alkoxy, $C_1$–$C_{10}$alkoxy substituted by halogen, CN, $NO_2$, $C_1$–$C_6$alkoxy or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy or substituted or unsubstituted aryl or aryloxy, $C_1$–$C_{10}$alkoxycarbonyl, $C_1$–$C_{10}$alkoxycarbonyl substituted by halogen, CN, $NO_2$, $C_1$–$C_6$alkoxy or substituted or unsubstituted aryl or aryloxy, $C_1$–$C_{10}$alkylcarbonyloxy or $C_1$–$C_{10}$alkylcarbonyloxy substituted by halogen, CN, $NO_2$, $C_1$–$C_6$alkoxy or substituted or unsubstituted aryl or aryloxy, or $R_{97}$ is $(R_{94})_2N$—, $(R_{95})_2N$—CO—, aryl, aryloxy, arylcarbonyl or aryloxycarbonyl;

the radicals $R_{94}$ independently of one another are hydrogen, $C_1$–$C_4$alkyl, $C_3$–$C_8$cycloalkyl, $C_1$–$C_5$alkylcarbonyl or substituted or unsubstituted arylcarbonyl; and the radicals $R_{95}$ independently of one another are hydrogen, $C_1$–$C_3$alkyl or $C_3$–$C_6$cycloalkyl.

Especially preferred individual compounds from the scope of formula I are:

3-amino-5-pentafluorophenoxy-1-(trans-3,3,5-trimethylcyclohexanolyl)thiatriazine;

3-amino-5-pentafluorophenoxy-1-[(N-cis-3,3,5-trimethylcyclohexyl)methylamino]thiatriazine;

3-amino-5-pentafluorophenoxy-1-octamethyleneimino-thiatriazine;

3-amino-5-pentafluorophenoxy-1-decahydroquinolyl-thiatriazine;

3-amino-5-pentafluorophenoxy-1-tetrahydroisoquinolyl-thiatriazine; and the compound of the formula

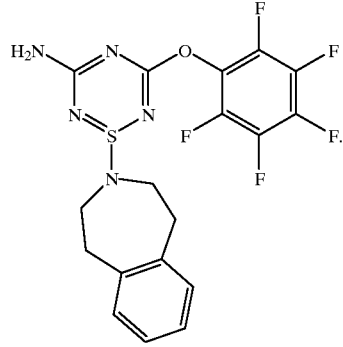

The compounds of the formula I can be prepared on the one hand by process steps known per se using known starting materials, and on the other hand by processes which are not known per se. The latter processes which are not known per se comprise a procedure in which, for preparation of compounds of the formula I in which $R_1$ is the group $R_7$; $R_2$ and $R_3$ independently of one another are halogen, $C_1$–$C_{10}$alkoxy, $C_1$–$C_{10}$alkoxy substituted by halogen, CN, $NO_2$, $C_1$–$C_6$alkoxy, $C_1$–$C_6$alkylthio, $C_3$–$C_6$alkenyloxy, $C_1$–$C_6$alkoxycarbonyl, heterocyclyl or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylthio, $C_1$–$C_{10}$alkylthio substituted by halogen, CN, $NO_2$, $C_1-C_6$alkoxy, $C_3-C_6$alkenyloxy, $C_1-C_6$alkoxycarbonyl or substituted or unsubstituted aryl or aryloxy, $C_3-C_{10}$alkenylthio or $C_3-C_{10}$alkenylthio substituted by halogen, CN, $NO_2$, $C_1-C_6$alkoxy, $C_3-C_6$alkenyloxy, $C_1-C_6$alkoxycarbonyl or substituted or unsubstituted aryl or aryloxy, or $R_2$ and $R_3$ independently of one another are $C_3-C_5$alkynyloxy, $C_3-C_5$alkynylthio, $C_3-C_8$cycloalkyl-X—, $C_8-C_{12}$bicycloalkyl-X—, heterocyclyl-X—, alicyclyl-X—, aryl-X—, phthalidyl-X—, biphenyl-X— or heteroaryl-X—, and X is as defined under formula I, $a_1$) 1,3,5-trichlorthiatriazine is used as the starting substance, and this is converted with an alcohol of the formula XVII

   $R_7$—OH   (XVII), in which $R_7$ is as defined under formula I,
if appropriate in the presence of an equimolar amount of base and an inert organic solvent, into the compound of the formula VII

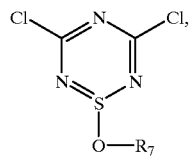 (VII)

in which $R_7$ is as defined,
and this compound is then either $b_1$) reacted with a compound of the formula XXIII

   $R_{14}$—$X_1$H   (XXIII), in which $R_{14}$ is $C_1-C_{10}$alkyl, $C_1-C_{10}$alkyl substituted by halogen, CN, $NO_2$, $C_1-C_6$alkoxy, $C_1-C_6$alkylthio, $C_3-C_6$alkenyloxy, $C_1-C_6$alkoxycarbonyl, heterocyclyl or substituted or unsubstituted aryl or aryloxy, $C_3-C_{10}$alkenyl or $C_3-C_{10}$alkenyl substituted by halogen, CN, $NO_2$, $C_1-C_6$alkoxy, $C_3-C_6$alkenyloxy, $C_1-C_6$alkoxycarbonyl or substituted or unsubstituted aryl or aryloxy, $C_3-C_5$alkynyl, $C_3-C_8$cycloalkyl, $C_6-C_{12}$bicycloalkyl, heterocyclyl or alicyclyl and $X_1$ is oxygen or sulfur,
in the presence of an equimolar amount of base and an inert organic solvent, or $b_2$) converted with a compound of the formula XVI

   $R_{12}$—$X_1$H   (XVI), in which $R_{12}$ is an aryl, phthalidyl, biphenyl or heteroaryl radical; and
$X_1$ is oxygen or sulfur,
in the presence of an equimolar amount of base and an aprotic solvent, into the compound of the formula VI

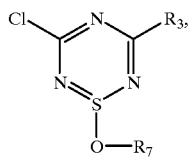 (VI)

in which $R_3$ is —$X_1$—$R_{12}$,
and this compound is either $c_2$) reacted with the compound of the formula XXIII

   $R_{14}$—$X_1$H   (XXIII), in which $R_{14}$ and $X_1$ are as defined above,
in the presence of an equimolar amount of base and an inert organic solvent, or $c_3$) converted with the compound of the formula XVI

   $R_{12}$—$X_1$H   (XVI), in which $R_{12}$ and $X_1$ are as defined above,
in the presence of an equimolar amount of base and an aprotic solvent, into the compound of the formula V

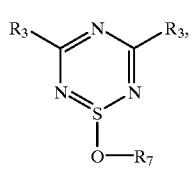 (V)

in which $R_3$ is —$X_1$—$R_{12}$ and
$R_7$, $X_1$ and $R_{12}$ are as defined above,
and this compound is then $d_3$) reacted with the compound of the formula XXIII

   $R_{14}$—$X_1$H   (XXIII), in which $R_{14}$ and $X_1$ are as defined,
in the presence of an equimolar amount of base and in an inert organic solvent, or the compound of the formula VII $b_3$) converted with 2 mol of compound of the formula XVI

   $R_{12}$—$X_1$H   (XVI), in which $R_{12}$ and $X_1$ are as defined,
in the presence of an equimolar amount of base and in an aprotic organic solvent, into the compound of the formula V, and this compound is then reacted in a manner analogous to that described under $d_3$), or $a_2$) 1,3,5-trichlorothiatriazine is converted with a $C_6-C_{12}$bicycloalkyl epoxide, a $C_6-C_{12}$bicycloalkyl epoxide substituted by $C_1-C_3$alkyl or an epoxide of the formula XVIII or XIX

(XVIII)

or

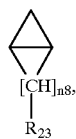

(XIX)

in which the radicals $R_{13}$ independently of one another are hydrogen, $C_3$–$C_8$alkenyl, $C_1$–$C_{14}$alkyl, $C_1$–$C_{14}$alkyl substituted by halogen, $NO_2$, CN, $C_1$–$C_5$alkoxy, aryloxy or $C_1$–$C_3$alkoxycarbonyl;

the radicals $R_{23}$ independently of one another are hydrogen or $C_1$–$C_6$alkyl;

$n_8$ is a number from 3–10; and $n_{11}$ is 1 or 2, in an inert organic solvent, into the compound of the formula VII in which $R_7$ is $C_2$–$C_{16}$-b-chloroalkyl, $C_2$–$C_{16}$-b-chloroalkyl substituted by halogen, $NO_2$, CN, $C_1$–$C_5$alkoxy, aryloxy or $C_1$–$C_3$alkoxycarbonyl, $C_5$–$C_{12}$-b-chlorocycloalkyl or $C_5$–$C_{12}$-b-chlorocycloalkyl substituted by $C_1$–$C_6$alkyl, and this compound reacted further in a manner analogous to that described under $b_1$); $b_2$) and $c_2$); $b_2$), $c_3$) and $d_3$); or $b_3$) and $d_3$), or $a_3$) 1,3,5-trichlorothiatriazine is reacted with an alcohol of the formula XVII $R_7$—OH (XVII), in which $R_7$ is $C_1$–$C_{10}$alkyl, $C_1$–$C_{10}$alkyl substituted by halogen, CN, $NO_2$, $C_1$–$C_5$alkoxy, $C_1$–$C_5$alkylthio, $C_3$–$C_6$alkenyloxy, $C_1$–$C_3$alkoxycarbonyl, heterocyclyl or substituted or unsubstituted aryl or aryloxy, $C_3$–$C_{10}$alkenyl, $C_3$–$C_{10}$alkenyl substituted by halogen, $C_1$–$C_3$alkoxy or substituted or unsubstituted aryl or aryloxy, $C_3$–$C_5$alkynyl, $C_3$–$C_8$cycloalkyl, $C_6$–$C_{12}$bicycloalkyl, heterocyclyl or alicyclyl, if appropriate in an inert solvent in the presence of an eqimolar amount of base.

Another process according to the invention for the preparation of the compounds of the formula I in which $R_1$ is the group —$OR_7$;

$R_2$ is a group $R_{88}R_{89}N$—,

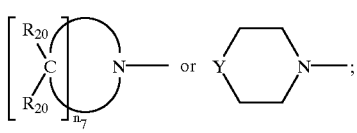

and $R_3$ is aryl-X—, phthalidyl-X—, biphenyl-X— or heteroaryl-X— comprises a procedure in which $c_4$) a compound of the formula VI

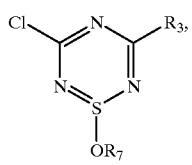

(VI)

in which $R_7$ is as defined under formula I and $R_3$ is as defined above, is reacted with an amine of the formula XIII, XIV or XV $R_{88}R_{89}NH$ (XIII),

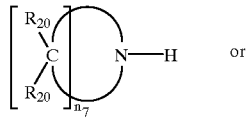

(XIV)

or

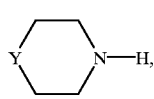

(XV)

in which $R_{20}$, $R_{88}$, $R_{89}$, Y and $n_7$ are as defined under formula I, if appropriate in a solvent; or $c_3$) the compound of the formula VI is first converted with a compound of the formula XVI $R_{12}$—$X_1H$ (XVI), in which $R_{12}$ is an aryl, phthalidyl, biphenyl or heteroaryl radical, and $X_1$ is oxygen or sulfur, in the presence of an equimolar amount of base and in an aprotic organic solvent, into the compound of the formula V

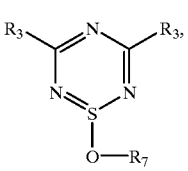

(V)

in which $R_3$ is —$X_1$—$R_{12}$ and $R_7$, $R_{12}$ and $X_1$ are as defined, and $d_4$) this is then reacted with an amine of the formula XIII, XIV or XV in a manner analogous to that described under $C_4$); or in whicha₄) 1,3,5-trichlorothiatriazine is converted with an alcoholate of the formula XVII₁

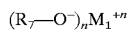 (XVII₁), in which $R_7$ is as defined under formula I;
$M_1^{+n}$ is an alkali metal or alkaline earth metal ion or a metal ion of the first or second sub-group of the Periodic Table; and
n is 1, 2, 3 or 4,
in the presence of an inert organic solvent, into the compound of the formula VII

 (VII)

in which $R_7$ is as defined, and
b₄) this is reacted with an amine of the formula XIII, XIV or XV
$R_{88}R_{89}NH$

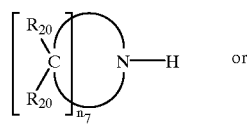 (XIV)

or

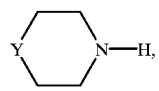 (XV)

in which $R_{20}$, $R_{88}$, $R_{89}$, Y and $n_7$ are as defined under formula I,
if appropriate in a solvent, to give the compound of the formula VIII

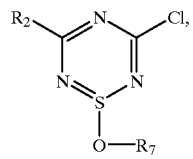 (VIII)

in which $R_2$ and $R_7$ are as defined, and
c₅) this is then reacted with a compound of the formula XVI

$—X_1H$ (XVI), in which $R_{12}$ is an aryl, phthalidyl, biphenyl or heteroaryl radical; and
$X_1$ is oxygen or sulfur,
in a solvent in the presence of a tertiary amine and, if appropriate, another base.

The process according to the invention for the preparation of the compounds of the formula I in which
$R_1$ is a group —$NR_{90}R_{91}$ or an N-heterocyclic radical onto which 1 or 2 further carbocyclic, heterocyclic or aromatic rings can be fused and which can contain further heteroatoms;
$R_2$ is a group $R_{88}R_{89}N$—, or ;

and $R_3$ is aryl-X—, phthalidyl-X—, biphenyl-X— or heteroaryl-X—
comprises a procedure in which
e) a compound of the formula III

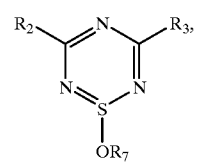 (III)

in which $R_7$ is as defined under formula I and
$R_2$ and $R_3$ are as defined,
is reacted with an amine of the formula XI or XII $R_{90}R_{91}NH$ or (XI)

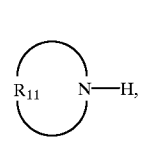 (XII)

in which $R_{90}$ and $R_{91}$ are as defined under formula I and
$R_{11}$ is a cyclic radical onto which 1 or 2 further carbocyclic, heterocyclic or aromatic rings can be fused and which can contain further heteroatoms,
if appropriate in a solvent; or in which
a₅) 1,3,5-trichlorothiatriazine is converted with an amine of the formula XI or XII $R_{90}R_{91}NH$ or (XI)

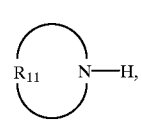 (XII)

in which $R_{90}$ and $R_{91}$ are as defined under formula I and
$R_{11}$ is a cyclic radical onto which 1 or 2 carbocyclic, heterocyclic or aromatic rings can be fused and which can contain further heteroatoms,
or with an amide of the formula XI₁ or XII₁, $(R_{90}R_{91}N^-)_nM_2^{+n}$ or (XI₁)

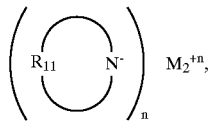

(XII₁)

in which $R_{90}$, $R_{91}$ and $R_{11}$ are as defined;

$M_2^{+n}$ is an alkali metal or alkaline earth metal ion or a metal ion of the first or second sub-group of the Periodic Table; and n is 1, 2, 3 or 4, in the presence of an inert organic solvent and if appropriate a base, into the compound of the formula IX

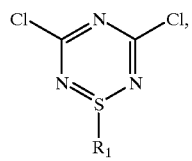

(IX)

in which $R_1$ is as defined, and b₅) this is reacted with an amine of the formula XIII, XIV or XV $R_{88}R_{89}NH$, (XIII)

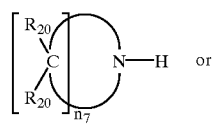

(XIV)

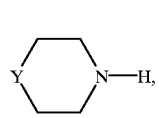

(XV)

in which $R_{20}$, $R_{88}$, $R_{89}$, Y and $n_7$ are as defined under formula I, if appropriate in a solvent, to give the compound of the formula X

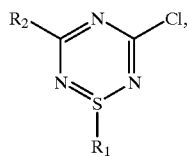

(X)

in which $R_1$ and $R_2$ are as defined, and c₆) this is then reacted with a compound of the formula XVI $R_{12}$—$X_1$H (XVI), in which $R_{12}$ is an aryl, phthalidyl, biphenyl or heteroaryl radical; and $X_1$ is oxygen or sulfur, in a solvent in the presence of a tertiary amine and a further equivalent amount of base.

Another process according to the invention for the preparation of compounds of the formula I in which $R_1$ is a group —$OR_7$;

$R_2$ is a group $R_{88}R_{89}N$—,

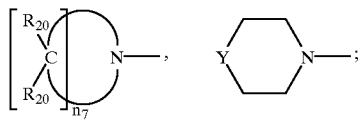

aryl-X—, phthalidyl-X—, biphenyl-X— or heteroaryl-X—; and $R_3$ is aryl-X—, phthalidyl-X—, biphenyl-X— or heteroaryl-X—, comprises a procedure in which a compound of the formula I in which $R_1$ is a group —$OR_7$, in which $R_7$ is other than in the end product; and $R_2$ and $R_3$ are as defined is reacted with an alcohol of the formula XVII $R_7$—OH (XVII)

in which $R_7$ is other than in the starting substance of the formula I, in the presence of an inert organic solvent and a catalytic or equimolar amount of base.

The abovementioned processes according to the invention for the preparation of compounds of the formula I follow equations 1 and 2, the scope of the compounds of the formula I being composed of the scopes of the compounds of the formulae II, III and IV shown in the equations mentioned.

Equation 1:

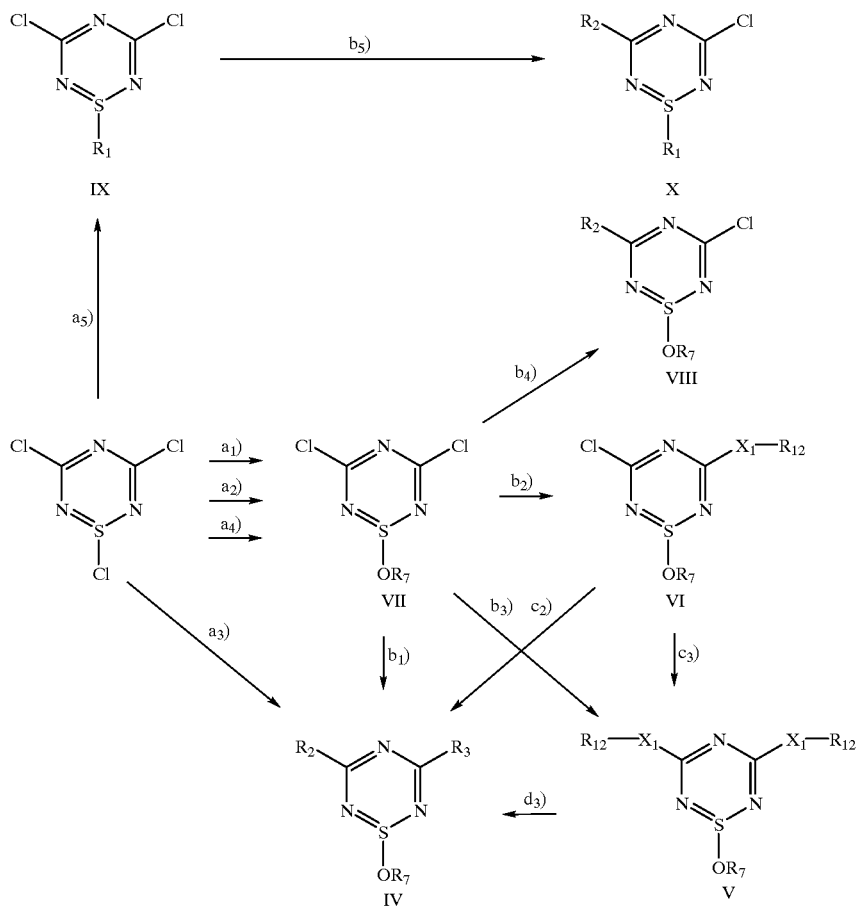

In equation 1 the following applies:
$a_1$) $R_7$—OH (XVII), solvent, $-60°-+80°$ C.;
$a_2$) Bicycloalkyl epoxides,

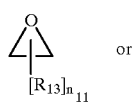

(XVIII)

or

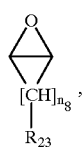

(XIX)

solvent, $0°-130°$ C.;
$a_3$) $R_7$—OH (XVII), solvent, base, for example NaH, $10°-40°$ C.;
$b_1$) $R_{14}$—$X_1$H (XXIII), solvent, base, for example NaH, $-60°-+80°$ C.;
$b_2$) $R_{12}$—$X_1$H (XVI), solvent, base, for example NaH, $-60°-+50°$ C.;
$b_3$) 2 mol $R_{12}$—$X_1$H (XVI), solvent, base, for example NaH, $-60°-+50°$ C.;
$c_2$) $R_{14}$—$X_1$H (XXIII), solvent, base, for example K tert-butylate, $-60°-+80°$ C.;

$c_3$) $R_{12}$—$X_1$H (XVI), solvent, base, for example NaH, $-60°-+50°$ C.; and
$d_3$) $R_{14}$—$X_1$H (XXIII), solvent, base, for example K tert-butylate, $-60°-+80°$ C.;
$a_4$) $(R_7$—$O^-)_n$ $M_1^{+n}$ (VII$_1$), for example $(R_7$—$O^-)$ $(MgCl)^+$, solvent, for example tetrahydrofuran, $-78°-0°$ C.;
$b_4$) $R_{88}R_{89}$NH (XIII),

(XIV)

or

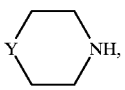

(XV)

solvent, $-78°-+40°$ C.;

$a_5$) $R_{90}R_{91}NH$ (XI) or (XI)

base, for example $Et_3N$, solvent, or
$(R_{90}R_{91}N^-)_n \, M_2^{+n}$ (XI$_1$) or (XI$_1$)

solvent, $-78°$–$0°$ C.;
$b_5$) $R_{88}R_{89}NH$ (XIII), (XIV)

or (XV)

solvent, $-78°$–$+40°$ C.,
in which $R_7$, $R_{11}$, $R_{12}$, $R_{13}$, $R_{14}$, $R_{20}$, $R_{23}$, $R_{88}$, $R_{89}$, $R_{90}$, $R_{91}$, n, $n_7$, $n_8$, $n_{11}$, Y, $X_1$, $M_1^{+n}$ and $M_2^{+n}$ are as defined above.

Equation 2

In equation 2, the following applies:
$c_3$) $R_{12}$—$X_1H$ (XVI), solvent, base, for example NaH, $-60°$–$+50°$ C.;
$c_4$) $R_{88}R_{89}NH$ (XIII), (XIV)

or (XV)

solvent, $-50°$–$+50°$ C.;
$d_4$) $R_{88}R_{89}NH$ (XIII), (XIV)

or (XV)

solvent, $-20°$–$+100°$ C.;
e) $R_{90}R_{91}NH$ (XI) or (XII)

solvent, $20°$–$150°$ C.;
$c_5$) $R_{12}$—$X_1H$ (XVI), solvent, tertiary amine, for example $(CH_3)_3N$, if appropriate base, for example NaOH, $-10°$–$+70°$ C.;
$c_6$) $R_{12}$—$X_1H$ (XVI), solvent, tertiary amine, for example $(CH_3)_3N$, base, for example NaOH, $-10°$–$+70°$ C.;

p) R$_7$—OH (XVII), solvent, base$_{cat}$, for example NaH, −60°−+50° C.; and q) R$_7$—OH (XVII), solvent, base, for example NaH, 0°−+50° C.;

in which R$_7$, R$_{11}$, R$_{12}$, R$_{20}$, R$_{88}$, R$_{89}$, R$_{90}$, R$_{91}$, Y, n$_7$ and X$_1$ are as defined above.

The substitution of the most reactive chlorine atom on the sulfur of the 1,3,5-trichloro-thiatriazine leads on the one hand by a process variant a$_1$), by reaction with the alcohol of the formula XVII, by process variant a$_2$), by reaction with bicycloalkyl epoxides or epoxides of the formula XVIII or XIX, or by process variant a$_4$), by reaction with alcoholates of the formula XVII$_1$, to the compounds of the formula VII, and on the other hand by process variant a$_3$), by reaction with the alcohol of the formula XVII, directly to the compounds of the formula IV (equation 1).

Process variant a$_2$) always gives 1-b-chloroalkoxy derivatives of the formula VII here.

The reaction according to process variant a$_1$) is advantageously carried out in a non-polar organic solvent which is inert in the reaction, such as chlorinated hydrocarbons, for example methylene chloride, chloroform or carbon tetrachloride, aromatic hydrocarbons, for example benzene, toluene or xylenes, cyclic hydrocarbons, for example cyclohexane, or cyclic ethers, for example tetrahydrofuran or dioxane, at reaction temperatures of −60° C. to +80° C., preferably at temperatures of −30° C. to +50° C., if appropriate in the presence of an equimolar amount of base. Examples of suitable bases are organic bases, such as tertiary amines, for example trimethylamine, triethylamine, quinuclidine, 1,4-diazabicyclo-[2.2.2]octane, 1,5-diazabicyclo[4.3.0]non-5-ene or 1,5-diazabicyclo[5.4.0]undec-7-ene or alcoholates, for example potassium tert-butylate, sodium methylate or sodium ethylate. However, inorganic bases, such as hydrides, for example sodium or calcium hydride, hydroxides, such as sodium or potassium hydroxide, carbonates, such as sodium or potassium carbonate, or bicarbonates, such as potassium or sodium bicarbonate, can also be used as bases. In a preferred embodiment (Example H2), 2-chloroethanol and an equimolar amount of triethylamine are dissolved in carbon tetrachloride and a solution of 1,3,5-trichlorothiatriazine in carbon tetrachloride is added to this cooled solution (−15° C.), and the mixture is subsequently warmed to 0° C.

The reaction of 1,3,5-trichlorothiatriazine with bicycloalkyl epoxides or with epoxides of the formula XVIII or XIX is expediently carried out in the same solvents as listed under variant a$_1$) at reaction temperatures of 0° to 130° C., preferably at reaction temperatures of 25° to 80° C.

In a preferred embodiment (Example H1), 1,3,5-trichlorothiatriazine is dissolved in carbon tetrachloride and an equimolar amount of cyclohexene oxide is added at room temperature.

In process variant a$_4$), 1,3,5-trichlorothiatriazine is reacted with an alcoholate of the formula XVII$_1$

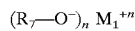 (R$_7$—O$^-$)$_n$ M$_1$$^{+n}$ (XVII$_1$), in which R$_7$ is as defined under formula I;

M$_1$$^{+n}$ is a mono- or polyvalent metal ion, for example an alkali metal or alkaline earth metal ion or a metal ion of the first or second sub-group of the Periodic Table, preferably lithium, magnesium, zinc, aluminium, silicon, fin or titanium, but especially preferably magnesium; and n is the number 1, 2, 3 or 4 (=oxidation number of the corresponding metal ion) in the presence of an inert organic solvent, such as ethers, for example diethyl ether or tetrahydrofuran (THF).

In the compounds of the formula XVII$_1$ in the case of polyvalent metal ions M$_1$$^{+n}$, if n>1, further substituents, for example halogen, C$_1$–C$_4$alkyl or cyano, are also possible in addition to one or more R$_7$—O$^-$ groups. Furthermore, the alcoholates of the formula XVII$_1$ can also be employed in combination With salts, for example aluminium, tin or zinc chloride or aluminium or zinc bromide.

The reaction temperatures for this reaction range from −70° to +20° C., but are preferably below 0° C.

The resulting compound of the formula VII can be isolated, if appropriate, or else used directly for the next reaction stage.

In process variant a$_3$), the most reactive chlorine atom on the sulfur of the thiatriazine ring is replaced in particular by the group —OR$_7$ with addition of an equimolar amount of base; the less reactive chlorine atoms on the carbon atoms in the 3- and 5-positions can also be partly or completely replaced by the group —OR$_7$, depending on the reaction conditions (for example low reaction temperatures; slow warming of the reaction mixture).

The replacement according to variant a$_3$) is advantageously carried out in the presence of a non-polar organic solvent which is inert in the reaction. Such solvents are listed under variants a$_1$) and a$_2$). The alcohol of the formula XVII is accordingly converted into the corresponding alcoholate in the solvent by treatment with a strong base, such as metal hydrides, for example sodium hydride, and this alcoholate solution is added dropwise to a solution of 1,3,5-trichlorothiatriazine at temperatures of 10° to 40° C., in particular at temperatures of 20° to 30° C., while cooling.

In a preferred embodiment (Example H9), the 1,3,5-trichlorothiatriazine is dissolved in tetrahydrofuran and a methanolic sodium methylate solution in tetrahydrofuran is added dropwise at 30° C., while cooling. Completely substituted 1,3,5-trimethoxythiatriazine is obtained.

Preparation of the thiatriazine derivatives of the formula VI (equation 1) according to process variant b$_2$) is advantageously carried out by reaction of the corresponding 3,5-dichloro-thiatriazine of the formula VII with an alcohol of the formula XVI

 R$_{12}$—X$_1$H (XVI), 

in which R$_{12}$ and X$_1$ are as defined, in the presence of an organic solvent which is inert in the reaction, such as cyclic ethers, for example tetrahydrofuran or dioxane, and an equimolar amount of base, for example alkali metal hydrides, preferably sodium or lithium hydride, or alcoholates, for example potassium tert-butylate. The reaction temperatures range from −60° to +50° C., preferably from +40° to −10° C.

In a preferred embodiment (Example H4), ethyl salicylate is dissolved in tetrahydrofuran together with the equimolar amount of sodium hydride, 1-chloroethoxy-3,5-dichlorothiatriazine is added dropwise at −30° C. and the mixture is then warmed to room temperature.

The substitution of the remaining chlorine atom in the thiatriazine derivative of the formula VI with a further radical —X$_1$R$_{12}$ is carried out in accordance with process variant c$_3$). This reaction advantageously proceeds analogously to variant b$_2$), and leads to symmetrically or asymmetrically substituted thiatriazine derivatives of the formula V, depending on the compound of the formula XVI employed (equation 1).

The thiatriazine derivatives of the formula V can also be prepared directly from the compounds of the formula VII according to process variant b$_3$), and leads exclusively to symmetrically substituted derivatives being formed. The reaction according to process variant $b_3$) is advantageously carried out analogously to process variant $b_2$) or $c_3$), but with the difference that two molar equivalents of the compound of the formula XVI and accordingly two molar equivalents of base are employed.

The preparation of the thiatriazine derivatives of the formula IV (equation 1), in which $R_2$, $R_3$ and $R_7$ are as defined, is advantageously carried out in accordance with process variant $d_3$) from the thiatriazine derivatives of the formula V by reaction with alcohols or thiols of the formula XXIII $$R_{14}\text{—}X_1H \qquad (XXIII),$$

in which $R_{14}$ and $X_1$ are as defined, in an inert organic solvent analogously to process variant $a_1$) at temperatures of $-60°$ to $+80°$ C., preferably $-50°$ C. to room temperature, in the presence of an equimolar amount of base. Suitable bases are, for example, organic bases, such as tertiary amines, for example triethylamine, alcoholates, for example potassium tert-butylate, or inorganic bases, such as alkali metal hydrides, for example sodium or lithium hydride. If appropriate, the alcohol of the formula XXIII can also be used as the solvent. Partial or complete exchange can take place both on the sulfur atom (1-position) and on the carbon atoms in the 3- and 5-positions, depending on the reaction conditions (reaction temperature, reaction time) and the ease of substitution of the substituents in the starting compound of the formula V. In a preferred embodiment (Example H10), 1-(b-chloroethoxy)-3,5-di(2',5'-difluorophenoxy)-thiatriazine is dissolved in methanol and a sodium methylate solution in methanol is added dropwise at low temperatures ($-60°$ C.). The derivative substituted by methoxy in the 1-position is first formed by this procedure and is converted into 1,3-dimethoxy-5-(2',5'-di-fluorophenoxy)thiatriazine when the reaction solution is warmed.

In another preferred embodiment (Example H11), 1-(b-chloroethoxy)-3,5-di(2',4'-dichlorophenoxy)thiatriazine is dissolved in tetrahydrofuran and a solution of 2,2,2-trichloroethanol and sodium hydride is added dropwise at low temperatures ($-50°$ C.). After the reaction mixture has been warmed up, the derivative of the formula IV substituted by 2,2,2-trichloroethoxy in the 3- and 5-positions on the thiatriazine ring is isolated.

The reactions according to process variants $b_1$) and $c_2$) (equation 1) starting from the thiatriazine intermediates of the formulae VII and VI also give thiatriazines of the formula IV. Both variants $b_1$) and $c_2$) are advantageously carried out analogously to process variant $d_3$) by reaction of the thiatriazine intermediates of the formula VII or VI with alcohols or thiols of the formula XXIII in organic solvents which are inert in the reaction at reaction temperatures of $-60°$ to $+80°$ C.

In these two process variants $b_1$) and $c_2$) also, partial or complete exchange of the substituents in the 1-, 3- and 5-positions can be obtained, depending on the reactivity of the substituents in the 1-, 3- and 5-positions of the thiatriazine intermediates of the formulae VII and VI and on the reaction conditions, for example the use of an equimolar amount of alcohol or thiol of the formula XXIII and an equimolar or catalytic amount of base.

In an embodiment preferred for variant $b_1$) (Example H12), 1-(b-chloroethoxy)-3,5-di-chlorothiatriazine is dissolved in tetrahydrofuran and a solution of 3 molar equivalents of tert-butylmercaptan and triethylamine in tetrahydrofuran is added dropwise at low temperatures ($-50°$ C.). After the reaction mixture has been warmed up to $0°$ C., a 4/1 product mixture comprising 1-(b-chloroethoxy)-3-chloro-5-tert-butylmercaptothiatriazine and 1-(b-chloroethoxy)-3,5-di-tert-butylmercaptothiatriazine is obtained.

The preparation of the thiatriazine derivatives of the formula VIII (equation 1) according to process variant $b_4$) is advantageously carried out by reaction of the 3,5-dichlorothiatriazine of the formula VII with an amine of the formula XIII, XIV or XV, if appropriate in the presence of a solvent, preferably tetrahydrofuran or acetonitrile, if appropriate mixed with water, at reaction temperatures of $-78°$ to $+40°$ C.

In a preferred embodiment (Example H20), 3,5-dichloro-1-(3-hexyloxy)thiatriazine is reacted with ammonia in tetrahydrofuran at $0°$ C.

In process variant $a_5$) in equation 1, the most reactive chlorine atom on the sulfur atom of the trichlorothiatriazine is substituted by addition of an amine of the formula XI or XII in an inert organic solvent and if appropriate in the presence of a base, for example a tertiary amine, for example triethylamine. Suitable solvents for this substitution are ethers, for example tetrahydrofuran, at reaction temperatures of $-78°$ to $+25°$ C., but preferably at reaction temperatures below $-40°$ C.

Alternatively, instead of the amines of the formula XI or XII, the amides of the formula $XI_1$ or $XII_1$

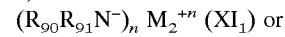

or

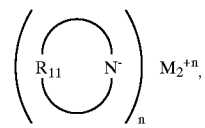

in which $R_{90}$ and $R_{91}$ are as defined under formula I;

$R_{11}$ is a cyclic radical onto which 1 or 2 carbocyclic, heterocyclic or aromatic rings can be fused and which can contain further heteroatoms;

$M_2^{+n}$ is an alkali metal or alkaline earth metal ion or a metal ion of the first or second sub-group of the Periodic Table; and n is the number 1, 2, 3 or 4 (=oxidation number of the corresponding metal ion), can be reacted with the 1,3,5-trichlorothiatriazine in an organic solvent, for example an ether, for example diethyl ether or, preferably tetrahydrofuran.

The reaction temperatures range from $-78°$ to $0°$ C., but are preferably below $-40°$ C. In the compounds of the formula $XI_1$ or $XII_1$, in the case of polyvalent metal ions $M^{2+n}$ if $n>1$, further substituents, for example halogen or $C_1$-$C_4$alkyl, are also possible in addition to one or more amide groups.

The compound of the formula IX can be isolated, if appropriate, or else used directly for the next reaction stage ($b_5$)).

In a preferred embodiment (Example H21), a mixture comprising equimolar amounts of octahydroindole and triethylamine is added dropwise to 1,3,5-trichlorothiatriazine in diethyl ether at $-70°$ to $-60°$ C.

Further reaction of the thiatriazine of the formula IX in accordance with process variant $b_5$) in equation 1 gives the thiatriazine of the formula X. This process variant is advantageously carried out analogously to process variant $b_4$).

In a preferred embodiment (Example H23), an aqueous ammonia solution is added to 3,5-dichloro-1-(octahydroindol-1-yl)thiatriazine in tetrahydrofuran.

In another preferred embodiment (Example H22), a suspension of piperidine and n-butyllithium is added dropwise to a solution of trichlorothiatriazine in tetrahydrofuran which has been cooled to −60° C., and the mixture is subsequently treated further with ammonia gas at −10° C. until the conversion is complete.

In the reactions according to process variants p) and q) (equation 2), only the substituent in the 1-position, i.e. on the sulfur atom of the thiatriazine ring, is substituted selectively.

The thiatriazine derivatives of the formula III can be obtained either by reaction of the 3-chlorothiatriazine derivatives of the formula VI with the amines of the formula XIII, XIV or XV in accordance with process variant $c_4$), or by reaction of the 5-chlorothiatriazine derivatives of the formula VIII with an alcohol of the formula XVI in accordance with process variant $c_5$) (equation 2).

The substitution reaction according to variant $c_4$) can advantageously be carried out in an inert organic solvent, such as a cyclic ether, for example tetrahydrofuran or dioxane, at temperatures of −50° to +50° C., preferably at temperatures of −20° to +20° C.

In a preferred embodiment (Example H15), 3-chloro-1-(b-chloroethoxy)-5-(2'-carboethoxyphenoxy)thiatriazine is dissolved in tetrahydrofuran, and dimethylamine is passed in at 0° C. until conversion is complete.

The substitution reaction according to variant $c_5$) can advantageously be carried out in an organic solvent, such as an ether, for example tetrahydrofuran, or a halogenated hydrocarbon, for example methylene chloride, to which water is admixed, if appropriate, in the presence of a catalytic to excess amount of a tertiary amine, for example trimethylamine, and in the presence or absence of a further base, for example sodium hydroxide, at temperatures from −10° to +70° C., preferably at 0° to 25° C.

In a preferred embodiment (Example H16), a mixture of 3-amino-5-chloro-1-(3-hexyloxy)thiatriazine, difluorophenol and trimethylamine in methylene chloride is allowed to react at 20° C.

Another possibility for the preparation of the thiatriazines of the formula III starts from the thiatriazine intermediates of the formula V, one of the radicals —$X_1R_{12}$ being substituted by amines of the formula XIII, XIV or XV according to process variant $d_4$) (equation 2). This substitution reaction is advantageously carried out analogously to variant $c_4$) in an inert organic solvent at temperatures from −20° to +100° C., preferably at 0° to 50° C.

According to process variant e), in equation 2, the group —$OR_7$ bonded to the sulfur of the thiatriazine ring of the formula III can be substituted selectively by an amino group. As a result, compounds of the formula II in which
  $R_1$ is a group —$NR_{90}R_{91}$ or an N-heterocyclic radical, are obtained. This reaction is advantageously carried out with amines of the formula XI or XII in an inert organic solvent, such as an aromatic hydrocarbon, for example toluene or xylenes, at temperatures of 20° to 150° C., preferably at temperatures of 50° to 100° C.

In a preferred embodiment (Example H18), 1-(2'-chlorocyclohexanolyl)-3-amino-5-(2',6'-difluorophenoxy) thiatriazine is heated at 80°–90° C. together with decahydroquinoline in toluene until conversion is complete.

Another possibility for the preparation of the thiatriazines of the formula II starts from the 1,3-disubstituted 5-chlorothiatriazines of the formula X, the 5-chlorine atom being replaced by alcohols of the formula XVI according to process variant $c_6$) in equation 2. This replacement is advantageously carried out in the presence of a catalytic to excess amount of a tertiary amine, for example trimethylamine, and a further equivalent amount of base, for example sodium hydroxide, in an organic solvent, such as an ether, for example tetrahydrofuran, or a halogenated hydrocarbon, for example methylene chloride, to which water is admixed if appropriate. The reaction temperatures are −10° to +70° C., preferably 0° to 25° C.

In a preferred embodiment (Example H19), 3-amino-5-chloro-1-(piperidin-1-yl)thiatriazine and pentafluorophenol are brought together in methylene chloride with 2N sodium hydroxide solution and aqueous trimethylamine and allowed to react. In the thiatriazine derivatives of the formulae V and III, the group —$OR_7$ bonded to the sulfur can be substituted selectively by another alcohol of the formula XVII

$$R_7\text{—OH} \qquad\qquad\qquad (XVII),$$

in which $R_7$ is as defined under formula I, according to process variants p) and q) in equation 2.

Other compounds of the formulae V and III and of the formula I can be prepared in this way and by customary derivatzation.

In the case of the compounds of the formula V, this exchange is advantageously carried out according to process variant p) with an excess of alcohol, but at least the equimolar amount of alcohol, in an inert organic solvent, such as a cyclic ether, for example tetrahydrofuran or dioxane, at temperatures from −60° to +50° C., preferably at temperatures from −40° to +10° C., in the presence of a catalytic amount of base, for example 1–30 mol %, preferably 5–20 mol %. Suitable bases are, for example, metal hydrides, such as sodium hydride, or alcoholates, such as potassium tert-butylate.

The exchange of the group —$OR_7$ in the case of the compounds of the formula III in accordance with process variant q) can be carried out analogously to process variant p), with the difference that reaction temperatures of 0° to 50° C., preferably 10° to 30° C., are used and that the amount of base used for the exchange reaction is less critical. Equimolar amounts of bases are preferably used.

In a preferred embodiment (Example H14), isopropanol and sodium hydride are initially introduced into tetrahydrofuran and 3-amino-1-(b-chloroethoxy)-5-(2',5'-difluorophenoxy)thiatriazine is added to this suspension at room temperature.

The thiatriazines of the formula I or of the formulae II, III and IV, in which
  $R_2$ and/or $R_3$ is aryl-X—, phthalidyl-X—, biphenyl-X— or heteroaryl-X—; and
  X is sulfur,
    obtained in the process variants described above can subsequently be oxidized to give the corresponding sulfoxides and sulfone derivatives of the formula I or of the formulae II, III and IV, in which
  $R_2$ and/or $R_3$ is aryl-X—, phthalidyl-X—, biphenyl-X— or heteroaryl-X—; and
  X is —SO— or —$SO_2$—,
    analogously to known standard processes, for example with hydrogen peroxide or m-chloroperbenzoic acid. In order to avoid undesirable side reactions, the conditions for this oxidation must be evaluated in respect of the reactivities of the other substituents on the thiatriazine ring. Examples of such sulfur oxidations are described in Houben-Weyl, "Methoden der Organischen Chemie" [Methods of Organic Chemistry], Fourth edition, Volume IV, Georg Thieme Verlag Stuttgart.

The present processes according to the invention have the following advantages:
1. Easy accessibility of the 1,3,5-trichlorothiatriazine and of the other starting compounds of the formulae XVII, XVIII, XIX, XVI, XXIII, XI, XII, XIII, XIV and XV, and of the bicycloalkyl epoxides from the scope of formula I;
2. Low number of synthesis stages;
3. Selectivity of the exchange reactions on the thiatriazine ring;
4. Wide possibilities for derivatization in respect of the choice of substituents $R_1$, $R_2$ and $R_3$ on the thiatriazine ring and associated wide possibilities of variation for the thiatriazines of the formula I; and
5. Exchange reactions are carried out under mild reaction conditions (for example low temperatures) and are compatible for a large number of functional groups.

The thiatriazine derivatives of the formulae V, VI, VII, VII, IX and X are novel. They are important intermediates for the synthesis of the compounds of the formula 1. The invention therefore also relates to these novel compounds and processes for their preparation, and to the use of the compounds of the formulae V, VI, VII, VIII, IX and X for the preparation of compounds of the formula I, excluding the compounds

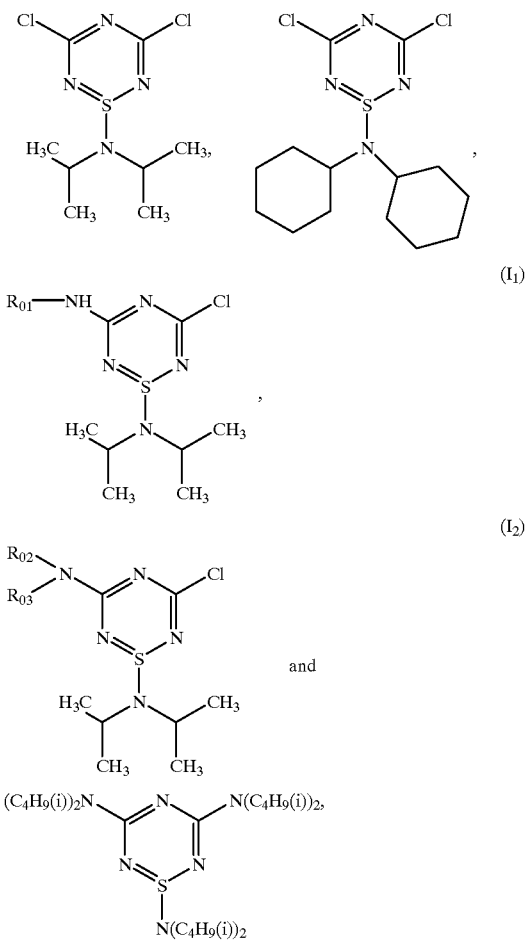

wherein $R_{01}$ is hydrogen, methyl, ethyl, n-propyl, i-butyl or cyclohexyl; and $R_{02}$ and $R_{03}$ are ethyl or benzyl.

For the intermediates of the formulae V, VI, VII, VIII, IX and X, the same preferences apply in respect of $R_3$ and $R_7$ as for the compounds of the formula I.

The starting compounds of the formulae XVII, XVIII and XIX required in process variants $a_1$), $a_2$), $a_3$), p) and q) and the corresponding bicycloalkyl epoxides from the scope of formula I either are obtainable commercially or can be prepared by generally known methods. The preparation of such compounds is described, for example, in Houben-Weyl, "Methoden der Organischen Chemie" [Methods of Organic Chemistry], Fourth edition, Volume VI and VI/3, Georg Thieme Verlag Stuttgart.

The starting compounds of the formulae XVI and XXIII required in process variants $b_1$), $b_2$), $b_3$), $c_2$), $c_3$) and $d_3$) either are obtainable commercially or can be prepared by generally known methods. The preparation of such compounds is described, for example, in Houben-Weyl, "Methoden der Organischen Chemie" [Methods of Organic Chemistry], Fourth edition, Volume VI and IX, Georg Thieme Verlag Stuttgart.

The amines of the formulae XI, XII, XIII, XIV and XV required in process variants $c_4$), $d_4$) and e) either are obtainable commercially or can be prepared analogously to known standard processes. The preparation of such compounds is described, for example, in Houben-Weyl, "Methoden der Organischen Chemie" [Methods of Organic Chemistry], Fourth edition, Volume XI, Georg Thieme Verlag Stuttgart.

The alcoholates of the formula $XVII_1$ required in process variant $a_4$) can be prepared analogously to known standard processes, for example by reaction of the corresponding alcohol of the formula XVII with an $M_1$-organometallic compound, for example $C_1$–$C_4$alkyllithium or $C_1$–$C_8$alkylmagnesium halide, or by reaction with an $M_1$-metal compound which contains at least one leaving group, for example cyano or, preferably, halogen, and if appropriate one or more $C_1$–$C_4$alkyl groups, in the presence of a base. The compounds of the formula $XVII_1$ do not have to be isolated in a pure form, but can be further used directly.

The amides of the formulae $XI_1$ and $XII_1$ required in process variant $a_5$) can be prepared analogously to known standard processes, for example by reaction of the corresponding amines of the formula XI and XII with an $M_2$-organometallic compound, for example $C_1$–$C_4$alkyllithium or $C_1$–$C_8$alkylmagnesium halide, or by reaction with an $M_2$-metal compound which has at least one leaving group, for example halogen, and where appropriate one or more $C_1$–$C_4$alkyl groups, in the presence of a base.

The preparation of the starting compound 1,3,5-trichlorothiatriazine is described in DD-A-113 006 (Example 1).

The resulting compounds of the formula I can be isolated in the customary manner by concentration or evaporation of the solvent, and purified by recrystallization or trituraaon of the solid residue in solvents in which they do not dissolve readily, such as ethers or aliphatic hydrocarbons, by distillation or by means of column chromatography with a suitable eluting agent.

If no controlled synthesis is carried out for isolation of pure isomers or diastereomers, the product can be obtained as a mixture of two or more isomers or diastereomers. The isomers or diastereomers can be separated by methods known per se. If desired, for example, pure optically active isomers or diastereomers can also be prepared by synthesis from corresponding optically active starting materials, for example cis- or trans-decalin, cis- or trans-2,6-dimethylmorpholine or cis- or trans-decahydro(iso)quinoline.

The end products of the formula I can be isolated in the customary manner by concentration and/or evaporation of the solvent and purified by recrystallization or trituration of the solid residue in solvents in which they do not dissolve readily, such as ethers, aromatic hydrocarbons or chlorinated hydrocarbons.

For use according to the invention of the compounds of the formula I, including the compounds of the formulae $I_1$ to $I_7$, or compositions comprising these, all the methods of application customary in agriculture, for example preemergence and postemergence application, as well as various methods and techniques such as, for example, controlled release of the active compound, are suitable. For this, the active compound is adsorbed in solution onto mineral granule carriers or polymerized granules (urea/formaldehyde) and the granules are dried. If appropriate, a coating can additionally be applied (coated granules), allowing the active compound to be released in a metered form over a certain period of time.

The compounds of the formula I, including the compounds of the formulae $I_1$ to $I_7$, can be employed in unchanged form, i.e. as they are obtained in the synthesis, but they are preferably processed in the customary manner with the auxiliaries customary in formulation technology, for example to give emulsifiable concentrates, solutions which can be sprayed or diluted directly, dilute emulsions, wettable powders, soluble powders, dusts, granules or microcapsules. The methods of application, such as spraying, atomizing, dusting, wetting, scattering or pouring, like the nature of the compositions, are chosen according to the required aims and the given circumstances.

The formulations, i.e. the compositions, formulations, preparations, combinations or mixtures comprising the active compound of the formula I or at least one active compound of the formula I, including the compounds of the formulae $I_1$ to $I_7$ and as a rule one or more solid or liquid formulation auxiliaries, are prepared in a known manner, for example by intimate mixing and/or grinding of the active compounds with the formulation auxiliaries, for example solvents or solid carriers. Surface-active compounds (surfactants) can, furthermore, additionally be used in the preparation of the formulations.

Solvents can be: aromatic hydrocarbons, preferably fractions $C_8$ to $C_{12}$, for example xylene mixtures or substituted naphthalenes phthalic acid esters, such as dibutyl or dioctylphthalate, aliphatic hydrocarbons, such as cyclohexane or paraffins, alcohols and glycols, and ethers and esters thereof, such as ethanol, ethylene glycol or ethylene glycol monomethyl or -ethyl ether, ketones, such as cyclohexanone, strongly polar solvents, such as N-methyl-2-pyrrolidone, dimethyl sulfoxide or N,N-dimethylformamide, and epoxidized or non-epoxidized vegetable oils, such as epoxidized coconut oil or soya oil; or water.

Solid carriers, for example for dusts and dispersable powders, which are used are as a rule natural rock powders, such as calcite, talc, kaolin, montmorillonite or attapulgite. Highly disperse silicic acid or highly disperse absorbent polymers can also be added to improve the physical properties of the formulation. Granular adsorptive carriers for granules are porous types, for example pumice, crushed brick, sepiolite or bentonite, and non-sorbent carrier materials are, for example, calcite or sand. A large number of pregranulated materials of inorganic or organic nature, such as, in particular, dolomite or comminuted plant residues, can moreover be used.

Surface-active compounds are nonionic, cationic and/or anionic surfactants and surfactant mixtures having good emulsifying, dispersing and wetting properties, depending on the nature of the active compound of the formula I to be formulated Suitable anionic surfactants can be both so-called water-soluble soaps and water-soluble synthetic surface-active compounds.

Soaps are the alkali metal, alkaline earth metal or substituted or unsubstituted ammonium salts of higher fatty acids ($C_{10}$–$C_{22}$), for example the Na or K salts of oleic or stearic acid, or of naturally occurring fatty acid mixtures, which can be obtained, for example, from coconut oil or tallow oil. They are also the fatty acid methyl-taurine salts.

However, so-called synthetic surfactants are more frequently used, in particular fatty alcohol sulfonates, fatty alcohol sulfates, sulfonated benzimidazole derivatives or alkylarylsulfonates.

The fatty alcohol sulfonates or sulfates are as a rule in the form of alkali metal, alkaline earth metal or substituted or unsubstituted ammonium salts and contain an alkyl radical having 8 to 22 C atoms, alkyl also including the alkyl moiety of acyl radicals, for example the Na or Ca salt of ligninsulfonic acid, of dodecyl-sulfuric acid ester or of a fatty alcohol sulfate mixture prepared from naturally occurring fatty acids. These also include the salts of the sulfuric acid esters and sulfonic acids of fatty alcohol-ethylene oxide adducts. The sulfonated benzimidazole derivatives preferably contain 2 sulfonic acid groups and a fatty acid radical having 8–22 C atoms. Alkylarylsulfonates are, for example, the Na, Ca or triethanolamine salts of dodecylbenzenesulfonic acid, of dibutyinaphthalenesulfonic acid or of a naphthalenesulfonic acid-formaldehyde condensation product.

Salts can furthermore also be corresponding phosphates, for example salts of the phosphoric acid ester of a p-nonylphenol-(4–14)-ethylene oxide adduct, or phospholipids.

Nonionic surfactants are, in particular, polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Other suitable nonionic surfactants are the water-soluble adducts, containing 20 to 250 ethylene glycol ether groups and 10 to 100 propylene glycol ether groups, of polyethylene oxide on polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit.

Examples of nonionic surfactants are nonylphenolpolyethoxyethanols, castor oil polyglycol ether, polypropylene-polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, can also be used.

The cationic surfactants are, in particular, quaternary ammonium salts, which contain at least one alkyl radical having 8 to 22 C atoms as N substituents and lower, halogenated or non-halogenated alkyl, benzyl) or lower hydroxyalkyl radicals as further substituents. The salts are preferably in the form of halides, methyl sulfates or ethyl sulfates, for example stearyltrimethylammonium chloride or benzyldi(2-chloroethyl)ethyl ammonium bromide.

The surfactants customary in formulation technology which can also be used in the compositions according to the invention are described, inter alia, in "Mc Cutcheon's Detergents and Emulsifiers Annual", MC Publishing Corp., Ridgewood N.J., 1981, Stache, H., "Tensid-Taschenbuch" [Surfactant Handbook], Carl Hanser Verlag, Munich/

Vienna, 1981 and M. and J. Ash, "Encyclopedia of Surfactants", Volume I–III, Chemical Publishing Co., New York, 1980–81.

The herbicidal formulations as a rule comprise 0.1 to 99% by weight, in particular 0.1 to 95% by weight, of herbicide, 1 to 99.9% by weight, in particular 5 to 99.8% by weight, of a solid or liquid formulation auxiliary and 0 to 25% by weight, in particular 0.1 to 25% by weight, of a surfactant.

While concentrated compositions are more preferable as commercial goods, the end user as a rule uses dilute compositions.

The compositions can also comprise further additives, such as stabilizers, for example epoxidized or nonepoxidized vegetable oils (epoxidized coconut oil, rapeseed oil or soya oil), defoamers, for example silicone oil, preservatives, viscosity regulators, binders, tackifiers and fertilizers or other active compounds.

In particular, preferred formulations have the following composition:

(%=per cent by weight)
Emulsifiable Concentrates:
  Active compound: 1 to 90%, preferably 5 to 50%
  Surface-active agent: 5 to 30%, preferably 10 to 20%
  Solvent: 15 to 94%, preferably 70 to 85%
Dusts:
  Active compound: 0.1 to 50%, preferably 0.1 to 1%
  Solid carrier: 99.9 to 90%, preferably 99.9 to 99%
Suspension Concentrates:
  Active compound: 5 to 75%, preferably 10 to 50%
  Water: 94 to 24%, preferably 88 to 30%
  Surface-active agent: 1 to 40%, preferably 2 to 30%
Wettable Powders:
  Active compound: 0.5 to 90%, preferably 1 to 80%
  Surface-active agent: 0.5 to 20%, preferably 1 to 15%
  Solid carrier material: 5 to 95%, preferably 15 to 90%
Granules:
  Active compound: 0.1 to 30%, preferably 0.1 to 15%.
  Solid carrier: 99.5 to 70%, preferably 97 to 85%

The active compounds of the formula I, including the compounds of the formulae $I_1$ to $I_7$, are as a rule successfully employed on the plants or their environment with rates of application of 0.001 to 4 kg/ha, in particular 0.005 to 2 kg/ha. The dosage required for the desired action can be determined by experiments. It depends on the mode of action, the stage of development of the crop plant and the weed and on the application (location, time, method), and can vary within relatively wide limits as a result of these parameters.

The compounds of the formula I, including the compounds of the formulae $I_1$ to $I_7$, have herbicidal and growth-inhibiting properties which enable them to be used in crops of useful plants, in particular in cereals, cotton, soya, sugar beet, sugar cane, plantation crops, oilseed rape, maize and rice.

Crops are also to be understood as those which have been rendered tolerant to herbicides or classes of herbicide by conventional breeding or genetic engineering methods.

The weeds to be controlled can be both monocotyledon and dicotyledon weeds, for example Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola and Veronica.

The following examples illustrate the invention further, without limiting it.

PREPARATION EXAMPLES

Example H1

Preparation of 1-(trans-2-chlorocyclohexyloxy)-3,5-dichlorothiatriazine (process $a_2$)

(Compound No. 1.15)

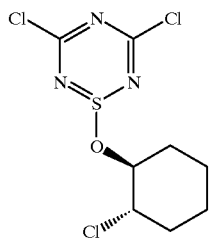

5.11 g (0.025 mol) of 1,3,5-trichlorothiatriazine are dissolved in 50 ml of carbon tetrachloride, and 2.94 g (0.03 mol) of cyclohexene oxide are added at 25° C. The weakly exothermic reaction is carried out at 25–35° C. and has ended after 30 minutes. The cloudy solution formed is filtered and the filtrate is concentrated. 8.7 g of crude product are obtained as a residue, recrystallization of which from a mixture of ethyl acetate and hexane gives 6.75 g (89% of theory) of the desired product of melting point 82–83° C.

Example H2

Preparation of 1-(2-chloroethoxy)-3,5-dichlorothiatriazine (process $a_1$)

(Compound No. 1.7)

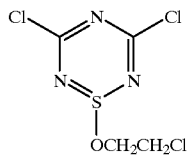

0.80 g (0.01 mol) of 2-chloroethanol and 1.21 g (0.012 mol) of triethylamine are dissolved in 30 ml of carbon tetrachloride and the solution is cooled to −15° C. Thereafter, a solution of 2.04 g (0.01 mol) of 1,3,5-trichlorothiatriazine in 5 ml of carbon tetrachloride is added dropwise at this temperature and the temperature is then allowed to rise to 0° C. The triethylamine hydrochloride is filtered off and the filtrate is concentrated to give 1.85 g of crude product. Recrystallization from 10 ml of hexane gives 1.65 g (67% of theory) of the desired product of melting point 54–55° C.

Example H3

Preparation of 1-methoxy-3,5-dichlorothiatriazine (process $a_1$)

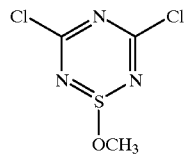

(Compound No. 1.1)

4.09 g (0.02 mol) of 1,3,5-trichlorothiatriazine are stirred as a suspension in 50 ml of carbon tetrachloride at −25° C., and a solution of 0.70 g (0.022 mol) of methanol in a little carbon tetrachloride is added dropwise. During this operation, the trichlorothiatriazine dissolves apart from a little insoluble product. The mixture is then warmed to 0° C. and filtered and the filtrate is concentrated on a rotary evaporator at a maximum of 50° C. 3.25 g of the desired product, which, according to the $^{13}$C-NMR spectrum and thin layer chromatogram (silica gel; eluting agent ethyl acetate/hexane 1/3), contains practically no further impurities, are obtained as the residue. The compound is unstable and decomposes within a few hours when left to stand.

The compounds listed in the following Table I can be prepared analogously to Examples H1 to H3.

TABLE 1

Compounds of the formula VII

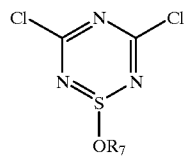

(VII)

| Comp. No. | $R_7$ | Process | Physical data |
|---|---|---|---|
| 1.1 | —CH$_3$ | $a_1$ | $^{13}$C-NMR: 167.5 ppm; 52.6 ppm |
| 1.2 | —C$_2$H$_5$ | | |
| 1.3 | —C$_5$H$_{11}$(n) | | |
| 1.4 | —C$_{10}$H$_{21}$(n) | | |
| 1.5 | —CH(CH$_3$)$_2$ | | |
| 1.6 | —CH$_2$CH(CH$_3$)$_2$ | | |
| 1.7 | —CH$_2$CH$_2$Cl | $a_1$ | Melting point 54–55° C. |
| 1.8 | —CH$_2$CHBrCH$_2$Br | | |
| 1.9 | —CH$_2$CH$_2$F | | |
| 1.10 | —CH$_2$CH$_2$(CF$_2$)$_3$CF$_3$ | | |
| 1.11 | cyclopentyl-CH$_2$CN | | |
| 1.12 | —CH$_2$CHCl$_2$ | $a_1$ | $^{13}$C-NMR: 167.7 ppm; 71.1 ppm; 68.6 ppm |
| 1.13 | —CH(CH$_3$)(CH$_2$)$_5$CH$_3$ | | |
| 1.14 | cyclohexyl-CH$_2$CH$_2$CN | | |
| 1.15 | trans-2-chlorocyclohexyl | $a_2$ | Melting point 82–83° C. |
| 1.16 | cyclopentyl | | |

TABLE 1-continued
Compounds of the formula VII
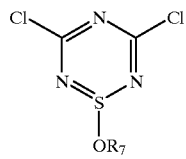
(VII)
| Comp. No. | R₇ | Process | Physical data |
|---|---|---|---|
| 1.17 | cyclododecyl | | |
| 1.18 | cyclobutyl | | |
| 1.19 | 2-chlorocyclooctyl | a₂ | $^{13}$C-NMR: 166.8 ppm; 88.9 ppm; 64.5 ppm; 33.1 ppm; 31.2 ppm; 25.7 ppm; 25.3 ppm; 25.1 ppm; 24.1 ppm |
| 1.20 | cyclohexyl | a₁ | $^{13}$C-NMR: 166.5 ppm; 82.8 ppm; 33.4 ppm; 25.2 ppm; 23.4 ppm: |
| 1.21 | 2-chlorocyclopentyl | a₂ | $^{13}$C-NMR: 167.2 ppm; 88.6 ppm; 62.5 ppm; 33.2 ppm; 30.8 ppm; 21.0 ppm |
| 1.22 | cyclooctyl | a₁ | $^{13}$C-NMR: 166.5 ppm; 85.9 ppm; 33.2 ppm; 26.8 ppm; 22.5 ppm |
| 1.23 | —CH₂—phenyl | | |
| 1.24 | indanyl | | |
| 1.25 | bornyl | | |

TABLE 1-continued
Compounds of the formula VII
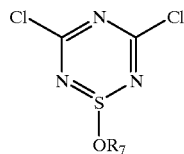
(VII)
| Comp. No. | R₇ | Process | Physical data |
|---|---|---|---|
| 1.26 | 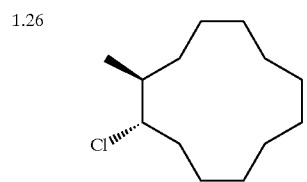 | | |
| 1.27 | 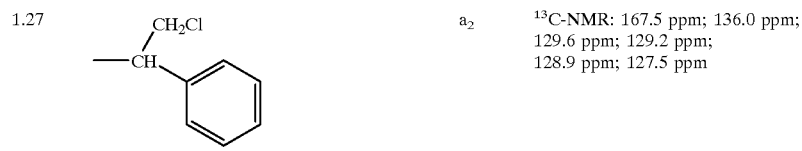 | a₂ | $^{13}$C-NMR: 167.5 ppm; 136.0 ppm; 129.6 ppm; 129.2 ppm; 128.9 ppm; 127.5 ppm |
| 1.28 | 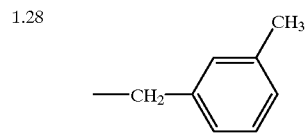 | | |
| 1.29 | 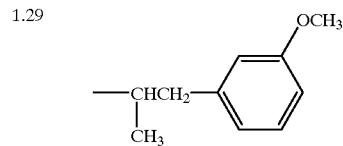 | | |
| 1.30 | 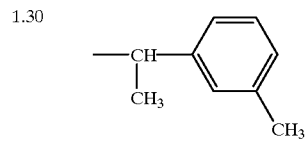 | | |
| 1.31 | —CH₂CH₂SC₂H₅ | | |
| 1.32 | —CH(CH₃)C₆F₅ | | |
| 1.33 | 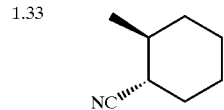 | | |
| 1.34 | —CH₂C≡CH | a₁ | $^{13}$C-NMR: 167.7 ppm; 79.0 ppm; 75.3 ppm; 55.5 ppm |
| 1.35 | 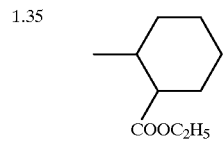 | | |

TABLE 1-continued
Compounds of the formula VII
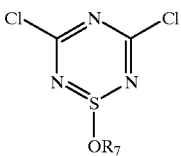
(VII)
| Comp. No. | $R_7$ | Process | Physical data |
|---|---|---|---|
| 1.36 | —CH$_2$—(3-NO$_2$-C$_6$H$_4$) | | |
| 1.37 | —CH(CH$_3$)—(2-OCHF$_2$-4-F-5-NO$_2$-C$_6$H$_2$) | | |
| 1.38 | —CH$_2$—(4-CF$_3$-C$_6$H$_4$) | | |
| 1.39 | —CH(CF$_2$)$_3$CF$_3$ \| C(CH$_3$)$_3$ | | |
| 1.40 | —CH$_2$CH$_2$COOC$_2$H$_5$ | | |
| 1.41 | (1,3,5-trimethyl-5-methylcyclohexyl, 3,3,5-trimethylcyclohexyl) | | |
| 1.42 | —CH(CH$_3$)CH$_2$OCH$_3$ | | |
| 1.43 | —C(CH$_3$)(C$_2$H$_5$)—(2,4-Cl$_2$-C$_6$H$_3$) | | |
| 1.44 | —CH$_2$CH=CH$_2$ | | |
| 1.45 | —CH(CF$_3$)—C$_6$H$_5$ | | |
| 1.46 | —CH$_2$—(2,6-F$_2$-C$_6$H$_3$) | | |

TABLE 1-continued

Compounds of the formula VII (VII)

*[Structure: 3,5-dichloro-1,2,4,6-thiatriazine with OR7 substituent on S]*

| Comp. No. | R7 | Process | Physical data |
|---|---|---|---|
| 1.47 | —CH2-cyclopropyl | | |
| 1.48 | 1-cyano-cyclohexyl | | |
| 1.49 | —CHCH2Cl with CH2CF2CHF2 | | |
| 1.50 | —C(CH3)(CH2Cl)-(4-F-C6H4) | | |
| 1.51 | —CHCH2Cl with C2H5 | a2 | $^{13}$C-NMR: 167.0 ppm; 166.8 ppm; 84.3 ppm; 45.7 ppm; 26.4 ppm; 9.5 ppm |
| 1.52 | —CH2CH2OCH3 | | |
| 1.53 | —CH2CH2Br | | |
| 1.54 | —CH2CHCl with C2H5 | a2 | $^{1}$H-NMR: 3.9–4.1 ppm (3 H); 1.6–2.0 ppm (2 H); 1.05 ppm (3 H) |
| 1.55 | —CHCH2Cl with (CH2)6CH3 | | |
| 1.56 | trans-2-chloro-1-methylcycloheptyl | | |
| 1.57 | 2-methyl-cycloheptyl-CH2CH2CN | | |
| 1.58 | —CH2-(2-furyl) | | |
| 1.59 | —CH2-(tetrahydrofuran-2-yl) | | |

TABLE 1-continued

Compounds of the formula VII (VII)

[Structure: 1,3,5-triazine ring with Cl at 4-position, Cl at 6-position, N atoms at 1,3,5, and S at position bearing OR7]

| Comp. No. | R₇ | Process | Physical data |
|---|---|---|---|
| 1.60 | 3-methyl-tetrahydrothiopyran-yl | | |
| 1.61 | 5-methyl-1,3-dioxan-yl | | |
| 1.62 | —CH₂—(3-chloro-2-nitrophenyl) (—CH₂— attached to phenyl with Cl and O₂N substituents) | | |
| 1.63 | —CH₂CH=CH—phenyl | | |
| 1.64 | 2-methyl-6-(trifluoromethyl)cyclohexyl | | |
| 1.65 | 2-methyl-5-(2-cyanoethyl)cyclopentyl (CH₂CH₂CN) | | |
| 1.66 | —CH₂-(2-thienyl) | | |
| 1.67 | —CH₂-(tetrahydropyran-2-yl) | | |
| 1.68 | —CH(4-chlorophenyl)(2,4-dimethoxyphenyl) | | |

TABLE 1-continued
Compounds of the formula VII
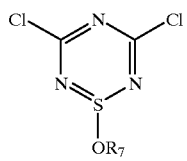
(VII)
| Comp. No. | R₇ | Process | Physical data |
|---|---|---|---|
| 1.69 | 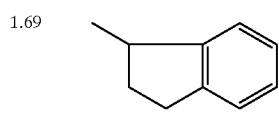 | | |
| 1.70 | 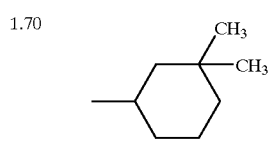 | | |
| 1.71 | 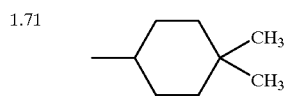 | | |
| 1.72 |  | | |
| 1.73 |  | | |
| 1.74 |  | | |
| 1.75 | 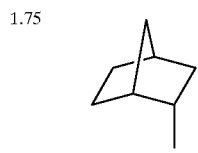 | | |
| 1.76 | 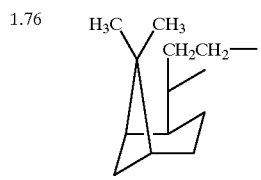 | | |
| 1.77 |  | a₂ | Melting point 67–68° C. |

TABLE 1-continued
Compounds of the formula VII
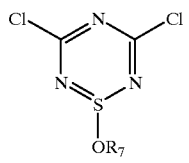
(VII)
| Comp. No. | R$_7$ | Process | Physical data |
|---|---|---|---|
| 1.78 | 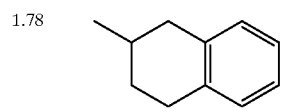 | | |
| 1.79 | 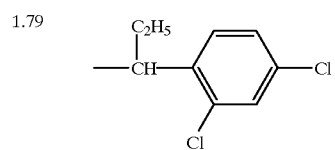 | | |
| 1.80 | 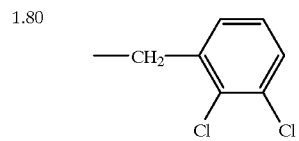 | | |
| 1.81 | 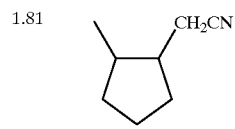 | | |
| 1.82 | 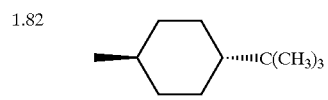 | | |
| 1.83 | —(CH$_2$)$_7$CH$_3$ | | |
| 1.84 | 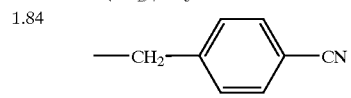 | | |
| 1.85 | 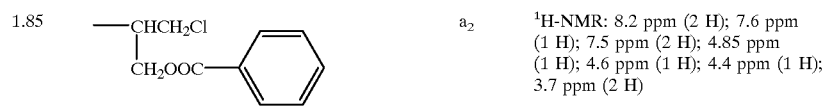 | a$_2$ | $^1$H-NMR: 8.2 ppm (2 H); 7.6 ppm (1 H); 7.5 ppm (2 H); 4.85 ppm (1 H); 4.6 ppm (1 H); 4.4 ppm (1 H); 3.7 ppm (2 H) |
| 1.86 | —CH(CH$_2$Cl)$_2$ | | |
| 1.87 | 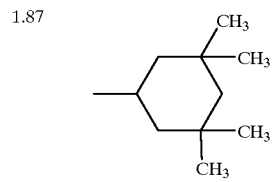 | | |
| 1.88 | —CH$_2$-adamantyl | | |

TABLE 1-continued
Compounds of the formula VII
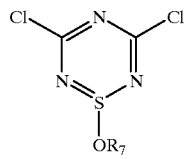
(VII)
| Comp. No. | $R_7$ | Process | Physical data |
|---|---|---|---|
| 1.89 | 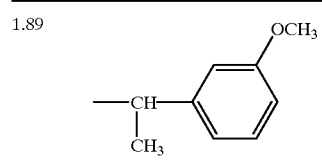 | | |
| 1.90 | 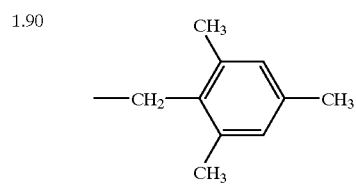 | | |
| 1.91 | —CH$_2$CH$_2$CN | | |
| 1.92 | 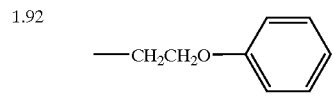 | | |
| 1.93 | 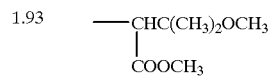 | | |
| 1.94 | 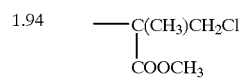 | | |
| 1.95 | 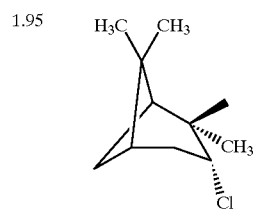 | | |
| 1.96 | 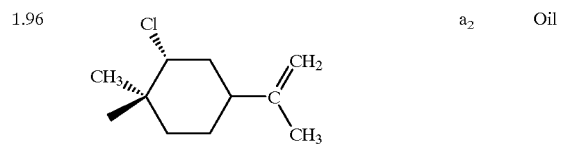 | a$_2$ | Oil |
| 1.97 | 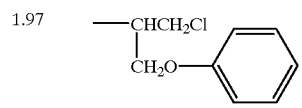 | | |

TABLE 1-continued
Compounds of the formula VII
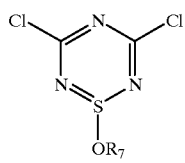
(VII)
| Comp. No. | R₇ | Process | Physical data |
|---|---|---|---|
| 1.98 | 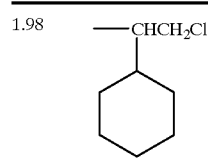 | | |
| 1.99 | 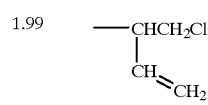 | | |
| 1.100 | —CH₂CH₂CH(C₂H₅)₂ | | |
| 1.101 | —CH(C₂H₅)₂ | | |
| 1.102 | —CH₂CH(CH₃)Cl | | |
| 1.103 | 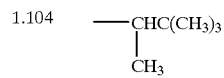 | | |
| 1.104 | 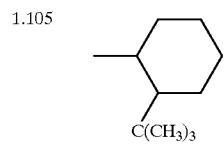 | | |
| 1.105 | 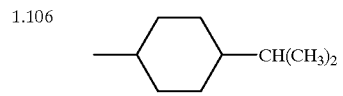 | | |
| 1.106 | 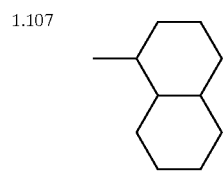 | | |
| 1.107 | 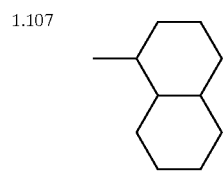 | | |
| 1.108 | 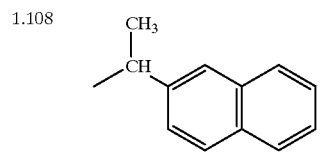 | | |
| 1.109 | 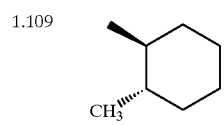 | | |

TABLE 1-continued

Compounds of the formula VII (VII)

[Structure: 1,2,4,6-thiatriazine ring with Cl at 3 and 5 positions, N at 2,4,6, S at 1, and OR$_7$ substituent on S]

| Comp. No. | R$_7$ | Process | Physical data |
|---|---|---|---|
| 1.110 | —CH$_2$-(2-fluorophenyl) | | |
| 1.111 | 2-methyl-1,1-dimethoxycyclohexyl | | |
| 1.112 | 3,5,5-trimethylcyclohexyl (1,3-dimethyl, 5,5-dimethyl) | | |
| 1.113 | —C(CH$_3$)(CH$_2$Cl)-(4-fluorophenyl) | | |
| 1.114 | 2-methyl-4-isopropyl-cyclohexyl with CH$_3$ | | |
| 1.115 | —CH$_2$C$_6$F$_5$ | | |
| 1.116 | —CH(CH=CH$_2$)(CH$_2$)$_4$CH$_3$ | | |
| 1.117 | —CH$_2$CH$_2$Si(CH$_3$)$_3$ | | |
| 1.118 | —CH(4-chlorophenyl)(phenyl) | | |

TABLE 1-continued
Compounds of the formula VII
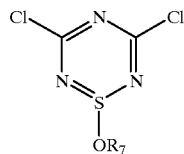
(VII)
| Comp. No. | R₇ | Process | Physical data |
|---|---|---|---|
| 1.119 | 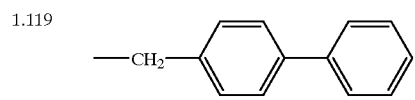 | | |
| 1.120 | 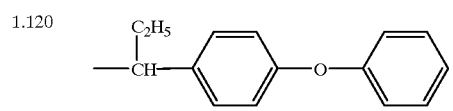 | | |
| 1.121 | 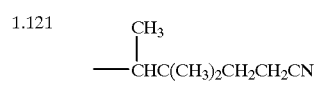 | | |
| 1.122 | 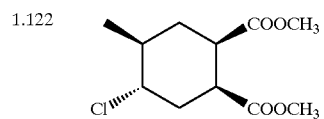 | | |
| 1.123 | 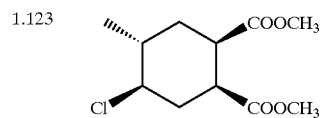 | | |
| 1.124 | 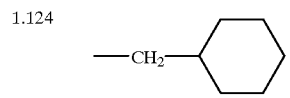 | | |
| 1.125 | —CH₂CH₂OCOCH₃ | | |
| 1.126 | 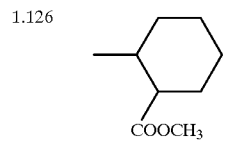 | | |
| 1.127 | 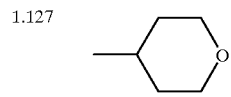 | | |
| 1.128 | 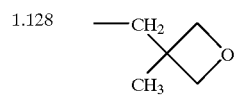 | | |
| 1.129 | 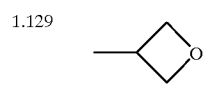 | | |

TABLE 1-continued

Compounds of the formula VII (VII)

| Comp. No. | R₇ | Process | Physical data |
|---|---|---|---|
| 1.130 | —CHCH₂Cl<br>   \|<br>   COOC₂H₅ | | |
| 1.131 | 2-chloro-3,3,5,5-tetramethylcyclohexanone | | |
| 1.132 | —CH₂CH₂—cyclohexyl | | |
| 1.133 | 2-methylcyclohexyl-cyclohexyl | | |
| 1.134 | 3-methylcyclohex-1-enyl | | |
| 1.135 | 3-(trifluoromethyl)cyclohexyl (1,3-substituted) | | |
| 1.136 | —CHCH₂Cl<br>   \|<br>   CH₂OC(CH₃)₃ | | |
| 1.137 | 2-(cyanomethyl)cyclohexyl | | |

Example H4

Preparation of 1-chloroethoxy-2-chloro-3-(2'-carboethoxyphenoxy)thiatriazine (Compound No. 2.4)

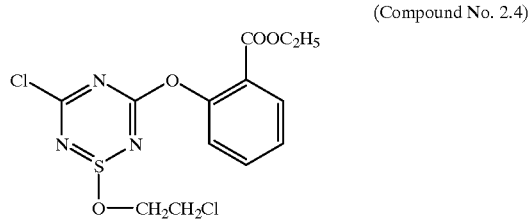

3.32 g (0.02 mol) of ethyl salicylate are stirred with 0.96 9 of 55% sodium hydride (0.022 mol) in 50 ml of tetrahydrofuran under nitrogen. With evolution of hydrogen, a clear solution forms, which is added dropwise to a solution of 4.97 g (0.02 mol) of 1-chloroethoxy-3,5-dichlorothiatriazine at −30° C. The mixture is warmed to room temperature and extracted with water and ethyl acetate at pH 6, with addition of a little acetic acid. After the solvent has been evaporated, 7.2 g of crude product are obtained, which is chromatographed on silica gel with a mixture of ethyl acetate and hexane 3/7. The desired product is obtained as an oil in a yield of 6.6 g (95% of theory).

The compounds listed in the following Table 2 can be prepared analogously to Example H4.

TABLE 2

Compounds of the formula VI

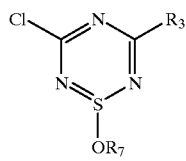

(VI)

| Comp. No. | $R_7$ | $R_3$ | Physical Data |
|---|---|---|---|
| 2.1 | —$C_5H_{11}$(n) | ![3-cyanophenoxy] | |
| 2.2 | —$CH_2CHCl_2$ | —$SC_6Cl_5$ | Melting point 128–129° C. |
| 2.3 | trans-4-tert-butylcyclohexyl | 2,5-dimethylphenoxy | |
| 2.4 | —$CH_2CH_2Cl$ | 2-(carboethoxy)phenoxy | $^1$H-NMR: 7.2–8.1 ppm (4 H); 3.6–4.4 ppm (6 H); 1.4 ppm (3 H) |
| 2.5 | —$CH_2CH(C_2H_5)$-(2,4-dichlorophenyl) | —S-phenyl | |
| 2.6 | —$CH_2CH\!=\!CH$-phenyl | —S-(2-pyridyl) | |

TABLE 2-continued

Compounds of the formula VI

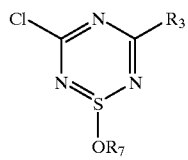

(VI)

| Comp. No. | $R_7$ | $R_3$ | Physical Data |
|---|---|---|---|
| 2.7 | 1-methylindanyl | —$OC_6F_5$ | |
| 2.8 | —$CH_2CH_2Cl$ | —O—phenyl | $^{13}$C-NMR: 169.8 ppm; 166.5 ppm; 150.9 ppm; 129.7 ppm; 126.7 ppm; 121.5 ppm; 66.1 ppm; 41.4 ppm |
| 2.9 | —$CH_2C\equiv CH$ | —O—(3-$CF_3$-phenyl) | |
| 2.10 | methylcyclooctyl | —O—(2,3,5,6-tetrafluorophenyl) | $^{13}$C-NMR: 169.2 ppm; 164.8 ppm; 139–148 ppm; 103.7 ppm; 84.5 ppm |
| 2.11 | 3,3,5-trimethylcyclohexyl | —$OC_6F_5$ | |
| 2.12 | —$CH_2$-(2,6-difluorophenyl) | —O-(2,4,6-trimethylphenyl) | |
| 2.13 | cyclohexyl | —O—(4-$NO_2$-phenyl) | $^{13}$C-NMR: 168.9 ppm; 165.2 ppm; 155.7 ppm; 145.7 ppm; 125.4 ppm; 122.7 ppm; 81.4 ppm; 33.4 ppm; 24.8 ppm; 23.5 ppm |
| 2.14 | —$CH_2CH_2OCH_3$ | —O—(3-Cl-phenyl) | |

TABLE 2-continued

Compounds of the formula VI

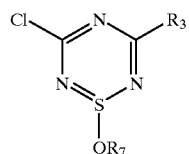

(VI)

| Comp. No. | $R_7$ | $R_3$ | Physical Data |
|---|---|---|---|
| 2.15 | —CH₂-(tetrahydrofuran-2-yl) | 2-methoxyphenoxy | |
| 2.16 | —CH₂CH=CH₂ | 4,6-dimethoxypyrimidin-2-ylthio | |
| 2.17 | 2-(7,7-dimethylbicyclo[2.2.1]heptyl)ethyl | 2-formylphenoxy | |
| 2.18 | —CH(CH₃)CH₂Cl-phenyl (1-chloromethyl-2-phenylethyl) | naphthalen-2-yloxy | ¹³C-NMR: 169.7 ppm; 167.0 ppm; 118.6–148.6 ppm; 70.0 ppm; 59.5 ppm |
| 2.19 | —CH₂-(thiophen-2-yl) | 2,3,4-trifluorophenoxy | |
| 2.20 | —CH(CH₃)C(CH₃)₃ | 2,6-difluorophenoxy | |
| 2.21 | menthyl (2-isopropyl-5-methylcyclohexyl) | naphthalen-1-yloxy | |

TABLE 2-continued

Compounds of the formula VI

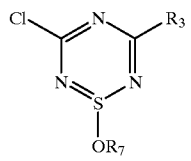

(VI)

| Comp. No. | $R_7$ | $R_3$ | Physical Data |
|---|---|---|---|
| 2.22 | —CH₂—(4-biphenyl) | —S—(2-COOCH₃-phenyl) | |
| 2.23 | —CH₂CH₂OC(O)CH₃ | —SC₆F₅ | |
| 2.24 | —CH(CH₂Cl)(CH₂Br) | —O—(3-N(CH₃)₂-phenyl) | $^{13}$C-NMR: 169.7 ppm; 166.4 ppm; 152.1 ppm; 151.6 ppm; 130.0 ppm; 110.6 ppm; 108.8 ppm; 105.0 ppm |
| 2.25 | 4-tetrahydropyranyl | —O—(3-NO₂-phenyl) | |
| 2.26 | —CH(CH₂Br)(CH₂Cl) | —O—(4-I-phenyl) | |
| 2.27 | —CH₂—(3-pyridyl) | —O—(4-phenoxyphenyl) | |
| 2.28 | bornyl-Cl derivative | —O—(4-F-phenyl) | |
| 2.29 | —CH₂COOC₂H₅ | —O—(3,4-dimethylphenyl) | |
| 2.30 | trans-2-chlorocyclooctyl | —S—(3-OCH₃-phenyl) | $^1$H-NMR: 6.9–7.3 ppm (4 H); 4.4 ppm (1 H); 4.0 ppm (1 H); 3.8 ppm (3 H); 1.2–2.2 ppm (12 H) |

TABLE 2-continued
Compounds of the formula VI
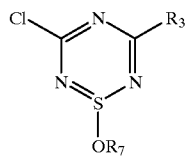
(VI)
| Comp. No. | $R_7$ | $R_3$ | Physical Data |
|---|---|---|---|
| 2.31 | —CH(CH$_3$)$_2$ | —O—C$_6$H$_4$—Cl (4-Cl) | |
| 2.32 | —CH$_2$CH$_2$Cl | —SC$_6$F$_5$ | Melting point 72–73° C. |
| 2.33 | —CH$_2$CH$_2$Cl | —O—C$_6$H$_3$(2-Cl)(4-Cl) | |
| 2.34 | —CH$_2$CH$_2$Cl | —O—C$_6$H$_2$(2-F)(3-F)(4-F) | |
| 2.35 | —CH$_2$CH$_2$Cl | —O—C$_6$H$_4$—Br (4-Br) | |
| 2.36 | —CH$_2$CH$_2$Cl | —O—C$_6$F$_5$ | |
| 2.37 | —CH$_2$CH$_2$Cl | —O—C$_6$H$_2$(2-F)(3-F)(4-F) | |
| 2.38 | —CH$_2$CH$_2$Cl | —O—C$_6$H$_2$(3-F)(4-F)(5-F) | |
| 2.39 | —CH$_2$CH$_2$Cl | —O—C$_6$H$_3$(2-Cl)(5-Cl) | |

TABLE 2-continued

Compounds of the formula VI

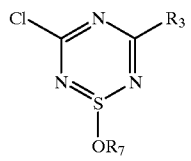

(VI)

| Comp. No. | $R_7$ | $R_3$ | Physical Data |
|---|---|---|---|
| 2.40 | —CH$_2$CH$_2$Cl | 2,6-dichlorophenoxy | |
| 2.41 | —CH(CH$_3$)CH$_2$Cl | —OC$_6$F$_5$ | |
| 2.42 | —CH(C$_2$H$_5$)CH$_2$Cl | 2,3,5,6-tetrafluorophenoxy | |
| 2.43 | —CH(C$_3$H$_7$)CH$_2$Cl | 2,5-difluorophenoxy | |
| 2.44 | trans-2-chlorocyclohexyl | —OC$_6$F$_5$ | |
| 2.45 | —CH(C$_6$H$_5$)CH$_2$Cl | —OC$_6$F$_5$ | |
| 2.46 | —CH(CH$_3$)CH$_2$Cl | —SC$_6$F$_5$ | |
| 2.47 | —CH$_2$CH$_2$Cl | 3-(methoxycarbonyl)pyridin-2-ylthio | |
| 2.48 | —CH$_2$CH$_2$Cl | (4-methyl-6-cyclopropylpyrimidin-2-yl)thio | |

TABLE 2-continued

Compounds of the formula VI

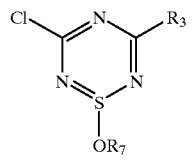

(VI)

| Comp. No. | R$_7$ | R$_3$ | Physical Data |
|---|---|---|---|
| 2.49 | —CH$_2$CH$_2$Cl | 3-methyl-7-(methylthio)-isobenzofuran-1(3H)-one | $^1$H-NMR: 7.5–7.8 ppm (3 H); 5.55 ppm (1 H); 4.2 ppm (1 H); 3.9 ppm (1 H); 3.15 ppm (2 H); 1.6 ppm (3 H) |
| 2.50 | —CH$_3$ | 4-ethyl-5-chloro-6-(methylthio)pyrimidine | |
| 2.51 | —CH(CH$_3$)$_2$ | 5-methoxypyrimidine | |
| 2.52 | —CH$_2$CH$_2$F | 3-(trifluoromethyl)-2-(methylthio)pyridine | |
| 2.53 | —CHCH$_2$Cl<br>      \|<br>      C$_2$H$_5$ | 1-methoxynaphthalene | |
| 2.54 | —CH$_2$CH$_2$Cl | 3-(methylthio)naphthalene | |
| 2.55 | —CH$_2$CH$_2$Cl | 5-(trifluoromethyl)-3-chloro-2-(methylthio)pyridine | |
| 2.56 | —CH$_2$CH$_2$Cl | 3-methyl-7-(methylthio)-isobenzofuran-1(3H)-one | |

TABLE 2-continued

Compounds of the formula VI

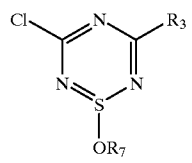

(VI)

| Comp. No. | R$_7$ | R$_3$ | Physical Data |
|---|---|---|---|
| 2.57 | —CH$_2$CH$_2$Cl | (3-methoxy-3-methyl-1-oxo-1,3-dihydroisobenzofuran-4-yl methoxy group) | |
| 2.58 | cycloheptyl | methyl 2-(methylthio)nicotinate-3-yl | |
| 2.59 | —CH$_2$CH$_2$Br | 4-methyl-2-isopropyl-6-(methylthio)pyrimidin-5-yl | |
| 2.60 | —CH$_2$CH$_2$Cl | 4,6-dimethyl-2-(methylthio)pyrimidin-5-yl | |
| 2.61 | —CH$_2$CH$_2$Cl | 4-methyl-6-cyclopropyl-2-(methylthio)pyrimidin-5-yl | |
| 2.62 | cyclooctyl | 5,6-dimethyl-3-(methylthio)-1,2,4-triazin-yl | |
| 2.63 | —CH$_2$CH$_2$Cl | 1-acetyl-2-methoxynaphth-yl | |

TABLE 2-continued
Compounds of the formula VI
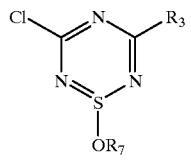
(VI)
| Comp. No. | R₇ | R₃ | Physical Data |
|---|---|---|---|
| 2.64 | —CH₂CH₂Cl | (CH₃)₃C—C₆H₄—S— | |
| 2.65 | —CH(C₂H₅)CH₂Cl | 4-OCF₃-6-Cl-2-pyrimidinyl-S— | |
| 2.66 | —CH(C₂H₅)CH₂Cl | 2-COCH₃-3,5-difluoro-6-methoxyphenyl-O— | |
| 2.67 | —CH₂CH₂Br | C₆F₅S— | |
| 2.68 | —CH₂CH₂Cl | 4-methoxyphenyl-O-phenyl-O— | |
| 2.69 | —CH₂CH₂Cl | 4-CH₃-6-CF₃-2-pyrimidinyl-S— | |
| 2.70 | —CH₂CH₂Cl | 3,5-dichloro-2-methoxyphenyl—O— | |
| 2.71 | —CH₂CH₂Cl | 2,4-dibromo-phenyl-O— | |
| 2.72 | —CH₂CH₂Cl | 5-CF₃-2-pyridyl-S— | |

TABLE 2-continued

Compounds of the formula VI

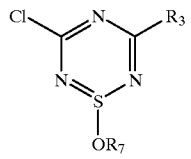

(VI)

| Comp. No. | R₇ | R₃ | Physical Data |
|---|---|---|---|
| 2.73 | —CH$_2$CH$_2$F | 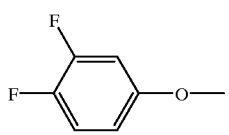 | |
| 2.74 | —CH$_2$CH$_2$Cl | 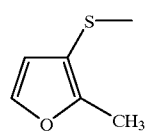 | |
| 2.75 | —CH$_2$CH$_2$OCH$_3$ | C$_6$F$_5$O— | |
| 2.76 | —CH$_2$CH=CH$_2$ | 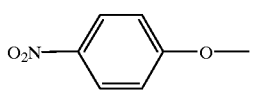 | |
| 2.77 | 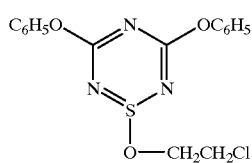 | C$_6$F$_5$O— | |

Example H5

Preparation of 1-(b-chloroethoxy)-3,5-diphenoxythiatriazine (process b$_3$)

(Comp. No. 3.1)

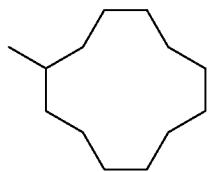

2.07 g (0.022 mol) of phenol are dissolved in 30 ml of tetrahydrofuran under nitrogen at a temperature of 40° C. to 45° C., and 0.90 g (0.0225 mol) of 60% sodium hydride is added. When no further hydrogen is evolved, the mixture is cooled to −40° C., 2.5 g (0.01 mol) of 1-(b-chloroethoxy)-3,5-dichlorothiatriazine are added in portions and the exothermic reaction is allowed to proceed at −30° C. to −40° C. The temperature is then allowed to rise to 0° C. and the reaction mixture is extracted with water and ethyl acetate. After removal of the solvent, 4.5 g of crude product are obtained, which, after purification by chromatography (silica gel; ethyl acetate/hexane 1/1) and recrystallization from 10 ml of ethyl acetate and 15 ml of hexane, gives 3.35 g (92% of theory) of the desired pure product of melting point 89–90° C.

Analysis: C$_{16}$H$_{14}$ClN$_3$O$_3$S;

| | calculated [%] | found [%] |
|---|---|---|
| N | 11.55 | 11.69 |
| Cl | 9.74 | 9.73 |

Example H6

Preparation of 1-cyclohexyloxy-3-(p-nitrophenoxy)-5-(a-naphthoxy)thiatriazine (process c₃)

(Comp. No. 3.31)

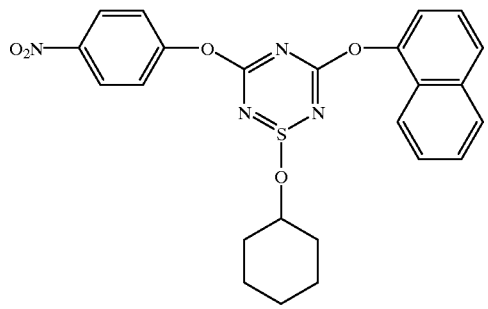

0.65 g (0.0045 mol) of a-naphthol is dissolved in 40 ml of tetrahydrofuran, and 0.196 g (0.0045 mol) of 55% sodium hydride is added, under nitrogen. When the exothermic reaction has ended, the mixture is cooled to room temperature (23° C.) and a solution of 1.60 g (0.0043 mol) of 1-cyclohexyloxy-3-chloro-5-(p-nitrophenoxy)thiatriazine in a little tetrahydrofuran is added dropwise. During this operation, the temperature rises from 23° C. to 31° C. The mixture is extracted with water and ethyl acetate, the extract is concentrated and the residue is chromatographed (silica gel; ethyl acetate/hexane 1/9). This gives 1.05 g of the desired pure product, which is recrystallized from 5 ml of ethyl acetate and 5 ml of hexane. The yield of crystalline product of melting point 115–116° C. is 0.87 g. The $^{13}$C-NMR spectrum in CDCl₃ shows, in addition to the lines for the a-naphthyl radical (118–156 ppm), 4 lines for the cyclohexyl radical (79.3 ppm; 33.4 ppm; 24.9 ppm and 23.6 ppm) and 2 lines for the two C atoms of the thiatriazine ring (169.3 ppm and 168.2 ppm).

Example H7

Preparation of 1-(n-butoxy)-3,5-di(2',5'-dichlorophenoxy)thiatriazine (process p)

(Comp. No. 3.7)

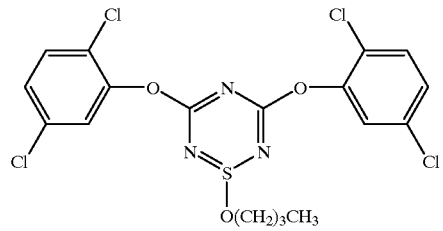

0.75g (0.0015 mol) of 1-(b-chloroethoxy)-3,5-di(2',5'-dichlorophenoxy)thiatriazine and 2.22 g (0.03 mol) of n-butanol are dissolved in 15 ml of tetrahydrofuran, the solution is cooled to −40° C. and 3.1 ml of a 0.098 molar solution of potassium tert-butylate in tetrahydrofuran (0.00030 mol) are added. After 45 minutes, the reaction has ended. The reaction mixture is extracted with water and ethyl acetate, the extract is concentrated and the residue is chromatographed (silica gel; ethyl acetate/hexane 8/92). The yield is 0.64 g (92% of theory) of a resin, the 300 MHz $^1$H-NMR spectrum of which confirms the structure of the desired compound.

Example H8

Preparation of 1-(2,2-dimethylpropoxy)-3,5-di(pentafluorophenoxy)thiatriazine (process p)

(Comp. No. 3.84)

0.74 g (0.001494 mol) of 1-methoxy-3,5-di(pentafluorophenoxy)thiatriazine is dissolved with 5.27 g (0.0598 mol) of 2,2-dimethyl-1-propanol in 15 ml of tetrahydrofuran, and 0.30 ml of a 0.0982 molar solution (2.94×10⁻⁵ mol) of potassium tert-butylate in tetrahydrofuran is added at −60° C. After 30 minutes, the reaction has ended. The mixture is extracted with water and ethyl acetate, the extract is concentrated on a rotary evaporator and the residue is treated under a high vacuum at 50° C. The yield is 0.75 g (91% of theory) of a resin, the 300 MHz $^1$H— and $^{13}$C-NMR spectra of which are in agreement with the structure of the desired compound.

The compounds listed in the following Table 3 can be prepared analogously to Examples H5 to H8.

TABLE 3
Compounds of the formula V
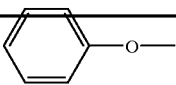
(V)
| Comp. No. | Process | R₇ | R₃ |
|---|---|---|---|
| 3.1 | b₃ | —CH₂CH₂Cl | 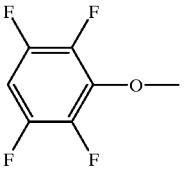 |
| 3.2 | | —CH₂CH₂Cl | 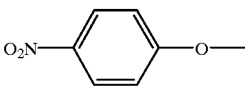 |
| 3.3 | b₃ | —CH₂CH₂Cl | C₆F₅O— |
| 3.4 | | —CH₂CH₂Cl | 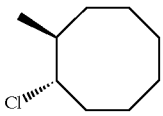 |
| 3.5 | b₃ | 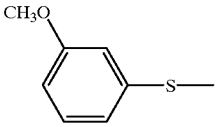 | 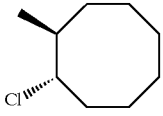 |
| 3.6 | b₃ | 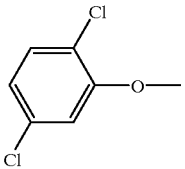 | C₆F₅O— |
| 3.7 | p | —(CH₂)₃CH₃ | 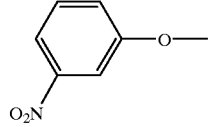 |
| 3.8 | | —CH₂CH₂Cl | 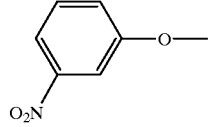 |
| 3.9 | | —CH₂CH₂Cl | 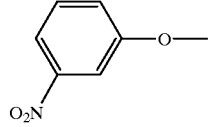 |

TABLE 3-continued

Compounds of the formula V $$\text{(V)}$$

| No. | | $R_{12}X_1$— | $R_3$ |
|---|---|---|---|
| 3.10 | p | —CH$_2$CH$_2$C$_6$H$_5$ | 2,6-difluoro-phenoxy (—O—C$_6$H$_3$F$_2$) |
| 3.11 | | —CH$_2$CH$_2$Cl | 2-nitro-phenoxy |
| 3.12 | | —CH$_2$CH$_2$Cl | 2,4-dinitro-phenoxy |
| 3.13 | b$_3$ | —CH$_2$CH$_2$Cl | (3-methyl-1-oxo-1,3-dihydroisobenzofuran-7-yl)oxy |
| 3.14 | | —CH$_2$C$_6$H$_5$ | 2,4-difluoro-phenoxy |
| 3.15 | | —CH$_2$CH$_2$Cl | 4-nitro-phenoxy |
| 3.16 | | —CH$_2$CH$_2$Cl | 4-nitro-phenoxy |
| 3.17 | | —CH$_2$CH$_2$Cl | 2,4-dinitro-phenoxy |
| 3.18 | | —CH(CH$_3$)CH$_2$Cl | C$_6$F$_5$O— |

TABLE 3-continued

Compounds of the formula V $$R_{12}X_1-\overset{N}{\underset{N-S-N}{\bigtriangleup}}-R_3$$
$$\overset{|}{OR_7}$$
(V)

| | | $R_{12}X_1$ | $R_3$ |
|---|---|---|---|
| 3.19 | b₃ | —CH₂CH₂Cl | 2-COOCH₃, phenyl-O— (with O-methoxy) |
| 3.20 | | —CH₂CH₂F | C₆F₅O— |
| 3.21 | | —CH₂CH₂Cl | 3-O₂N-phenyl-O— |
| 3.22 | | —CH₂CH₂Cl | 2-COOCH₃-phenyl-S— |
| 3.23 | b₃ | —CH₂CH₂Cl | C₆F₅S— |
| 3.24 | c₃ | cyclooctyl | 2,3,5,6-tetrafluoro-4-methoxy-phenyl-O— |
| 3.25 | | —CH₂CH₂Cl | 4,6-dimethoxy-pyrimidin-2-yl-S— |
| 3.26 | | —CHCH₂Cl, C₂H₅ | 4-methoxy-1-acetyl-naphthyl |
| 3.27 | | —CHCH₂Cl, CH₃ | 2,3,5,6-tetrafluoro-phenyl-S—methyl |

TABLE 3-continued
Compounds of the formula V
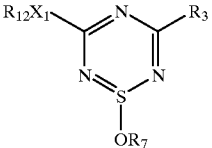
(V)
| | | | |
|---|---|---|---|
| 3.28 | b₃ | —CH₂CH₂Cl | 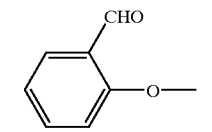 |
| 3.29 | | —CH₂CH₂Cl | 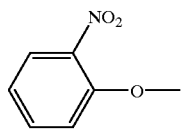 |
| 3.30 | | —CH₂CH₂Cl | 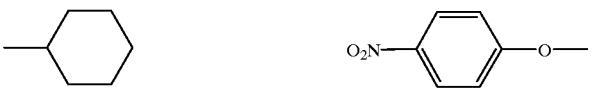 |
| 3.31 | c₃ |  |  |
| 3.32 | | —CHCH₂Cl<br>   \|<br>   C₂H₅ | 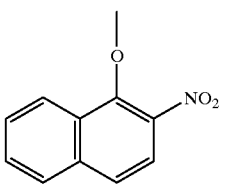 |
| 3.33 | | —CH₂C≡CH | 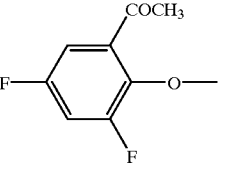 |
| 3.34 | | —CH₂CH₂Cl | |
| 3.35 | | —CH₂CH₂Cl | |

TABLE 3-continued

Compounds of the formula V (V)

| No. | | $R_{12}X_1$— | $R_3$ |
|---|---|---|---|
| 3.36 | p | 3,3,5-trimethylcyclohexyl | 7-methoxy-3-methyl-phthalid-3-yl |
| 3.37 | | —CH$_2$CH$_2$Cl | 4-methoxy-2-nitrophenyl |
| 3.38 | | —CH$_2$CH$_2$Cl | 3,5-bis(trifluoromethyl)phenylthiomethyl |
| 3.39 | | —CHCH$_2$Cl<br>  \|<br>  C$_6$H$_5$ | 2-methoxyphenoxy-(2-methoxy) |
| 3.40 | p | 3,3,5-trimethylcyclohexyl | C$_6$F$_5$S— |
| 3.41 | | —CH$_2$CH$_2$Cl | 2,3,6-trifluoro-methoxyphenyl |
| 3.42 | | —CH$_2$CH$_2$Cl | 4,6-dimethyl-2-(methylthio)pyrimidinyl |
| 3.43 | | —CH$_2$CH$_2$Cl | 4-methoxy-2-nitrophenyl |

TABLE 3-continued

Compounds of the formula V $$\text{(V)}$$

R$_{12}$X$_1$—, R$_3$, OR$_7$ on 1,2,4,6-thiatriazine ring

| No. | | R$_{12}$X$_1$— | R$_3$ |
|---|---|---|---|
| 3.44 | | —CH$_2$CH$_2$Cl | 3,5-bis(CF$_3$)-phenyl-O— |
| 3.45 | b$_3$ | —CH$_2$CH$_2$Cl | 2-(COOC$_2$H$_5$)-phenyl-O— |
| 3.46 | | 1-indanyl-CH— | C$_6$F$_5$O— |
| 3.47 | | —CH$_2$CH$_2$Cl | 2,4-dinitro-phenyl-O— |
| 3.48 | p | —CH(CH$_3$)(C$_6$H$_5$) | 2,5-difluoro-phenyl-O— |
| 3.49 | | —CH$_2$CH$_2$Cl | 2,3,4-trifluoro-phenyl-O— |
| 3.50 | b$_3$ | —CH$_2$CH$_2$Cl | 4-[CH(CH$_3$)(COOC$_2$H$_5$)]-phenyl-O— |

TABLE 3-continued

Compounds of the formula V (V)

[Structure: 1,2,4,6-thiatriazine ring with R12X1- at position 5, R3 at position 3, and OR7 at position 2]

| No. | X1 | R12 | R3 |
|---|---|---|---|
| 3.51 | | —CH2CH2Cl | 1-methoxy-2,4-dichloronaphthalen-3-yl (4-methoxy-1,3-dichloronaphthyl) — structure with OCH3 and two Cl on naphthalene |
| 3.52 | | —CH2CH2Cl | CF3O—C6H4—S— (4-trifluoromethoxyphenylthio) |
| 3.53 | | (−)-bornyl (1,7,7-trimethylbicyclo[2.2.1]heptyl) | 2-methoxybenzaldehyde-yl (o-OCH3-C6H4-CHO) |
| 3.54 | | —CH2CH2Cl | C6F5O— |
| 3.55 | | —CH2CH2Cl | 2-isopropyl-4-methyl-6-(methylthio)pyrimidin-yl [(CH3)2CH–pyrimidine with CH3 and S–CH3] |
| 3.56 | | —CHCH2Cl<br>   \|<br>   CH3 | 3-CF3-2-(methylthio)pyridin-yl |
| 3.57 | c3 | —CHCH2Cl<br>   \|<br>   C6H5 | C6F5O— |
| 3.58 | | —CH2CH2Cl | 2,4-dimethoxy-6-(methylthio)pyrimidin-yl (OCH3, CH3O, S–CH3 on pyrimidine) |
| 3.59 | | —CHCH2Cl<br>   \|<br>   C6H5 | 1-methoxy-2-methylnaphthalen-yl (OCH3, CH3 on naphthalene) |

TABLE 3-continued

Compounds of the formula V $$R_{12}X_1 - \underset{\underset{OR_7}{\overset{N}{\underset{S}{\bigtriangleup}}}}{\overset{N}{\underset{N}{\bigtriangleup}}} - R_3 \quad (V)$$

| | | $R_{12}X_1$ | $R_3$ |
|---|---|---|---|
| 3.60 | | —CH$_2$CH$_2$Cl | 2,4-dimethyl-6-methoxyphenyl (2,5-dimethylphenyl-O—) |
| 3.61 | p | —CH$_3$ | 2,5-difluorophenyl-O— |
| 3.62 | | —CHCH$_2$Cl<br>    \|<br>  C$_2$H$_5$ | 2-phenoxyphenyl-S— (OC$_6$H$_5$, S—) |
| 3.63 | | —CH$_2$CH$_2$Cl | 4-nitrophenyl-O— (O$_2$N—C$_6$H$_4$—O—) |
| 3.64 | | —CH$_2$CH$_2$Cl | 4-nitrophenyl-O— (O$_2$N—C$_6$H$_4$—O—) |
| 3.65 | | —CH$_2$CH$_2$Cl | 4-ethyl-5-chloro-6-(methylthio)pyrimidinyl |
| 3.66 | | —CH$_2$CH$_2$Cl | 4-chloro-1-methoxynaphthyl |
| 3.67 | b$_3$ | 2-chlorocyclopentyl | C$_6$F$_5$O— |

TABLE 3-continued
Compounds of the formula V
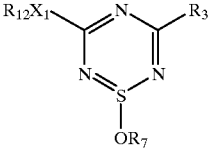
(V)
| | | | |
|---|---|---|---|
| 3.68 | b₃ | —CH₂CH₂Cl | 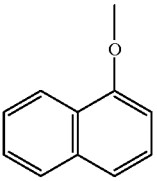 |
| 3.69 | | —CH₂CH₂Cl | 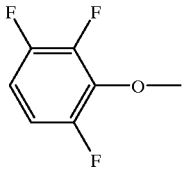 |
| 3.70 | | —CH₂CH₂Cl | 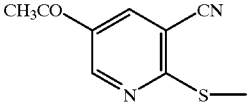 |
| 3.71 | | 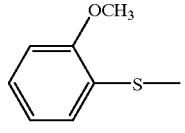 | 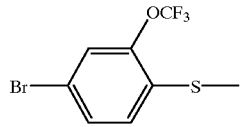 |
| 3.72 | p | —CH₃ | C₆F₅O— |
| 3.73 | | —CH₂CH₂Cl | 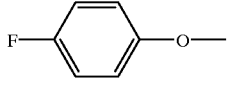 |
| 3.74 | | —CH₂CH₂Cl | 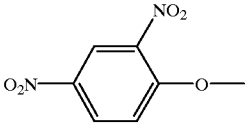 |
| 3.75 | | —CH₂CH₂Cl | 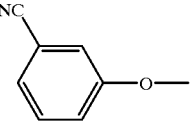 |
| 3.76 | | —CHCH₂Cl<br>\|<br>C₆H₅ | (3-cyanophenyl)-O— |

TABLE 3-continued

Compounds of the formula V $$\text{(V)}$$

R₁₂X₁—, —R₃, with central 1,2,4,6-thiatriazine ring bearing —OR₇

| No. | | R₁₂X₁— | R₃ |
|---|---|---|---|
| 3.77 | b₃ | —CH₂CH₂Cl | 2-methyl-5-methoxy-pyridin-yl |
| 3.78 | | —CH₂CH₂Cl | 4-nitro-phenoxy (O₂N—C₆H₄—O—) |
| 3.79 | | —CH₂CH₂Cl | NC—C₆H₄—O—C₆H₄—S— |
| 3.80 | | —CHCH₂Cl<br>\|<br>C₆H₅ | 2,4,6-trimethyl-phenoxy |
| 3.81 | | —CH₂CH₂Cl | 3,5-dichloro-phenoxy |
| 3.82 | b₃ | —CH₂CH₂Cl | 2-(methylthio)-benzoic acid methyl ester |
| 3.83 | | —CH₂CH₂Cl | 2,4-dimethyl-6-(methylthio)-pyrimidin-yl |
| 3.84 | p | —CH₂C(CH₃)₃ | C₆F₅O— |
| 3.85 | | —CH₂CH₂Cl | 2,3,4-trifluoro-phenoxy |
| 3.86 | | —CHCH₂Cl<br>\|<br>CH₃ | (CH₃)₂CH—C₆H₄—O— |

TABLE 3-continued

Compounds of the formula V $$R_{12}X_1 - \overset{N}{\underset{N-S-N}{\bigcirc}} - R_3 \quad (V)$$
$$\overset{|}{OR_7}$$

| | | R$_{12}$X$_1$ | R$_3$ |
|---|---|---|---|
| 3.87 | | —CH$_2$CH$_2$Cl | 2,4-dinitro-methoxyphenyl (O$_2$N, NO$_2$, OMe) |
| 3.88 | | —CH$_2$CH$_2$Cl | 2,4-dinitro-methoxyphenyl |
| 3.89 | b$_3$ | cyclohexyl | 4-nitro-methoxyphenyl |
| 3.90 | | —CH$_2$CH$_2$Cl | 5,6-dimethyl-3-methylthio-1,2,4-triazine |
| 3.91 | | —CH$_2$CH$_2$Cl | 4-CF$_3$-methoxyphenyl |
| 3.92 | | —CH$_2$CH$_2$Cl | 2,6-dibromo-methoxyphenyl |
| 3.93 | b$_3$ | —CH$_2$CH$_2$Cl | 3-methyl-7-methylthio-phthalide |
| 3.94 | | —CH$_2$CH$_2$Cl | 2,3,6-trifluoro-methoxyphenyl |
| 3.95 | | —CH$_2$CH$_2$Cl | CH$_2$=CHCH$_2$O—C$_6$H$_4$—O— |

TABLE 3-continued

Compounds of the formula V $$R_{12}X_1 \text{—} \underset{\underset{OR_7}{|}}{\overset{N}{\underset{N}{\bigvee}}} \text{—} R_3 \qquad (V)$$

| | | | |
|---|---|---|---|
| 3.96 | | —CH₂CH₂Cl | 4-OCF₃, 2-CH₃, 6-SCH₃ pyrimidinyl |
| 3.97 | b₃ | trans-2-chlorocyclohexyl | 2,6-difluoro-phenoxy |
| 3.98 | | —CH₂CH₂Cl | 2,4-dibromo-phenoxy |
| 3.99 | | —CHCH₂Cl, C₆H₅ | 2,4-dinitro-phenoxy |
| 3.100 | | —CH₂CH₂Br | C₆F₅O— |
| 3.101 | | —CH₂CH₂Cl | 4-phenoxy-phenoxy |
| 3.102 | | —CH₂CH₂Cl | 2,4-difluoro-phenoxy |
| 3.103 | p | —CH₃ | 2,4-difluoro-phenoxy |
| 3.104 | | —CH₂CH₂Cl | 2,3,5-trifluoro-phenoxy |

TABLE 3-continued

Compounds of the formula V $$R_{12}X_1 - \underset{\underset{OR_7}{|}}{\overset{N=\underset{N}{\overset{}{\bigtriangleup}}=N}{\bigtriangleup}} - R_3 \quad (V)$$

| No. | | $R_{12}X_1$ | $R_3$ |
|---|---|---|---|
| 3.105 | $b_3$ | —CH$_2$CH$_2$Cl | 4,6-dimethylpyrimidin-2-ylthio |
| 3.106 | | —CH$_2$CH$_2$Cl | 2,4-dichlorophenoxy |
| 3.107 | | —CH$_2$CH$_2$Cl | 4-bromophenoxy |
| 3.108 | | —CH$_2$CH$_2$Cl | 4-nitrobenzyl-4′-thiophenyl |
| 3.109 | $c_3$ | cyclooctyl | 2,3,5,6-tetrafluoro-4-phenoxy |
| 3.110 | | —CH$_2$CH$_2$Cl | 2,4-difluorophenoxy |
| 3.111 | | —CH$_2$CH$_2$Cl | 2,4-difluorophenoxy |
| 3.112 | $b_3$ | —CH$_2$CH$_2$Cl | pyridin-2-ylthio |
| 3.113 | | —CH$_2$CH$_2$Cl | 2-chlorophenoxy |

TABLE 3-continued
Compounds of the formula V
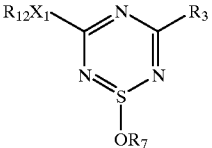
(V)
| | | | |
|---|---|---|---|
| 3.114 | | —CHCH₂Cl<br>  \|<br>  C₆H₅ | 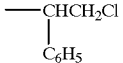 |
| 3.115 | | —CH₂CH₂Cl | 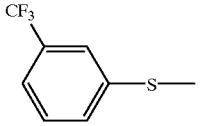 |
| 3.116 | | —CH₂CH₂Cl | 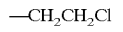 |
| 3.117 | | —CH₂CH₂Cl | 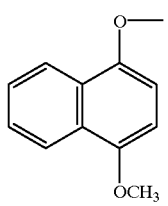 |
| 3.118 | | —CH₂CH₂Cl | 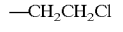 |
| 3.119 | b₃ | —CHCH₂Cl<br>  \|<br>  C₆H₅ |  |
| 3.120 | |  | 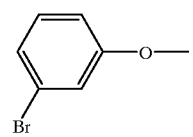 |
| 3.121 | | —CH₂CH₂Cl | 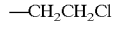 |

TABLE 3-continued

Compounds of the formula V $$R_{12}X_1\text{—}\underset{\underset{OR_7}{|}}{\underset{N\text{—}S\text{—}N}{\overset{N\text{—⟨⟩—}N}{}}}\text{—}R_3 \qquad (V)$$

| No. | | $R_{12}X_1$ | $R_3$ |
|---|---|---|---|
| 3.122 | | —CH$_2$CH$_2$Cl | 2-(methylthio)-4-methyl-6-(trifluoromethyl)pyrimidine |
| 3.123 | | —CH$_2$CH$_2$Cl | 2-fluoro-6-methoxyphenyl |
| 3.124 | p | —CH(CH$_3$)(CH$_2$)$_5$CH$_3$ | 2,4-dichloro-6-methoxyphenyl |
| 3.125 | | —CH$_2$CH$_2$Cl | 2,4-dinitro-6-methoxyphenyl |
| 3.126 | | —CH$_2$CH$_2$Cl | 2-(methylthio)-4-methyl-6-(trifluoromethyl)pyrimidine |
| 3.127 | | —CH$_2$CH$_2$Cl | 2-nitro-6-methoxyphenyl |
| 3.128 | | —CH$_2$CH$_2$Cl | 3-chloro-6-methoxyphenyl |
| 3.129 | b$_3$ | —CH$_2$CH$_2$Cl | 3,5-dimethoxy-6-methoxyphenyl |

TABLE 3-continued

Compounds of the formula V $$R_{12}X_1 - \underset{\underset{OR_7}{S}}{\overset{N}{\underset{N}{\bigvee}}} - R_3 \quad (V)$$

| | | | |
|---|---|---|---|
| 3.130 | b$_3$ | (structure: chloro-methyl-isopropenyl cyclohexane) | —OC$_6$F$_5$ |
| 3.131 | b$_3$ | (structure: chloro-methyl-isopropenyl cyclohexane) | —OC$_6$F$_5$ |
| 3.132 | | —CH$_2$CH$_2$Cl | 2,5-difluoro methoxyphenyl |
| 3.133 | | —CH$_2$CH$_2$Cl | 2-bromo methoxyphenyl |
| 3.134 | | —CH$_2$CH$_2$Cl | 3-nitro methoxyphenyl |
| 3.135 | | —CH$_2$CH$_2$Cl | 2-nitro methoxyphenyl |
| 3.136 | b$_3$ | —CH$_2$CH$_2$Cl | 2,4-dichloro methoxyphenyl |
| 3.137 | | —CH$_2$CH$_2$Cl | 3-fluoro methoxyphenyl |

TABLE 3-continued

Compounds of the formula V $$R_{12}X_1 - \underset{\underset{OR_7}{\overset{N}{\underset{S}{\bigtriangleup}}}}{\overset{N}{\bigtriangleup}} - R_3 \quad (V)$$

| | | | |
|---|---|---|---|
| 3.138 | | —CH$_2$CH$_2$Cl | 4-NO$_2$-2-methoxyphenyl (NO$_2$, O—) |
| 3.139 | | —CH$_2$CH$_2$Cl | 4-methoxy-(O$_2$N-phenyl)—O— |
| 3.140 | b$_3$ | —CH$_2$CH$_2$Cl | tetrafluoro-methoxyphenyl |
| 3.141 | | —CH$_2$CH$_2$Cl | 2-fluorophenyl-S— |
| 3.142 | b$_3$ | —CH$_2$CH$_2$Cl | 2,5-dichloro-methoxyphenyl |
| 3.143 | | —CHCH$_2$Cl<br>\|<br>C$_6$H$_5$ | 1-acetyl-2-methoxynaphthyl (COCH$_3$, O—) |
| 3.144 | | —CH$_2$CH$_2$Cl | 2-(SC$_2$H$_5$)-methoxyphenyl |
| 3.145 | | —CH$_2$CH$_2$Cl | 5-bromo-2-(methylthio)pyrimidine |
| 3.146 | | —CH$_2$CH$_2$Cl | C$_6$F$_5$O— |
| 3.147 | b$_3$ | —CH—CH$_2$Cl<br>\|<br>CH$_2$Br | 3-(dimethylamino)-methoxyphenyl ((CH$_3$)$_2$N, O—) |

TABLE 3-continued

Compounds of the formula V $$\text{(V)}$$

Structure: 1,2,4,6-thiatriazine ring with $R_{12}X_1$ at position 5, $R_3$ at position 3, and $OR_7$ at sulfur.

| No. | | $R_{12}X_1$ | $R_3$ |
|---|---|---|---|
| 3.148 | | —CH$_2$CH$_2$Cl | 4-F-C$_6$H$_4$-O— |
| 3.149 | | —CH$_2$CH$_2$Cl | 2-NO$_2$-6-methylphenyl (2-NO$_2$, 3-methyl) |
| 3.150 | | —CH$_2$CH$_2$Cl | 4-O$_2$N-C$_6$H$_4$-O— |
| 3.151 | | —CH$_2$CH$_2$Cl | C$_6$F$_5$O— |
| 3.152 | | —CH$_2$CH$_2$Cl | 2,4-Cl$_2$-C$_6$H$_3$-O— |
| 3.153 | | —CHCH$_2$Cl<br>\|<br>C$_2$H$_5$ | 3-CH$_3$-C$_6$H$_4$-S— |
| 3.154 | | —CH$_2$CH$_2$Cl | 4-F-C$_6$H$_4$-O— |
| 3.155 | b$_3$ | —CH$_2$CH$_2$Cl | 2,6-F$_2$-C$_6$H$_3$-O— |
| 3.156 | | —CH$_2$CH$_2$Cl | 4-O$_2$N-C$_6$H$_4$-O— |
| 3.157 | | —CHCH$_2$Cl<br>\|<br>C$_2$H$_5$ | 1,6-dibromo-2-naphthyl-O— |

TABLE 3-continued

Compounds of the formula V $$\underset{OR_7}{R_{12}X_1-\overset{N}{\underset{N-S-N}{\bigtriangleup}}-R_3}$$ (V)

| | | | |
|---|---|---|---|
| 3.158 | | —CH$_2$CH$_2$Cl | 4-cyclopropyl-6-methyl-2-(methylthio)pyrimidin-yl (structure with CH$_3$, —S—, cyclopropyl) |
| 3.159 | | —CHCH$_2$Cl \| C$_2$H$_5$ | 2-(CON(C$_2$H$_5$)$_2$)phenyl-O— |
| 3.160 | b$_3$ | —CH$_2$CH$_2$Cl | 2,5-difluorophenyl-O— |
| 3.161 | | —CH$_2$CH$_2$Cl | C$_6$F$_5$O— |
| 3.162 | | —CH$_2$CH$_2$Cl | 2-methoxyphenyl-S— |
| 3.163 | | —CHCH$_2$Cl \| C$_6$H$_5$ | 3-methoxy-2-(COOCH$_3$)naphthyl-O— |
| 3.164 | | —CH$_2$CH$_2$Cl | C$_6$H$_5$—O— |
| 3.165 | | —CH$_2$CH$_2$Cl | 2,4-dinitrophenyl-O— (O$_2$N, NO$_2$) |
| 3.166 | | —CH$_2$CH$_2$Cl | pyridyl-O— |
| 3.167 | | —CH$_2$CH$_2$Cl | 4-O$_2$N-phenyl-O— |

TABLE 3-continued

Compounds of the formula V $$R_{12}X_1 - \underset{\underset{OR_7}{\overset{N}{\underset{N}{\bigtriangleup}}}}{\overset{N}{\bigtriangleup}} - R_3 \quad (V)$$

| No. | R₃ | R₁₂X₁ | OR₇ |
|---|---|---|---|
| 3.168 | c₃ | methylcyclooctyl | 2,3,5,6-tetrafluorophenoxy |
| 3.169 | p | —CH₂CH₂CH₃ | 3-methyl-7-oxy-phthalide |
| 3.170 | | —CH₂CH₂Cl | 3-nitro-anisyloxy |
| 3.171 | | —CH₂CH₂Cl | C₆F₅O— |
| 3.172 | | —CH₂CH₂Cl | 1-(methylthio)naphthyloxy |
| 3.173 | | —CH₂CH₂Cl | 2,3-dichlorophenoxy |
| 3.174 | | —CHCH₂Cl<br>\|<br>C₂H₅ | 3,4-dimethoxyphenoxy (with CH₃O) |
| 3.175 | | —CH₂CH₂Cl | 4-fluorophenoxy |
| 3.176 | | CH₂CH₂Cl | 2,4-dinitrophenoxy |

TABLE 3-continued

Compounds of the formula V $$\underset{\underset{OR_7}{|}}{R_{12}X_1 \text{—} \overset{N}{\underset{N}{\diagup}} \overset{}{\underset{S}{\diagdown}} \overset{N}{\underset{}{\diagdown}} \text{—} R_3}$$ (V)

| | | | |
|---|---|---|---|
| 3.177 | | —CH$_2$CH$_2$Cl | 5-CF$_3$, 2-(SCH$_3$)-pyridin-yl |
| 3.178 | | —CH$_2$CH$_2$Cl | 2,4-difluoro-6-methoxyphenyl (2,5-F$_2$-C$_6$H$_2$-OCH$_3$) |
| 3.179 | b$_3$ | —CH$_2$CH$_2$Cl | 2-OCH$_3$-C$_6$H$_4$-O— |
| 3.180 | | —CH$_2$CH$_2$Cl | C$_6$F$_5$O— |
| 3.181 | | —CH$_2$CH$_2$Cl | 2-NO$_2$-C$_6$H$_4$-O— |
| 3.182 | | —CHCH$_2$Cl<br>    \|<br>    C$_2$H$_5$ | 2,5-Cl$_2$-C$_6$H$_3$-S— |
| 3.183 | | —CH$_2$CH$_2$Cl | 4-F-C$_6$H$_4$-CO-C$_6$H$_4$-4-O— |
| 3.184 | | —CHCH$_2$Cl<br>    \|<br>    C$_6$H$_5$ | 2,5-F$_2$-C$_6$H$_3$-O— |
| 3.185 | | —CH$_2$CH$_2$Cl | CH$_3$OCO-C$_6$H$_4$-4-O— |

TABLE 3-continued

Compounds of the formula V $$\underset{OR_7}{R_{12}X_1-\overset{N}{\underset{N}{\bigtriangleup}}\overset{R_3}{\underset{N}{\bigtriangleup}}}$$ (V)

| No. | | R₁₂X₁— | R₃ |
|---|---|---|---|
| 3.186 | p | —CH₂—C₆H₅ | 2,5-difluoro-methoxyphenyl |
| 3.187 | | —CH₂CH₂Cl | 2-nitro-methoxyphenyl |
| 3.188 | | —CH₂CH₂Cl | methyl 2-(methylthio)pyridine-3-carboxylate |
| 3.189 | p | cyclopentyl | C₆F₅O— |
| 3.190 | | —CH₂CH₂Cl | 2,4-dinitro-methoxyphenyl |
| 3.191 | | —CHCH₂Cl<br>  \|<br>  CH₃ | 2-fluoro-4-methoxy-methoxyphenyl |
| 3.192 | | —CH₂CH₂Cl | 4-nitro-methoxyphenyl |
| 3.193 | | —CH₂CH₂Cl | 2-chloro-4-fluoro-methoxyphenyl |
| 3.194 | | —CHCH₂Cl<br>  \|<br>  C₆H₅ | 2-nitro-methoxyphenyl |

TABLE 3-continued

Compounds of the formula V $$R_{12}X_1-\underset{\underset{\underset{OR_7}{|}}{S}}{\overset{N}{\underset{N}{\bigcirc}}}-R_3 \quad (V)$$

| | | R₁₂X₁— | R₃ |
|---|---|---|---|
| 3.195 | | —CH₂CH₂Cl | 2,3,5,6-tetrafluoro-4-methoxyphenyl (F,F,F,F, —O—) |
| 3.196 | b₃ | —CH₂CH₂Cl | 2-methyl-6-methoxyphenyl (CH₃, —O—) |
| 3.197 | | —CH₂CH₂Cl | 2,6-dichloro-phenoxy (Cl, Cl, —O—) |
| 3.198 | | —CHCH₂Cl<br>    \|<br>   C₆H₅ | 3,5-dimethylphenylthio (CH₃, CH₃, —S—) |
| 3.199 | | —CH₂CH₂Cl | 2,4,6-triiodo-methoxyphenyl (I, I, I, —O—) |
| 3.200 | | —CHCH₂Cl<br>    \|<br>   C₂H₅ | 2,4-dinitro-methoxyphenyl (NO₂, O₂N, —O—) |
| 3.201 | | —CH₂CH₂Cl | (CH₃OOC, CN, CH₃OCH₂, S, pyridinyl derivative) |
| 3.202 | p | —C₂H₅ | 2,5-difluoro-methoxyphenyl (F, F, —O—) |

TABLE 3-continued

Compounds of the formula V $$\text{(V)}$$

R₁₂X₁—[1,2,4,6-thiatriazine ring with N, N, S, N]—R₃, with OR₇ on S

| | | |
|---|---|---|
| 3.203 | —CH₂CH₂Cl | 3-O₂N, methoxyphenyl (O—) |
| 3.204 | —CH₂CH₂Cl | C₆F₅O— |
| 3.205 | —CH₂CH₂Cl | 3-O₂N, methoxyphenyl (O—) |
| 3.206 | —CH₂CH₂Cl | 2,4-(CH₃)₂-phenyl-S— |
| 3.207 p | —(CH₂)₄CH₃ | 2,5-F₂-phenyl-O— |
| 3.208 | —CH₂CH₂Cl | 4-O₂N-phenyl-O— |
| 3.209 | —CH₂CH₂Cl | 5-CH₃-3-CN-pyridin-2-yl-S— |
| 3.210 | —CHCH₂Cl<br>    C₆H₅ | 1-Br-naphthalen-2-yl-O— |
| 3.211 | —CH₂CH₂Cl | 4-O₂N-phenyl-O— |
| 3.212 | —CH₂CH₂Cl | 5-NO₂-pyrimidin-2-yl-S— |

TABLE 3-continued
Compounds of the formula V
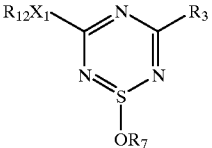
(V)
| | | |
|---|---|---|
| 3.213 | —CH₂CH₂Cl | 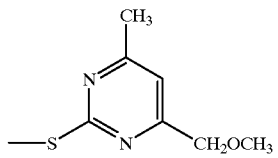 |
| 3.214 | —CHCH₂Cl<br>    \|<br>    CH₃ | 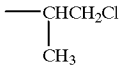 |
| 3.215 | —CH₂CH₂Cl | 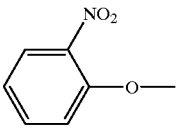 |
| 3.216 | —CH₂CH₂Cl | 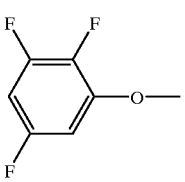 |
| 3.217 | —CHCH₂Cl<br>    \|<br>    C₂H₅ | 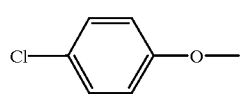 |
| 3.218 | —CH₂CH₂Cl | 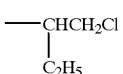 |
| 3.219 p | 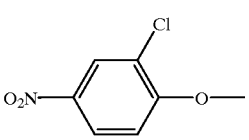 | 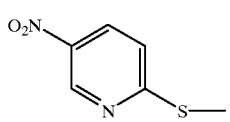 |
| 3.220 | —CH₂CH₂Cl | 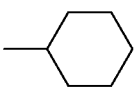 |

TABLE 3-continued

Compounds of the formula V (V)

R₁₂X₁—[triazine-S ring]—R₃, with OR₇

| | | |
|---|---|---|
| 3.221 | —CH₂CH₂Cl | isobenzofuranone with OCH₃, CH₃, CH₃O substituents |
| 3.222 | —CH₂CH₂Cl | isobenzofuranone with S—, CH₃, CH₃O substituents |
| 3.223 | —CH₂-furan | C₆F₅O— |
| 3.224 | tetrahydropyranyl | C₆F₅O— |
| 3.225 | 1,3-dioxanyl | 2,4-difluoro-methoxyphenyl |
| 3.226 | —CH₂-naphthyl | 2,6-dichloro-methoxyphenyl |
| 3.227 | —CH₂-thienyl | C₆F₅O— |
| 3.228 | —CH₂-tetrahydrofuryl | C₆F₅O— |
| 3.229 | N-acetylpiperidinyl | Br-methoxyphenyl |
| 3.230 | cycloheptyl | C₆F₅O— |

TABLE 3-continued

Compounds of the formula V $$\underset{\underset{OR_7}{|}}{R_{12}X_1-\overset{N}{\underset{N\diagdown S\diagup N}{\diagdown}}-R_3}\quad(V)$$

| No. | X₁ | R₁₂ | R₃ |
|---|---|---|---|
| 3.231 | | [methylcyclododecyl] | [4-nitrophenoxy: O₂N-C₆H₄-O-] |
| 3.232 | p | [2-(7,7-dimethylbicyclo[2.2.1]hept-2-en-1-yl)ethyl] | —OC₆F₅ |
| 3.233 | p | —CH₂CH₂Si(CH₃)₃ | —OC₆F₅ |
| 3.234 | p | —CH₂-(2-nitro-6-chlorophenyl) | —OC₆F₅ |
| 3.235 | p | —(CH₂)₃Si(CH₃)₃ | —OC₆F₅ |
| 3.236 | p | trans-4-tert-butylcyclohexyl | —OC₆F₅ |
| 3.237 | p | —CH₂CH₂-N(3,4-dimethyl-2,5-dioxo-2,5-dihydropyrrol-1-yl) | —OC₆F₅ |
| 3.238 | p | —CH₂C₆F₅ | —OC₆F₅ |
| 3.239 | p | cis-4-tert-butylcyclohexyl | —OC₆F₅ |
| 3.240 | p | —CH₂-(1-adamantyl) | —OC₆F₅ |
| 3.241 | p | —CH₂Si(CH₃)₃ | —OC₆F₅ |

TABLE 3-continued

Compounds of the formula V (V)

$$R_{12}X_1 \text{—}\underset{\underset{\underset{OR_7}{|}}{S}}{\overset{N}{\underset{N}}}\text{—}R_3$$

| | | | |
|---|---|---|---|
| 3.242 | p | (1-methyl-tetrahydronaphthyl) | —OC₆F₅ |
| 3.243 | p | (cyclopentyl with CH₂CH₂CN) | —OC₆F₅ |
| 3.244 | p | (cyclopentyl with CH₂CH₂CN) | —OC₆F₅ |
| 3.245 | p | —CH(CH₃)C₆F₅ | —OC₆F₅ |
| 3.246 | p | (cyclohexyl with CH₃) | —OC₆F₅ |
| 3.247 | p | (cyclohexyl with CH₃) | —OC₆F₅ |
| 3.248 | p | —CH(CH₃)Si(CH₃)₃ | —OC₆F₅ |
| 3.249 | p | —CHSi(CH₃)₃ with CH=CH₂ | —OC₆F₅ |
| 3.250 | | —CH(CH₃)COOCH₃ | —OC₆F₅ |
| 3.251 | b₃ | —CH₂CH₂Cl | (methoxy-phthalide with CH₃) |
| 3.252 | p | —C₂H₅ | —SC₆F₅ |
| 3.253 | p | —CH₃ | —SC₆F₅ |
| 3.254 | p | —CH(CH₃)₂ | —SC₆F₅ |
| 3.255 | p | —CH₂CH₂Si(CH₃)₃ | —OCH₂CH₂Cl |
| 3.256 | p | —CH₂CH₂CH₂Si(CH₃)₃ | —OCH₂CH₂Cl |
| 3.257 | p | Adamantyl | —OCH₂CH₂Cl |
| 3.258 | p | —CH₂Si(CH₃)₃ | —OCH₂CH₂Cl |
| 3.259 | p | (cyclohexyl with CH₃) | —OC₆F₅ |
| 3.260 | p | —CH(CH₃)Si(CH₃)₃ | —OC₆F₅ |

TABLE 3-continued
Compounds of the formula V
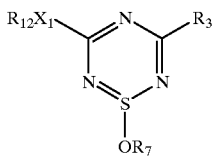
(V)
| | | | |
|---|---|---|---|
| 3.261 | p | 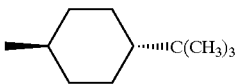 | 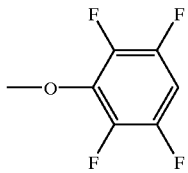 |
| 3.262 | p | 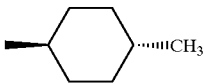 | 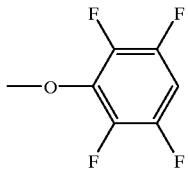 |
| 3.263 | p | 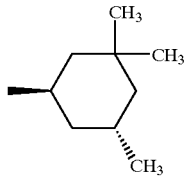 | 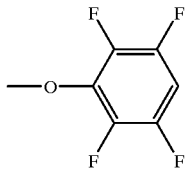 |
| 3.264 | p | —CH$_2$Si(CH$_3$)$_3$ | 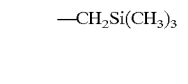 |
| 3.265 | p | 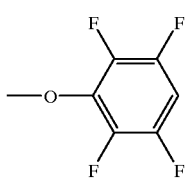 | 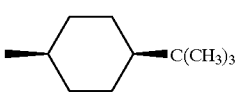 |
| 3.266 | | 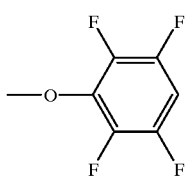 | 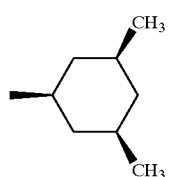 |
| 3.267 | p | 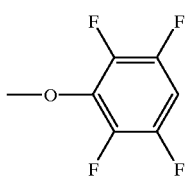 | 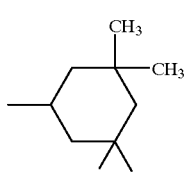 |

TABLE 3-continued
Compounds of the formula V
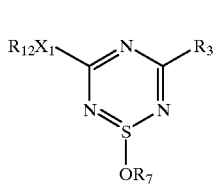
(V)
| | | | |
|---|---|---|---|
| 3.268 | p | 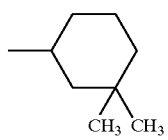 | 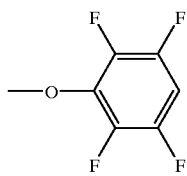 |
| 3.269 | p | 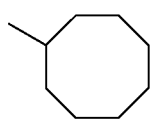 | 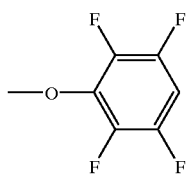 |
| 3.270 | p | 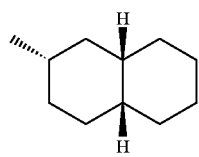 | —OC$_6$F$_5$ |
| 3.271 | | 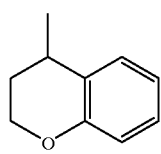 | —OC$_6$F$_5$ |
| 3.272 | |  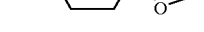 | —OC$_6$F$_5$ |
| 3.273 | p | 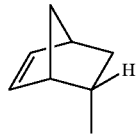 | —OC$_6$F$_5$ |
| 3.274 | p | 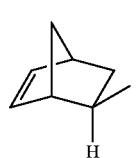 | —OC$_6$F$_5$ |
| 3.275 | p | 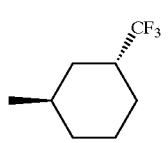 | —OC$_6$F$_5$ |

TABLE 3-continued

Compounds of the formula V $$\text{(V)}$$

R₁₂X₁—, N, R₃ on a 1,2,4-thiadiazine ring with OR₇

| No. | R₁₂X₁ | R₃ (structure) | OR₇ |
|---|---|---|---|
| 3.276 | p | norbornenyl-CH₂– (with H) | —OC₆F₅ |
| 3.277 | p | norbornyl (with H) | —OC₆F₅ |
| 3.278 | p | norbornyl (with H) | —OC₆F₅ |
| 3.279 | p | 2-(trifluoromethyl)cyclohexyl (CF₃) | —OC₆F₅ |
| 3.280 | | 4-tert-butyl-1-methylcyclohexenyl (C(CH₃)₃, CH₃) | —OC₆F₅ |
| 3.281 | p | pinanyl (CH₃, CH₃, CH₃) | —OC₆F₅ |
| 3.282 | | pinenyl (CH₃, CH₃, CH₃) (S) | —OC₆F₅ |
| 3.283 | | pinanyl (CH₃, CH₃, CH₃) | —OC₆F₅ |

TABLE 3-continued

Compounds of the formula V $$R_{12}X_1 - \underset{\underset{OR_7}{\overset{N}{\underset{N}{\bigvee}}}}{\overset{N}{\underset{N}{\bigvee}}} - R_3 \quad (V)$$

| | | R₁₂X₁– | R₃ |
|---|---|---|---|
| 3.284 | p | (trans-decalin, methyl) | —OC₆F₅ |
| 3.285 | p | (cis/trans-decalin, methyl) | —OC₆F₅ |
| 3.286 | p | —CH₂—C(CH₂CH₂CN)₂<br>    \|<br>    CH₃ | —OC₆F₅ |
| 3.287 | p | (cyclopentyl, methyl, CH₂CN) | —OC₆F₅ |
| 3.288 | p | (cyclopentyl, methyl, CH₂CN) | —OC₆F₅ |
| 3.289 |   | (bicyclic lactone with CH₃) | —OC₆F₅ |
| 3.290 |   | (isopropyl naphthalene) | —OC₆F₅ |
| 3.291 |   | (isopropyl m-methylphenyl) | —OC₆F₅ |

TABLE 3-continued

Compounds of the formula V $$\text{(V)}$$

(structure: 1,2,4,6-thiatriazine ring with R$_{12}$X$_1$ at 3-position, R$_3$ at 5-position, OR$_7$ on S)

| | | | |
|---|---|---|---|
| 3.292 | p | —CH$_2$—(2,3-dichlorophenyl) | —OC$_6$F$_5$ |
| 3.293 | | —CH(CH$_3$)—(2-OCHF$_2$, 4-F, 5-NO$_2$ phenyl) | —OC$_6$F$_5$ |
| 3.294 | | —CH(C$_2$H$_5$)—(4-phenoxyphenyl) | —OC$_6$F$_5$ |
| 3.295 | p | —CH(CH$_3$)—CH$_2$—(2-OCH$_3$ phenyl) | —OC$_6$F$_5$ |
| 3.296 | p | —CH$_2$—CH(C$_5$H$_7$(n))—(2,4-dichlorophenyl) | —OC$_6$F$_5$ |
| 3.297 | | —CH< (CH$_2$)$_9$ > (cycloundecyl) | —OC$_6$F$_5$ |
| 3.298 | | —CH< (CH$_2$)$_{11}$ > (cyclotridecyl) | —OC$_6$F$_5$ |
| 3.299 | p | —CH$_2$—(3-fluorophenyl) | —OC$_6$F$_5$ |

TABLE 3-continued

Compounds of the formula V $$\text{(V)}$$

| No. | R₁₂X₁– | R₃ |
|---|---|---|
| 3.300 | –CH₂CH₂–C₆F₅ (pentafluorophenyl) | –OC₆F₅ |
| 3.301 | –CH₂–cyclohexyl | –OC₆F₅ |
| 3.302 | 2-(n-propylthio)cyclooctyl | –OC₆F₅ |
| 3.303 | 2-methoxycyclopentyl | –OC₆F₅ |
| 3.304 | –CH(CH₃)–C₆H₄–(4-Cl) with phenyl | –OC₆F₅ |
| 3.305 | decahydronaphthyl with CN | –OC₆F₅ |
| 3.306 | decahydronaphthyl with CN | –OC₆F₅ |
| 3.307 | 2-(n-propoxy)cyclohexyl | –OC₆F₅ |

TABLE 3-continued

Compounds of the formula V (V)

| 3.308 | [cycloheptane with SCH₃ and CH₃ substituents] | —OC₆F₅ |
|---|---|---|

| Comp. No. | $R_{12}$—$X_1$ |
|---|---|
| 3.1 | C₆H₅—O— |
| 3.2 | 4-O₂N-C₆H₄—O— |
| 3.3 | C₆F₅O— |
| 3.4 | C₆F₅S— |
| 3.5 | 3-CH₃O-C₆H₄—S— |
| 3.6 | C₆F₅O— |
| 3.7 | 2,5-Cl₂-C₆H₃—O— |
| 3.8 | C₆F₅—O— |
| 3.9 | 2,6-F₂-C₆H₃—O— |

TABLE 3-continued

Compounds of the formula V $$\begin{array}{c} R_{12}X_1-\underset{N}{\overset{N}{\diagdown}}\underset{S}{\overset{}{\diagdown}}\underset{N}{\overset{}{\diagup}}R_3 \\ | \\ OR_7 \end{array}$$ (V)

| | R₃ |
|---|---|
| 3.10 | 2,6-difluoro-methoxyphenyl (2,6-F₂-C₆H₃-O—) |
| 3.11 | 2,5-difluoro-methoxyphenyl |
| 3.12 | C₆F₅S— |
| 3.13 | 3-methyl-7-methoxy-phthalide |
| 3.14 | 2,4-difluoro-methoxyphenyl |
| 3.15 | C₆F₅S— |
| 3.16 | 2,3,4-trifluoro-methoxyphenyl |
| 3.17 | C₆Cl₅O— |
| 3.18 | C₆F₅O— |
| 3.19 | 2-(methoxycarbonyl)-phenoxymethyl |
| 3.20 | C₆F₅O— |
| 3.21 | 2,3,4-trifluoro-methoxyphenyl |

TABLE 3-continued
Compounds of the formula V
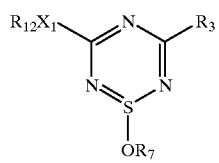
| | | |
|---|---|---|
| 3.22 | | 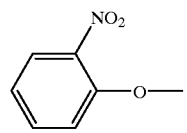 |
| 3.23 | | $C_6F_5S-$ |
| 3.24 | | 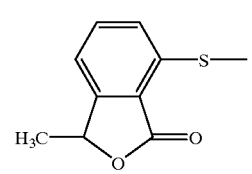 |
| 3.25 | | 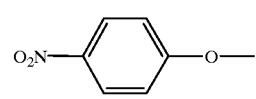 |
| 3.26 | | 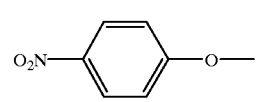 |
| 3.27 | | 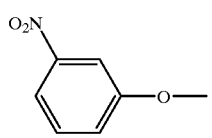 |
| 3.28 | | 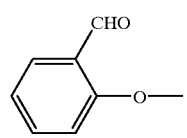 |
| 3.29 | | 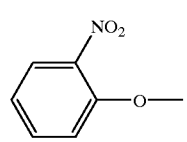 |
| 3.30 | | 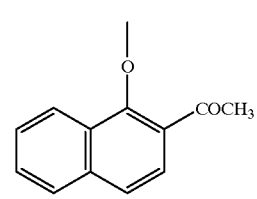 |

TABLE 3-continued
Compounds of the formula V
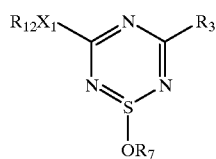
(V)
| | |
|---|---|
| 3.31 | 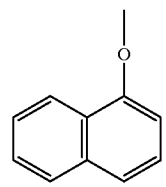 |
| 3.32 | 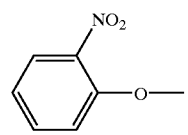 |
| 3.33 | 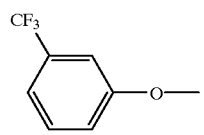 |
| 3.34 | 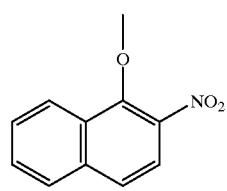 |
| 3.35 | 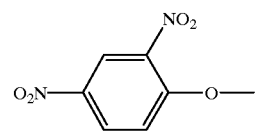 |
| 3.36 | 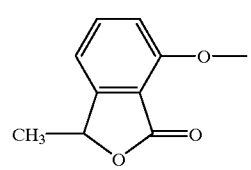 |
| 3.37 | 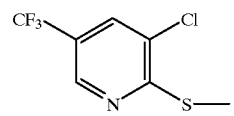 |
| 3.38 |  |

TABLE 3-continued

Compounds of the formula V $$\text{(V)}$$

Structure: 1,2,4,6-thiatriazine ring with $R_{12}X_1$– at one position, $R_3$ at another, and $OR_7$ at the sulfur position.

| No. | R₃ |
|---|---|
| 3.39 | 2,4-dichloro-1-methoxyphenyl (–O– linkage) |
| 3.40 | $C_6F_5S$— |
| 3.41 | 2-nitro-phenoxy |
| 3.42 | 2,4-dinitro-phenoxy |
| 3.43 | 3-methyl-phenoxy |
| 3.44 | 2,4-dinitro-phenoxy |
| 3.45 | 2-(ethoxycarbonyl)phenoxy |
| 3.46 | $C_6F_5O$— |
| 3.47 | 2,3,6-trifluoro-phenoxy |
| 3.48 | 2,4-difluoro-phenoxy |

TABLE 3-continued

Compounds of the formula V $$R_{12}X_1-\overset{N}{\underset{N-S-N}{\bigtriangleup}}-R_3 \quad (V)$$
$$\underset{OR_7}{|}$$

| 3.49 | 2,3,4-trifluoro-6-methoxyphenyl (F,F,F-C6H2-O–) |
| 3.50 | ethyl 2-(4-methoxyphenyl)propanoate group (C2H5OOC-CH(CH3)-C6H4-O–) |
| 3.51 | 2,4-dinitro-methoxyphenyl (O2N, NO2-C6H3-O–) |
| 3.52 | 2,4-dinitro-methoxyphenyl (O2N, NO2-C6H3-O–) |
| 3.53 | 2-methoxybenzaldehyde group (CHO-C6H4-O–) |
| 3.54 | 2-(methylthio)pyrimidine (–S-pyrimidine) |
| 3.55 | 4-nitro-methoxyphenyl (O2N-C6H4-O–) |
| 3.56 | 4-nitro-methoxyphenyl (O2N-C6H4-O–) |
| 3.57 | 2-methoxynaphthyl |

TABLE 3-continued

Compounds of the formula V $$\text{(V)}$$

Structure: 1,2,4,6-thiatriazine ring with $R_{12}X_1$ at position 5, $R_3$ at position 3, and $OR_7$ at position 2 (S).

| No. | Structure |
|---|---|
| 3.58 | 3-chloro-4-methoxy-nitrobenzene group (2-Cl, 1-OMe, 4-NO$_2$) |
| 3.59 | 2,5-difluoro-methoxyphenyl (1-OMe, 2-F, 5-F) |
| 3.60 | 4-methoxy-nitrobenzene (1-OMe, 4-NO$_2$) |
| 3.61 | 2,5-difluoro-methoxyphenyl |
| 3.62 | 4-methoxy-nitrobenzene |
| 3.63 | pentafluoro(trifluoromethyl)thiomethyl benzene: CF$_3$ and SMe on perfluorinated ring |
| 3.64 | 5-methoxypyrimidine |
| 3.65 | 4-methoxy-nitrobenzene |
| 3.66 | 1-methoxy-4-chloronaphthalene |

TABLE 3-continued

Compounds of the formula V $$\text{(V)}$$

R₁₂X₁—[1,2,4,6-thiatriazine ring with N, N, S, N]—R₃, with OR₇ on S

| | |
|---|---|
| 3.67 | C₆F₅O— |
| 3.68 | 1-methoxynaphthalen-8-yl (naphthalene with OCH₃) |
| 3.69 | 3-nitro-phenyl-O— (O₂N, —O—) |
| 3.70 | 4-nitro-phenyl-O— (O₂N—⟨⟩—O—) |
| 3.71 | 2-methoxy-phenyl-S— (OCH₃, —S—) |
| 3.72 | C₆F₅O— |
| 3.73 | 2,4-dichloro-phenyl-O— (Cl, Cl, —O—) |
| 3.74 | 4-tert-butyl-phenyl-O— ((CH₃)₃C—⟨⟩—O—) |
| 3.75 | 4-phenoxy-phenyl-O— (⟨⟩—O—⟨⟩—O—) |
| 3.76 | 4-nitro-phenyl-O— (O₂N—⟨⟩—O—) |
| 3.77 | 6-methyl-pyridin-3-yl-O— (H₃C—pyridine—O—) |

TABLE 3-continued

Compounds of the formula V (V)

$$\text{R}_{12}\text{X}_1\text{—ring with N, S, N, N, OR}_7, \text{R}_3$$

| 3.78 | 2,3,6-trifluoro-4-methoxyphenyl (F, F, F on ring with –O–) |
| 3.79 | 2,4-difluoro-methoxyphenyl |
| 3.80 | 2-nitro-methoxyphenyl |
| 3.81 | 4-[(C$_2$H$_5$O)$_2$CH]–phenyl–O– |
| 3.82 | 2-(methylthio)-methyl benzoate (COOCH$_3$, S—) |
| 3.83 | 4-nitro-phenyl–O– (O$_2$N) |
| 3.84 | C$_6$F$_5$O— |
| 3.85 | 2,3,6-trifluoro-4-methoxyphenyl |
| 3.86 | 2,4-dibromo-methoxyphenyl (Br, Br) |
| 3.87 | 2-acetyl-methoxyphenyl (COCH$_3$) |

TABLE 3-continued

Compounds of the formula V (V)

| | | |
|---|---|---|
| | 3.88 | 2,4-dimethoxy with OCH₃ (2,4,5-trimethoxyphenyl) |
| | 3.89 | 4-methoxy-1-nitrophenyl |
| | 3.90 | 2-nitro-1-methoxyphenyl |
| | 3.91 | 2,4-dinitro-1-methoxyphenyl |
| | 3.92 | 2,6-dibromo-1-methoxyphenyl |
| | 3.93 | 3-methyl-7-(methylthio)-isobenzofuran-1(3H)-one |
| | 3.94 | 2,3,6-trifluoro-1-methoxyphenyl |
| | 3.95 | 2-nitro-1-methylphenyl |
| | 3.96 | 4-methoxy-1-nitrophenyl |

TABLE 3-continued
Compounds of the formula V
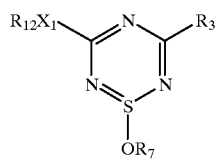
(V)
| 3.97 | 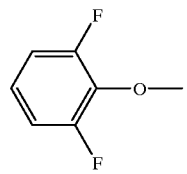 |
| 3.98 | 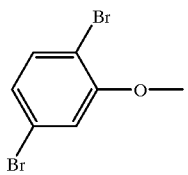 |
| 3.99 | 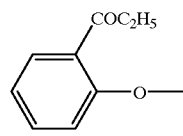 |
| 3.100 | C$_6$F$_5$O— |
| 3.101 | 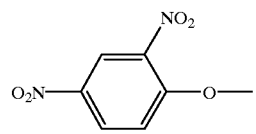 |
| 3.102 | 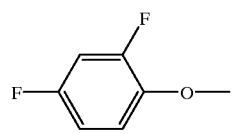 |
| 3.103 | 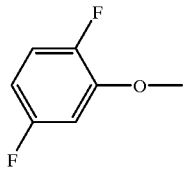 |
| 3.104 | 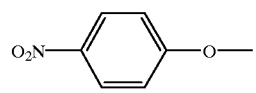 |
| 3.105 | 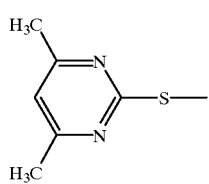 |

TABLE 3-continued
Compounds of the formula V
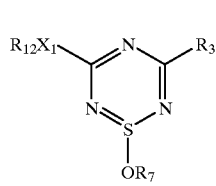
(V)
| | | |
|---|---|---|
| 3.106 | | 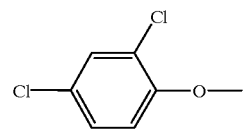 |
| 3.107 | | 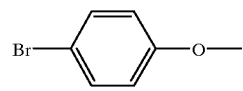 |
| 3.108 | | 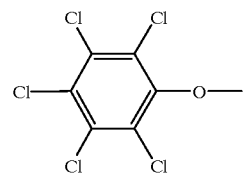 |
| 3.109 | | —$SC_6F_5$ |
| 3.110 | | 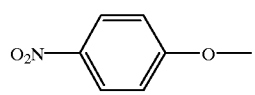 |
| 3.111 | | 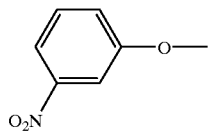 |
| 3.112 | | 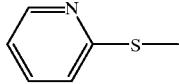 |
| 3.113 | | 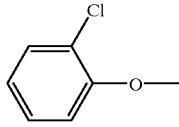 |
| 3.114 | | 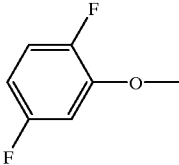 |

TABLE 3-continued
Compounds of the formula V
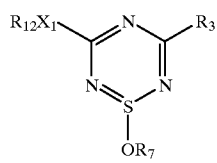
(V)
| | | |
|---|---|---|
| 3.115 | | 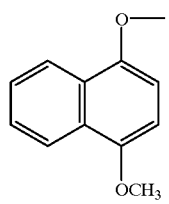 |
| 3.116 | | 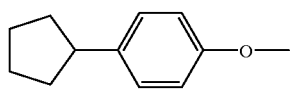 |
| 3.117 | | 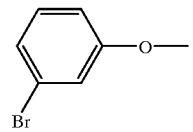 |
| 3.118 | | 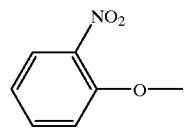 |
| 3.119 | | 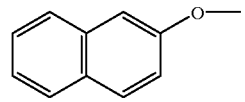 |
| 3.120 | | 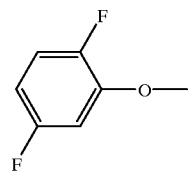 |
| 3.121 | | 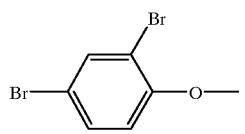 |
| 3.122 | | 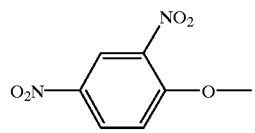 |

TABLE 3-continued
Compounds of the formula V
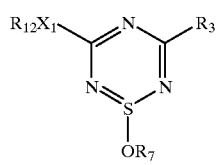
(V)
| | |
|---|---|
| 3.123 | 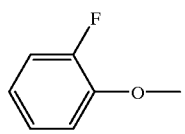 |
| 3.124 | 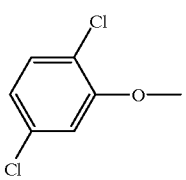 |
| 3.125 | 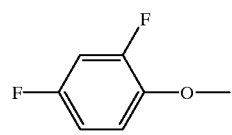 |
| 3.126 | 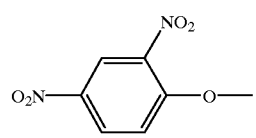 |
| 3.127 | 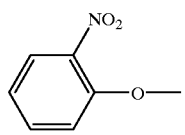 |
| 3.128 | 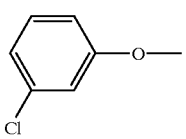 |
| 3.129 | 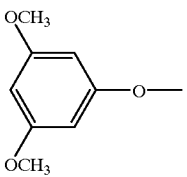 |
| 3.130 | —$OC_6F_5$ |
| 3.131 | —$OC_6F_5$ |
| 3.132 |  |

TABLE 3-continued

Compounds of the formula V $$\text{(V)}$$

R₁₂X₁—, N, R₃ on a 1,2,4,6-thiatriazine ring with OR₇

| No. | R₃ group |
|---|---|
| 3.133 | 2-bromo-6-methoxyphenyl |
| 3.134 | 3-nitro-5-methoxyphenyl (3-O₂N, 5-OMe) |
| 3.135 | 2-fluoro-6-methoxyphenyl |
| 3.136 | 2,4-dichloro-6-methoxyphenyl |
| 3.137 | 3-fluoro-5-methoxyphenyl |
| 3.138 | 4-nitro, methoxy (O₂N—C₆H₄—O—) |
| 3.139 | 3-fluoro-5-methoxyphenyl |
| 3.140 | 2,3,5,6-tetrafluoro-4-methoxyphenyl |
| 3.141 | 4-nitro, methoxy (O₂N—C₆H₄—O—) |

TABLE 3-continued

Compounds of the formula V $$R_{12}X_1 - \underset{\underset{OR_7}{\overset{N}{\underset{S}{\bigvee}}}}{\overset{N}{\bigvee}} - R_3 \quad (V)$$

| | | |
|---|---|---|
| 3.142 | | 2,5-dichloro-methoxyphenyl |
| 3.143 | | 2,4-dinitro-methoxyphenyl |
| 3.144 | | 3-nitro-methoxyphenyl |
| 3.145 | | 4-nitro-methoxyphenyl |
| 3.146 | | 2-(n-propyl)-4-methyl-6-(methylthio)pyrimidine |
| 3.147 | | 3-(dimethylamino)-methoxyphenyl |
| 3.148 | | 4-fluoro-methoxyphenyl |
| 3.149 | C₆F₅S— | |
| 3.150 | C₆F₅O— | |
| 3.151 | | 2-nitro-methoxyphenyl |
| 3.152 | | 4-fluoro-(methylthio)phenyl |

TABLE 3-continued

Compounds of the formula V $$\text{(V)}$$

| No. | Structure |
|---|---|
| 3.153 | 3-chloro-4-methoxy-fluorophenyl (2-Cl, 4-F, 1-OMe) |
| 3.154 | 2,4-dinitro-1-methoxyphenyl |
| 3.155 | 2,6-difluoro-1-methoxyphenyl |
| 3.156 | 2-(methylthio)naphthyl |
| 3.157 | 4-nitro-1-methoxyphenyl |
| 3.158 | 4-nitro-1-methoxyphenyl |
| 3.159 | 2,4-dinitro-1-methoxyphenyl |
| 3.160 | 2,4-difluoro-1-methoxyphenyl (2-OMe, 1,4-diF reading) |
| 3.161 | 3-nitro-1-methoxyphenyl |

TABLE 3-continued

Compounds of the formula V $$R_{12}X_1-\text{[ring]}-R_3, \text{ring with N-S-N and OR}_7$$ (V)

| | | |
|---|---|---|
| | 3.162 | 2-NO₂, 1-O— phenyl (o-nitroanisole-type: OCH₃ with ortho NO₂) |
| | 3.163 | 4-O₂N-C₆H₄-O— |
| | 3.164 | C₆F₅O— |
| | 3.165 | 4-OCH₃-2,5-(NO₂)... (2,4-dinitro anisole type with O₂N at 4 and NO₂) |
| | 3.166 | 4-O₂N-C₆H₄-O— |
| | 3.167 | 3-CH₃O-C₆H₄-S— |
| | 3.168 | —C₆F₅S— |
| | 3.169 | 3-methyl-7-methoxy-phthalide-type (isobenzofuranone with OCH₃ and H₃C) |
| | 3.170 | C₆F₅O— |
| | 3.171 | C₆F₅S— |
| | 3.172 | 2,4-(O₂N)₂-C₆H₃-O— with additional NO₂ |
| | 3.173 | 2,3-Cl₂-C₆H₃-O— |

TABLE 3-continued

Compounds of the formula V (V)

Structure: R12X1-C(=N)-N=S(OR7)-N=C(R3) six-membered ring (1,2,4,6-thiatriazine with OR7 on S)

| 3.174 | 4-nitrophenoxy (O2N-C6H4-O-) |
| 3.175 | 4-nitrophenoxy (O2N-C6H4-O-) |
| 3.176 | 4-methoxyphenoxy (CH3O-C6H4-O-) |
| 3.177 | 4-nitrophenoxy (O2N-C6H4-O-) |
| 3.178 | 2,4-dinitrophenoxy |
| 3.179 | 2-methoxyphenoxy |
| 3.180 | 2,4-dinitrophenoxy |
| 3.181 | 2-pyridylthio |
| 3.182 | 4-nitrophenoxy |
| 3.183 | 2,4-dinitrophenoxy |

TABLE 3-continued

Compounds of the formula V $$\text{(V)}$$

[Structure: 1,2,4,6-thiatriazine ring with R$_{12}$X$_1$ at 3-position, R$_3$ at 5-position, and OR$_7$ on S]

| No. | R$_3$ |
|---|---|
| 3.184 | 4-CH$_3$O-C$_6$H$_4$-O— |
| 3.185 | 4-O$_2$N-C$_6$H$_4$-O— |
| 3.186 | 2,4-F$_2$-C$_6$H$_3$-O— |
| 3.187 | C$_6$F$_5$-O— (2,3,5,6-tetrafluoro) |
| 3.188 | 4-O$_2$N-C$_6$H$_4$-O— |
| 3.189 | C$_6$F$_5$O— |
| 3.190 | 2,3,4-F$_3$-C$_6$H$_2$-O— |
| 3.191 | 4-O$_2$N-C$_6$H$_4$-O— |
| 3.192 | 2-CF$_3$-C$_6$H$_4$-O— |
| 3.193 | 2-NO$_2$-C$_6$H$_4$-O— |

TABLE 3-continued

Compounds of the formula V $$R_{12}X_1-\underset{\underset{OR_7}{|}}{\overset{N}{\underset{N}{\overset{||}{C}}}}\overset{R_3}{\underset{N}{\overset{||}{C}}}$$ (V)

| | |
|---|---|
| 3.194 | 2,5-dimethoxy-3,6-dimethylphenyl (CH₃O, CH₃, OCH₃, CH₃ substituted benzene with O—) |
| 3.195 | 2,4-dinitro-methoxyphenyl |
| 3.196 | 2-methylphenyl-O— |
| 3.197 | 2,6-dichlorophenyl-O— |
| 3.198 | 2,6-difluorophenyl-O— |
| 3.199 | 2,4-dinitro-methoxyphenyl |
| 3.200 | 1-CHO-2-methoxynaphthyl |
| 3.201 | 2,4-dinitro-methoxyphenyl |

TABLE 3-continued

Compounds of the formula V $$\text{(V)}$$

[Structure: 1,2,4,6-thiatriazine ring with R$_{12}$X$_1$ at one position, R$_3$ at another, and OR$_7$ on sulfur]

| No. | R |
|---|---|
| 3.202 | 2,5-difluorophenyl-O— (methoxy on difluorobenzene) |
| 3.203 | 2,3,5-trifluoro-phenyl-O— |
| 3.204 | 4-methyl-6-trifluoromethyl-pyrimidin-2-yl-S—CH$_3$ |
| 3.205 | 3-methoxy-naphthalen-2-yl (with COOCH$_3$)—O— |
| 3.206 | 4-nitrophenyl-O— |
| 3.207 | 2,5-difluorophenyl-O— |
| 3.208 | 2,3,5-trifluorophenyl-O— |
| 3.209 | 2,4-dinitrophenyl-O— |

TABLE 3-continued

Compounds of the formula V (V)

R₁₂X₁—, R₃ substituents on a 1,2,4,6-thiatriazine ring with OR₇

| No. | Substituent |
|---|---|
| 3.210 | 4-O₂N-C₆H₄-O— |
| 3.211 | 3-CF₃-C₆H₄-O— |
| 3.212 | 2,4-(O₂N)₂-C₆H₃-O— |
| 3.213 | C₆F₅O— |
| 3.214 | 4-(CH₃)₃C-C₆H₄-S— |
| 3.215 | 2-O₂N-C₆H₄-O— |
| 3.216 | 4-Cl-C₆H₄-O— |
| 3.217 | (4,6-dimethyl-3-cyanopyridin-2-yl)-S— |
| 3.218 | 4-O₂N-C₆H₄-O— |
| 3.219 | 2,5-F₂-C₆H₃-O— |

TABLE 3-continued

Compounds of the formula V $$R_{12}X_1 - \text{[triazine-thiadiazine ring with } R_3, OR_7\text{]} \quad (V)$$

| | | |
|---|---|---|
| 3.220 | | 2,3,5-trifluoro-6-methoxyphenyl (F,F,F substituted methoxybenzene) |
| 3.221 | | 2-NO₂, 4-NO₂ methoxybenzene |
| 3.222 | | 2-NO₂, 4-NO₂ methoxybenzene |
| 3.223 | C₆F₅O— | |
| 3.224 | C₆F₅O— | |
| 3.225 | | 2,4-difluoro methoxybenzene |
| 3.226 | | 2,6-dichloro methoxybenzene |
| 3.227 | C₆F₅O— | |
| 3.228 | C₆F₅O— | |
| 3.229 | | 4-bromo methoxybenzene |
| 3.230 | C₆F₅O— | |
| 3.231 | | 4-nitro methoxybenzene |
| 3.232 | —OC₆F₅ | |
| 3.233 | —OC₆F₅ | |
| 3.234 | —OC₆F₅ | |
| 3.235 | —OC₆F₅ | |
| 3.236 | —OC₆F₅ | |
| 3.237 | —OC₆F₅ | |
| 3.238 | —OC₆F₅ | |

TABLE 3-continued

Compounds of the formula V (V)

| | | |
|---|---|---|
| | 3.239 | —OC$_6$F$_5$ |
| | 3.240 | —OC$_6$F$_5$ |
| | 3.241 | —OC$_6$F$_5$ |
| | 3.242 | —OC$_6$F$_5$ |
| | 3.243 | —OC$_6$F$_5$ |
| | 3.244 | —OC$_6$F$_5$ |
| | 3.245 | —OC$_6$F$_5$ |
| | 3.246 | —OC$_6$F$_5$ |
| | 3.247 | —OC$_6$F$_5$ |
| | 3.248 | —OC$_6$F$_5$ |
| | 3.249 | —OC$_6$F$_5$ |
| | 3.250 | —OC$_6$F$_5$ |
| | 3.251 | (methoxy-phthalide-methyl structure) |
| | 3.252 | —SC$_6$F$_5$ |
| | 3.253 | —SC$_6$F$_5$ |
| | 3.254 | —SC$_6$F$_5$ |
| | 3.255 | —OC$_6$F$_5$ |
| | 3.256 | —OC$_6$F$_5$ |
| | 3.257 | —OC$_6$F$_5$ |
| | 3.258 | —OC$_6$F$_5$ |
| | 3.259 | —OC$_6$F$_5$ |
| | 3.260 | —OC$_6$F$_5$ |
| | 3.261 | —O—(2,3,5,6-tetrafluorophenyl) |
| | 3.262 | —O—(2,3,5,6-tetrafluorophenyl) |
| | 3.263 | —O—(2,3,5,6-tetrafluorophenyl) |

TABLE 3-continued

Compounds of the formula V $$R_{12}X_1-\underset{\underset{OR_7}{\overset{N}{\underset{S}{\bigtriangleup}}}N}{\overset{N}{\bigtriangleup}}R_3 \quad (V)$$

| | | |
|---|---|---|
| | 3.264 | —O—C₆F₄ (tetrafluorophenyl ether) |
| | 3.265 | —O—C₆F₄ |
| | 3.266 | —O—C₆F₄ |
| | 3.267 | —O—C₆F₄ |
| | 3.268 | —O—C₆F₄ |
| | 3.269 | —O—C₆F₄ |
| | 3.270 | —OC₆F₅ |
| | 3.271 | —OC₆F₅ |
| | 3.272 | —OC₆F₅ |
| | 3.273 | —OC₆F₅ |
| | 3.274 | —OC₆F₅ |
| | 3.275 | —OC₆F₅ |
| | 3.276 | —OC₆F₅ |
| | 3.277 | —OC₆F₅ |
| | 3.278 | —OC₆F₅ |
| | 3.279 | —OC₆F₅ |
| | 3.280 | —OC₆F₅ |

TABLE 3-continued

Compounds of the formula V $$R_{12}X_1\text{—[ring]—}R_3, \text{OR}_7 \quad (V)$$

| Comp. No. | |
|---|---|
| 3.281 | —OC$_6$F$_5$ |
| 3.282 | —OC$_6$F$_5$ |
| 3.283 | —OC$_6$F$_5$ |
| 3.284 | —OC$_6$F$_5$ |
| 3.285 | —OC$_6$F$_5$ |
| 3.286 | —OC$_6$F$_5$ |
| 3.287 | —OC$_6$F$_5$ |
| 3.288 | —OC$_6$F$_5$ |
| 3.289 | —OC$_6$F$_5$ |
| 3.290 | —OC$_6$F$_5$ |
| 3.291 | —OC$_6$F$_5$ |
| 3.292 | —OC$_6$F$_5$ |
| 3.293 | —OC$_6$F$_5$ |
| 3.294 | —OC$_6$F$_5$ |
| 3.295 | —OC$_6$F$_5$ |
| 3.296 | —OC$_6$F$_5$ |
| 3.297 | —OC$_6$F$_5$ |
| 3.298 | —OC$_6$F$_5$ |
| 3.299 | —OC$_6$F$_5$ |
| 3.300 | —OC$_6$F$_5$ |
| 3.301 | —OC$_6$F$_5$ |
| 3.302 | —OC$_6$F$_5$ |
| 3.303 | —OC$_6$F$_5$ |
| 3.304 | —OC$_6$F$_5$ |
| 3.305 | —OC$_6$F$_5$ |
| 3.306 | —OC$_6$F$_5$ |
| 3.307 | —OC$_6$F$_5$ |
| 3.308 | —OC$_6$F$_5$ |

Physical data of compounds in Table 3:

| Comp. No. | Physical Data |
|---|---|
| 3.1 | Melting point 89–90° C. |
| 3.3 | Melting point 82–83° C. |
| 3.5 | $^1$H-NMR: 6.9–7.3 ppm (8H); 4.3 ppm (1H); 3.95 ppm (1H); 3.8 ppm (6H); 1.2–2.2 ppm (12H) |
| 3.6 | Melting point 104–105° C. |
| 3.7 | $^1$H-NMR: 7.3 ppm (2H); 7.1 ppm (4H); 3.8 ppm (2H); 1.6 ppm (2H); 1.4 ppm (2H); 0.9 ppm (3H) |
| 3.10 | $^1$H-NMR: 6.8–7.4 ppm (6H); 3.9 ppm (2H); 3.0 ppm (2H) |
| 3.13 | Melting point 184–186° C. |
| 3.19 | $^1$H-NMR: 7.1–8.0 ppm (8H); 4.1 ppm (2H); 3.6 ppm (2H); 3.35 ppm (3H) |
| 3.23 | Melting point 89–90° C. |
| 3.24 | $^1$H-NMR: 7.6 ppm (2H); 7.4 ppm (1H); 6.9 ppm (1H); 5.5 ppm (1H); 4.4 ppm (1H); 1.4–1.9 ppm (14H) |
| 3.28 | $^1$H-NMR: 10.05 ppm (2H); 7.1–7.9 ppm (8H); 4.1 ppm (2H); 3.65 ppm (2H) |
| 3.31 | Melting point 115–116° C. |
| 3.36 | $^1$H-NMR: 7.6–7.7 ppm (2H); 7.1–7.3 ppm (4H); 5.3–5.5 ppm (1H); 4.3–4.5 ppm (1H) |
| 3.40 | $^{13}$C-NMR: 173.8 ppm; 135–150 ppm; 79.0 ppm 22.0–47.4 ppm (7 signals) |
| 3.45 | Melting point 83–84° C. |
| 3.48 | $^1$H-NMR: 6.5–7.4 ppm (11H); 5.7 ppm (1H); 1.6 ppm (3H) |
| 3.50 | $^1$H-NMR: 7.05 ppm (2H); 6.85 ppm (2H); 4.7 ppm (2H); 4.2 ppm (4H); 4.0 ppm (2H); 3.6 ppm (2H); 1.6 ppm (6H); 1.3 ppm (6H) |
| 3.57 | $^1$H-NMR: 7.1–7.9 ppm (12H); 4.95 ppm (1H); 4.1 ppm (2H) |
| 3.61 | Melting point 100–102° C. |
| 3.67 | $^{13}$C-NMR: 167.9 ppm; 136–143 ppm; 86.7 ppm; 62.5 ppm; 33.4 ppm; 30.6 ppm; 21.0 ppm |
| 3.68 | Melting point 141–142° C. |
| 3.72 | Melting point 86–87° C. |
| 3.77 | $^1$H-NMR: 8.85 ppm (2H); 7.4 ppm (2H); 7.15 ppm (2H); 4.05 ppm (2H); 3.6 ppm (2H); 2.6 ppm (6H) |
| 3.82 | $^1$H-NMR: 7.9 ppm (2H); 7.6 ppm (2H); 7.4 ppm (4H); 4.0 ppm (2H); 3.9 ppm (6H); 3.6 ppm (2H) |
| 3.84 | $^{13}$C-NMR: 168.2 ppm; 136–143 ppm; 73.8 ppm; 31.6 ppm; 25.9 ppm |
| 3.89 | Melting point 126–127° C. |
| 3.93 | Melting point 173–174° C. |
| 3.97 | Melting point 108–109° C. |
| 3.103 | Melting point 100–102° C. |
| 3.105 | Melting point 169–170° C. |
| 3.109 | $^{13}$C-NMR: 177.9 ppm; 162.9 ppm; 103.2 ppm; 83.5 ppm |
| 3.112 | $^1$H-NMR: 8.6 ppm (2H); 7.7 ppm (4H); 7.3 ppm (2H); 4.0 ppm (2H); 3.6 ppm (2H) |
| 3.119 | Melting point 80–81° C. |
| 3.124 | $^1$H-NMR: 7.1–7.3 ppm (6H); 4.35 ppm (1H); 1.6 ppm (2H); 1.3 ppm (11H); 0.9 ppm (3H) |

| Comp. No. | Physical Data |
|---|---|
| 3.129 | $^1$H-NMR: 6.4 ppm (2H); 6.3 ppm (4H); 4.0 ppm (2H); 3.8 ppm (12H); 3.6 ppm (2H) |
| 3.130 | $^{13}$C-NMR: 167.4 ppm; 147.7 ppm; 109.7 ppm; 88.2 ppm; 62.2 ppm; 36.5 ppm; 34.0 ppm; 32.0 ppm; 26.3 ppm; 25.4 ppm; 20.6 ppm |
| 3.131 | $^{13}$C-NMR: 167.4 ppm; 147.8 ppm; 109.5 ppm; 83.1 ppm; 68.1 ppm; 37.1 ppm; 35.7 ppm; 33.0 ppm; 29.5 ppm; 26.2 ppm; 20.5 ppm |
| 3.136 | Melting point 96–97° C. |
| 3.140 | Melting point 86–87° C. |
| 3.142 | $^1$H-NMR: 7.3 ppm (2H); 7.15 ppm (4H); 4.0 ppm (2H); 3.6 ppm (2H) |
| 3.147 | $^1$H-NMR: 7.2 ppm (2H); 6.6 ppm (2H); 6.4 ppm (2+2H); 4.4 ppm (1H); 3.7 ppm (2H); 3.5 ppm (2H); 2.9 ppm (12H) |
| 3.155 | Melting point 101–102° C. |
| 3.160 | $^1$H-NMR: 7.1 ppm (2H); 6.9 ppm (4H); 4.0 ppm (2H); 3.6 ppm (2H) |
| 3.168 | $^{13}$C-NMR: 177.9 ppm; 162.9 ppm; 103.2 ppm; 83.5 ppm |
| 3.169 | Melting point 197–198° C. |
| 3.179 | Melting point 100–101° C. |
| 3.186 | $^1$H-NMR: 6.8–7.4 ppm (6H); 4.7 ppm (2H) |
| 3.189 | $^{13}$C-NMR: 167.8 ppm; 136.2–143.1 ppm; 83.2 ppm; 34.0 ppm; 23.2 ppm |
| 3.196 | Melting point 106–108° C. |
| 3.202 | Melting point 89–90° C. |
| 3.207 | $^1$H-NMR: 6.9–7.2 ppm (6H); 3.7 ppm (2H) 1.7 ppm (2H); 1.3 ppm (4H); 0.9 ppm (3H) |
| 3.219 | $^1$H-NMR: 6.8–7.1 ppm (6H); 4.15 ppm (1H) 1.2–1.9 ppm (10H) |
| 3.224 | Melting point 85–86° C. |
| 3.232 | $^{13}$C-NMR: 168.2 ppm; 142.4 ppm; 120.3 ppm; 63.3 ppm; 45.6 ppm; 40.6 ppm; 38.0 ppm; 36.3 ppm; 31.5 ppm; 31.3 ppm; 26.1 ppm; 21.0 ppm |
| 3.233 | $^{13}$C-NMR: 168.1 ppm; 136–143 ppm; 64.2 ppm; 18.2 ppm; −1.9 ppm |
| 3.234 | Melting point 126–127° C. |
| 3.235 | $^{13}$C-NMR: 168.1 ppm; 136–143 ppm; 68.0 ppm; 24.0 ppm; 12.3 ppm; −1.99 ppm |
| 3.236 | Melting point 99–100° C. |
| 3.237 | $^{13}$C-NMR: 171.4 ppm; 168.2 ppm; 137.6 ppm; 136.2–142.8 ppm; 62.0 ppm; 36.8 ppm; 8.6 ppm |
| 3.239 | Melting point 113–114° C. |
| 3.240 | Melting point 93–94° C. |
| 3.241 | $^{13}$C-NMR: 168.53 ppm; 54.59 ppm; −3.54 ppm; |
| 3.243 | $^{13}$C-NMR: 167.9 ppm; 167.6 ppm; 119.1 ppm; 84.1 ppm; 44.2 ppm; 33.6 ppm; 28.4 ppm; 24.9 ppm; 21.7 ppm; 15.8 ppm |
| 3.244 | $^{13}$C-NMR: 168.0 ppm; 167.7 ppm; 119.0 ppm; 85.8 ppm; 45.7 ppm; 32.6 ppm; 28.7 ppm; 28.5 ppm; 22.1 ppm; 21.7 ppm; 15.8 ppm |
| 3.246 | $^{13}$C-NMR: 167.7 ppm; 81.2 ppm; 33.6 ppm; 33.0 ppm; 31.2 ppm; 21.5 ppm |
| 3.247 | $^{13}$C-NMR: 167.7 ppm; 78.2 ppm; 31.3 ppm; 30.9 ppm; 28.6 ppm; 21.7 ppm |
| 3.248 | Melting point 48–49° C. |
| 3.249 | $^1$H-NMR: 5.8 ppm (1H); 5.0 ppm (2H); 4.2 ppm (1H); 0 ppm (9H) |
| 3.251 | Melting point 185–186° C. |
| 3.252 | $^{13}$C-NMR: 174.5 ppm; 62.5 ppm; 15.0 ppm; |
| 3.253 | Melting point 90–92° C. |
| 3.254 | $^{13}$C-NMR: 173.8 ppm; 75.7 ppm; 23.6 ppm; |
| 3.255 | $^1$H-NMR: 4.55 ppm (2H); 3.2 ppm (4H); 1.0 ppm (2H); 0 ppm (9H) |
| 3.256 | $^1$H-NMR: 4.6 ppm (2H); 3.75 ppm (2H); 3.6 ppm (2H); 1.6 ppm (2H); 0.5 ppm (2H); 0 ppm (9H) |
| 3.257 | $^1$H-NMR: 4.6 ppm (2H); 3.8 ppm (2H); 3.2 ppm (2H); 2.0 ppm (3H); 1.4–1.8 ppm (6H) |
| 3.258 | $^1$H-NMR: 4.5 ppm (2H); 3.7 ppm (2H); 3.0 ppm (2H); 0 ppm (9H) |
| 3.259 | $^{13}$C-NMR: 167.7 ppm; 78.2 ppm; 31.3 ppm; 30.9 ppm; 28.6 ppm; 21.7 ppm |
| 3.260 | Melting point 48–49° C. |
| 3.261 | Melting point 95–96° C. |
| 3.262 | Melting point 131–132° C. |
| 3.263 | $^1$H-NMR: 7.0 ppm (2H); 4.55 ppm (1H); 0.8–2.0 ppm (16H) |
| 3.264 | Melting point 83–84° C. |
| 3.265 | Melting point 103–104° C. |
| 3.267 | $^{13}$C-NMR: 167.7 ppm; 138.9–147.6 ppm; 103.1–103.7 ppm; 51.0 ppm; 46.3 ppm; 34.7 ppm; 32.9 ppm; 27.5 ppm |
| 3.268 | Melting point 74–75° C. |
| 3.269 | Melting point 112–113° C. |
| 3.270 | $^{13}$C-NMR: 167.7 ppm; 136–143 ppm; 81.9 ppm; 35.0 ppm; 34.4 ppm; 33.9 ppm; 31.2 ppm; 28.9 ppm; 26.1 ppm; 21.1 ppm |
| 3.273 | $^{13}$C-NMR: 168.0 ppm; 167.8 ppm; 139.0 ppm; 130.7 ppm; 125–143.0 ppm; 79.6 ppm; 47.6 ppm; 47.5 ppm; 42.2 ppm; 35.1 ppm |
| 3.274 | $^{13}$C-NMR: 168.0 ppm; 187.8 ppm; 142.3 ppm; 131.6 ppm; 80.4 ppm; 49.0 ppm; 46.0 ppm; 40.7 ppm; 35.3 ppm |
| 3.275 | $^{13}$C-NMR: 167.8 ppm; 125–143 ppm; 75.9 ppm; 36.3 ppm (q); 30.8 ppm; 30.7 ppm; 29.6 ppm; 23.7 ppm; 18.4 ppm |
| 3.276 | $^{13}$C-NMR: 168.1 ppm; 138.3 ppm; 131.4 ppm; 125–143 ppm; 68.4 ppm; 49.4 ppm; 43.7 ppm; 42.3 ppm; 38.2 ppm; 29.1 ppm |
| 3.277 | $^{13}$C-NMR: 167.8 ppm; 125–143 ppm; 80.7 ppm; 42.0 ppm; 37.4 ppm; 37.3 ppm; 36.4 ppm; 29.0 ppm; 20.6 ppm |
| 3.278 | $^{13}$C-NMR: 167.8 ppm; 125–143 ppm; 83.1 ppm; 43.3 ppm; 40.3 ppm; 35.4 ppm; 34.9 ppm; 27.8 ppm; 24.1 ppm |
| 3.279 | $^{13}$C-NMR: 167.7 ppm; 127–143 ppm; 73.5 ppm; 45.5 ppm (q); 31.8 ppm; 23.9 ppm; 19.8 ppm; 19.5 ppm |
| 3.281 | $^{13}$C-NMR: 167.9 ppm; 167.4 ppm; 125–143 ppm; 81.8 ppm; 47.5 ppm; 44.8 ppm; 41.4 ppm; 38.4 ppm; 36.8 ppm; 33.9 ppm; 27.2 ppm; 23.7 ppm; 19.4 ppm |
| 3.284 | Melting point 123–124° C. |
| 3.285 | Melting point 117–118° C. |
| 3.286 | Melting point 109–110° C. |
| 3.287 | $^{13}$C-NMR: 167.9 ppm; 167.7 ppm; 136–143 ppm; 119.1 ppm; 83.0 ppm; 41.6 ppm; 33.4 ppm; 28.8 ppm; 21.8 ppm; 17.2 ppm |
| 3.288 | $^{13}$C-NMR: 167.9 ppm; 167.7 ppm; 136–143 ppm; 117.4 ppm; 84.3 ppm; 42.8 ppm; 32.5 ppm; 28.6 ppm; 21.9 ppm; 19.8 ppm |
| 3.292 | Melting point 82–83° C. |
| 3.295 | $^{13}$C-NMR: 167.5 ppm; 157.7 ppm; 136–143 ppm; 131.5 ppm; 128.6 ppm; 124.3 ppm; 120.5 ppm; 110.3 ppm; 78.6 ppm; 55.1 ppm; 38.8 ppm; 30.4 ppm; 21.4 ppm |
| 3.296 | $^{13}$C-NMR: 168.3 ppm; 126–143 ppm; 136.3 ppm; 135.2 ppm; 133.4 ppm; 129.6 ppm; 128.9 ppm; 127.5 ppm; 67.0 ppm; 39.9 ppm; 33.3 ppm; 20.0 ppm; 13.8 ppm |
| 3.299 | $^{13}$C-NMR: 168.4 ppm; 126–143 ppm; 65.9 ppm; |

Example H9

Preparation of 1,3,5-trimethoxythiatriazine (process a₃)

(Compound No. 4.2)

2.04 g (0.02 mol) of trichlorothiatriazine are dissolved in 15 ml of tetrahydrofuran and a solution of 5.94 g (0.033 mol) of 30% methanolic sodium methylate solution in 20 ml of tetrahydrofuran is added dropwise at 30° C., while cooling. After 15 minutes, the reaction mixture is extracted with water and ethyl acetate, the extract is concentrated and the residue is chromatographed over silica gel with ethyl acetate/hexane 1/3 as the eluting agent. The yield of the desired product is 1.70 g (89% of theory).

Analysis: $C_5H_9N_3O_3S$;

|   | calculated [%] | found [%] |
|---|---|---|
| N | 21.98 | 21.98 |
| S | 16.77 | 16.25 |

Example H10

Preparation of 1,3-dimethoxy-5-(2',5'-difluorophenoxy)thiatriazine (process $d_3$)

(Compound No. 4.5)

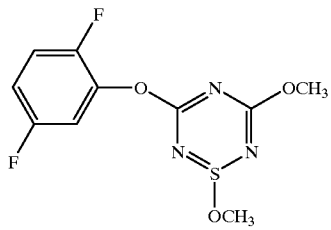

3.05 g (0.007 mol) of 1-(β-chloroethoxy)-3,5-di(2',5'-difluorophenoxy)thiatriazine are dissolved in 20 ml of methanol. 10.4 ml of a 1.35 molar sodium methylate solution in methanol are slowly added dropwise at −60° C., the intermediate 1-methoxy-3,5-di(2',5'-difluorophenoxy)thiatriazine crystallizing out. The mixture is warmed gradually to +5° C., the intermediate reacting further to give the desired end product. The reaction mixture is extracted with water and ethyl acetate, the extract is concentrated and the residue is chromatographed over silica gel. The yield of desired product is 1.38 g (68% of theory). After recrystallization from a mixture of cyclohexane/toluene 6/1, the product melts at 75–76° C.

Analysis: $C_{10}H_9N_3O_3F_2S$;

|   | calculated [%] | found [%] |
|---|---|---|
| C | 41.52 | 41.68 |
| H | 3.14 | 3.19 |
| N | 14.53 | 14.44 |

0.30 g of 1,3,5-trimethoxythiatriazine (Example H9) is isolated as a by-product.

Example H11

Preparation of 1-(β-chloroethoxy)-3,5-di(trichloroethoxy)thiatriazine (process $d_3$)

(Compound No. 4.38)

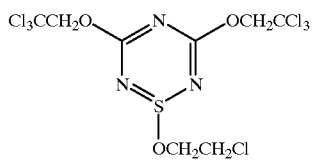

1.80 g (0.0036 mol) of 1-(β-chloroethoxy)-3,5-di(2',4'-dichlorophenoxy)thiatriazine are dissolved in 20 ml of tetrahydrofuran and the solution is cooled to −50° C. A solution prepared from 1.12 g (0.0075 mol) of trichloroethanol and 0.33 g of 55% sodium hydride (0.0075 mol) is added dropwise to this solution. The reaction is exothermic. The reaction mixture is warmed to 0° C., extracted with water and ethyl acetate, and the product is chromatographed over silica gel. The yield is 1.62 g (95% of theory). The desired compound is a resin, the $^1$H— and $^{13}$C-NMR spectra of which confirm the structure.

Example H12

Preparation of 1-(β-chloroethoxy)-3,5-di-tert-butylmercaptothiatriazine and 1-(β-chloroethoxy)-3-chloro-5-tert-butylmercaptothiatriazine (process $b_1$)

(Compound No. 4.49)

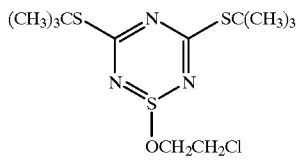

and (Compound No. 4.22)

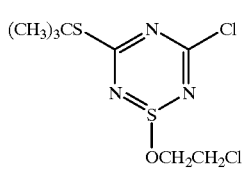

3.00 g (0.012 mol) of 1-(β-chloroethoxy)-3,5-dichlorothiatriazine are dissolved in 20 ml of tetrahydrofuran, and a solution of 3.25 g (0.036 mol, of tert-butylmercaptan and 3.64 g (0.036 mol) of trethylamine in 15 ml of tetrahydrofuran is added dropwise at −50° C. Thereafter, the mixture warmed to 0° C., extracted with water and ethyl acetate, and the substance mixture is separated over silica gel with ethyl acetate/hexane 3/1 as the eluting agent. 1.05 g of 1-(β-chloroethoxy)-3-chloro-5-tert-butylmercaptothiatriazine and 0.25 g of 1-(β-chloroethoxy)-3,5-di-tert-butylmercaptothiatriazine are obtained as resins. The $^1$H-NMR spectra and the mass spectra confirm the structures.

The compounds listed in the following Table 4 can be prepared analogously to Examples H9 to H12.

TABLE 4
Compounds of the formula IV
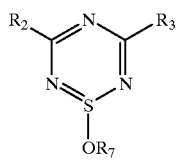
(IV)
| Comp. No. | Process | R₇ | R₃ | R₂ |
|---|---|---|---|---|
| 4.1 | c₂ | —CH₃ | phenyl—O— | —OCH₃ |
| 4.2 | a₃ | —CH₃ | —OCH₃ | —OCH₃ |
| 4.3 | | —CH(CH₃)CH₂Cl | —OCH₃ | 1-naphthyl—S— |
| 4.4 | b₁ | —CH₂CH₂Cl | Cl | —SCH(CH₃)₂ |
| 4.5 | d₃ | —CH₃ | 2,5-difluoro-phenyl—O— | —OCH₃ |
| 4.6 | | —C₂H₅ | —OC₂H₅ | pyrimidin-5-yl—O— |
| 4.7 | | —CH₃ | 1-acetyl-2-methoxy-naphthalen-1-yl | —OCH₃ |
| 4.8 | d₃ | —CH₂CH₂Cl | —OC₂H₅ | —OC₂H₅ |
| 4.9 | d₃ | —CH₃ | 2,6-difluoro-phenyl—O— | —OCH₃ |
| 4.10 | | —CH(C₂H₅)CH₂Cl | —SCH₃ | 3-cyano-4,6-dimethyl-2-(methylthio)pyridin-yl |

TABLE 4-continued

Compounds of the formula IV

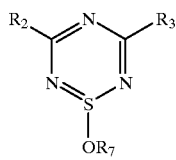

(IV)

| Comp. No. | Process | R₇ | R₃ | R₂ |
|---|---|---|---|---|
| 4.11 | | —CH₂CH=CH₂ | —OCH₂CH=CH₂ | 2,4-dimethylphenyl-S— |
| 4.12 | d₃ | —CH₃ | 2,5-difluorophenyl-O— | —OCH₂C≡CH |
| 4.13 | | —CH₂CH₂Cl | —SCH₃ | 2,6-dichlorophenyl-O— |
| 4.14 | | —CH₂CH₂Cl | 4-ethyl-5-chloro-6-methylthiopyrimidinyl | —SCH₃ |
| 4.15 | a₃ | —CH₂CH₂CH₃ | Cl | —OCH₂CH₂CH₃ |
| 4.16 | d₃ | —CH₃ | C₆F₅O— | —OCH₃ |
| 4.17 | | —CH₃ | —OCH₃ | 1-naphthyl-S— |
| 4.18 | b₁ | —CH₂CH₂Cl | —SCH(CH₃)₂ | —SCH(CH₃)₂ |
| 4.19 | | —cyclopentyl | 4-nitrophenyl-O— | —O-cyclopentyl |
| 4.20 | d₃ | —C₂H₅ | 2,5-difluorophenyl-O— | —OC₂H₅ |

TABLE 4-continued

Compounds of the formula IV

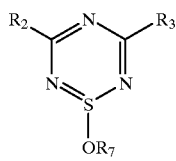

(IV)

| Comp. No. | Process | R₇ | R₃ | R₂ |
|---|---|---|---|---|
| 4.21 | | 2-chlorocyclohexyl (methyl-substituted) | —OCH₃ | 2-naphthyl-S—CH₃ |
| 4.22 | b₁ | —CH₂CH₂Cl | Cl | —SC(CH₃)₃ |
| 4.23 | d₃ | —CH₂CH₂Cl | —OCH₂CF₃ | —OCH₂CF₃ |
| 4.24 | | —CH₃ | 5-methoxypyrimidinyl | —OCH₃ |
| 4.25 | | cyclohexyl | —SC₂H₅ | 2,3-dichloro-methoxyphenyl |
| 4.26 | a₃ | —CH₂CH₂CH₃ | —OCH₂CH₂CH₃ | —OCH₂CH₂CH₃ |
| 4.27 | | —CH₃ | tetrafluoromethoxyphenyl | —OCH₃ |
| 4.28 | | —CH(CH₃)₂ | —O—CH(CH₃)₂ | 3-CF₃-2-(SCH₃)-pyridinyl |
| 4.29 | d₃ | —CH₂CH₂Cl | —OCH₂CBr₃ | —OCH₂CBr₃ |
| 4.30 | | —CH₂CH₂Cl | —SCH₃ | 1-methoxynaphthyl |
| 4.31 | | —CH₃ | 2,3,5-trifluoro-6-methoxyphenyl | cyclohexyloxy |

TABLE 4-continued
Compounds of the formula IV
(IV)
| Comp. No. | Process | $R_7$ | $R_3$ | $R_2$ |
|---|---|---|---|---|
| 4.32 | | —C$_4$H$_9$(n) | —OC$_4$H$_9$(n) | 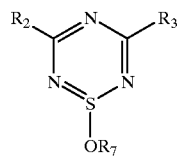 |
| 4.33 | d$_3$ | —C$_2$H$_5$ | —OCH$_3$ | —OCH$_3$ |
| 4.34 | | —C$_2$H$_5$ | 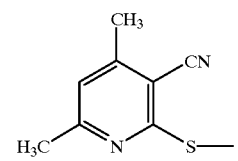 | —OC$_2$H$_5$ |
| 4.35 | | —CH$_3$ | —OC$_6$F$_5$ | 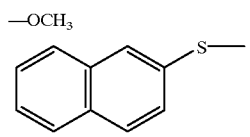 |
| 4.36 | | —CH$_2$CH$_2$Cl | —OC(CH$_3$)$_3$ | 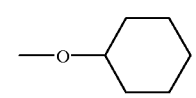 |
| 4.37 | | —CH$_3$ | 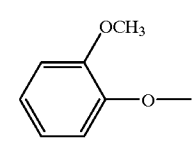 | —OCH$_3$ |
| 4.38 | d$_3$ | —CH$_2$CH$_2$Cl | —OCH$_2$CCl$_3$ | —OCH$_2$CCl$_3$ |
| 4.39 | | 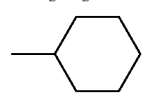 | —SCH$_3$ | —SCH$_3$ |
| 4.40 | | —CH(CH$_3$)$_2$ | —O—CH(CH$_3$)$_2$ | 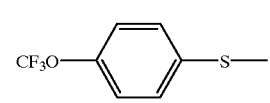 |
| 4.41 | d$_3$ | —C$_2$H$_5$ | 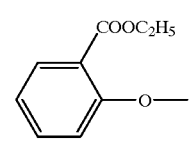 | —OC$_2$H$_5$ |
| 4.42 | | —CH$_3$ | —OCH$_3$ | 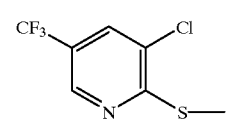 |

TABLE 4-continued

Compounds of the formula IV

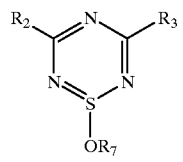

(IV)

| Comp. No. | Process | R₇ | R₃ | R₂ |
|---|---|---|---|---|
| 4.43 | d₃ | —CH₃ | 2,4-dichloro-methoxyphenyl | —OCH₃ |
| 4.44 | | —CH₃ | —OCH₃ | 3-chloro-methoxyphenyl |
| 4.45 | d₃ | cyclopentylmethyl | C₆F₅O— | —CH₂CH₂Cl |
| 4.46 | | 3,3,5-trimethylcyclohexyl | —SC₂H₅ | —SC₂H₅ |
| 4.47 | | —CH₃ | 1-methoxy-2-acetylnaphthyl | —OCH₃ |
| 4.48 | | —CH(CH₃)₂ | —O—CH(CH₃)₂ | 7-methoxy-3-methylphthalid-yl |
| 4.49 | b₁ | —CH₂CH₂Cl | —SC(CH₃)₃ | —SC(CH₃)₃ |
| 4.50 | d₃ | —C₂H₅ | —OC₂H₅ | —OC₂H₅ |
| 4.51 | | trans-4-isopropylcyclohexyl | —OCH₃ | —OCH₃ |
| 4.52 | | —CH₂CH₂Cl | C₆F₅O— | —SCH₃ |
| 4.53 | | —CH₂CH₂Cl | 3-methoxycarbonyl-2-methylthiopyridyl | —OCH₃ |

TABLE 4-continued

Compounds of the formula IV $$\text{(IV)}$$

| Comp. No. | Process | R₇ | R₃ | R₂ |
|---|---|---|---|---|
| 4.54 | | —CH₂CH₂Cl | 3-COOCH₃, 2-SCH₃-pyridinyl | —SCH(CH₃)₂ |
| 4.55 | | —CH(CH₃)₂ | 3-COOCH₃, 2-SCH₃-pyridinyl | —OCH(CH₃)₂ |
| 4.56 | | 3,3,5-trimethylcyclohexyl | —SCH₃ | —SCH₃ |
| 4.57 | | —CH₃ | 5,6-dimethyl-3-SCH₃-1,2,4-triazinyl | —OCH₃ |
| 4.58 | | cyclopentylmethyl | —OC₂H₅ | 2,3,5,6-tetrafluoro-4-methoxyphenyl |
| 4.59 | | —CH₂CH₂Cl | —SCH₃ | 4-methyl-2-isopropyl-6-SCH₃-pyrimidinyl |
| 4.60 | | —CH₂C≡CH | C₆F₅O— | —OCH₃ |
| 4.61 | | —CH₂C≡CH | 2,4,6-trifluoro-3-methoxyphenyl | —OCH₃ |

TABLE 4-continued
Compounds of the formula IV
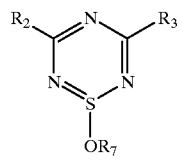
(IV)
| Comp. No. | Process | $R_7$ | $R_3$ | $R_2$ |
|---|---|---|---|---|
| 4.62 | | cyclohexyl | $C_6F_5O-$ | $-SCH_3$ |
| 4.63 | | $-C_2H_5$ | -S-(4,6-dimethylpyrimidin-2-yl) | $-OC_2H_5$ |
| 4.64 | | $-CH_2CH_2Cl$ | $-SCH_3$ | -S-(4,6-dimethoxypyrimidin-2-yl) |
| 4.65 | | $-CH_3$ | $-OCH_3$ | -S-(4,6-dimethoxypyrimidin-2-yl) |
| 4.66 | | $-CH_3$ | $(CH_3)_3C-C_6H_4-S-$ | $-OCH_3$ |
| 4.67 | | cyclohexyl | $-S-CH(CH_3)_2$ | $-S-CH(CH_3)_2$ |
| 4.68 | | $-CH_3$ | $-OCH_3$ | -S-(4-OCF$_3$-2-methylpyrimidin-6-yl) |
| 4.69 | | cyclohexyl | $C_6F_5O-$ | $-OCH_3$ |
| 4.70 | | $-CH_2CH_2Cl$ | $(CH_3)_3C-C_6H_4-S-$ | $-SCH_3$ |

TABLE 4-continued

Compounds of the formula IV

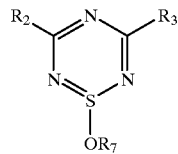

(IV)

| Comp. No. | Process | R₇ | R₃ | R₂ |
|---|---|---|---|---|
| 4.71 | | —CH₂CH₂Cl | 2,4-dichloro-1-methoxynaphthalen-3-yl | —OCH(CH₃)C₂H₅ |
| 4.72 | | cyclopentylmethyl | —SC(CH₃)₂ | —SC(CH₃)₃ |
| 4.73 | | —CH₃ | —OCH₃ | 4-methoxyphenyl-CH(OC₂H₅)₂ |
| 4.74 | | —CH₃ | 2-methoxy-3,5-difluoro-6-acetylphenyl | —OCH₃ |
| 4.75 | | —C₂H₅ | —OC₂H₅ | 5-nitro-2-(methylthio)pyridin-2-yl |
| 4.76 | | —CH(CH₃)₂ | 4-fluorophenoxy | —O—CH(CH₃)₂ |
| 4.77 | | —CH₃ | —SCH₃ | phenylthio |
| 4.78 | | —CH₃ | —OCH₃ | 4-bromo-2-(difluoromethoxy)phenylthio |
| 4.79 | | —C₃H₇(n) | 2,4-dichloro-1-methoxynaphthalen-3-yl | —OC₃H₇(n) |

TABLE 4-continued

Compounds of the formula IV

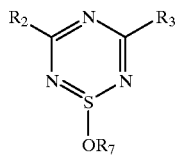

(IV)

| Comp. No. | Process | R₇ | R₃ | R₂ |
|---|---|---|---|---|
| 4.80 | | cycloheptyl | —SCH₃ | —SCH₃ |
| 4.81 | | —CH₃ | 4-methoxyphenoxyphenyl | —OCH₃ |
| 4.82 | | —CH₃ | —OCH₃ | pentafluorophenyl-S— |
| 4.83 | | trans-2-chlorocyclohexyl | —SC₂H₅ | —SC₂H₅ |
| 4.84 | | —CH₂CH₂Cl | 5-CF₃-2-(methylthio)pyridin-yl | —SCH₃ |
| 4.85 | | —CH₂CH₂Cl | 2,5-dibromo-3-methoxyphenyl | —O-cyclohexyl |
| 4.86 | d₃ | —CH₃ | —OCH₃ | 3-methyl-7-(methylthio)phthalide |
| 4.87 | | —CHCH₂Cl<br>   \|<br>   CH₃ | 3-CF₃-phenyl-S-methyl | —SC₄H₉(n) |

TABLE 4-continued

Compounds of the formula IV

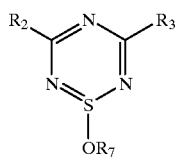

(IV)

| Comp. No. | Process | $R_7$ | $R_3$ | $R_2$ |
|---|---|---|---|---|
| 4.88 | | —CH$_3$ | 3-(CF$_3$)-phenyl-S— | —OCH$_3$ |
| 4.89 | | cyclohexyl | —O-cyclohexyl | 1-bromo-2-methoxy-naphthyl |
| 4.90 | | —CH(CH$_3$)C$_2$H$_5$ | —OCH(CH$_3$)C$_2$H$_5$ | 2,3-difluoro-4-methoxy-phenyl |
| 4.91 | | cyclooctyl | C$_6$F$_5$O— | —OCH$_3$ |
| 4.92 | | —CH$_3$ | 4-methyl-6-cyclopropyl-2-(methylthio)pyrimidinyl | —OCH$_3$ |
| 4.93 | | —CH$_2$CH=CH$_2$ | —SCH$_3$ | —SCH$_3$ |
| 4.94 | | —CH$_2$CH=CH$_2$ | 2,5-difluoro-6-methoxy-phenyl | —OCH$_3$ |
| 4.95 | | trans-4-tert-butylcyclohexyl | C$_6$F$_5$O— | —OCH$_3$ |

TABLE 4-continued
Compounds of the formula IV
$$\text{(IV)}$$
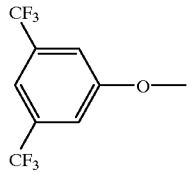
| Comp. No. | Process | R₇ | R₃ | R₂ |
|---|---|---|---|---|
| 4.96 | | —CH₂CH₂Cl | —OCH₃ | 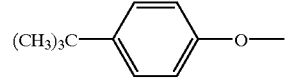 |
| 4.97 | | —CH₂CH₂Cl | 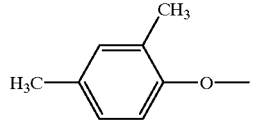 | —SCH₃ |
| 4.98 | | —C₂H₅ | —OC₂H₅ | 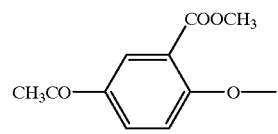 |
| 4.99 | | —CH₃ | 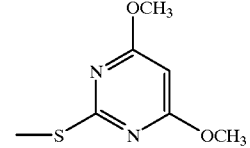 | —OCH₃ |
| 4.100 | | —CH₃ | 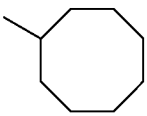 | —SCH₃ |
| 4.101 | | 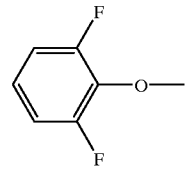 | —SC₂H₅ | 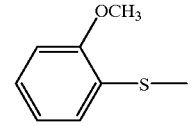 |
| 4.102 | | —CH(CH₃)₂ | 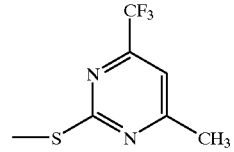 | —O—CH(CH₃)₂ |
| 4.103 | | —CH₃ | —OCH₃ |  |

TABLE 4-continued

Compounds of the formula IV

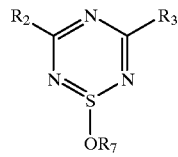

(IV)

| Comp. No. | Process | R₇ | R₃ | R₂ |
|---|---|---|---|---|
| 4.104 | | cyclohexyl | 3-methoxy-methylphenyl (H₃C, —O—) | —O-cyclohexyl |
| 4.105 | | —CH₂CH₂OCH₃ | —SC₄H₉(i) | 2,4-dimethoxyphenoxy with OCH₃ (CH₃O—, OCH₃, —O—) |
| 4.106 | | —CH₂-phenyl | —OCH₃ | —OCH₃ |
| 4.107 | | cyclopentyl | —O-cyclopentyl | —O-cyclopentyl |
| 4.108 | | —C₂H₅ | 4,6-dimethoxypyrimidin-2-ylthio (—S-pyrimidine with OCH₃, OCH₃) | —OC₂H₅ |
| 4.109 | | —CH₃ | 2,4-dichloro-phenoxy-methyl (Cl, Cl, —O—) | —OCH₂-phenyl |
| 4.110 | | —CH₂CH₂Cl | C₆F₅O— | —OCH₂-furyl |
| 4.111 | | —C₂H₅ | —OCH₂-phenyl | —OC₂H₅ |
| 4.112 | | —CH(CH₃)-phenyl | —SCH₃ | —SCH₃ |
| 4.113 | | cyclohexyl | —OCH₂-thienyl | —SC₂H₅ |

TABLE 4-continued

Compounds of the formula IV

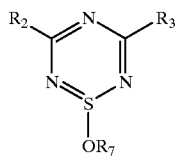
(IV)

| Comp. No. | Process | R₇ | R₃ | R₂ |
|---|---|---|---|---|
| 4.114 | | 4-methyl-1,1-dimethylcyclohexyl | $C_6F_5O-$ | $-OCH_3$ |
| 4.115 | | trans-4-(C(CH₃)₂C₂H₅)cyclohexyl | $C_6F_5O-$ | $-SCH_3$ |
| 4.116 | | $-CH_3$ | tetrahydrothiopyran-3-yloxy | $C_6F_5O-$ |
| 4.117 | | 2-methyl-1-methoxy-1-methoxycyclohexyl | $-SCH_3$ | $-SCH_3$ |
| 4.118 | | $-CH_3$ | $C_6F_5O-$ | indan-2-yloxy |
| 4.119 | | $-CH_2C\equiv CH$ | bornyl-2-oxy | $C_6F_5O-$ |
| 4.120 | | $-CH_2CH_2F$ | 4,6-difluoro-2-methoxyphenyl | $-OCH_2CH_2F$ |
| 4.121 | | $-C_7H_{15}(n)$ | $-SCH_3$ | $-SCH_3$ |
| 4.122 | | $-C_5H_{11}(n)$ | $-OC_5H_{11}(n)$ | 2,4-dibromo-1-methoxyphenyloxy |
| 4.123 | | $-CHCH_2Cl$<br>$\|$<br>$C_6H_5$ | $-S-CH(CH_3)_2$ | $-S-CH(CH_3)_2$ |

TABLE 4-continued
Compounds of the formula IV
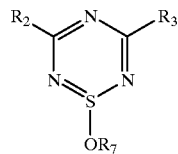
| Comp. No. | Process | R₇ | R₃ | R₂ |
|---|---|---|---|---|
| 4.124 | | 2,6-difluorobenzyl (—CH₂—C₆H₃F₂) | —SC₂H₅ | —SC₂H₅ |
| 4.125 | | —CH(C₆H₅)(4-ClC₆H₄) | —SCH₃ | —SCH₃ |
| 4.126 | | —CH₂-(4-biphenyl) | —S—CH(CH₃)₂ | —S—CH(CH₃)₂ |
| 4.127 | | —CH₂CH₂Cl | —OCH₂-(tetrahydrofuran-3-yl) | —OCH₂-(tetrahydrofuran-3-yl) |
| 4.128 | | —CH₃ | —S—C₆H₅ | —OCH₂CH₂SC₂H₅ |
| 4.129 | | tetrahydropyran-4-yl | 2,5-difluoro-3-methoxyphenyl-O— | —SCH₃ |
| 4.130 | | bornyl | —O—CH(CH₃)₂ | —O—CH(CH₃)₂ |
| 4.131 | | bornyl | —SCH₃ | —SCH₃ |

TABLE 4-continued

Compounds of the formula IV

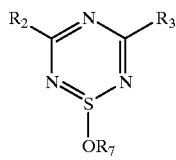

(IV)

| Comp. No. | Process | $R_7$ | $R_3$ | $R_2$ |
|---|---|---|---|---|
| 4.132 | | —CH(CH$_3$)$_2$ | —O—CH(CH$_3$)$_2$ | Br—C$_6$H$_4$—O— (4-bromophenoxy) |
| 4.133 | | —C$_2$H$_5$ | 2-fluorophenoxy | —OC$_2$H$_5$ |
| 4.134 | | —CH$_2$-(2-naphthyl) | —SCH$_3$ | —SCH$_3$ |
| 4.135 | | —CH$_2$-(1-naphthyl) | —OCH$_2$CF$_3$ | —OCH$_2$CF$_3$ |
| 4.136 | | —CH$_3$ | —OCH$_3$ | —OCH$_2$-(2-naphthyl) |
| 4.137 | | cyclohexyl | Cl | —OCH$_3$ |
| 4.138 | | cyclohexyl | Cl | —S—CH(CH$_3$)$_2$ |
| 4.139 | | —CH$_3$ | —OCH$_3$ | Cl |
| 4.140 | | —CH$_2$C≡CH | Cl | —OCH$_2$-phenyl |
| 4.141 | | —CH$_2$C≡CH | Cl | —SC$_3$H$_7$(n) |
| 4.142 | | —CH$_3$ | Cl | —SC(CH$_3$)$_3$ |
| 4.143 | | cycloheptyl | Cl | —OC$_3$H$_7$(n) |

TABLE 4-continued

Compounds of the formula IV

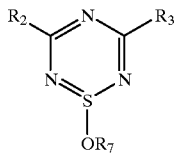

(IV)

| Comp. No. | Process | R₇ | R₃ | R₂ |
|---|---|---|---|---|
| 4.144 | | —CH₂CH₂F | —OCH₂-(2-furyl) | Cl |
| 4.145 | | cyclooctyl-CH₂— | Cl | —OCH₃ |
| 4.146 | | cyclooctyl-CH₂— | Cl | —SC₂H₅ |
| 4.147 | | cyclopentyl-CH₂— | —SCH₂CH(CH₃)C₂H₅ | Cl |
| 4.148 | | —CH₂CH₂Br | Cl | —SCH₂CH=CH₂ |
| 4.149 | | —C₂H₅ | Cl | —OC₂H₅ |
| 4.150 | | —CH₂C≡CH | —SCH₂CF₃ | Cl |
| 4.151 | | —C₄H₉(n) | Cl | —OC₄H₉(n) |
| 4.152 | | —C₄H₉(n) | Cl | —SC₄H₉(n) |
| 4.153 | | cyclooctyl-CH₂— | —OC₂H₅ | —OC₂H₅ |
| 4.154 | | —CH(CH₃)₂ | —SCH₂CF₃ | —SCH₂CF₃ |
| 4.155 | | —CH₂-phenyl | —SCH₂-(2-naphthyl) | Cl |
| 4.156 | d₃ | pinanyl-CH₂CH₂— | —OC₆F₅ | —OCH₂CH₂Cl |
| 4.157 | d₃ | —CH₂CH₂Si(CH₃)₃ | —OC₆F₅ | —OCH₂CH₂Cl |
| 4.158 | d₃ | —(CH₂)₃Si(CH₃)₃ | —OC₆F₅ | —OCH₂CH₂Cl |
| 4.159 | d₃ | adamantyl-CH₂— | —OC₆F₅ | —OCH₂CH₂Cl |
| 4.160 | d₃ | —CH₂Si(CH₃)₃ | —OC₆F₅ | —OCH₂CH₂Cl |

TABLE 4-continued

Compounds of the formula IV

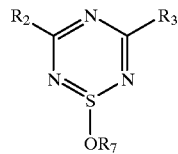

(IV)

| Comp. No. | Process | $R_7$ | $R_3$ | $R_2$ |
|---|---|---|---|---|
| 4.161 | $d_3$ | —CH$_3$ | —OCH$_3$ | ![2-methylphenoxy] |
| 4.162 | $d_3$ | —C$_2$H$_5$ | —OC$_2$H$_5$ | ![phenoxy] |
| 4.163 | $d_3$ | —CH$_3$ | —OCH$_3$ | ![2-methoxyphenoxy] |
| 4.164 | $d_3$ | —C$_2$H$_5$ | —SC$_6$F$_5$ | —OC$_2$H$_5$ |
| 4.165 | $d_3$ | ![pinene-ethyl] | —OC$_6$F$_5$ | —OCH$_2$CH$_2$Cl |
| 4.166 | $d_3$ | ![trimethylcyclohexyl] | ![tetrafluorophenoxy] | —OCH$_2$CH$_2$Cl |
| 4.167 | $d_3$ | ![pinanyl] | —OC$_6$F$_5$ | —OCH$_2$CH$_2$Cl |
| 4.168 | $d_3$ | —OCH$_2$CH$_2$Cl | —OC$_6$F$_5$ | —OCH$_2$CH$_2$Cl |
| 4.169 | $d_3$ | ![decalinyl] | —OC$_6$F$_5$ | —OCH$_2$CH$_2$Cl |

Physical data of compounds in Table 4:

| Comp. No. | Physical data |
|---|---|
| 4.1 | $^1$H-NMR: 7.4 ppm (2H); 7.25 ppm (1H); 7.15 ppm (2H); 3.9 ppm (3H); 3.5 ppm (3H) |
| 4.2 | $^{13}$C-NMR: 169.5 ppm; 54.7 ppm; 49.1 ppm |
| 4.4 | $^{13}$C-NMR: 181.8 ppm; 164.9 ppm; 65.9 ppm; 41.6 ppm; 36.5 ppm; 22.9 ppm |
| 4.5 | Melting point 75–76° C. |
| 4.8 | $^1$H-NMR: 4.6 ppm (2H); 4.4 ppm (2H); 3.3 ppm (4H); 1.35 ppm (3H); 1.25 ppm (3H) |
| 4.9 | $^1$H-NMR: 7.2 ppm (1H); 7.0 ppm (2H); 3.9 ppm (3H); 3.4 ppm (3H) |
| 4.12 | $^1$H-NMR: 7.1 ppm (1H); 6.9 ppm (2H); 4.9 ppm (2H); 3.4 ppm (3H); 2.5 ppm (1H) |
| 4.15 | $^1$H-NMR: 4.3 ppm (2H); 3.7 ppm (2H); 1.4–1.9 ppm (4H); 0.9–1.1 ppm (6H) |
| 4.16 | $^{13}$C-NMR: 170.0 ppm; 167.9 ppm; 136.0–143.2 ppm; 125.9 ppm; 55.2 ppm; 49.1 ppm |
| 4.18 | $^1$H-NMR: 3.95 ppm (2H); 3.85 ppm (2H); 3.6 ppm (2H); 1.4 ppm (6H) |
| 4.20 | $^1$H-NMR: 7.1 ppm (1H); 6.9 ppm (2H); 4.3 ppm (2H); 3.7 ppm (2H); 1.3 ppm (6H) |
| 4.22 | $^1$H-NMR: 4.0 ppm (2H); 3.7 ppm (2H); 1.6 ppm (9H) |
| 4.23 | $^{13}$C-NMR: 160.0 ppm; 122.6 ppm; 65.1 ppm; 63.6 ppm; 41.6 ppm |
| 4.26 | $^1$H-NMR: 4.3 ppm (4H); 3.6 ppm (2H); 1.8 ppm (4H); 1.6 ppm (2H); 1.0 ppm (6H); 0.9 ppm (3H) |
| 4.29 | $^1$H-NMR: 5.2 ppm (4H); 4.0 ppm (2H); 3.6 ppm (2H) |
| 4.33 | $^1$H-NMR: 3.95 ppm (6H); 3.7 ppm (2H); 1.3 ppm (3H) |
| 4.38 | $^{13}$C-NMR: 168.2 ppm; 94.3 ppm; 76.5 ppm; 64.9 ppm; 41.6 ppm |
| 4.41 | $^1$H-NMR: 7.2–8.0 ppm (4H); 4.35 ppm (2H); 4.25 ppm (2H); 3.7–3.9 ppm (2H); 1.2–1.4 ppm (9H) |
| 4.43 | $^1$H-NMR: 7.5 ppm (1H); 7.3 ppm (1H); 7.1 ppm (1H); 3.9 ppm (3H); 3.4 ppm (3H) |
| 4.45 | $^{13}$C-NMR: 168.5 ppm; 167.2 ppm; 136.1–143.0 ppm; 125.8 ppm; 81.7 ppm; 67.2 ppm; 40.7 ppm; 33.8 ppm |
| 4.49 | $^1$H-NMR: 3.95 ppm (2H); 3.65 ppm (2H); 1.6 ppm (18H) |
| 4.50 | $^1$H-NMR: 4.4 ppm (4H); 3.7 ppm (2H); 1.4 ppm (6H); 1.3 ppm (3H) |
| 4.86 | Melting point 141–142° C. |
| 4.156 | $^{13}$C-NMR: 169.0 ppm; 167.7 ppm; 142.8 ppm; 119.9 ppm; 67.3 ppm; 62.8 ppm; 45.6 ppm; 40.8 ppm; 40.6 ppm; 38.0 ppm; 36.5 ppm; 31.5 ppm; 31.3 ppm; 26.1 ppm; 21.0 ppm |
| 4.157 | $^{13}$C-NMR: 169.0 ppm; 167.6 ppm; 67.3 ppm; 63.7 ppm; 40.9 ppm; 18.4 ppm; −1.7 ppm |
| 4.158 | $^1$H-NMR: 4.6 ppm (2H); 3.75 ppm (2H); 3.6 ppm (2H); 1.65 ppm (2H); 0.5 ppm (2H); 0.0 ppm (9H) |
| 4.159 | $^1$H-NMR: 4.6 ppm (2H); 3.8 ppm (2H); 3.2 ppm (2H); 2.0 ppm (3H); 1.6–1.8 ppm (6H); 1.5 ppm (6H) |
| 4.160 | $^1$H-NMR: 4.55 ppm (2H); 3.7 ppm (2H); 3.0 ppm (2H); 0.0 ppm (9H) |
| 4.161 | $^1$H-NMR: 7.3–7.0 ppm (3H); 3.95 ppm (3H); 3.4 ppm (3H); 2.25 ppm (3H) |
| 4.162 | $^1$H-NMR: 7.1–7.4 ppm (5H); 4.35 ppm (2H); 3.75 ppm (2H); 1.2–1.4 ppm (6H) |
| 4.163 | $^1$H-NMR: 6.9–7.3 ppm (4H); 3.95 ppm (3H); 3.8 ppm (3H); 3.4 ppm (3H) |
| 4.164 | $^1$H-NMR: 5.2 ppm (4H); 4.0 ppm (2H); 3.65 ppm (2H) |
| 4.165 | $^1$H-NMR: 5.3 ppm (1H); 4.6 ppm (2H); 3.8 ppm (2H); 3.6 ppm (2H); 1.9–2.4 ppm (7H); 1.25 ppm (3H); 1.1 ppm (1 H); 0.8 ppm (3H) |
| 4.166 | $^1$H-NMR: 7.0 ppm (1H); 4.55 ppm (1H+2H); 3.75 ppm (2H); 0.8–1.9 ppm (16H) |
| 4.167 | $^{13}$C-NMR: 168.8 ppm; 168.4 ppm; 167.6 ppm; 167.1 ppm; 125–143 ppm; 80.5 ppm; 80.3 ppm; 67.3 ppm; 47.5 ppm; 44.8 ppm; 41.4 ppm; 40.7 ppm; 38.4 ppm; 37.0 ppm; 33.9 ppm; 27.3 ppm; 23.8 ppm; 19.6 ppm |
| 4.168 | $^{13}$C-NMR: 169.0 ppm; 167.7 ppm; 125–143 ppm; 67.7 ppm; 64.7 ppm; 41.4 ppm; 40.8 ppm |
| 4.169 | $^{13}$C-NMR: 168.4 ppm; 167.1 ppm; 84.8 ppm; 67.3 ppm; 47.9 ppm; 41.8 ppm; 40.8 ppm; 34.5 ppm; 33.4 ppm; 32.6 ppm; 29.2 ppm; 26.0 ppm; 25.7 ppm; 23.9 ppm |

Example H13

Preparation of 3-amino-1-(β-chloroethoxy)-5-(2',4'-dichlorophenoxy)thiatriazine (process $d_4$)

(Compound No. 5.333)

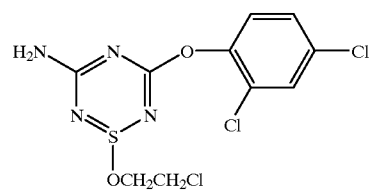

6.5 g (0.013 mol) of 1-(β-chloroethoxy)-3,5-di(2',4'-dichlorophenoxy)thiatriazine are dissolved in 100 ml of tetrahydrofuran. Thereafter, ammonia gas is passed in at 20° C. until the starting material can no longer be detected in a thin layer chromatogram (about 15 minutes). The reaction mixture is concentrated on a rotary evaporator and hexane is added to the still hot residue until crystallization starts. The crystals formed are filtered off with suction, washed with hexane and dried. 4.00 g (86.5% of theory) of the desired compound are obtained as crystals of melting point 141–142° C. Cl analysis: 29.3% (calculated 29.9%); $^1$H-NMR (300 MHz, CDCl$_3$): 7.2–7.5 ppm (3H), 6.6 and 6.3 ppm (2H), 3.9 ppm (2H), 3.6 ppm (2H).

Example H14

Preparation of 3-amino-1-isopropoxy-5-(2',5'-difluorophenoxy)thiatriazine (process g)

(Compound No. 5.3)

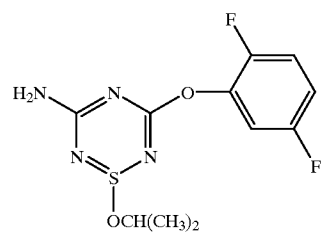

0.50 g (0.0084 mol) of isopropanol is reacted with 0.37 g (0.0084 mol) of 55% sodium hydride in oil in 30 ml of tetrahydrofuran. 2.60 g (0.008 mol) of 3-amino-1-(β-chloroethoxy)-5-(2',5'-difluorophenoxy)thiatriazine are added to the resulting suspension of the sodium isopropanolate at room temperature, and a slightly exothermic reaction takes place.

Extraction of the reaction mixture with water and ethyl acetate gives 2.0 g of crude product, which is recrystallized from a mixture of ethyl acetate/hexane 3/5. Yield of desired product 1.82 g (75% of theory) of melting point 163–164° C.

Analysis: $C_{11}H_{12}F_2N_4O_2S$;

|   | calculated. [%] | found [%] |
|---|---|---|
| C | 43.7 | 43.3 |
| H | 4.0 | 4.0 |
| N | 18.5 | 18.4 |

$^1$H-NMR (300 MHz, CDCl$_3$): 6.8–7.2 ppm (3H); 5.1–5.5 ppm (1H); 4.4 ppm (1H); 1.3 ppm (6H).

Example H15

Preparation of 3-dimethylamino-1-(β-chloroethoxy)-5-(2'-carboethoxyphenoxy)thiatriazine (process c$_4$)

(Compound No. 5.22)

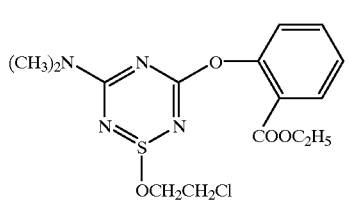

2.22 g (0.0064 mol) of 3-chloro-1-(β-chloroethoxy)-5-(2'-carboethoxyphenoxy)thiatriazine are dissolved in 30 ml of tetrahydrofuran. Dimethylamine is passed in at 0° C. until the conversion is complete, the reaction mixture is extracted with water and ethyl acetate, the extract is concentrated and the crude product is purified by means of chromatography (silica gel; ethyl acetate/hexane mixture). The desired product is obtained as an oil in a yield of 1.40 g (57% of theory).

The $^1$H-NMR spectrum is in agreement with the structure of the desired compound; mass spectrum: [M$^+$]386.

Example H16

Preparation of 3-amino-5-(2,5-difluorophenoxy)-1-(3-hexyloxy)thiatriazine (Compound No. 5.340)

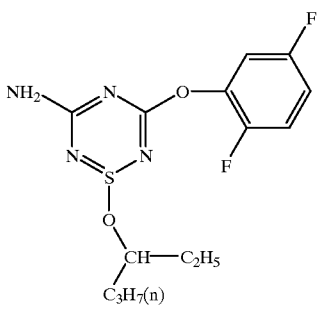

2.1 g of trimethylamine solution (40% in water) are added to a mixture of 3.6 g of 3-amino-5-chloro-1-(3-hexyloxy)thiatriazine (0.014 mol), 70 ml of methylene chloride and 2.05 g of 2,5-difluorophenol (0.01 6 mol). The reaction mixture is stirred at 20° C. until the conversion is complete, and is then evaporated. Water is added to the resulting residue and the residue is filtered off with suction. The resulting solid is stirred in diethyl ether and filtered off, the clear ether solution is concentrated and pentane is added to the residue. The desired product precipitates in the form of white crystals of melting point 171–172° C.

The compounds listed in the following Table 5 can be prepared analogously to Examples H13 to H16.

TABLE 5

Compounds of the formula III

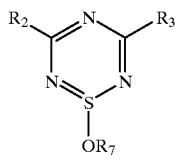

(III)

| Comp. No. | Process | R$_7$ | R$_3$ | R$_2$ |
|---|---|---|---|---|
| 5.1 | d$_4$ | —CH$_2$CH$_2$Cl | C$_6$H$_5$O— | —NH$_2$ |
| 5.2 | d$_4$ | —CH$_2$CH$_2$C$_6$H$_5$ | 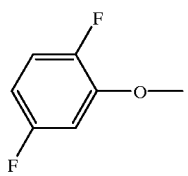 | —N(CH$_3$)C$_4$H$_9$(n) |

TABLE 5-continued

Compounds of the formula III

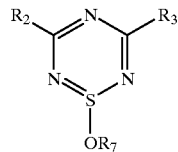
(III)

| Comp. No. | Process | R₇ | R₃ | R₂ |
|---|---|---|---|---|
| 5.3 | q | —CH(CH₃)₂ | 2,5-difluorophenoxy | —NH₂ |
| 5.4 | d₄ | —CH₂CH₂Cl | 2-methoxyphenoxy | —NH₂ |
| 5.5 | d₅ | —CH₂CH₂Cl | 2,5-dichlorophenoxy | —NH₂ |
| 5.6 | d₄ | —CH₂CH₂Cl | C₆F₅O— | —N(CH₃)₂ |
| 5.7 | q | —CH₂-(2,3-dichlorophenyl) | 2,5-difluorophenoxy | —NH₂ |
| 5.8 | q | cyclohexyl | cyclohexyloxy-tetrafluoro-methoxyphenoxy | —NH₂ |
| 5.9 | | 2-(ethoxycarbonyl)cyclohex-1-enyl | C₆F₅O— | —NH₂ |
| 5.10 | d₄ | —CH₂CH₂C₆H₅ | 2,5-difluorophenoxy | bornylamino |
| 5.11 | d₄ | —CH₂CH₂Cl | C₆H₅O— | —N(CH₃)₂ |

TABLE 5-continued

Compounds of the formula III

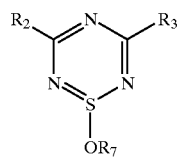

(III)

| Comp. No. | Process | $R_7$ | $R_3$ | $R_2$ |
|---|---|---|---|---|
| 5.12 | | 1-methylcyclohexyl | $C_6F_5O-$ | $-NH_2$ |
| 5.13 | $d_4$ | $-CH_2CH_2Cl$ | $C_6F_5O-$ | $-NH_2$ |
| 5.14 | q | 1-methyldecahydronaphthyl (trans) | 2,5-difluoro-methoxyphenyl | $-NH_2$ |
| 5.15 | $d_4$ | $-CH_2CH_2Cl$ | 2,5-difluoro-methoxyphenyl | $-NHC(CH_3)_3$ |
| 5.16 | | 1-methylindanyl | $C_6F_5O-$ | $-NH_2$ |
| 5.17 | $d_4$ | $-CH_2CH_2Cl$ | 2,4-dichloro-methoxyphenyl | morpholinyl |
| 5.18 | | 1-(4-methoxyphenyl)-1-(4-chlorophenyl)ethyl | $C_6F_5O-$ | $-NH_2$ |

TABLE 5-continued

Compounds of the formula III

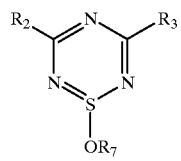

(III)

| Comp. No. | Process | $R_7$ | $R_3$ | $R_2$ |
|---|---|---|---|---|
| 5.19 | q | (1,1,3-trimethyl-4-methylcyclohexyl) | 2,5-difluoro-3-methoxyphenyl | —$NH_2$ |
| 5.20 | | —$CH_2CH_2Cl$ | 1-methoxynaphthalen-2-yl | —$NH_2$ |
| 5.21 | | 3-methylcyclopentyl-1-carbonitrile | 3-methyl-5-methoxyphenyl | —$NH_2$ |
| 5.22 | $c_4$ | —$CH_2CH_2Cl$ | 2-methoxy-6-(ethoxycarbonyl)phenyl | —$N(CH_3)_2$ |
| 5.23 | $d_4$ | —$CH_2CH_2Cl$ | 2,6-difluoro-3-methoxyphenyl | —$N(CH_3)_2$ |
| 5.24 | | —$CH_2CH_2Cl$ | $C_2H_5OOC$—CH(CH$_3$)—O—(4-methoxyphenyl) | —$NH_2$ |
| 5.25 | | —CH(CH$_3$)CH$_2$OCH$_3$ | (CH$_3$)$_3$C—(4-methoxyphenyl) | —$NH_2$ |
| 5.26 | | 4-methylcyclohexyl | $C_6F_5O$— | —$NH_2$ |

TABLE 5-continued

Compounds of the formula III

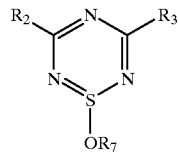

(III)

| Comp. No. | Process | R₇ | R₃ | R₂ |
|---|---|---|---|---|
| 5.27 | | ![cyclohexyl-CH₂CH(CH₃)₂] | $C_6F_5O-$ | $-NH_2$ |
| 5.28 | $d_4$ | $-CH_2CH_2Cl$ | ![2-methoxy-3-methylphenyl] | $-NH_2$ |
| 5.29 | | $-CH_2CH_2Cl$ | ![2,6-difluoro-methoxyphenyl] | ![piperidinyl] |
| 5.30 | q | ![menthyl (+)] | $C_6F_5O-$ | $-NH_2$ |
| 5.31 | $d_4$ | ![1-phenylethyl] | ![2,5-difluoro-methoxyphenyl] | $-NH_2$ |
| 5.32 | | $-CH_2CH_2Cl$ | ![2,6-dimethoxy-methoxyphenyl] | $-NH_2$ |
| 5.33 | | $-CH_2CH=CH_2$ | $C_6F_5O-$ | $-NH_2$ |
| 5.34 | | ![2-tert-butylcyclohexyl] | $C_6F_5O-$ | $-NH_2$ |

TABLE 5-continued

Compounds of the formula III

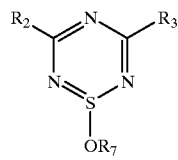

(III)

| Comp. No. | Process | R₇ | R₃ | R₂ |
|---|---|---|---|---|
| 5.35 | d₄ | —CH₂—C₆H₅ (benzyl) | 2,5-difluoro-methoxyphenyl | —NH-cyclopentyl |
| 5.36 | | —(CH₂)₆CH₃ | C₆F₅O— | —NH₂ |
| 5.37 | | trans-2-isocyanocyclohexyl | 2,5-difluoro-methoxyphenyl | —NH₂ |
| 5.38 | d₄ | cyclopentylmethyl | C₆F₅O— | —NH₂ |
| 5.39 | | —CH₂-(2-furyl) | 2,5-difluoro-methoxyphenyl | —NH₂ |
| 5.40 | | —CH₂CH₂NO₂ | 2,5-difluoro-methoxyphenyl | —NH₂ |
| 5.41 | | —CH₂C₆F₅ | 2,5-difluoro-methoxyphenyl | —NH₂ |
| 5.42 | d₄ | cyclohexylmethyl | 4-nitro-methoxyphenyl | —NH₂ |

TABLE 5-continued
Compounds of the formula III
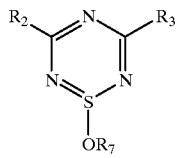
(III)
| Comp. No. | Process | R₇ | R₃ | R₂ |
|---|---|---|---|---|
| 5.43 | | -CH(C₂H₅)-C₆H₄-O-C₆H₅ | 2,5-difluoro-phenyl-O- | —NH₂ |
| 5.44 | | -CH(CH₃)-CH₂-OOC-C₆H₅ | 2,5-difluoro-phenyl-O- | —NH₂ |
| 5.45 | q | —CH₃ | 2,5-dichloro-phenyl-O- | —NHCH₂CH₂CH₃ |
| 5.46 | q | trans-2-methylcyclohexyl (Diastereomer 1) | $C_6F_5O-$ | —NH₂ |
| 5.47 | q | trans-2-methylcyclohexyl (Diastereomer 2) | $C_6F_5O-$ | —NH₂ |
| 5.48 | d₄ | —CH₂CH₂Cl | 2,6-difluoro-phenyl-O- | —NH₂ |
| 5.49 | | —CH₂CH₂Cl | $C_6F_5O-$ | —N(piperidinyl) |

TABLE 5-continued

Compounds of the formula III

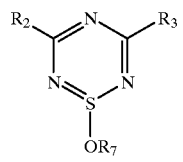
(III)

| Comp. No. | Process | R$_7$ | R$_3$ | R$_2$ |
|---|---|---|---|---|
| 5.50 | | -CH(C$_2$H$_5$)-(2,4-dichlorophenyl) | 2,5-difluoro-phenyl-O- | -NH$_2$ |
| 5.51 | q | -CH$_3$ | 2,6-difluoro-phenyl-O- | -N(CH$_3$)$_2$ |
| 5.52 | q | 4,4-dimethylcyclohexyl | C$_6$F$_5$O- | -NH$_2$ |
| 5.53 | | -CH$_2$-(pyridin-3-yl) | C$_6$F$_6$O- | -NH$_2$ |
| 5.54 | q | -CH$_3$ | 2,5-dichloro-phenyl-O- | -NH$_2$ |
| 5.55 | d$_4$ | -CH$_2$CH$_2$Cl | 3,6-difluoro-phenyl-O- | -N(CH$_3$)$_2$ |
| 5.56 | | cyclohept-3-enyl | C$_6$F$_5$O- | -NH$_2$ |
| 5.57 | | 1,2,3,4-tetrahydronaphthalen-2-yl | C$_6$F$_5$O- | -NH$_2$ |

TABLE 5-continued

Compounds of the formula III

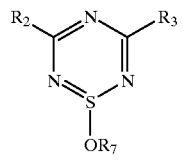

(III)

| Comp. No. | Process | $R_7$ | $R_3$ | $R_2$ |
|---|---|---|---|---|
| 5.58 | q | cyclohexyl-CH₂- | 2,6-difluorophenyl-O- | —NH₂ |
| 5.59 | q | trans-4-(1,1-dimethylpropyl)cyclohexyl- | $C_6F_5O$— | —NH₂ |
| 5.60 | $d_4$ | —CH₂CH₂Cl | 2,6-difluorophenyl-O- | —NHCH₂CH₂CH₃ |
| 5.61 |  | 1-methyl-4,5,6,7-tetrahydroindol-4-yl- | $C_6F_5O$— | —NH₂ |
| 5.62 |  | —CH₂-(1-methylindol-3-yl) | $C_6F_5O$— | —NH₂ |
| 5.63 |  | 2-methylcyclopentyl-CH₂-NC | $C_6F_5O$— | —NH₂ |
| 5.64 | q | —CH₃ | 2,6-difluorophenyl-O- | —NHCH₂CH₂CH₃ |
| 5.65 | q | 3-tetrahydrothiopyranyl- | $C_6F_5O$— | —NH₂ |

TABLE 5-continued

Compounds of the formula III

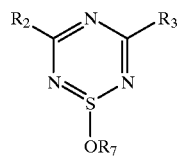

(III)

| Comp. No. | Process | $R_7$ | $R_3$ | $R_2$ |
|---|---|---|---|---|
| 5.66 | | —CH$_2$CH$_2$COOC$_2$H$_5$ | C$_6$F$_5$O— | —NH$_2$ |
| 5.67 | d$_4$ | (trans-2-chlorocyclohexyl) | (2,6-difluorophenoxy) | —NH$_2$ |
| 5.68 | | —CH$_2$C≡CH | C$_6$F$_5$O— | —NH$_2$ |
| 5.69 | | —CH$_2$-(2-thienyl) | C$_6$F$_5$O— | —NH$_2$ |
| 5.70 | | (1-tetralinyl) | C$_6$F$_5$O— | —NH$_2$ |
| 5.71 | q | —CH$_3$ | (2,6-difluorophenoxy) | —NH$_2$ |
| 5.72 | d$_4$ | —CH$_2$CH$_2$-phenyl | (2,5-difluoro-3-methoxyphenoxy) | —NH$_2$ |
| 5.73 | c$_4$ | (trans-2-chlorocyclooctyl) | (3-methoxyphenyl-thio, 2-OCH$_3$) | —NH$_2$ |
| 5.74 | d$_4$ | (trans-2-chlorocyclooctyl) | (3-methoxyphenyl-thio, 2-OCH$_3$) | —NHCH$_3$ |

TABLE 5-continued
Compounds of the formula III
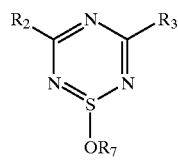
(III)
| Comp. No. | Process | R₇ | R₃ | R₂ |
|---|---|---|---|---|
| 5.75 | q | (3-methyloxetane) | 2,5-difluoro-methoxyphenyl | —NH₂ |
| 5.76 | | —CH₂-(2-chloro-6-nitrophenyl) | C₆F₅O— | —NH₂ |
| 5.77 | | —CH₂CH₂CCl₃ | C₆F₅O— | —NH₂ |
| 5.78 | q | 3,3,5-trimethylcyclohexyl | C₆F₅O— | —NH₂ |
| 5.79 | | 1-(naphthalen-2-yl)ethyl | C₆F₅O— | —NH₂ |
| 5.80 | | 1-(naphthalen-2-yl)ethyl | C₆F₅O— | —NH₂ |
| 5.81 | | 3,3,5-trimethylcyclohexyl | 2,3,5,6-tetrafluoro-methoxyphenyl | —NH₂ |

TABLE 5-continued
Compounds of the formula III
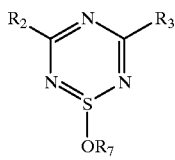
(III)
| Comp. No. | Process | $R_7$ | $R_3$ | $R_2$ |
|---|---|---|---|---|
| 5.82 | | 1-(1-naphthyl)ethyl | $C_6F_5O$— | —$NH_2$ |
| 5.83 | q | 3,5,5-trimethylcyclohex-2-enyl | $C_6F_5O$— | —$NH_2$ |
| 5.84 | q | 1-methoxy-2-methylcyclohexyl (with OCH$_3$) | $C_6F_5O$— | —$NH_2$ |
| 5.85 | | —$CH_2$-Adamantyl | $C_6F_5O$— | —$NH_2$ |
| 5.86 | q | 3,3,5-trimethylcyclohexyl | —$C_6F_5O$— | —$NH_2$ |
| 5.87 | | 3,3,5-trimethylcyclohexyl | $C_6F_5S$— | —$NH_2$ |
| 5.88 | $d_4$ | cyclooctyl | $C_6F_5S$— | —$NH_2$ |
| 5.89 | $d_4$ | —$CH_2CH_2Cl$ | $C_6F_5S$— | —$NH_2$ |

TABLE 5-continued

Compounds of the formula III

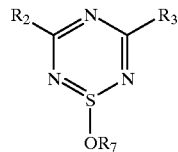

(III)

| Comp. No. | Process | $R_7$ | $R_3$ | $R_2$ |
|---|---|---|---|---|
| 5.90 | q | (bornyl group with CH₃, CH₃, CH₃, H) (+) | $C_6F_5O$— | —$NH_2$ |
| 5.91 | | —$CH_2$—(trimethyl azulenyl) | $C_6F_5O$— | —$NH_2$ |
| 5.92 | q | (2-indanyl) | $C_6F_5O$— | —$NH_2$ |
| 5.93 | | —$CH_2$—(tetrahydrofuran-2-yl) | $C_6F_5O$— | —$NH_2$ |
| 5.94 | $c_4$ | (chloro-methyl-cyclooctyl) | (3-methoxyphenyl-SCH₃) | (3-ethylpiperidin-1-yl) |
| 5.95 | | (2-trifluoromethylcyclohexyl-methyl) | $C_6F_5O$— | —$NH_2$ |
| 5.96 | q | —$CH_2CH_2OCH_3$ | (2,5-difluorophenoxy) | —$NH_2$ |
| 5.97 | | (pinanyl-CH₂—) | (4-chlorophenoxy) | —$NHC_4H_9(n)$ |

TABLE 5-continued

Compounds of the formula III

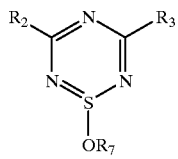

(III)

| Comp. No. | Process | R₇ | R₃ | R₂ |
|---|---|---|---|---|
| 5.98 | d₄ | (trans-2-methyl-1-chlorocyclopentyl) | $C_6F_5O-$ | $-NH_2$ |
| 5.99 |  | (2-methyl-1-ethoxycarbonylcyclohexyl) | $C_6F_5O-$ | $-NH_2$ |
| 5.100 |  | (3,5-dimethyl-5,5-... trimethylcyclohexyl with CH₃ groups) | $C_6F_5S-$ | $-NH_2$ |
| 5.101 |  | (tetramethylcyclohexyl) | $C_6F_5O-$ | $-NH_2$ |
| 5.102 | q | $-CH_2CH_2F$ | (2,5-difluorophenyl-O-methyl) | $-NH_2$ |
| 5.103 | q | (methyloxetanyl) | (2,6-difluorophenyl-O-methyl) | $-NH_2$ |
| 5.104 |  | (2-methyl-1-(2-cyanoethyl)cyclopentyl, NCCH₂CH₂) | $C_6F_5O-$ | $-NH_2$ |

TABLE 5-continued
Compounds of the formula III
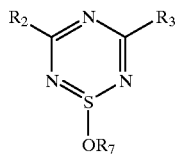
(III)
| Comp. No. | Process | R₇ | R₃ | R₂ |
|---|---|---|---|---|
| 5.105 | | —(CH₂)₇CH₃ | 3-Br-phenoxy (Br, —O—) | —NHCH₃ |
| 5.106 | | —CH₂-(2-furyl) | C₆F₅O— | —NH₂ |
| 5.107 | q | —C₂H₅ | 2,6-difluoro-phenoxy | —NH₂ |
| 5.108 | q | 3,3,5-trimethylcyclohexyl | 2,6-difluoro-phenoxy | —NH₂ |
| 5.109 | | —CH(CH₃)C₂H₅ | 3-I-phenoxy | —NH₂ |
| 5.110 | q | —C(CH₃)₃ | 3,6-difluoro-phenoxy | —NH₂ |
| 5.111 | | 3-methyl-cyclohexyl-CN | C₆F₅O— | —NH₂ |
| 5.112 | | 2-methyl-3-chloro-cyclodecyl | C₆F₅O— | —NH₂ |

TABLE 5-continued
Compounds of the formula III
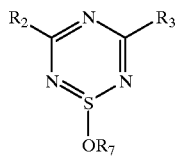
(III)
| Comp. No. | Process | R₇ | R₃ | R₂ |
|---|---|---|---|---|
| 5.113 | q | —CH₃ | 2,5-difluorophenoxy | —NHC(CH₃)₃ |
| 5.114 | | 4-methyltetrahydropyran | C₆F₅O— | —NH₂ |
| 5.115 | | 2-methylbicyclopentyl | C₆F₅O— | —NH₂ |
| 5.116 | q | bornyl (CH₃, CH₃, CH₃, H(-)) | 2,5-difluorophenoxy | —NH₂ |
| 5.117 | | norbornylmethyl | C₆F₅O— | —NH₂ |
| 5.118 | | NCCH₂CH₂-cyclododecyl-methyl | C₆F₅O— | —NH₂ |
| 5.119 | q | —CH₃ | 2,5-difluorophenoxy | —NH₂ |

TABLE 5-continued

Compounds of the formula III

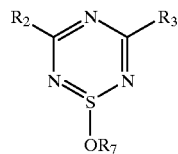

(III)

| Comp. No. | Process | R₇ | R₃ | R₂ |
|---|---|---|---|---|
| 5.120 | q | cis/trans-3,5-dimethylcyclohexyl (with CH₃, CH₃) | $C_6F_5O-$ | $-NH_2$ |
| 5.121 | d₄ | $-CH_2-C_6H_5$ (benzyl) | 2,5-difluoro-methoxyphenyl | $-NHCH(CH_3)CH_2OCH_3$ |
| 5.122 | d₄ | $-CHCH_2Cl$ / $C_6H_5$ | 6-methoxy-2-naphthyl | $-NH_2$ |
| 5.123 |   | 2-(2-cyanoethyl)cyclooctyl ($CH_2CH_2CN$) | $C_6F_5O-$ | $-NH_2$ |
| 5.124 |   | 3-(trifluoromethyl)cyclohexyl ($CF_3$) | $C_6F_5O-$ | $-NH_2$ |
| 5.125 | q | $-C_2H_5$ | 3,5-difluoro-methoxyphenyl | $-NH_2$ |
| 5.126 | d₄ | 3,3-dimethylcyclohexyl ($CH_3$, $CH_3$) | 2,3,5,6-tetrafluoro-4-methoxyphenyl | $-NH_2$ |
| 5.127 |   | trans-4-tert-butylcyclohexyl ($-C(CH_3)_3$) | $C_6F_5O-$ | $-NH_2$ |

TABLE 5-continued

Compounds of the formula III

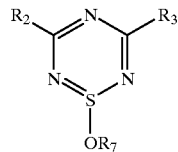

(III)

| Comp. No. | Process | R₇ | R₃ | R₂ |
|---|---|---|---|---|
| 5.128 | | —CH₂—(2,6-difluorophenyl) | C₆F₅O— | —NH₂ |
| 5.129 | q | —CH(C₆H₅)—(4-chlorophenyl) | 2,5-difluoro-3-methoxyphenyl | —NH₂ |
| 5.130 | q | cyclopentylmethyl | 2,5-difluoro-3-methoxyphenyl | —NH₂ |
| 5.131 | q | (1,1,3-trimethylcyclohexyl) | C₆F₅O— | —NH₂ |
| 5.132 | d₄ | (trans-2-chlorocyclooctyl)methyl | C₆F₅O— | —NH₂ |
| 5.133 | d₄ | cyclooctylmethyl | 3-methyl-7-(methylthio)-1(3H)-isobenzofuranone | —NH₂ |
| 5.134 | | —CH₂-(4-biphenyl) | C₆F₅O— | —NH₂ |
| 5.135 | q | —CH₂-(tetrahydropyran-2-yl) | C₆F₅O— | —NH₂ |

TABLE 5-continued

Compounds of the formula III

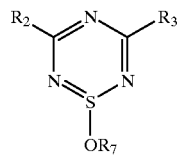
(III)

| Comp. No. | Process | R₇ | R₃ | R₂ |
|---|---|---|---|---|
| 5.136 | | cyclohexyl-CH₂CH₂CN | $C_6F_5O-$ | $-NH_2$ |
| 5.137 | | cyclohexyl-COOC₂H₅ | $C_6F_5O-$ | $-NH_2$ |
| 5.138 | d₄ | $-CH(CH_3)$-phenyl | 2,5-difluoro-methoxyphenyl | $-NHCH_3$ |
| 5.139 | | $-CH_2$-(2-F-phenyl) | $C_6F_5O-$ | $-NH_2$ |
| 5.140 | | 3-tetrahydrofuranyl | $C_6F_5O-$ | $-NH_3$ |
| 5.141 | q | trans-1,3-dimethylcyclohexyl | $C_6F_5O-$ | $-NH_2$ |
| 5.142 | | cyclohex-2-enyl | $C_6F_5O-$ | $-NH_2$ |
| 5.143 | q | $-CH(C(CH_3)_2$-triazolyl)-CH_2$-(4-Cl-phenyl) | 2,5-difluoro-methoxyphenyl | $-NH_2$ |

TABLE 5-continued

Compounds of the formula III

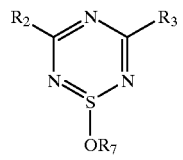

(III)

| Comp. No. | Process | R$_7$ | R$_3$ | R$_2$ |
|---|---|---|---|---|
| 5.144 | d$_4$ | methylcyclooctyl | 2,3,5,6-tetrafluoro-4-methoxyphenyl | —NH$_2$ |
| 5.145 | q | cyclohexyl | C$_6$F$_5$O— | —NH$_2$ |
| 5.146 | q | 3,3,5,5-tetramethylcyclohexyl | C$_6$F$_5$O— | —NH$_2$ |
| 5.147 | d$_4$ | 3,3,5-trimethylcyclohexyl | 2,3,5,6-tetrafluoro-4-methoxyphenyl | —NH$_2$ |
| 5.148 | q | 1-ethynyl-1-methylcyclohexyl | C$_6$F$_5$O— | —NH$_2$ |
| 5.149 |  | 4-(C(CH$_3$)$_2$C$_2$H$_5$)cyclohexyl | 2,3,5,6-tetrafluoro-4-methoxyphenyl | —NH$_2$ |
| 5.150 | d$_4$ | methylcyclooctyl | C$_6$F$_5$S— | —NH$_2$ |
| 5.151 | d$_4$ | 2-chlorocyclopentyl | C$_6$F$_5$O— | —NHC$_2$H$_5$ |

TABLE 5-continued

Compounds of the formula III

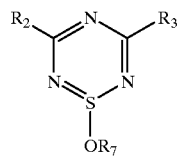
(III)

| Comp. No. | Process | R₇ | R₃ | R₂ |
|---|---|---|---|---|
| 5.152 | d₄ | (1-chloro-1-methyl-cyclohexyl with isopropenyl substituent) | $C_6F_5O-$ | $-NH_2$ |
| 5.153 | d₄ | (chloro, methyl cyclohexyl with isopropenyl) | $C_6F_5O-$ | $-NH_2$ |
| 5.154 | q | (bornyl/camphyl structure with H(−)) | $C_6F_5O-$ | $-NH_2$ |
| 5.155 | | (1,3-dioxane with methyl) | $C_6F_5O-$ | $-NH_2$ |
| 5.156 | q | $-(CH_2)_4CH_3$ | (2,5-difluorophenyl methyl ether) | $-NH_2$ |
| 5.157 | q | (methylcyclohexyl) | (2,5-difluorophenyl methyl ether) | $-NH_2$ |
| 5.158 | | $-CH_2-$ (norbornenyl) | $C_6F_5O-$ | $-NH_2$ |

TABLE 5-continued

Compounds of the formula III

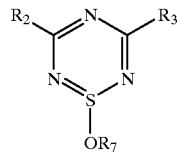

(III)

| Comp. No. | Process | R₇ | R₃ | R₂ |
|---|---|---|---|---|
| 5.159 | | (1,3,5-trimethylcyclohexyl) | 2,3,4,5-tetrafluoro-6-methoxyphenyl | —NH₂ |
| 5.160 | q | —CH₂CH₂SC₂H₅ | 2,5-difluoro-6-methoxyphenyl | —NH₂ |
| 5.161 | d₄ | —CH₂CH₂Si(CH₃)₃ | C₆F₅O— | —NH₂ |
| 5.162 | q | —(CH₂)₉CH₃ | 2,5-difluoro-6-methoxyphenyl | —NH₂ |
| 5.163 | | (4-isopropylcyclohexyl) | C₆F₅O— | —NH₂ |
| 5.164 | | (chloro-methyl-dicarbomethoxycyclohexyl) | C₆F₅O— | —NH₂ |
| 5.165 | | (chloro-methyl-dicarbomethoxycyclohexyl) | C₆F₅O— | —NH₂ |
| 5.166 | | (4-methylchroman-4-yl) | C₆F₅O— | —NH₂ |
| 5.167 | | —CH₂CH₂Cl | 3-trifluoromethyl-methoxyphenyl | —NH₂ |

TABLE 5-continued

Compounds of the formula III

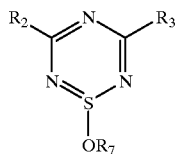

(III)

| Comp. No. | Process | $R_7$ | $R_3$ | $R_2$ |
|---|---|---|---|---|
| 5.168 | q | —(CH$_2$)$_2$(CF$_2$)$_3$CF$_3$ | 2,5-difluorophenoxy | —NH$_2$ |
| 5.169 | | 2-methylcycloheptyl-NCCH$_2$ | C$_6$F$_5$O— | —NH$_2$ |
| 5.170 | | —CH$_2$CH(C$_6$H$_5$)$_2$ | C$_6$F$_5$O— | —NH$_2$ |
| 5.171 | | tetrahydropyran-4-yl | C$_6$F$_5$O— | —NH$_2$ |
| 5.172 | q | —CH$_2$—C$_6$H$_5$ | 2,5-difluorophenoxy | —NH$_2$ |
| 5.173 | | 2-(trichloromethyl)cyclohexyl | C$_6$F$_5$O— | —NH$_2$ |
| 5.174 | d$_4$ | —CH$_2$CH$_2$Cl | 2-methoxy-3-(methoxycarbonyl)phenyl | —NH$_2$ |
| 5.175 | | 2-(CH$_2$CH$_2$COOC$_2$H$_5$)cyclohexyl | C$_6$F$_5$O— | —NH$_2$ |
| 5.176 | q | cyclooctyl | C$_6$F$_5$O— | —NH$_2$ |

TABLE 5-continued

Compounds of the formula III

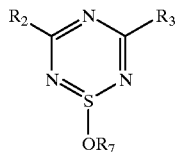

(III)

| Comp. No. | Process | R₇ | R₃ | R₂ |
|---|---|---|---|---|
| 5.177 | d₄ | —CH₂CH₂Cl | 2-methyl-5-methoxy-pyridin-yl | —NH₂ |
| 5.178 | d₄ | —CH₂CH₂Cl | 2,5-dichloro-4-methoxy-phenyl | —NHCH₂CH₂CH₃ |
| 5.179 |  | 3,5-dimethyl-cyclohexyl | 4-cyano-phenoxy via methylene | —NHC₄H₉(n) |
| 5.180 | d₄ | pinanyl-ethyl | C₆F₅O— | —NH₂ |
| 5.181 |  | 1-ethyl-3-methyl-piperidinyl | C₆F₅O— | —NH₂ |
| 5.182 | d₄ | —CH₂CH₂Cl | 3-methyl-7-methoxy-phthalide-yl | —NHCH(CH₃)₂ |
| 5.183 | d₄ | —CH₂CH₂Cl | 3-methyl-7-methoxy-phthalide-yl | —N(C₂H₅)₂ |

TABLE 5-continued

Compounds of the formula III

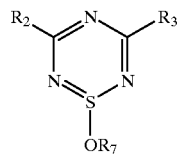

(III)

| Comp. No. | Process | R₇ | R₃ | R₂ |
|---|---|---|---|---|
| 5.184 | d₄ | —CH₂CH₂Cl | 2,5-difluoro-phenyl methyl ether | —NH₂ |
| 5.185 | | 2,6-dimethylcyclohexyl | C₆F₅O— | —NH₂ |
| 5.186 | | 8-methoxy-1,5-dimethyl-tetrahydronaphthyl | C₆F₅O— | —NH₂ |
| 5.187 | | 2-methyl-3-(2-cyanoethyl)cycloheptyl | C₆F₅O— | —NH₂ |
| 5.188 | d₄ | —CH₂CH₂Cl | 2,5-difluoro-phenyl methyl ether | —NHCH₂C₆H₅ |
| 5.189 | | —CH₂CH₂Cl | 2-methylthio-3-methoxycarbonyl-pyridine | —NH₂ |
| 5.190 | | —CH₂CH₂Cl | 2-methylthio-5-methylpyrimidine | —NH₂ |
| 5.191 | | 2,7,7-trimethyl-bicyclic terpene | C₆F₅O— | —NH₂ |

TABLE 5-continued

Compounds of the formula III

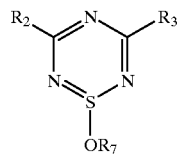

(III)

| Comp. No. | Process | R$_7$ | R$_3$ | R$_2$ |
|---|---|---|---|---|
| 5.192 | d$_4$ | —CH$_2$CH$_2$Cl | 7-methoxy-3-methyl-phthalide-3-yl | —NH$_2$ |
| 5.193 | d$_4$ | —CH$_2$CH$_2$Cl | 7-methoxy-3-methyl-phthalide-3-yl | —N(CH$_3$)$_2$ |
| 5.194 | | 2-methylcyclohexyl-cyclohexyl | C$_6$F$_5$O— | —NH$_2$ |
| 5.195 | q | bornyl | C$_6$F$_5$O— | —NH$_2$ |
| 5.196 | | 4-tert-butyl-1-methylcyclohexyl | C$_6$F$_5$O— | —NH$_2$ |
| 5.197 | q | —CH$_2$-phenyl | C$_6$F$_5$O— | —NH$_2$ |
| 5.198 | | hexahydro-methyl-phthalide-yl | C$_6$F$_5$O— | —NH$_2$ |
| 5.199 | | —CH$_2$CH$_2$Cl | 4-cyano-phenoxymethyl (NC-C$_6$H$_4$-O—) | —NH$_2$ |

TABLE 5-continued

Compounds of the formula III

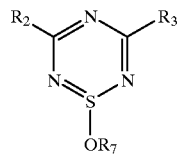

(III)

| Comp. No. | Process | $R_7$ | $R_3$ | $R_2$ |
|---|---|---|---|---|
| 5.200 | | —CH$_2$CH$_2$Cl | (phenyl-O-phenyl-OCH$_3$) | —NH$_2$ |
| 5.201 | | (2-methylcyclohexyl-CH$_2$CN) | C$_6$F$_5$O— | —NH$_2$ |
| 5.202 | | (2-methyltetralinyl) | C$_6$F$_5$O— | —NH$_2$ |
| 5.203 | | —CH$_2$CH$_2$Cl | (2-methoxyphenyl-CH(OCH$_3$)$_2$) | —NH$_2$ |
| 5.204 | | —CHCH$_2$Cl / C$_2$H$_5$ | (3-methyl-7-(methylthio)isobenzofuran-1(3H)-one) | —NH$_2$ |
| 5.205 | | —CHCH$_2$Cl / C$_6$H$_5$ | (4-cyclopropyl-6-methyl-2-(methylthio)pyrimidine) | —NH$_2$ |
| 5.206 | | —CH$_2$CH$_2$Cl | (3,5-difluoro-2-methoxyphenyl-COCH$_3$) | —NH$_2$ |
| 5.207 | | (ethylnorbornyl) | C$_6$F$_5$O— | —NH$_2$ |

TABLE 5-continued

Compounds of the formula III (III)

| Comp. No. | Process | R₇ | R₃ | R₂ |
|---|---|---|---|---|
| 5.208 | | —CHCH₂Cl<br>\|<br>CH₃ | 3,5-bis(CF₃)-phenyl-O— | —NH₂ |
| 5.209 | | —CHCH₂Cl<br>\|<br>CH₃ | (5-bromopyrimidin-2-yl)-S— | —NH₂ |
| 5.210 | | —CH₂CH₂Cl | 2,3-dimethylphenyl-O— | —NH₂ |
| 5.211 | | —CH₂CH₂Cl | 4-(tert-butyl)phenyl-O— | —NH₂ |
| 5.212 | | —CH₂CH₂Cl | 2,3,5,6-tetrafluorophenyl-S— | —NH₂ |
| 5.213 | | —CHCH₂Cl<br>\|<br>C₂H₅ | 4-(tert-butyl)phenyl-S— | —NH₂ |
| 5.214 | | —CHCH₂Cl<br>\|<br>C₂H₅ | 1-acetyl-2-methoxynaphthyl-O— | —NH₂ |
| 5.215 | | —CH₂CH₂Cl | (4,6-dimethoxypyrimidin-2-yl)-S— | —NH₂ |

TABLE 5-continued

Compounds of the formula III

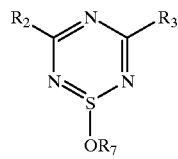

(III)

| Comp. No. | Process | R₇ | R₃ | R₂ |
|---|---|---|---|---|
| 5.216 | | —CH₂CH₂Cl | 4-chloro-1-naphthyloxy (with OCH₃ at 1, Cl at 4) | —NH₂ |
| 5.217 | | —CH₂CH₂Cl | 3,4-dimethoxy-phenyl with CH₃O substituent | —NH₂ |
| 5.218 | | —CH₂CH₂Cl | fluoro-methoxy-methoxyphenyl | —NH₂ |
| 5.219 | | —CHCH₂Cl (with C₆H₅) | phenoxy-methoxyphenyl | —NH₂ |
| 5.220 | | —CH₂CH₂Cl | benzyloxy-methoxyphenyl | —NH₂ |
| 5.221 | | —CH₂CH₂Cl | substituted isobenzofuranone with SCH₃ | —NH₂ |
| 5.222 | | —CH₂CH₂Cl | 2-methoxy-phenyl with SC₂H₅ | —NH₂ |
| 5.223 | | —CH₂CH₂Cl | 1-bromo-2-methoxynaphthyl | —NH₂ |

TABLE 5-continued

Compounds of the formula III

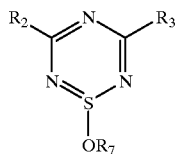

(III)

| Comp. No. | Process | R_7 | R_3 | R_2 |
|---|---|---|---|---|
| 5.224 | | —CH$_2$CH$_2$Cl | 2,4-dimethoxy-6-(methylthio)pyrimidine | —NH$_2$ |
| 5.225 | | 2-chloro-1-methylcyclohexyl | 6-(methylthio)naphthalen-2-yl | —NH$_2$ |
| 5.226 | | —CH$_2$CH$_2$Cl | methyl 1-methoxynaphthalene-2-carboxylate | —NH$_2$ |
| 5.227 | | —CHCH$_2$Cl<br>　　C$_2$H$_5$ | 2-isopropyl-4-methyl-6-(methylthio)pyrimidine | —NH$_2$ |
| 5.228 | | —CH$_2$CH$_2$Cl | 4-(heptyloxy)-1-methoxybenzene | —NH$_2$ |
| 5.229 | | —CH$_2$CH$_2$Cl | 4,6-dimethyl-2-(methylthio)pyrimidine | —NH$_2$ |
| 5.230 | | —CH$_2$CH$_2$Cl | 2,4-dichloro-1-methoxynaphthalene | —NH$_2$ |
| 5.231 | | —CH$_2$CH$_2$Cl | 1-cyclopentyl-4-methoxybenzene | —NH$_2$ |

TABLE 5-continued

Compounds of the formula III

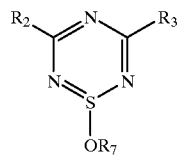

(III)

| Comp. No. | Process | R₇ | R₃ | R₂ |
|---|---|---|---|---|
| 5.232 | | —CH₂CH₂Cl | 2-(methylthio)pyrimidine | —NH₂ |
| 5.233 | | —CH₂CH₂Cl | 2,5-dimethyl-4-methoxyphenyl | —NH₂ |
| 5.234 | | —CH₂CH₂Cl | 3-methoxy-benzonitrile | —NH₂ |
| 5.235 | | —CH₂CH₂Cl | 1-methoxy-2-methylnaphthyl | —NH₂ |
| 5.236 | | —CH₂CH₂Cl | 5,6-dimethyl-3-(methylthio)-1,2,4-triazine | —NH₂ |
| 5.237 | | —CHCH₂Cl<br>   CH₃ | 2,3,5-trimethyl-4-methoxyphenyl | —NH₂ |
| 5.238 | | —CHCH₂Cl<br>   CH₃ | 3-hydroxy-3-methyl-4-methoxy-isobenzofuranone | —NH₂ |

TABLE 5-continued

Compounds of the formula III

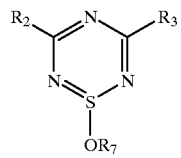
(III)

| Comp. No. | Process | R₇ | R₃ | R₂ |
|---|---|---|---|---|
| 5.239 | | —CH₂CH₂Cl | 4-CF₃-2-methyl-6-(methylthio)pyrimidin-5-yl | —NH₂ |
| 5.240 | | —CH₂CH₂Cl | 4-methyl-2-methyl-6-(methylthio)pyrimidin-5-yl | —NH₂ |
| 5.241 | | —CH(C₆H₅)CH₂Cl | 2-methoxy-6-[CH(OCH₃)₂]phenyl | —NH₂ |
| 5.242 | | —CH₂CH₂Cl | 1-methoxy-2-(COCH₃)naphthyl | —NH₂ |
| 5.243 | | —CH₂CH₂Cl | 4-C₂H₅-5-Cl-2-(n)C₃H₇-6-(methylthio)pyrimidin-5-yl | —NH₂ |
| 5.244 | | —CH₂CH₂Cl | 4-methoxy-α,α-diethylbenzyl | —NH₂ |
| 5.245 | | —CH₂CH₂Cl | 2-COCH₃-3,6-dimethoxy-4-methoxyphenyl | —NH₂ |
| 5.246 | | —CH₂CH₂Cl | 3,5-dichloro-2-(CH₃CO)-4-methoxyphenyl | —NH₂ |

TABLE 5-continued

Compounds of the formula III

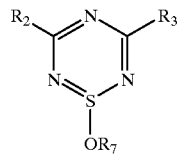

(III)

| Comp. No. | Process | $R_7$ | $R_3$ | $R_2$ |
|---|---|---|---|---|
| 5.247 | | —CH$_2$CH$_2$Cl | 4-methyl-6-(methylthio)pyrimidin-yl | —NH$_2$ |
| 5.248 | | —CH$_2$CH$_2$Cl | 1,4-dimethoxynaphthalen-2-yl | —NH$_2$ |
| 5.249 | | —CH$_2$CH$_2$Cl | 1-formyl-2-methoxynaphthalen-yl | —NH$_2$ |
| 5.250 | | —CH$_2$CH$_2$Cl | 5-methyl-2-(methylthio)pyrimidin-yl | —NH$_2$ |
| 5.251 | | —CH$_2$CH$_2$Cl | 3,5-bis(trifluoromethyl)-(methylthio)phenyl | —NH$_2$ |
| 5.252 | | —CH$_2$CH$_2$Cl | 2-phenoxy-6-(methylthio)phenyl | —NH$_2$ |
| 5.253 | | —CH$_2$CH$_2$Cl | 3-hydroxy-3-methyl-7-(methylthio)-3H-isobenzofuran-1-one-yl | —NH$_2$ |

TABLE 5-continued

Compounds of the formula III

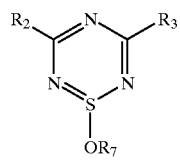

(III)

| Comp. No. | Process | $R_7$ | $R_3$ | $R_2$ |
|---|---|---|---|---|
| 5.254 | | —CH$_2$CH$_2$Cl | 4-methyl-6-(trifluoromethyl)pyrimidin-2-ylthio | —NH$_2$ |
| 5.255 | | —CH$_2$CH$_2$Cl | naphthalen-1-ylthio | —NH$_2$ |
| 5.256 | | —CH$_2$CH$_2$Cl | 4-(trifluoromethoxy)phenylthio | —NH$_2$ |
| 5.257 | | —CH$_2$CH$_2$Cl | 4-acetyl-1-naphthyloxy | —NH$_2$ |
| 5.258 | | —CH$_2$CH$_2$Cl | 6-bromo-1-naphthyloxy | —NH$_2$ |
| 5.259 | | —CH$_2$CH$_2$Cl | 4,6-dimethyl-5-nitropyrimidin-2-ylthio | —NH$_2$ |
| 5.260 | | —CH$_2$CH$_2$Cl | 3-(trifluoromethyl)phenylthio | —NH$_2$ |

TABLE 5-continued
Compounds of the formula III
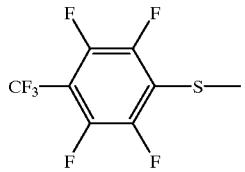
(III)
| Comp. No. | Process | R₇ | R₃ | R₂ |
|---|---|---|---|---|
| 5.261 | | —CH₂CH₂Cl | 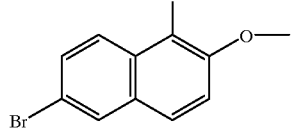 | —NH₂ |
| 5.262 | | —CH₂CH₂Cl | 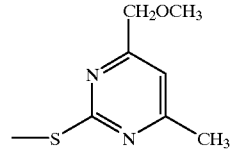 | —NH₂ |
| 5.263 | | —CH₂CH₂Cl | 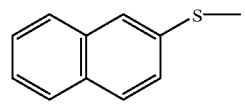 | —NH₂ |
| 5.264 | | —CH₂CH₂Cl | 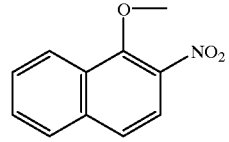 | —NH₂ |
| 5.265 | | —CH₂CH₂Cl | 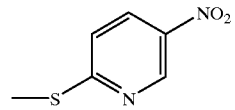 | —NH₂ |
| 5.266 | | —CH₂CH₂Cl | 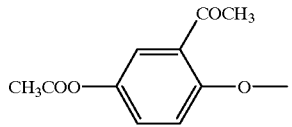 | —NH₂ |
| 5.267 | | —CH₂CH₂Cl | 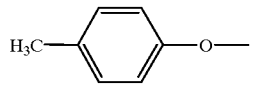 | —NH₂ |
| 5.268 | | —CH₂CH₂Cl | 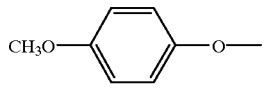 | —NH₂ |
| 5.269 | | —CH₂CH₂Cl | CH₃O—⟨⟩—O— | —NH₂ |

TABLE 5-continued

Compounds of the formula III

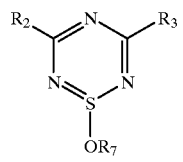

(III)

| Comp. No. | Process | $R_7$ | $R_3$ | $R_2$ |
|---|---|---|---|---|
| 5.270 | | —CH$_2$CH$_2$Cl | 5-F, 2-OCH$_3$, 1-COCH$_3$-phenyl | —NH$_2$ |
| 5.271 | | —CH$_2$CH$_2$Cl | 3-F, 4-OCH$_3$, 6-OCH$_3$-phenyl | —NH$_2$ |
| 5.272 | | —CH$_2$CH$_2$Cl | 5-OCH$_3$, 2-OCH$_3$, 1-COOCH$_3$-phenyl | —NH$_2$ |
| 5.273 | | —CH$_2$CH$_2$Cl | 5-CH$_3$, 3-CN, 2-SCH$_3$-pyridyl | —NH$_2$ |
| 5.274 | | —CH$_2$CH$_2$Cl | 5-CF$_3$, 2-SCH$_3$-pyridyl | —NH$_2$ |
| 5.275 | | —CH$_2$CH$_2$Cl | 3-CF$_3$, 2-SCH$_3$-pyridyl | —NH$_2$ |
| 5.276 | | —CH$_2$CH$_2$Cl | 5-OCH$_3$-pyrimidyl | —NH$_2$ |
| 5.277 | | —CH$_2$CH$_2$Cl | 4-NC-C$_6$H$_4$-CO-C$_6$H$_4$-S— | —NH$_2$ |
| 5.278 | | —CH$_2$CH$_2$Cl | 4-O$_2$N-C$_6$H$_4$-CH$_2$-C$_6$H$_4$-S— | —NH$_2$ |

TABLE 5-continued

Compounds of the formula III $$\text{(III)}$$

| Comp. No. | Process | R$_7$ | R$_3$ | R$_2$ |
|---|---|---|---|---|
| 5.279 | | —CH$_2$CH$_2$Cl | 2-Cl, 6-(SCH$_3$), CN-phenyl | —NH$_2$ |
| 5.280 | | —CH$_2$CH$_2$Cl | 4-F, (SCH$_3$)-phenyl | —NH$_2$ |
| 5.281 | | —CH$_2$CH$_2$Cl | 2-OCH$_3$, (SCH$_3$)-phenyl | —NH$_2$ |
| 5.282 | | —CH$_2$CH$_2$Cl | 3,5-(CH$_3$)$_2$, (SCH$_3$)-phenyl | —NH$_2$ |
| 5.283 | | —CH$_2$CH$_2$Cl | 2-F, (SCH$_3$)-phenyl | —NH$_2$ |
| 5.284 | | —CH$_2$CH$_2$Cl | 2,5-(CH$_3$)$_2$, 4-OCH$_3$-phenyl | —NH$_2$ |
| 5.285 | | —CH$_2$CH$_2$Cl | 3,5-(OCH$_3$)$_2$-phenyl | —NH$_2$ |
| 5.286 | | trans-2-(OC$_3$H$_7$(n))cyclohexyl | C$_6$F$_5$O— | —NH$_2$ |

TABLE 5-continued

Compounds of the formula III

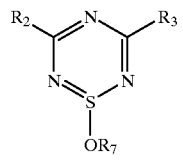

(III)

| Comp. No. | Process | R₇ | R₃ | R₂ |
|---|---|---|---|---|
| 5.287 | | cycloheptyl with CH₃ and CH₃S substituents | $C_6F_5O-$ | $-NH_2$ |
| 5.288 | | indanyl with $OC_2H_5$ and CH₃ | $C_6F_5O-$ | $-NH_2$ |
| 5.289 | | cyclopentyl with CH₃ and OCH₃ | $C_6F_5O-$ | $-NH_2$ |
| 5.290 | | cyclooctyl with CH₃ and SC₃H₇(n) | $C_6F_5O-$ | $-NH_2$ |
| 5.291 | | tetrahydroindanyl with two CH₃ | $C_6F_5O-$ | $-NH_2$ |
| 5.292 | | tetrahydroindanyl with CH₃ and C₃H₇(n) | $C_6F_5O-$ | $-NH_2$ |
| 5.293 | | tetrahydroindanyl with CH₃ and C₂H₅ | $C_6F_5O-$ | $-NH_2$ |
| 5.294 | | cyclopentenyl with three CH₃ | $C_6F_5O-$ | $-NH_2$ |
| 5.295 | | tetrahydronaphthyl with two CH₃ | $C_6F_5O-$ | $-NH_2$ |

TABLE 5-continued

Compounds of the formula III

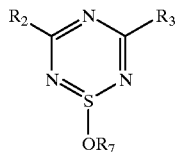

(III)

| Comp. No. | Process R$_7$ | R$_3$ | R$_2$ |
|---|---|---|---|
| 5.296 | —⟨cyclohexyl⟩—⟨cyclohexyl⟩ | C$_6$F$_5$O— | —NH$_2$ |
| 5.297 | cyclohexyl with C$_2$H$_5$, C$_2$H$_5$, C$_2$H$_5$ substituents | C$_6$F$_5$O— | —NH$_2$ |
| 5.298 | cyclohexyl with CH$_3$, CH$_3$, CH$_3$, CH$_3$ substituents | C$_6$F$_5$O— | —NH$_2$ |
| 5.299 | cyclohexyl with C$_4$H$_9$(n) | C$_6$F$_5$O— | —NH$_2$ |
| 5.300 | cyclohexyl with CH$_3$, CH$_3$, CH$_3$ | C$_6$F$_5$O— | —NH$_2$ |
| 5.301 | cyclohexyl—Si(CH$_3$)$_3$ | C$_6$F$_5$O— | —NH$_2$ |
| 5.302 | cyclohexyl with CH(CH$_3$)$_2$ | C$_6$F$_5$O— | —NH$_2$ |
| 5.303 | cyclohexyl—CF$_3$ | C$_6$F$_5$O— | —NH$_2$ |

TABLE 5-continued

Compounds of the formula III

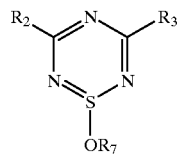

(III)

| Comp. No. | Process R$_7$ | R$_3$ | R$_2$ |
|---|---|---|---|
| 5.304 | 2-(SCH$_3$)cyclohexyl | C$_6$F$_5$O— | —NH$_2$ |
| 5.305 | 2-(CH$_2$C$_6$H$_5$)cyclohexyl | C$_6$F$_5$O— | —NH$_2$ |
| 5.306 | 2-(CH(CH$_3$)$_2$)cyclohexyl | C$_6$F$_5$O— | —NH$_2$ |
| 5.307 | 2-(C$_2$H$_5$)cyclopentyl | C$_6$F$_5$O— | —NH$_2$ |
| 5.308 | 2,2-(CH$_3$)$_2$cyclopentyl | C$_6$F$_5$O— | —NH$_2$ |
| 5.309 | 2,2,4-(CH$_3$)$_3$cyclopentyl | C$_6$F$_5$O— | —NH$_2$ |
| 5.310 | 2,4,4-(CH$_3$)$_3$cyclopentyl | C$_6$F$_5$O— | —NH$_2$ |
| 5.311 | 2-(C$_6$H$_{13}$(n))cyclopentyl | C$_6$F$_5$O— | —NH$_2$ |
| 5.312 | 3-(C(CH$_3$)$_2$C$_2$H$_5$)cyclopentyl | C$_6$F$_5$O— | —NH$_2$ |

TABLE 5-continued
Compounds of the formula III
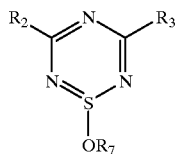
(III)
| Comp. No. | Process | $R_7$ | $R_3$ | $R_2$ |
|---|---|---|---|---|
| 5.313 | | ![](cyclopentane with 4 CH3 groups) | $C_6F_5O-$ | $-NH_2$ |
| 5.314 | | ![](cyclopentane with 4 CH3 groups) | $C_6F_5O-$ | $-NH_2$ |
| 5.315 | $d_4$ | $-(CH_2)_3Si(CH_3)_3$ | $C_6F_5O-$ | $-NH_2$ |
| 5.316 | $d_4$ | $-C(CH_3)_3$ | $C_6F_5O-$ | $-NH_2$ |
| 5.317 | $c_5$ | $CH_3$ | $C_6F_5O-$ | $-NH_2$ |
| 5.318 | $c_5$ | $CH_3$ | | $-NH_2$ |
| 5.319 | $d_4$ | ![]($-CH_2CH_2-N$ dimethylmaleimide) | $C_6F_5O-$ | $-NH_2$ |
| 5.320 | $d_4$ | ![]($-CH_2-$ 2-nitro-3-chlorophenyl) | $C_6F_5O-$ | $-NH_2$ |
| 5.321 | $d_4$ | $-CH_2Si(CH_3)_3$ | $C_6F_5O-$ | $-NH_2$ |

TABLE 5-continued

Compounds of the formula III

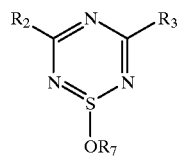

(III)

| Comp. No. | Process | $R_7$ | $R_3$ | $R_2$ |
|---|---|---|---|---|
| 5.322 | $d_4$ | trans-4-C(CH$_3$)$_3$-cyclohexyl | $C_6F_5O$— | —NHC$_2$H$_5$ |
| 5.323 | $d_4$ | cis-4-C(CH$_3$)$_3$-cyclohexyl | $C_6F_5O$— | —NHCH$_3$ |
| 5.324 | $d_4$ | trans-2-CH$_2$CH$_2$CN-cyclopentyl | $C_6F_5O$— | —NH$_2$ |
| 5.325 | $d_4$ | cis-2-CH$_2$CH$_2$CN-cyclopentyl | $C_6F_5O$— | —NH$_2$ |
| 5.326 | $d_4$ | cis-4-CH$_3$-cyclohexyl | $C_6F_5O$— | —NH$_2$ |
| 5.327 | $d_4$ | trans-4-CH$_3$-cyclohexyl | $C_6F_5O$— | —NH$_2$ |
| 5.328 | $d_4$ | —CH(Si(CH$_3$)$_3$)—CH=CH$_2$ | $C_6F_5O$— | —NH$_2$ |
| 5.329 | $d_4$ | —CH(CH$_3$)—Si(CH$_3$)$_3$ | $C_6F_5O$— | —NH$_2$ |
| 5.330 | q | —CH$_3$ | $C_6F_5O$— | —NH$_2$ |
| 5.331 | | —CH(CH$_3$)COOCH$_3$ | $C_6F_5O$— | —NH$_2$ |
| 5.332 | $c_5$ | —CH(C$_2$H$_5$)(C$_3$H$_7$(n)) | $C_6F_5O$— | —NH$_2$ |
| 5.333 | $d_4$ | —CH$_2$CH$_2$Cl | 2,4-dichloro-phenoxy-methyl | —NH$_2$ |

TABLE 5-continued

Compounds of the formula III

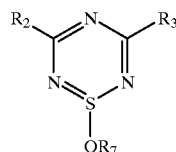
(III)

| Comp. No. | Process | R₇ | R₃ | R₂ |
|---|---|---|---|---|
| 5.334 | | —CH₂CH₂S—cyclohexyl | 2,5-difluoro-methoxyphenyl | —NH₂ |
| 5.335 | q | —CH₂CH₂Cl | CF₃CH₂O— | —NH₂ |
| 5.336 | q | —CH₂CH₂Cl | (CF₃)₂CHO— | —NH₂ |
| 5.337 | q | —CH₂CH₂Cl | CF₃CCl₂CH₂O— | —NH₂ |
| 5.338 | d₄ | cyclohexyl | 4-methoxy-2-nitrophenyl | —NH₂ |
| 5.339 | c₅ | —CH[CH₂CH(CH₃)₂]₂ | C₆F₅O— | —NH₂ |
| 5.340 | c₅ | —CH(C₂H₅)(C₃H₇(n)) | 2,5-difluoro-methoxyphenyl | —NH₂ |
| 5.341 | d₄ | trans-4-tert-butylcyclohexyl | 2,3,5,6-tetrafluoro-4-methoxyphenyl | —NH₂ |
| 5.342 | d₄ | trans-4-methylcyclohexyl | 2,3,5,6-tetrafluoro-4-methoxyphenyl | —NH₂ |
| 5.343 | d₄ | —CH₂Si(CH₃)₃ | 2,3,5,6-tetrafluoro-4-methoxyphenyl | —NH₂ |

TABLE 5-continued

Compounds of the formula III

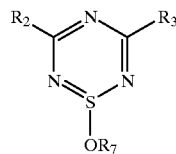

(III)

| Comp. No. | Process | R₇ | R₃ | R₂ |
|---|---|---|---|---|
| 5.344 | d₄ | (trans-decalin with methyl, stereochem) | $C_6F_5O$— | —$NH_2$ |
| 5.345 | d₄ | (decalin with methyl, stereochem) | $C_6F_5O$— | —$NH_2$ |
| 5.346 | d₄ | (decalin with methyl, stereochem) | $C_6F_5O$— | —$NH_2$ |
| 5.347 | | (isopropyl-m-tolyl group) | $C_6F_5O$— | —$NH_2$ |
| 5.348 | | (methyl-cyclohexanone ethylene ketal) | $C_6F_5O$— | —$NH_2$ |
| 5.349 | d₄ | (norbornenyl group) | $C_6F_5O$— | —$NH_2$ |
| 5.350 | d₄ | (norbornenyl group) | $C_6F_5O$— | —$NH_2$ |
| 5.351 | d₄ | (norbornenyl-methyl group) | $C_6F_5O$— | —$NH_2$ |

TABLE 5-continued

Compounds of the formula III

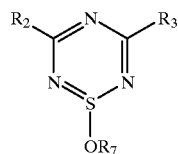

(III)

| Comp. No. | Process | $R_7$ | $R_3$ | $R_2$ |
|---|---|---|---|---|
| 5.352 | $d_4$ | (1R,2S,5R)-2,6,6-trimethylbicyclo[3.1.1]heptyl | $C_6F_5O-$ | $-NH_2$ |
| 5.353 | | 2,6,6-trimethylbicyclo[3.1.1]heptyl | $C_6F_5O-$ | $-NH_2$ |
| 5.354 | | 2,6,6-trimethylbicyclo[3.1.1]hept-2-enyl | $C_6F_5O-$ | $-NH_2$ |
| 5.355 | $d_4$ | trans-4-(trifluoromethyl)cyclohexyl | $C_6F_5O-$ | $-NH_2$ |
| 5.356 | $d_4$ | 2-(trifluoromethyl)cyclohexyl, Diastereomer 1 | $C_6F_5O-$ | $-NH_2$ |
| 5.357 | $d_4$ | $-CH_2-$(2,3-dichlorophenyl) | $C_6F_5O-$ | $-NH_2$ |
| 5.358 | $d_4$ | $-CH_2-C(CH_3)(CH_2CH_2CN)_2$ | $C_6F_5O-$ | $-NH_2$ |
| 5.359 | $d_4$ | 2-(cyanomethyl)cyclopentyl | $C_6F_5O-$ | $-NH_2$ |

TABLE 5-continued

Compounds of the formula III

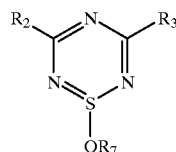

(III)

| Comp. No. | Process | R₇ | R₃ | R₂ |
|---|---|---|---|---|
| 5.360 | d₄ | (1,2-cyclopentyl with CH₂CN) | C₆F₅O— | —NH₂ |
| 5.361 | | 2-(OCHF₂)-4-isopropyl-5-NO₂-fluorophenyl (–CH(CH₃)–) | C₆F₅O— | —NH₂ |
| 5.362 | | –CH(C₂H₅)–(4-phenoxyphenyl) | C₆F₅O— | —NH₂ |
| 5.363 | d₄ | –CH(CH₃)–CH₂–(2-OCH₃-phenyl) | C₆F₅O— | —NH₂ |
| 5.364 | d₄ | –CH₂–C(C₃H₇(n))(CN)–(2,4-dichlorophenyl) | C₆F₅O— | —NH₂ |
| 5.365 | | –CH(CH₂)₉ (cycloundecyl) | C₆F₅O— | —NH₂ |
| 5.366 | d₄ | —CH₂CH₂Cl | 2,3,5,6-tetrafluoro-4-methoxyphenyl | —NH₂ |
| 5.367 | | –CH(CH₂)₆ (cyclooctyl) | C₆F₅O— | —NH₂ |

TABLE 5-continued

Compounds of the formula III

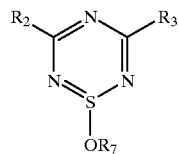

(III)

| Comp. No. | Process | $R_7$ | $R_3$ | $R_2$ |
|---|---|---|---|---|
| 5.368 | | —CH((CH$_2$)$_{11}$) (cyclododecyl) | $C_6F_5O$— | —$NH_2$ |
| 5.369 | $d_4$ | —CH$_2$-(3-CF$_3$-C$_6$H$_4$) | $C_6F_5O$— | —$NH_2$ |
| 5.370 | | —CH$_2$CH$_2$C$_6$F$_5$ | $C_6F_5O$— | —$NH_2$ |
| 5.371 | | —CH$_2$-cyclohexyl | $C_6F_5O$— | —$NH_2$ |
| 5.372 | | —CH(C$_6$H$_5$)(4-Cl-C$_6$H$_4$) | $C_6F_5O$— | —$NH_2$ |
| 5.373 | | 2-methyl-8a-cyano-decahydronaphthyl | $C_6F_5O$— | —$NH_2$ |
| 5.374 | | 2-methyl-8a-cyano-decahydronaphthyl (isomer) | $C_6F_5O$— | —$NH_2$ |
| 5.375 | $d_4$ | trans-4-tert-butylcyclohexyl | 2,3,5,6-tetrafluoro-4-methoxyphenyl-O— | —$NH_2$ |
| 5.376 | $d_4$ | 3,3,5,5-tetramethylcyclohexyl | 2,3,5,6-tetrafluoro-4-methoxyphenyl-O— | —$NH_2$ |

TABLE 5-continued

Compounds of the formula III

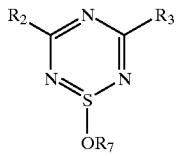

(III)

| Comp. No. | Process | R₇ | R₃ | R₂ |
|---|---|---|---|---|
| 5.377 | d₄ | [CF₃-cyclohexyl, Diastereomer 2] | [2,3,5,6-tetrafluorophenyl-O-] | —NH₂ |

Physical data of compounds in Table 5:

| Comp. No. | Physical data |
|---|---|
| 5.1 | Melting point 152–153° C. |
| 5.2 | ¹H-NMR: 6.8–7.3 ppm (8H); 3.7–4.0 ppm (2H); 3.2–3.6 ppm (2H); 2.8–3.0 ppm (5H); 0.8–1.6 ppm (7H) |
| 5.3 | Melting point 163–164° C. |
| 5.4 | Melting point 167–168° C. |
| 5.5 | Melting point 141–142° C. |
| 5.6 | ¹H-NMR: 3.8–4.0 ppm (2H); 3.6 ppm (2H); 3.2 ppm (3H); 3.0 ppm (3H) |
| 5.7 | Melting point 145–146° C. |
| 5.8 | Melting point 148–149° C. |
| 5.10 | ¹H-NMR: 6.8–7.3 ppm (8H); 5.3–5.5 ppm (1H); 4.0–4.3 ppm (1H); 3.8 ppm (2H); 2.9 ppm (2H) |
| 5.11 | ¹H-NMR: 7.1–7.4 ppm (5H); 3.9 ppm (2H); 3.6 ppm (2H); 3.13 ppm (3H); 3.05 ppm (3H) |
| 5.13 | Melting point 127–128° C. |
| 5.14 | Melting point 140–141° C. |
| 5.15 | ¹H-NMR: 6.5–7.2 ppm (3H); 5.3 ppm (1H); 3.6–4.0 ppm (4H); 1.45 ppm (9H) |
| 5.17 | ¹H-NMR: 7.1–7.5 ppm (3H); 3.6–4.0 ppm (12H) |
| 5.19 | Melting point 179–180° C. |
| 5.22 | ¹H-NMR: 7.2–8.0 ppm (4H); 4.3 ppm (2H); 3.8–4.1 ppm (2H); 3.6 ppm (2H); 3.1 ppm (3H); 3.0 ppm (3H); 1.3 ppm (3H) |
| 5.23 | ¹H-NMR: 6.9–7.2 ppm (3H); 3.8–4.0 ppm (2H); 3.6 ppm (2H); 3.15 ppm (3H); 3.0 ppm (3H) |
| 5.28 | Melting point 130–131° C. |
| 5.30 | Melting point 207–208° C. |
| 5.31 | Melting point 159–160° C. (decomposition) |
| 5.35 | ¹H-NMR: 6.8–7.4 ppm (8H); 5.5 ppm (1H); 4.7 ppm (2H); 4.2 ppm (1H); 1.9 ppm (4H); 1.4–1.7 ppm (4H) |
| 5.38 | Melting point 163–164° C. |
| 5.42 | Melting point 181–182° C. |
| 5.45 | Melting point 98–99° C. |
| 5.46 | Melting point 147–148° C. |
| 5.47 | Melting point 125–126° C. |
| 5.48 | Melting point 161–162° C. |
| 5.51 | Melting point 87–88° C. |
| 5.52 | Melting point 138–139° C. |
| 5.54 | Melting point 215–216° C. |
| 5.55 | ¹H-NMR: 6.8–7.1 ppm (3H); 3.8–4.0 ppm (2H); 3.6 ppm (2H); 3.15 ppm (3H); 3.0 ppm (3H) |
| 5.58 | Melting point 202–203° C. |
| 5.59 | Melting point 123–124° C. |
| 5.60 | ¹H-NMR: 6.9–7.2 ppm (3H); 3.7–4.0 ppm (2H); 3.6 ppm (2H); 3.4 ppm (2H); 1.6 ppm (2H); 0.9 ppm (3H) |
| 5.64 | Melting point 112–113° C. |
| 5.65 | Melting point 103–104° C. |
| 5.67 | Melting point 176–177° C. |
| 5.71 | Melting point 204–206° C. (decomposition) |
| 5.72 | Melting point 178–179° C. |
| 5.73 | Melting point 173–174° C. |
| 5.74 | ¹H-NMR: 6.8–7.3 ppm (4H); 4.3 ppm (1H); 4.0 ppm (1H); 3.8 ppm (3H); 2.8–3.0 ppm (3H); 1.2–2.2 ppm (12H) |
| 5.75 | Melting point 167–168° C. |
| 5.76 | Melting point 175–176° C. (decomposition) |
| 5.78 | Melting point 165–166° C. |
| 5.83 | Oil |
| 5.84 | Melting point 109–110° C. |
| 5.85 | Melting point 175–176° C. (decomposition) |
| 5.86 | Melting point 165–166° C. |
| 5.88 | Melting point 115–116° C. |
| 5.89 | Melting point 91–92° C. |
| 5.90 | Melting point 179–180° C. (decomposition) |
| 5.92 | Melting point 212–213° C. |
| 5.94 | ¹H-NMR: 6.9–7.3 ppm (4H); 3.8–4.6 ppm (6H); 3.8 ppm (3H); 0.7–2.9 ppm (22H) |
| 5.96 | Melting point 108–109° C. |
| 5.98 | Melting point 138–139° C. |
| 5.101 | Melting point 182–183° C. |
| 5.102 | Melting point 145–146° C. |
| 5.103 | Melting point 183–185° C. |
| 5.107 | Melting point 190–191° C. |
| 5.108 | Melting point 204–205° C. |
| 5.110 | Melting point 124–125° C. |
| 5.113 | ¹H-NMR: 6.5–7.2 ppm (3H); 5.3 ppm (1H); 3.4 ppm (3H); 1.45 ppm (9H) |
| 5.114 | Melting point 137–138° C. |
| 5.116 | Melting point 216–217° C. |
| 5.117 | Melting point 161–162° C. |
| 5.119 | Melting point 194–196° C. (decomposition) |
| 5.120 | Melting point 156–157° C. |
| 5.121 | ¹H-NMR: 7.3 ppm (5H); 7.1 ppm (1H); 6.9 ppm (2H); 5.6 ppm (1H); 4.7 ppm (2H); 4.2 ppm (1H); 3.2–3.4 ppm (5H); 1.2 ppm (3H) |
| 5.122 | Melting point 103–104° C. |
| 5.125 | Melting point 162–163° C. |
| 5.126 | Melting point 197–198° C. |

-continued

| Comp. No. | Physical data |
|---|---|
| 5.127 | Melting point 118–119° C. |
| 5.129 | Melting point 140–141° C. |
| 5.130 | Melting point 167–168° C. |
| 5.131 | Melting point 140–141° C. |
| 5.132 | Melting point 147–148° C. |
| 5.133 | Melting point 139–140° C. |
| 5.135 | $^{13}$C-NMR: 166.0 ppm; 165.2 ppm; 75.6 ppm; 68.5 ppm; 66.2 ppm; 27.8 ppm; 25.6 ppm; 22.9 ppm |
| 5.138 | Melting point 132–133° C. |
| 5.141 | Melting point 115–116° C. |
| 5.143 | Melting point 105–106° C. |
| 5.144 | Melting point 183–184° C. |
| 5.145 | Melting point 106–107° C. |
| 5.146 | Melting point 182–184° C. |
| 5.147 | Melting point 198–199° C. |
| 5.148 | Melting point 108–109° C. |
| 5.150 | Melting point 115–116° C. |
| 5.151 | Melting point 122–123° C. |
| 5.152 | Melting point 122–123° C. |
| 5.153 | Oil |
| 5.154 | Melting point 178–180° C. (decomposition) |
| 5.156 | Melting point 148–149° C. |
| 5.157 | Melting point 162–163° C. |
| 5.160 | Melting point 103–104° C. |
| 5.161 | Melting point 120–121° C. |
| 5.162 | Melting point 117–118° C. |
| 5.168 | Melting point 127–128° C. |
| 5.172 | Melting point 148–149° C. |
| 5.174 | Melting point 125–126° C. |
| 5.176 | Melting point 139–140° C. |
| 5.177 | $^{1}$H-NMR: 8.3 ppm (1H); 7.4 ppm (1H); 7.2 ppm (1H); 6.8 ppm (1H); 6.5 ppm (1H); 3.9 ppm (2H); 3.6 ppm (2H); 2.5 ppm (3H) |
| 5.178 | $^{1}$H-NMR: 7.1–7.4 ppm (3H); 3.8–4.0 ppm (2H); 3.6 ppm (2H); 3.3 ppm (2H); 1.4–1.7 ppm (2H); 0.8–1.0 ppm (3H) |
| 5.180 | Melting point 123–124° C. |
| 5.182 | Melting point 138–140° C. |
| 5.183 | $^{1}$H-NMR: 7.7 ppm (1H); 7.1–7.3 ppm (2H); 5.5 ppm (1H); 3.6–4.2 ppm (4H); 3.5 ppm (2H); 3.2 ppm (2H); 1.6 ppm (3H); 1.2 ppm (3H); 0.9 ppm (3H) |
| 5.184 | Melting point 146–147° C. |
| 5.188 | Melting point 123–124° C. |
| 5.192 | Melting point 182–183° C. |
| 5.193 | $^{1}$H-NMR: 7.7 ppm (1H); 7.2–7.3 ppm (2H); 5.5 ppm (1H); 3.6–4.2 ppm (4H); 3.1 ppm (3H); 2.9 ppm (3H); 1.6 ppm (3H) |
| 5.195 | Melting point 167–168° C. |
| 5.197 | Melting point 177–178° C. |
| 5.207 | Melting point 157–158° C. |
| 5.315 | Melting point 111–112° C. |
| 5.316 | Melting point 145–146° C. |
| 5.317 | Melting point 137–139° C. |
| 5.318 | Melting point 171–173° C. |
| 5.319 | Melting point 146–147° C. (decomposition) |
| 5.320 | Melting point 175–176° C. (decomposition) |
| 5.321 | Melting point 179–180° C. |
| 5.322 | Melting point 210–211° C. (decomposition) |
| 5.323 | solid |
| 5.324 | Melting point 112° C. (decomposition) |
| 5.325 | Melting point 116° C. (decomposition) |
| 5.326 | Melting point 118–119° C. |
| 5.327 | Melting point 148–149° C. |
| 5.328 | Melting point 129–130° C. (decomposition) |
| 5.329 | Melting point 157–158° C. (decomposition) |
| 5.330 | Melting point 142–143° C. |
| 5.332 | Melting point 142–143° C. |
| 5.333 | Melting point 141–142° C. |
| 5.334 | Melting point 124–125° C. |
| 5.335 | Melting point 137–140° C. |
| 5.336 | Resin; MS: [M$^+$] 360/362 |
| 5.337 | Melting point 162–163° C. |
| 5.338 | Melting point 181–182° C. |
| 5.339 | Melting point 112–114° C. |
| 5.340 | Melting point 171–172° C. |
| 5.341 | Melting point 154–155° C. |

-continued

| Comp. No. | Physical data |
|---|---|
| 5.342 | Melting point 178–179° C. |
| 5.343 | Melting point 223–224° C. |
| 5.344 | Melting point 163–164° C. |
| 5.345 | Melting point 167–168° C. |
| 5.346 | Melting point 117–118° C. |
| 5.349 | Melting point 151–152° C. |
| 5.350 | Melting point 146–147° C. |
| 5.351 | Melting point 124–125° C. |
| 5.352 | Melting point 134–135° C. |
| 5.355 | Melting point 164–165° C. |
| 5.356 | Melting point 145–146° C. |
| 5.357 | Melting point 186–187° C. |
| 5.358 | Melting point 169–170° C. |
| 5.359 | Melting point 164–165° C. |
| 5.360 | Melting point 136–137° C. |
| 5.363 | Melting point 183–184° C. |
| 5.364 | Melting point 118–119° C. |
| 5.366 | Melting point 131–132° C. (decomposition) |
| 5.369 | Melting point 146–147° C. |
| 5.375 | Melting point 188–189° C. |
| 5.376 | Melting point >225° C. |
| 5.377 | Melting point 156–157° C. |

Example H17

Preparation of 3-amino-1-dipropylamino-5-(2',5'-difluorophenoxy)thiatriazine (Comp. No. 6.48)

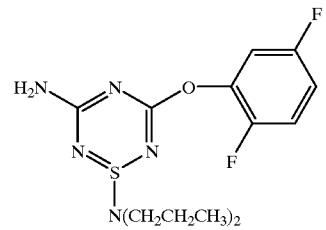

1.60 g (0.005 mol) of 3-amino-1-(β-chloroethoxy)-5-(2',5'-difluorophenoxy)thiatriazine are stirred in 20 ml of toluene with 0.53 9 (0.00525 mol) of dipropylamine at 70° C. for 3.5 hours. After the reaction mixture has cooled, it is extracted with ethyl acetate and water. On concentration of the reaction mixture on a rotary evaporator, the desired product crystallizes out. It is filtered off with suction, washed and dried. Yield 1.42 g (83% of theory); melting point 184–185° C.

Analysis: $C_{14}H_{19}F_2N_5OS$;

|  | calculated [%] | found [%] |
|---|---|---|
| C | 48.97 | 48.92 |
| H | 5.58 | 5.61 |
| N | 20.39 | 20.24 |

Example H18

Preparation of 3-amino-1-decahydroquinolinyl-5-(2′,6′-difluorophenoxy)thiatriazine (Compound No. 6.3)

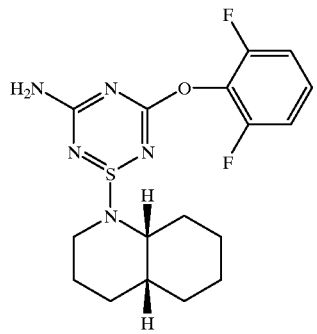

1.00 g (0.0027 mol) of 1-(trans-2′-chlorocyclohexanolyl)-3-amino-5-(2′,6′-difluorophenoxy)thiatriazine is heated at 80–90° C. with 0.49 g (0.0035 mol of decahydroquinoline (cis/trans mixture) in 20 ml of toluene until the conversion is complete. Thereafter, the mixture is concentrated on a rotary evaporator, the residue is dissolved in ethyl acetate, the clouding formed is filtered off with suction and the filtrate is concentrated. Recrystallization of the resulting residue from a mixture of ethyl acetate/hexane gives 0.85 g (82% of theory) of the desired product of melting point 194–195° C. (decomposition). The $^1$H— and $^{13}$C-NMR spectra are in agreement with the structure of the desired product.

Example H19

Preparation of 3-amino-5-pentafluorophenoxy-1-(piperidin-1-yl)thiatriazine (Compound No. 6.53)

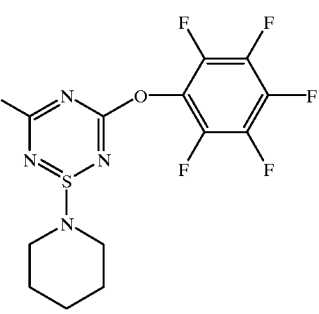

8.3 ml of 2N sodium hydroxide solution (0.0166 mol) and 2.2 g of trimethylamine solution (40% in water) (0.015 mol) are added to a mixture of 3.5 9 of 3-amino-5-chloro-1-(piperidin-1-yl)thiatriazine (0.015 mol) and 3.0 g of pentafluorophenol (0.0165 mol) in 100 ml of methylene chloride. After the mixture has been stirred for 20 hours, the organic phase is dried over sodium sulfate and filtered over silica gel, with subsequent elution with a 50/50 hexane/ethyl acetate mixture. After the collected fractions have been evaporated and the residue has been stirred in pentane, the desired product is isolated as slightly yellowish crystals of melting point 104–105° C. (decomposition).

The compounds listed in the following Table 6 can be prepared analogously to Examples H17 to H19.

TABLE 6

Compounds of the formula II

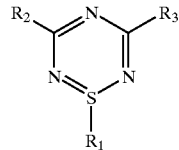

(II)

| Comp. No. | R$_1$ | R$_3$ | R$_2$ | Physical data |
|---|---|---|---|---|
| 6.1 | —NHCH$_2$CH$_2$CH$_3$ | 2,5-difluorophenoxy | —NH$_2$ | Melting point 132–133° C. |
| 6.2 | 3,4-dihydro-2H-pyridin-1-yl | 2,5-difluorophenoxy | —N(CH$_3$)$_2$ | $^1$H-NMR: 6.8–7.1 ppm (3H); 5.6–5.8 ppm (2H); 3.0–5.5 ppm (10 H); 2.2 ppm (2H) |

TABLE 6-continued

Compounds of the formula II

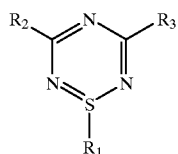

(II)

| Comp. No. | R₁ | R₃ | R₂ | Physical data |
|---|---|---|---|---|
| 6.3 | (decahydroquinoline with N-CH₃, 4aH, 8aH) | 2,6-difluoro-phenoxy | —NH₂ | Melting point 194–195° C. (decomposition) |
| 6.4 | —N(CH₃)(CH₂)₆CH₃ | 2,5-difluoro-phenoxy | —NH₂ | Melting point 121–122° C. |
| 6.5 | 2,6-dimethylmorpholin-4-yl | 2,5-difluoro-phenoxy | —NH₂ | Melting point 170–171° C. |
| 6.6 | octahydroindolizinyl (Diastereomer 1) | $C_6F_5O$— | —NH₂ | ¹³C-NMR: 165.7 ppm; 165.0 ppm; 63.7 ppm; 44.8 ppm; 43.3 ppm; 34.1 ppm; 32.2 ppm; 31.5 ppm; 24.5 ppm. |
| 6.7 | —N(CH₃)(C₆H₁₁(c)) | $C_6F_5O$— | —NH₂ | Melting point 201–202° C. |
| 6.8 | 2,6-dimethylmorpholin-4-yl | $C_6F_5O$— | —NH₂ | Melting point 162–163° C. |
| 6.9 | 4-trifluoromethylpiperidin-1-yl | $C_6F_5O$— | —NH₂ | Melting point 147–148° C. (decomposition) |

TABLE 6-continued

Compounds of the formula II

(II)

| Comp. No. | $R_1$ | $R_3$ | $R_2$ | Physical data |
|---|---|---|---|---|
| 6.10 | (pyrrolizidine, Diastereomer 2) | $C_6F_5O-$ | $-NH_2$ | $^{13}$C-NMR: 165.7 ppm. 165.0 ppm; 63.7 ppm. 45.1 ppm; 43.6 ppm; 34.4 ppm; 32.1 ppm; 31.6 ppm; 24.7 ppm |
| 6.11 | (2-methyl-1,2,3,4-tetrahydroisoquinolin-2-yl) | 2,5-difluoro-methoxyphenyl | $-NH_2$ | Melting point 167–168° C. |
| 6.12 | (3-ethyl-1-methylpiperidin-1-yl) | 2,5-difluoro-methoxyphenyl | $-NH_2$ | Melting point 148–149° C. |
| 6.13 | (1-methyldecahydroquinolin-1-yl) | $C_6F_5S-$ | $-NH_2$ | |
| 6.14 | (4-methylpiperazin-1-yl) | $C_6F_5O-$ | $-NH_2$ | Melting point 185–186° C. (decomposition) |
| 6.15 | $-N(CH_3)(CH_2)_3CH_3$ | $C_6F_5O-$ | $-NH_2$ | Melting point 102–103° C. |
| 6.16 | $-N(CH_2CH_2CN)_2$ | $C_6F_5O-$ | $-NH_2$ | $^{13}$C-NMR: 165.8 ppm; 164.7 ppm; 118.5 ppm; 117.4 ppm; 49.6 ppm; 43.0 ppm; 18.6 ppm; 17.4 ppm |
| 6.17 | $-NHC_6H_{11}(c)$ | $C_6F_5O-$ | $-NH_2$ | Melting point 136–137° C. |

TABLE 6-continued

Compounds of the formula II (II)

| Comp. No. | R₁ | R₃ | R₂ | Physical data |
|---|---|---|---|---|
| 6.18 | N-methyl trans-decahydroquinoline | $O_2N$—C₆H₄—O— | —NH₂ | Melting point 189–190° C. (decomposition) |
| 6.19 | N-methyl decahydroquinoline | $(CH_3)_3C$—C₆H₄—S— | —NH₂ | |
| 6.20 | —N(CH₃)(CH(CH₃)₂) | 4-methoxy-1-acetyl-naphthyl (—OCH₃ / —COCH₃) | —NH₂ | |
| 6.21 | —N(n-C₃H₇)₂ | C₆F₅O— | —NH₂ | Melting point 111–112° C. |
| 6.22 | —N(cycloheptyl)(cyclopentyl) with N-methyl | C₆F₅O— | —NH₂ | Melting point 137–138° C. |
| 6.23 | 1,3,5-trimethylpiperidinyl (3,5-dimethyl-1-piperidinyl, N-) | 2,5-difluoro-methoxyphenyl | —NH₂ | Melting point 190–191° C. |
| 6.24 | N-methyl octahydroindolyl | C₆F₅O— | —NH₂ | |
| 6.25 | —N⟨(CH₂)₇⟩ (azocane) | C₆F₅O— | —NH₂ | |

TABLE 6-continued

Compounds of the formula II

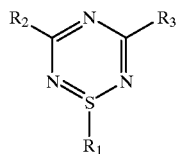

(II)

| Comp. No. | R₁ | R₃ | R₂ | Physical data |
|---|---|---|---|---|
| 6.26 | ![N-methylpiperidine with C₂H₅] | $C_6F_5O-$ | $-NH_2$ | |
| 6.27 | ![N-methyl bicyclic amine] | $C_6F_5O-$ | $-NH_2$ | Melting point 150–151° C. (decomposition) |
| 6.28 | ![N-methylpiperidine-2-COOC₂H₅] | ![2,5-difluoroanisole] | $-NH_2$ | Melting point 137–139° C. |
| 6.29 | ![N-methylpiperidine-3-COOC₂H₅] | ![2,5-difluoroanisole] | $-NH_2$ | Melting point 128–129° C. |
| 6.30 | ![N-methyl-2-ethylpiperidine] | $C_6F_5O-$ | $-NH_2$ | Melting point 161–162° C. |
| 6.31 | ![N-isopropyl-N-cyclohexyl] | $C_6F_5O-$ | $-NH_2$ | Melting point 173–174° C. |
| 6.32 | ![azacycloundecane (N-(CH₂)₉)] | $C_6F_5O-$ | $-NH_2$ | |
| 6.33 | ![N-methyl-2,3,3-trimethylpiperidine] | ![2,5-difluoroanisole] | $-NH_2$ | |

TABLE 6-continued

Compounds of the formula II $$\text{(II)}$$

(structure: 1,2,4,6-thiatriazine ring with R_2 and R_3 at 3,5-positions, R_1 on S)

| Comp. No. | R₁ | R₃ | R₂ | Physical data |
|---|---|---|---|---|
| 6.34 | N-methyl-3,3-dimethylpiperidinyl | C₆F₅O— | —NH₂ | Melting point 180–181° C. (decomposition) |
| 6.35 | N-(CH₂)₆ (hexamethyleneimino) | 3-(CF₃)C₆H₄—S— | —NH₂ | |
| 6.36 | —N[CH(CH₃)₂]₂ | 3,5-(OCH₃)₂C₆H₃—S— | —NH₂ | |
| 6.37 | N-methyl-trans-decahydroquinolinyl | C₆F₅O— | —NH₂ | Melting point 183–184° C. (decomposition) |
| 6.38 | —N(C₂H₅)₂ | 4,6-dimethylpyrimidin-2-yl-S— | —NH₂ | |
| 6.39 | —N(C₂H₅)C₄H₉(n) | 4-CH₃O-C₆H₄—O— | —NHCH₃ | |
| 6.40 | 4-phenyl-N-methylpiperidinyl | 2,5-difluoro-6-methoxyphenyl—O— | —NH₂ | Melting point 208–209° C. |

TABLE 6-continued

Compounds of the formula II

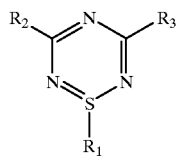

(II)

| Comp. No. | $R_1$ | $R_3$ | $R_2$ | Physical data |
|---|---|---|---|---|
| 6.41 | (2,6-dimethylmorpholin-4-yl) | $C_6F_5O-$ | $-NH_2$ | Melting point 162–163° C. |
| 6.42 | (decahydroazulenyl, cis-fused) | $C_6F_5O-$ | $-NH_2$ | MS: [M$^+$+H, 45%] 450. [M$^+$, 40%]449 |
| 6.43 | $-N(CH_3)_2$ | 2-(phenoxy)-6-(methylthio)phenyl | $-NHC_3H_6(n)$ | |
| 6.44 | (pyrrolidin-1-yl) | 2,4-dichloro-1-methoxyphenyl | $-NHCH(CH_3)_3$ | |
| 6.45 | (1-methyl-3-methoxycarbonyl-1,2,5,6-tetrahydropyridin-3-yl) | 2,5-difluoro-6-methoxyphenyl | $-NH_2$ | Melting point 159–160° C. |
| 6.46 | (2,5-dihydro-1H-pyrrol-1-yl) | $C_6F_5O-$ | $-NH_2$ | Melting point 203–204° C. |
| 6.47 | $-N(n-C_3H_7)_2$ | 2-(methylthio)pyridin-2-yl | $-NH_2$ | |
| 6.48 | $-N(n-C_3H_7)_2$ | 2,5-difluoro-6-methoxyphenyl | $-NH_2$ | Melting point 184–185° C. |

TABLE 6-continued

Compounds of the formula II

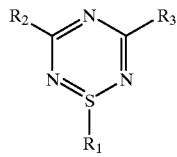

(II)

| Comp. No. | R₁ | R₃ | R₂ | Physical data |
|---|---|---|---|---|
| 6.49 | —N⟨(CH₂)₁₀⟩ | C₆F₅O— | —NH₂ | Melting point 134–135° C. |
| 6.50 | —N(CH₃)₂ | (methyl-phthalide-SMe group) | —NH₂ | |
| 6.51 | —N(CH₃)₂ | (1-naphthyl-SMe) | —N(CH₃)₂ | |
| 6.52 | —N(C₂H₅)₂ | (trimethyl-cyano-methylthio-pyridine) | —NH₂ | |
| 6.53 | —N(piperidinyl) | C₆F₅O— | —NH₂ | Melting point 104–105° C. |
| 6.54 | —NHCH₂CH₂CH₃ | (2,6-difluorophenoxy-methyl) | —NHCH₂CH₂CH₃ | Melting point 104–106° C. |
| 6.55 | —N(CH₃)(CH(CH₃)(2-naphthyl))(C₂H₅) (Diastereomer 1) | C₆F₅O— | —NH₂ | Melting point 184–185° C. |
| 6.56 | —N(CH₃)(CH(CH₃)(2-naphthyl))(C₂H₅) (Diastereomer 2) | C₆F₅O— | —NH₂ | Melting point 163–164° C. |

TABLE 6-continued

Compounds of the formula II (II)

| Comp. No. | R₁ | R₃ | R₂ | Physical data |
|---|---|---|---|---|
| 6.57 | N-methylazepane | 2,5-difluoro-methoxyphenyl | —NH₂ | Melting point 193–194° C. |
| 6.58 | —N(CH₃)(CH₂)₈ ring | CF₃O—C₆H₄—S— | —NH₂ | |
| 6.59 | —N(C₂H₅)₂ | 3,3-dimethoxy-7-(methylthio)-isobenzofuran-1(3H)-one | —NH₂ | |
| 6.60 | N-cyclooctyl-N-cyclohexyl-N-methyl | 2,5-difluoro-methoxyphenyl | —NH₂ | ¹³C-NMR: 166.0 ppm; 164.6 ppm, 159.7 + 156.5 ppm, 153.0 + 149.7 ppm, 105–117 ppm |
| 6.61 | N-methyl-7,8-dimethoxy-2,3,4,5-tetrahydro-1H-benzo[d]azepine | C₆F₅O— | —NH₂ | |
| 6.62 | —N(CH₃)₂ | 2,3-dimethyl-methoxyphenyl | —N(CH₃)₂ | |
| 6.63 | 2,5-dimethyl-N-methylpyrrolidine | C₆F₅O— | —NH₂ | Melting point 181–182° C. (Decomposition) |
| 6.64 | —N(CH₃)₂ | (CH₃)₂CH—C₆H₄—O— | —N(C₂H₅)₂ | |

TABLE 6-continued

Compounds of the formula II (II)

| Comp. No. | R₁ | R₃ | R₂ | Physical data |
|---|---|---|---|---|
| 6.65 | —NHCH₃ | NC—C₆H₄—O— (4-methoxy-benzonitrile) | —NHCH₃ | |
| 6.66 | —N(C₂H₅)₂ | 3,5-dimethylphenyl-S-CH₃ | —N(C₂H₅)₂ | |
| 6.67 | (trimethyl-methylazabicyclic group) | 2,5-difluoro-methoxyphenyl | —NH₂ | Melting point 208–209° C. |
| 6.68 | (N-methyl-decahydroquinoline) | tetrafluoro-methoxyphenyl | —NH₂ | |
| 6.69 | —N(CH₂)₁₂ (azacyclotridecane) | Br—C₆H₄—S— | —NH₂ | |
| 6.70 | —N(CH₃)₂ | 2,6-dimethyl-methoxyphenyl | —NHCH(CH₃)₂ | |
| 6.71 | —N(CH₃)₂ | phenoxy-methoxyphenyl | —NH₂ | |
| 6.72 | —NH(CH₂)₃CF₃ | 2,5-difluoro-methoxyphenyl | —NH₂ | Melting point 80–81° C. |

TABLE 6-continued

Compounds of the formula II

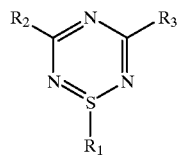

(II)

| Comp. No. | $R_1$ | $R_3$ | $R_2$ | Physical data |
|---|---|---|---|---|
| 6.73 | (N-methyl decahydrocycloocta[b]pyridine) | $C_6F_5O$— | —$NH_2$ | Melting point 175–176° C. |
| 6.74 | N,N-dimethylbenzylamine | 2,5-difluoro-methoxyphenyl | —$NH_2$ | Melting point 147–148° C. |
| 6.75 | (N-methyl dibenzazepine) | $C_6F_5O$— | —$NH_2$ | MS: [M$^+$+ H, 35%] 492, [M$^+$, 40%] 491 |
| 6.76 | (N-methyl benzazepine) | 2-methoxy-thiomethylphenyl | —$NH_2$ | |
| 6.77 | (N-methyl-N'-phenylpiperazine) | $C_6F_5O$— | —$NH_2$ | Melting point 198–199° C. (Decomposition) |
| 6.78 | —$N(CH_3)_2$ | 5-methyl-3-cyano-2-thiomethylpyridine | —$NHC_3H_7$ (n) | |
| 6.79 | (N-methyl-4-methoxy-3-cyano-tetrahydropyridine) | 4-bromo-methoxyphenyl | —$NH_2$ | |
| 6.80 | —$N(CH_3)_2$ | 2-methoxycarbonyl-methoxyphenyl | —$NHC_2H_5$ | |

TABLE 6-continued

Compounds of the formula II

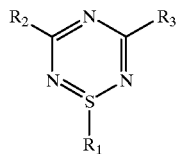

(II)

| Comp. No. | $R_1$ | $R_3$ | $R_2$ | Physical data |
|---|---|---|---|---|
| 6.81 | (N-methyl azabicyclic) | 2,5-difluorophenoxy | —NH$_2$ | Melting point >220° C. |
| 6.82 | (N-methyl decahydroisoquinolinyl) | 2,3,5,6-tetrafluoro-4-methoxyphenyl | —NH$_2$ | |
| 6.83 | —N(CH$_3$)CH$_2$COOC$_2$H$_5$ | 2,5-difluorophenoxy | —NH$_2$ | Melting point 133–134° C. |
| 6.84 | N(cyclooctyl)(cyclohexyl)(methyl) | C$_6$F$_5$O— | —NH$_2$ | $^{13}$C-NMR: 165.4 ppm; 164.5 ppm; 53.7 ppm; 53.4 ppm; 33.3 ppm; 27.3 ppm; 25.9 ppm; 25.4 ppm; 25.3 ppm; 24.3 ppm; 24.2 ppm |
| 6.85 | —N(CH$_3$)(CH$_2$)$_3$CH$_3$ | 2,5-difluorophenoxy | —NH$_2$ | Melting point 144–145°°C. |
| 6.86 | (N-methyl chloro-benzazepinyl) | C$_6$F$_5$O— | —NHhd 2 | |

TABLE 6-continued

Compounds of the formula II $$\text{(II)}$$

| Comp. No. | R₁ | R₃ | R₂ | Physical data |
|---|---|---|---|---|
| 6.87 | N-methyl-tetrahydroisoquinolinyl | 2,5-dichlorophenyl-S— | —NH₂ | |
| 6.88 | —N(CH₃)₂ | 5-methoxy-3-cyano-2-(methylthio)pyridinyl | —NHCH₃ | |
| 6.89 | N-methyl-azepanyl | 2,3,5,6-tetrafluoro-4-methoxyphenyl | —NH₂ | Melting point 187–188° C. |
| 6.90 | 1,2,2-trimethyl-3-methylpiperidinyl (with CH₃ groups) | C₆F₅O— | —NH₂ | Melting point 187–188° C. (Decomposition) |
| 6.91 | N(CH₂-cyclohexyl)(CH(CH₃)₂) | phenoxy | —N(CH₃)₂ | |
| 6.92 | N-methyl-4,4-dimethyl-6-methyl-azepanyl (Diastereomer 1) | C₆F₅O— | —NH₂ | ¹³C-NMR: 164.9 ppm; 165.2 ppm; 21.1–53.7 ppm |
| 6.93 | N-methyl-4,4-dimethyl-6-methyl-azepanyl (Diastereomer 2) | C₆F₅O— | —NH₂ | ¹³C-NMR: 165.7 ppm; 164.7 ppm; 21.2–53.6 ppm |

TABLE 6-continued

Compounds of the formula II

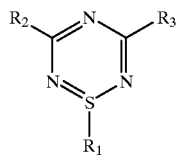

(II)

| Comp. No. | R₁ | R₃ | R₂ | Physical data |
|---|---|---|---|---|
| 6.94 | —N⏜(CH₂)₁₁ | C₆F₅O— | —NH₂ | |
| 6.95 | (N-methyl decahydroquinoline) | 2,3,4-trifluoro-methoxyphenyl | —NH₂ | |
| 6.96 | —N(CH₃)₂ | ethyl 2-cyano-3-(methylthio)-5-methylbenzoate | —NH₂ | |
| 6.97 | —N(C₄H₉(n))₂ | 2,5-dimethyl-4-methoxy-phenoxy (with CH₃CO—) | —NH₂ | |
| 6.98 | (trans N-methyl decahydroisoquinoline) | C₆F₅O— | —NH₂ | |
| 6.99 | (N-methyl-2,3,4,5-tetrahydro-1H-benzazepine) | C₆F₅S— | —NH₂ | Melting point 191° C. (Decomposition) |
| 6.100 | (N-methylquinuclidine) | 2,3,5,6-tetrafluoro-4-methoxyphenyl | —NH₂ | |
| 6.101 | (N-methyl-6-methoxy-2,3,4,5-tetrahydro-1H-benzazepine) | C₆F₅O— | —NH₂ | |

TABLE 6-continued

Compounds of the formula II

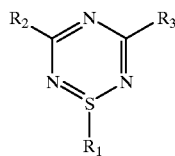

(II)

| Comp. No. | R₁ | R₃ | R₂ | Physical data |
|---|---|---|---|---|
| 6.102 | (decahydro-pyrido-cyclooctane with N–CH₃) | C₆F₅O— | —NH₂ | MS: [M⁺+H] 464 |
| 6.103 | —N(CH₂)₈ (azacyclic) | 4-F-C₆H₄-S— | —NH₂ | |
| 6.104 | N-methyl-2,3,4,5-tetrahydro-1H-benzo[c]azepine | 2,3,4-trifluoro-6-methoxyphenyl | —NH₂ | |
| 6.105 | —N(CH₃)(c-C₆H₁₁) | 2,5-difluoro-6-methoxyphenyl | —NH₂ | Melting point 165–166° C. |
| 6.106 | norbornenyl-CH₂N(CH₃)₃ | C₆F₅O— | —NH₂ | |
| 6.107 | N-piperidinyl | 2,5-difluoro-6-methoxyphenyl | —NH₂ | Melting point 191–192° C. |
| 6.108 | —N(C₂H₅)₂ | 2-acetyl-6-methoxyphenyl | —NH₂ | |
| 6.109 | —N(CH₃)₂ | 2,5-difluoro-6-methoxyphenyl | —NH₂ | Melting point 166–167° C. |

TABLE 6-continued

Compounds of the formula II (II)

| Comp. No. | R₁ | R₃ | R₂ | Physical data |
|---|---|---|---|---|
| 6.110 | —N(CH₃)₂ | 4-methoxy-biphenyl | —NH₂ | |
| 6.111 | N-methyl decahydroquinolinyl | (n)H₁₃C₆O—C₆H₄—O— | —NH₂ | |
| 6.112 | —N(CH₃)₂ | 3,3-dimethyl-7-(methylthio)-isobenzofuran-1(3H)-one | —NH₂ | |
| 6.113 | (2R,6S)-2,6-dimethyl-4-methylmorpholinyl | C₆F₅O— | —NH₂ | Melting point 174–175° C. |
| 6.114 | 1-methylaziridinyl | C₆F₅O— | —NH₂ | |
| 6.115 | 6,7-dimethoxy-2-methyl-1,2,3,4-tetrahydroisoquinolinyl | C₆F₅O— | —NH₂ | MS: [M⁺+ H] 489 |
| 6.116 | 1-methyl-1,2,3,6-tetrahydropyridinyl | 2,5-difluoro-methoxyphenyl | —NH₂ | Melting point 171–172° C. |
| 6.117 | N-methyl hexahydropyrrolo-indolyl | C₆F₅O— | —NH₂ | |

TABLE 6-continued

Compounds of the formula II

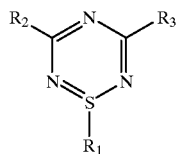

(II)

| Comp. No. | R₁ | R₃ | R₂ | Physical data |
|---|---|---|---|---|
| 6.118 | (N-methyl benzazepine) | C₆F₅O— | —NH₂ | |
| 6.119 | (N-methyl octahydroindole, H,H) | 2,5-difluorophenoxy | —NH₂ | ¹³C-NMR: 162.9 ppm; 161.8 ppm; 62.5 ppm; 42.8 ppm; 28.8 ppm 28.3 ppm; 27.9 ppm; 27.2 ppm |
| 6.120 | (N-methyl octahydroindole, H,H) (Diastereomer 1) | 2,5-difluorophenoxy | —NH₂ | Melting point 173–174° C.; ¹³C-NMR: 165.8 ppm; 164.6 ppm, 58.6 ppm; 37.6 ppm; 27.8 ppm; 27.6 ppm; 25.9 ppm; 22.1 ppm, 21.1 ppm |
| 6.121 | (N-methyl octahydroindole, H,H) (Diastereomer 2) | 2,5-difluorophenoxy | —NH₂ | Melting point 174–175° C. |
| 6.122 | (S)-2-methoxymethyl-N-methylpyrrolidine | C₆F₅O— | —NH₂ | |
| 6.123 | (N-methyl tetrahydro-β-carboline-like) | C₆F₅O— | —NH₂ | |
| 6.124 | (N-methyl-3,5-dimethylpiperidine) | C₆F₅O— | —NH₂ | Melting point 161–162° C. |

TABLE 6-continued

Compounds of the formula II (II)

| Comp. No. | R₁ | R₃ | R₂ | Physical data |
|---|---|---|---|---|
| 6.125 | —N(CH₃)₂ | 5-nitro-2-(methylthio)pyrazinyl | —N(CH₃)₂ | |
| 6.126 | —N(CH₃)₂ | 4-tert-butyl-2-methoxyphenyl | —NH₂ | |
| 6.127 | 1-methyl-3-(N,N-diethylcarbamoyl)piperidinyl | 2,5-difluoro-6-methoxyphenyl | —NH₂ | ¹H-NMR: 6.8–7.1 ppm (3H); 5.2 ppm (2H); 3.2–3.5 ppm (6H); 2.6–3.1 ppm (3H); 1.5–1.9 ppm (4H); 1.1–1.3 ppm (6H) |
| 6.128 | 1-aziridinyl | C₆F₅O— | —NH₂ | |
| 6.129 | 1-methyl-3,3-dimethylpiperidinyl | 2,5-difluoro-6-methoxyphenyl | —NH₂ | Melting point 201–202° C. (Decomposition) |
| 6.130 | N-benzyl-N-(indan-1-yl)amino | C₆F₅O— | —NH₂ | |
| 6.131 | 7-methoxy-2,3,4,5-tetrahydro-1H-2-benzazepin-2-yl | C₆F₅O— | —NH₂ | |
| 6.132 | 1-methyl-4-oxopiperidinyl | 2-chloro-3-cyano-6-(methylthio)phenyl | —NH₂ | |

TABLE 6-continued

Compounds of the formula II

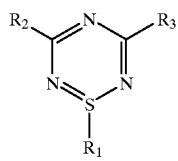

(II)

| Comp. No. | R₁ | R₃ | R₂ | Physical data |
|---|---|---|---|---|
| 6.133 | —N(CH₃)₂ | 4-Br-2-(OCF₃)-1-(SCH₃)-phenyl | —NH₂ | |
| 6.134 | (1,7,7-trimethylbicyclo-norbornyl)-N(CH₂CH₂CH(CH₃))— | C₆F₅O— | —NH₂ | |
| 6.135 | N-methyl-decahydroquinolinyl | 2,5-difluoro-6-methoxyphenyl | —NH₂ | Melting point 195–196° C. |
| 6.136 | 1-methyl-3-hydroxypyrrolidinyl | C₆F₅O— | —NH₂ | |
| 6.137 | 1-methyl-4-oxopiperidinyl | 2,5-difluoro-6-methoxyphenyl | —NH₂ | Melting point 151–152° C. |
| 6.138 | 2-azaspiro[5.5]undecyl | C₆F₅O— | —NH₂ | |
| 6.139 | 1-methyl-3-(hydroxymethyl)piperidinyl | 2,5-difluoro-6-methoxyphenyl | —NH₂ | Melting point 109–110° C. |

TABLE 6-continued

Compounds of the formula II

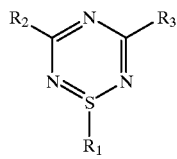

(II)

| Comp. No. | $R_1$ | $R_3$ | $R_2$ | Physical data |
|---|---|---|---|---|
| 6.140 | N(C₂H₅)-3,5-dimethyl-5-methylcyclohexyl | $C_6F_5O-$ | $-NH_2$ | Melting point 140–141° C. |
| 6.141 | N(CH₃)-3,5-dimethyl-5-methylcyclohexyl | 2,6-dichlorophenoxy | $-NH_2$ | |
| 6.142 | $-N(CH_3)_2$ | 2,4-dimethoxy-6-(methylthio)pyrimidine | $-NHCH_3$ | |
| 6.143 | 1-methyl-3-hydroxypiperidine | 2,5-difluorophenoxy | $-NH_2$ | Melting point 146–147° C. |
| 6.144 | norbornene-spiro-N-methylpiperidine | $C_6F_5O-$ | $-NH_2$ | |
| 6.145 | 2-methyl-1,2,3,4-tetrahydroisoquinoline | pentafluorophenoxy | $-NH-$ | Melting point 135–136° C. |
| 6.146 | $-N(CH_3)_2$ | 2,4-dimethyl-6-(methylthio)pyrimidine | $-N(CH_3)_2$ | |

TABLE 6-continued
Compounds of the formula II
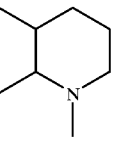
(II)
| Comp. No. | R₁ | R₃ | R₂ | Physical data |
|---|---|---|---|---|
| 6.147 | 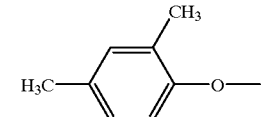 | 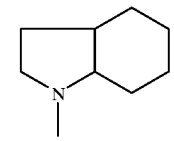 | —NH₂ | |
| 6.148 | 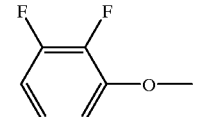 | 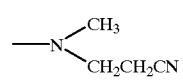 | —NH₂ | |
| 6.149 | 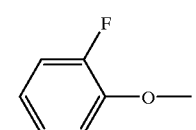 | 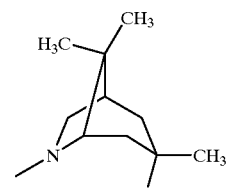 | —NH₂ | Melting point 167–168° C. |
| 6.150 | 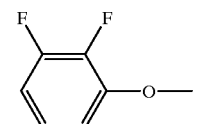 | 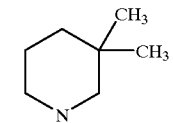 | —NH₂ | |
| 6.151 | 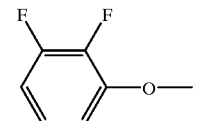 | 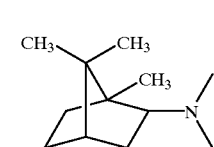 | —NH₂ | |
| 6.152 |  | C₆F₅O— | —NH₂ | |

TABLE 6-continued

Compounds of the formula II (II)

| Comp. No. | R₁ | R₃ | R₂ | Physical data |
|---|---|---|---|---|
| 6.153 | (Diastereomer 1) [bicyclic N-methyl amine with three CH₃ groups] | $C_6F_5O-$ | $-NH_2$ | Melting point 161–162° C. |
| 6.154 | (Diastereomer 2) [bicyclic N-methyl amine with three CH₃ groups] | $C_6F_5O-$ | $-NH_2$ | Melting point 166–167° C. |
| 6.155 | $-N(C_4H_9(n))_2$ | 2,6-dimethoxy-3-acetyl-phenoxy (CH₃O, COCH₃, OCH₃ substituted phenyl-O–) | $-N(CH_3)_2$ | |
| 6.156 | octahydrobenzoxazine N-methyl | 2,3,4-trifluorophenoxy | $-NH_2$ | |
| 6.157 | octahydroindole N-methyl, 2-CH₃ | 4-bromophenoxy | $-NH_2$ | |
| 6.158 | bornyl-N(CH₃)(CH₂C₆H₅) | $C_6F_5O-$ | $-NH_2$ | |
| 6.159 | trans-decahydroquinoline N-methyl, 4a-CH₃ | 2,5-difluorophenoxy | $-NH_2$ | Melting point 195–196° C. |

TABLE 6-continued

Compounds of the formula II

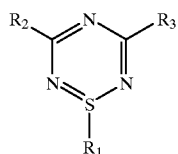

(II)

| Comp. No. | R₁ | R₃ | R₂ | Physical data |
|---|---|---|---|---|
| 6.160 | —N(CH₃)₂ | 2-fluoro-(methylthio)benzene | —N(CH₃)₂ | |
| 6.161 | 2-methyl-1,2,3,4-tetrahydroisoquinoline | 1-(methylthio)naphthalene | —NH₂ | |
| 6.162 | —N(CH₃)₂ | 3-methyl-methoxybenzene | —NHC₄H₉(n) | |
| 6.163 | —N(CH₃)₂ | 2-methoxybenzonitrile | —NHCH₃ | |
| 6.164 | 3-methyl-2,3,4,5-tetrahydro-1H-3-benzazepine | 2,5-difluoro-methoxybenzene | —NH₂ | Melting point 196–197° C. (Decomposition) |
| 6.165 | N-isobutyl-N-(3,3,5-trimethylcyclohexyl) | C₆F₅O— | —NH₂ | Resin; 2 diastereomers: ¹³C-NMR: 164.3–164.8 ppm (4 signals) |
| 6.166 | 1-methyloctahydroindole | 5-fluoro-2-methoxyacetophenone | —NH₂ | |

TABLE 6-continued
Compounds of the formula II
(II)
| Comp. No. | R₁ | R₃ | R₂ | Physical data |
|---|---|---|---|---|
| 6.167 | 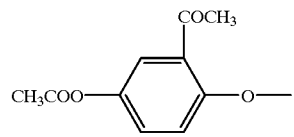 | 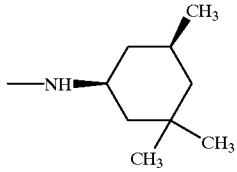 | —NH₂ | |
| 6.168 | 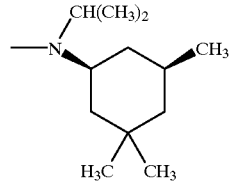 | C₆F₅O— | —NH₂ | Melting point 128–129° C. |
| 6.169 | 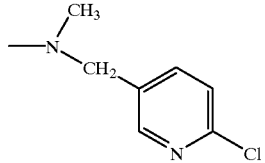 | C₆F₅O— | —NH₂ | |
| 6.170 | 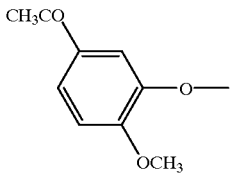 | C₆F₅O— | —NH₂ | Melting point 145–146° C. |
| 6.171 | —N(CH₃)₂ | 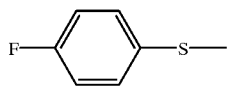 | —N(CH₃)₂ | |
| 6.172 | —N(C₂H₅)₂ | 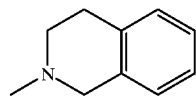 | —NH₂ | |
| 6.173 | 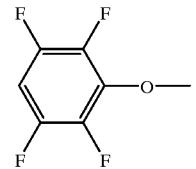 |  | —NH₂ | Melting point 139–140° C. |

TABLE 6-continued

Compounds of the formula II (II)

| Comp. No. | R₁ | R₃ | R₂ | Physical data |
|---|---|---|---|---|
| 6.174 | 2-methyl-1-piperidinyl (N-CH₃, with CH₃ on ring) | 2,5-difluoro-6-methoxyphenyl | —NH₂ | Melting point 192–193° C. |
| 6.175 | —N(CH₃)₂ | 4-(acetyloxy)-phenoxy (CH₃CO—O—C₆H₄—O—) | —N(C₂H₅)₂ | |
| 6.176 | —N(CH₃)₂ | 3-fluorophenylthio (F—C₆H₄—S—) | —NH₂ | |
| 6.177 | —N(CH₂)₁₂ (azacyclotridecane) | C₆F₅O— | —NH₂ | Melting point 124–125° C. |
| 6.178 | 1,2-dimethyloctahydroindol-1-yl | 4-(trifluoromethyl)phenoxy (CF₃—C₆H₄—O—) | —NH₂ | |
| 6.179 | —N(CH₃)₂ | 2-(trifluoromethyl)phenoxy | —NH₂ | |
| 6.180 | 3-methyl-2,3,4,5-tetrahydro-1H-3-benzazepin-3-yl | 2,3,5,6-tetrafluoro-4-methoxyphenyl | —NH₂ | |
| 6.181 | 4a-methyl-1-methyldecahydroquinolin-1-yl | C₆F₅O— | —NH₂ | Melting point 180–181° C. |

TABLE 6-continued

Compounds of the formula II $$\text{(II)}$$

Structure: 1,2,4,6-thiatriazine ring with $R_2$ and $R_3$ at the 3 and 5 positions (adjacent to N), $R_1$ on S.

| Comp. No. | $R_1$ | $R_3$ | $R_2$ | Physical data |
|---|---|---|---|---|
| 6.182 | —N(CH$_3$)$_2$ | 4-(benzyloxy)phenyl-O— (PhCH$_2$O–C$_6$H$_4$–O—) | —NH$_2$ | |
| 6.183 | —NHC$_3$H$_7$(n) | 2-methoxy-6-(ethylthio)phenyl (SC$_2$H$_5$, OCH$_3$ substituted phenyl) | —NH$_2$ | |
| 6.184 | —N(CH$_3$)$_2$ | 7-methoxy-3-methyl-1-indanon-yl | —NH$_2$ | |
| 6.185 | N-methylquinuclidinyl | C$_6$F$_5$O— | —NH$_2$ | Melting point 173–174° C. |
| 6.186 | —N(C$_2$H$_5$)$_2$ | 2-(methylthio)-3-(methoxycarbonyl)pyridin-yl (COOCH$_3$, SCH$_3$) | —NH$_2$ | |
| 6.187 | 1,2,3-trimethyl-3-methylpiperidinyl (H$_3$C, CH$_3$, CH$_3$) | 2,3-dimethoxyphenyl (OCH$_3$, O—) | —NH$_2$ | |
| 6.188 | —N(CH$_3$)$_2$ | 2-methoxy-6-cyanophenyl (CN) | —N(CH$_3$)$_2$ | |
| 6.189 | —N(C$_2$H$_5$)$_2$ | 4-methoxy-methylphenyl (H$_3$C—C$_6$H$_4$—O—) | —NH$_2$ | |

TABLE 6-continued

Compounds of the formula II

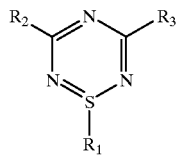

(II)

| Comp. No. | R₁ | R₃ | R₂ | Physical data |
|---|---|---|---|---|
| 6.190 | ![octahydrobenzothiazine with N-methyl] | 2,6-difluoro-3-methoxyphenyl | —NH₂ | |
| 6.191 | —N(CH₃)₂ | 3-chloro-5-(trifluoromethyl)-2-(methylthio)pyridinyl | —NH₂ | |
| 6.192 | —N(CH₃)(CH₂-phenyl) | C₆F₅O— | —NH₂ | Melting point 171–172° C. |
| 6.193 | bornyl-N(CH₃)(C₂H₄) | 2,3,5,6-tetrafluoro-4-methoxyphenyl | —NH₂ | |
| 6.194 | —N(CH₃)(3,3,5-trimethylcyclohexyl) | C₆F₅O— | —NH₂ | Melting point 168–169° C. |
| 6.195 | —N(CH₃)₂ | 3,3-dimethyl-4-methoxy-phthalide | —NH₂ | |
| 6.196 | —N(CH₃)₂ | 4-methyl-6-(trifluoromethyl)-2-(methylthio)pyrimidinyl | —NH₂ | |

TABLE 6-continued

Compounds of the formula II

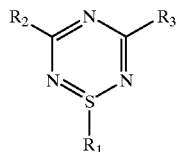

(II)

| Comp. No. | R₁ | R₃ | R₂ | Physical data |
|---|---|---|---|---|
| 6.197 | (1,3,3-trimethylpiperidin-2-yl, N-linked) H₃C, H₃C, CH₃ on N-methylpiperidine | 2-naphthylthio | —NH₂ | |
| 6.198 | 1-acetyl-decahydroquinoxalin-4-yl (N-methyl) | C₆F₅O— | —NH₂ | |
| 6.199 | —N(C₄H₉(n))₂ | phenoxy | —N(CH₃)₂ | |
| 6.200 | 3-methyl-2,3,4,5-tetrahydro-1H-3-benzazepin-3-yl | C₆F₅O— | —NH₂ | Melting point 160–161° C. (Decomposition) |
| 6.201 | 4-methyl-decahydroquinolin-1-yl | 3-methoxycarbonyl-pyridin-2-ylthio | —NH₂ | |
| 6.202 | —N(CH₃)₂ | 3-methoxyphenoxy | —N(C₂H₅)₂ | |
| 6.203 | —NH—C₄H₉(n) | 5-methylpyrimidin-2-ylthio | —NH₂ | |
| 6.204 | —N(CH₃)₂ | pyrimidin-2-ylthio | —NH₂ | |

TABLE 6-continued

Compounds of the formula II

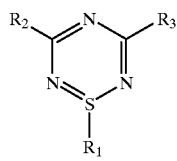

(II)

| Comp. No. | $R_1$ | $R_3$ | $R_2$ | Physical data |
|---|---|---|---|---|
| 6.205 | [1-methylpiperidin-4-yl]-COCH₃ | 2,5-difluoro-methoxyphenyl | —NH₂ | Melting point 160–161° C. |
| 6.206 | —N(CH₃)₂ | 1-bromo-2-methoxy-6-bromonaphthyl | —NH₂ | |
| 6.207 | —N(CH₃)₂ | 2,4-dinitro-methoxyphenyl | —NH₂ | |
| 6.208 | —N(C₂H₅)₂ | 2-methoxy-acetylphenyl | —NH₂ | |
| 6.209 | 3-methyl-2,3,4,5-tetrahydro-1H-3-benzazepinyl | pentafluoro-methoxyphenyl | —NH₂ | |
| 6.210 | 1,4-dimethyl-decahydroquinolinyl | C₆F₅O— | —NH₂ | |
| 6.211 | 1-methyl-decahydroquinolinyl | 3,5-bis(trifluoromethyl)-methoxyphenyl | —NH₂ | |

TABLE 6-continued

Compounds of the formula II

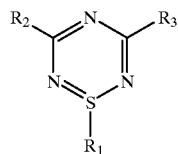

(II)

| Comp. No. | $R_1$ | $R_3$ | $R_2$ | Physical data |
|---|---|---|---|---|
| 6.212 | —N(C$_2$H$_5$)$_2$ | 2-fluorophenyl-S— | —N(C$_2$H$_5$)$_2$ | |
| 6.213 | —N(C$_2$H$_5$)$_2$ | 2-methoxynaphthalen-1-yl-CHO | —NHCH$_3$ | |
| 6.214 | —N(CH$_3$)$_2$ | 3-methoxy-5-cyanophenyl | —NH$_2$ | |
| 6.215 | (1S,2R,4R)-N,N,1,7,7-pentamethylbicyclo[2.2.1]heptan-2-amin-N-yl | C$_6$F$_5$O— | —NH$_2$ | Melting point 88–89° C. |
| 6.216 | 2-ethyl-1-methylpiperidin-1-yl | 2,5-difluoro-6-methoxyphenyl | —NH$_2$ | Melting point 179–180° C. |
| 6.217 | 1-methyl-azacyclododecan-1-yl | 2,3,5,6-tetrafluoro-4-methoxyphenyl | —NH$_2$ | |
| 6.218 | —N(C$_2$H$_5$)$_2$ | 2,4-dimethyl-5-(methylthio)phenyl | —N(CH$_3$)$_2$ | |
| 6.219 | —N(CH$_3$)$_2$ | 6-bromo-2-methoxynaphthalen-1-yl | —NHC$_3$H$_7$(n) | |

TABLE 6-continued
Compounds of the formula II
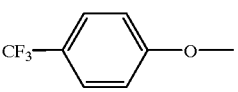
(II)
| Comp. No. | R₁ | R₃ | R₂ | Physical data |
|---|---|---|---|---|
| 6.220 | —NHCH₃ | 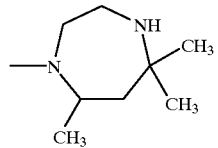 | —NHCH₃ | |
| 6.221 | 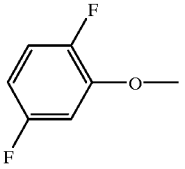 | 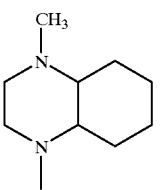 | —NH₂ | Melting point 169–170° C. (Decomposition) |
| 6.222 | 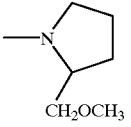 | C₆F₅O— | —NH₂ | |
| 6.223 | 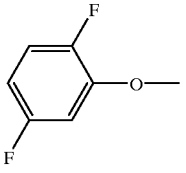 | 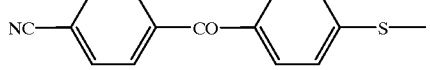 | —NH₂ | Melting point 168–169° C. |
| 6.224 | (CH₃)₂N— | 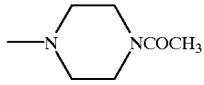 | —NH₂ | |
| 6.225 | 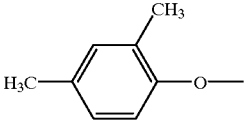 | 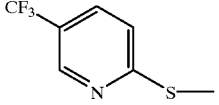 | —N(C₂H₅)₂ | |
| 6.226 | —N(C₂H₅)₂ | 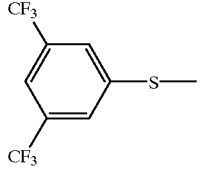 | —NHCH₃ | |
| 6.227 | —N(CH₃)₂ |  | —N(CH₃)₂ | |

TABLE 6-continued

Compounds of the formula II

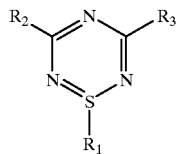

(II)

| Comp. No. | $R_1$ | $R_3$ | $R_2$ | Physical data |
|---|---|---|---|---|
| 6.228 | —N(C$_4$H$_9$(n))$_2$ | 3-F-C$_6$H$_4$-S-CH$_3$ | —NH$_2$ | |
| 6.229 | N-methylhexahydroazepinyl | C$_6$F$_5$O— | —NH$_2$ | Melting point 154–155° C. (Decomposition) |
| 6.230 | N-methyl-(3,3,5-trimethylcyclohexyl)amino | 2,3,5,6-tetrafluoro-4-methoxyphenyl | —NH$_2$ | Melting point 199–200° C. |
| 6.231 | 1-methyl-4-(4-fluorobenzoyl)piperidinyl | 2,5-difluoro-6-methoxyphenyl | —NH$_2$ | Melting point 181–182° C. |
| 6.232 | 1,2-dimethyloctahydroindolyl | 4-nitro-4'-methoxyphenyl | —NH$_2$ | |
| 6.233 | N-cyclopentyl-N-methyl-(3,3,5-trimethylcyclohexyl)amino | C$_6$F$_5$O— | —NH$_2$ | |
| 6.234 | 1-methyl-4-acetylpiperidinyl | 2,5-difluoro-6-methoxyphenyl | —NH$_2$ | Melting point 160–161° C. |

TABLE 6-continued

Compounds of the formula II

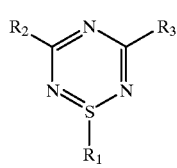

(II)

| Comp. No. | $R_1$ | $R_3$ | $R_2$ | Physical data |
|---|---|---|---|---|
| 6.235 | N-methyl decahydroquinoline | 2,6-dichlorophenoxy (methoxy) | —NH$_2$ | |
| 6.236 | $(CH_3)_2N$— | 2-chlorophenoxy | —NH$_2$ | |
| 6.237 | 1-methylpiperidine-4-COOCH$_3$ | 2,5-difluorophenoxy | —NH$_2$ | Melting point 176–177° C. |
| 6.238 | N-methylmorpholine | 4-CF$_3$-phenoxy | —N(CH$_3$)$_2$ | |
| 6.239 | 1-methyl-4-methylpiperidine | 2,5-difluorophenoxy | —NH$_2$ | Melting point 188–189° C. |
| 6.240 | —N(CH$_3$)$_2$ | CH$_3$O—phenoxy—O— | —N(C$_2$H$_5$)$_2$ | |
| 6.241 | —N(CH$_3$)$_2$ | 4-methyl-6-cyclopropyl-pyrimidin-2-ylthio | —NH$_2$ | |
| 6.242 | N-methylthiomorpholine | 2,5-difluorophenoxy | —NH$_2$ | Melting point 185–186° C. |

TABLE 6-continued
Compounds of the formula II
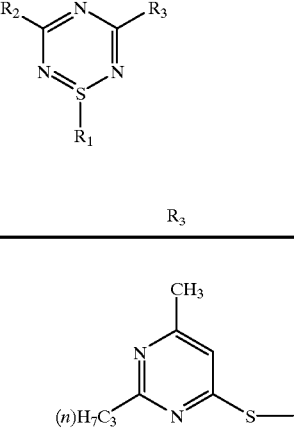
(II)
| Comp. No. | R₁ | R₃ | R₂ | Physical data |
|---|---|---|---|---|
| 6.243 | —N(CH₃)₂ | 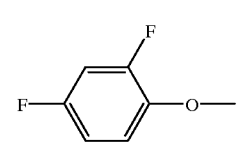 | —NH₂ | |
| 6.244 | —N(C₂H₅)₂ | 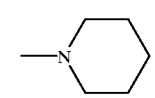 | —NHCH₃ | |
| 6.245 | 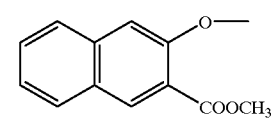 | 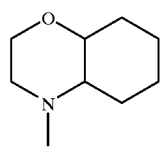 | —NH₂ | |
| 6.246 | 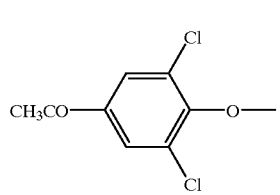 | C₆F₅O— | —NH₂ | |
| 6.247 | —N[CH(CH₃)₂]₂ | C₆F₅O— | —NH₂ | Melting point 153–154° C. |
| 6.248 | —N(CH₃)₂ | 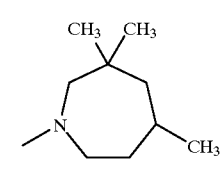 | —NH₂ | |
| 6.249 | 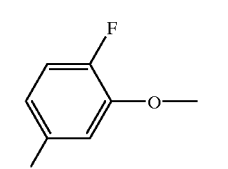 | 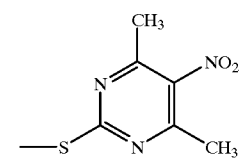 | —NH₂ | Melting point 175–176° C. |
| 6.250 | —N(CH₃)₂ |  | —N(CH₃)₂ | |

TABLE 6-continued

Compounds of the formula II (II)

[Structure: 1,2,4,6-thiatriazine ring with R2 at position 4, R3 at position 6, R1 at position 2 (on S)]

| Comp. No. | R₁ | R₃ | R₂ | Physical data |
|---|---|---|---|---|
| 6.251 | —N(C₂H₅)₂ | 1-bromo-2-methoxynaphthalen-yl | —NH₂ | |
| 6.252 | N-methyl-N-cyclohexyl | 2-acetyl-4,6-difluorophenoxy (COCH₃, F, O, F) | —NHCH₃ | |
| 6.253 | N-methyl octahydro-benzazepinyl | C₆F₅O— | —NH₂ | |
| 6.254 | —N(CH(CH₃)₂)(CH₂)₂NHC₂H₅ | 2,4-difluoro-6-methoxyphenyl | —NH₂ | Melting point 106–107° C. |
| 6.255 | —N(CH₃)₂ | 2-methyl-6-methoxyphenyl | —NH₂ | |
| 6.256 | 2-methylpiperidin-1-yl (H₃C) | 2-isopropyl-4-methyl-6-methylthio-pyrimidinyl | —NH₂ | |
| 6.257 | azacyclononyl —N(CH₂)₈ | C₆F₅O— | —NH₂ | Melting point 160–161° C. |
| 6.258 | —N(C₂H₅)₂ | 1-acetyl-2-methoxynaphthalen-yl (COCH₃) | —NHCH₃ | |

TABLE 6-continued

Compounds of the formula II (II)

| Comp. No. | R₁ | R₃ | R₂ | Physical data |
|---|---|---|---|---|
| 6.259 | —N(CH₃)₂ | (2-methylthio)phenyl with COOCH₃ | —N(CH₃)₂ | |
| 6.260 | N-methyl decahydroisoquinoline (trans) | 2-methoxy-3,6-difluorophenyl | —NH₂ | ¹H-NMR: 6.8–7.1 ppm (3H); 5.4 ppm (2H); 3.0–3.4 ppm (2H); 2.7 ppm (1H) |
| 6.261 | N-methyl hexahydrobenzothiazine | C₆F₅O— | —NH₂ | |
| 6.262 | —N(CH₃)₂ | 5,6-dimethyl-3-(methylthio)-1,2,4-triazine | —NH₂ | |
| 6.263 | —N(CH₃)₂ | 3-(trifluoromethyl)-2-(methylthio)pyridine | —NH₂ | |
| 6.264 | N-methyl-2,3,4,5-tetrahydro-1H-benzo[c]azepine | 2-chloro-4-fluoro-1-methoxyphenyl | —NH₂ | |
| 6.265 | 1,2,5-trimethylpyrrolidine | 2-methoxy-3,6-difluorophenyl | —NH₂ | Melting point 172–173° C. (Decomposition) |
| 6.266 | —N(CH₃)₂ | 5-methoxypyrimidine | —NH₂ | |

TABLE 6-continued

Compounds of the formula II

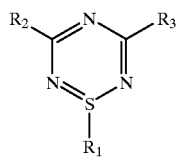

| Comp. No. | R₁ | R₃ | R₂ | Physical data |
|---|---|---|---|---|
| 6.267 | —N(CH₃)₂ | 3-methyl-(methylthio)phenyl | —N(C₃H₇(n))₂ | |
| 6.268 | —N(CH₃)₂ | 6-methyl-5-chloro-4-(methylthio)pyrimidinyl | —NH₂ | |
| 6.269 | —N(CH₂)₈ (azonane) | C₆F₅O— | —NH₂ | Melting point 145–146° C. (Decomposition) |
| 6.270 | N-methylisoindoline | 1-methoxy-2,4-dichloronaphthyl | —NH₂ | |
| 6.271 | N-methyl-di-cyclopentylamine | 2-methyl-6-methoxyphenyl | —N(CH₃)₂ | |
| 6.272 | —N(CH₃)₂ | 1-methoxy-4-chloronaphthyl | —NHC₄H₉(n) | |
| 6.273 | —N(CH₃)₂ | 6-ethyl-5-chloro-4-(methylthio)pyrimidinyl | —NH₂ | |

TABLE 6-continued

Compounds of the formula II

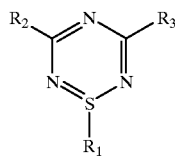

(II)

| Comp. No. | R₁ | R₃ | R₂ | Physical data |
|---|---|---|---|---|
| 6.274 | (3-methyl-N-methyl-octahydrobenzoxazine) | C₆F₅O— | —NH₂ | |
| 6.275 | (N-methyl-pyrrolidine-2-COOCH₃) | 2,5-difluoro-methoxyphenyl | —NH₂ | Melting point 153–154° C. |
| 6.276 | (N-methyl-octahydrobenzothiazine) | 2-CF₃-3,4,5,6-tetrafluoro-methoxyphenyl | —NH₂ | |
| 6.277 | —N(CH₃)₂ | 2-C(CH₃)₃-4-(CH₃)₃C-phenyl-S-CH₃ | —NH₂ | |
| 6.278 | (N-methyl-3-COOCH₃-piperidin-4-one) | 2,5-difluoro-methoxyphenyl | —NH₂ | Melting point 101–103° C. |
| 6.279 | —N(C₂H₅)₂ | 3,5-dimethylphenyl-S-CH₃ | —N(C₂H₅)₂ | |
| 6.280 | (N-methyl-Cl-tetrahydrobenzazepine) | 2-methyl-1-methoxynaphthyl | —NH₂ | |

TABLE 6-continued

Compounds of the formula II

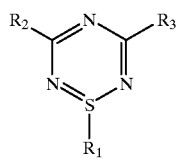

(II)

| Comp. No. | $R_1$ | $R_3$ | $R_2$ | Physical data |
|---|---|---|---|---|
| 6.281 | N-methyl-N-cyclododecyl | $C_6F_5O-$ | $-NH_2$ | MS: [M$^+$, 50%] 561, [M$^+$+H, 30%] 562 |
| 6.282 | (2-methyl-octahydroindole) | $C_6F_5O-$ | $-NH_2$ | Melting point 157–158° C. |
| 6.283 | (N-methyl-decahydrobenzazepine) | $C_6F_5O-$ | $-NH_2$ | Melting point 133–134° C. |
| 6.284 | (N-methyl-decahydroisoquinoline) | $C_6F_5O-$ | $-NH_2$ | |
| 6.285 | (4-methyl-decahydroquinoline, Diastereomer 1) | $C_6F_5O-$ | $-NH_2$ | Melting point 137–138° C. |
| 6.286 | (4-methyl-decahydroquinoline, Diastereomer 2) | $C_6F_5O-$ | $-NH_2$ | MS: [M$^+$, 50%] 449, [M$^+$+H, 40%] 450 |

TABLE 6-continued

Compounds of the formula II

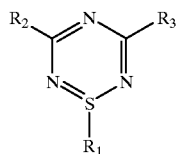

(II)

| Comp. No. | R₁ | R₃ | R₂ | Physical data |
|---|---|---|---|---|
| 6.287 | (Diastereomer 1) decahydroquinoline with CH₃ | $C_6F_5O-$ | $-NH_2$ | Melting point 129–130° C. |
| 6.288 | (Diastereomer 2) decahydroquinoline with CH₃ | $C_6F_5O-$ | $-NH_2$ | MS: [M⁺, 40%] 449, [M⁺+H, 40%] 450 |
| 6.289 | (Diastereomer 1 and 2) decahydroquinoline with CH₃ | $C_6F_5O-$ | $-NH_2$ | Melting point 157–158° C. (Decomposition) |
| 6.290 | (Diastereomer 1) decahydroquinoline with CH₃ | $C_6F_5O-$ | $-NH_2$ | Melting point 112–113° C. |
| 6.291 | (Diastereomer 2) decahydroquinoline with CH₃ | $C_6F_5O-$ | $-NH_2$ | Melting point 154–155° C. |
| 6.292 | (Diastereomer 1) decahydroquinoline with CH₃ | $C_6F_5O-$ | $-NH_2$ | Melting point 165–166° C. |

TABLE 6-continued

Compounds of the formula II

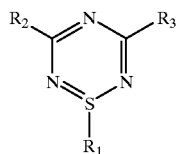

(II)

| Comp. No. | R₁ | R₃ | R₂ | Physical data |
|---|---|---|---|---|
| 6.293 | (Diastereomer 2) [structure: N-methyl decahydroquinoline with 3-CH₃] | C₆F₅O— | —NH₂ | $^{13}$C-NMR (ppm): 165.8; 164.5; 62.2; 47.7; 41.9; 31.9; 30.7; 29.5; 24.9; 24.8; 19.2 |
| 6.294 | (Diastereomerengem) [structure: N-methyl decahydroquinoline with 2-CH₃] | C₆F₅O— | —NH₂ | Melting point 181–182° C. |
| 6.295 | (Diastereomer 1) [structure: N-methyl octahydroindole with 3-CH₃] | C₆F₅O— | —NH₂ | Melting point 162–163° C. |
| 6.296 | (Diastereomer 2) [structure: N-methyl octahydroindole with 3-CH₃] | C₆F₅O— | —NH₂ | Melting point 147–148° C. |
| 6.297 | (Diastereomer 1) [structure: N-methyl octahydroindole with 5-CH₃] | C₆F₅O— | —NH₂ | Melting point 134–135° C. |
| 6.298 | (Diastereomer 2) [structure: N-methyl octahydroindole with 5-CH₃] | C₆F₅O— | —NH₂ | Melting point 158–159° C. |

TABLE 6-continued

Compounds of the formula II

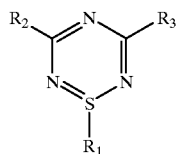

(II)

| Comp. No. | R₁ | R₃ | R₂ | Physical data |
|---|---|---|---|---|
| 6.299 | CH₃, CH₃, CH₃-substituted octahydroindole, N-methyl (Diastereomer mixture) | $C_6F_5O-$ | $-NH_2$ | Resin |
| 6.300 | 6,7-dimethoxy-N-methyl decahydroisoquinoline (Diastereomer mixture) | $C_6F_5O-$ | $-NH_2$ | Melting point 165–166° C. |
| 6.301 | 1,2-dimethyl-4,5,6,7-tetrahydroindole | $C_6F_5O-$ | $-NH_2$ | Melting point 177–178° C. (Decomposition) |
| 6.302 | N-methyl azonane ((CH₂)₈) | 2,3,5,6-tetrafluorophenoxy | $-NH_2$ | Melting point 174–175° C. |
| 6.303 | N-methyl-N-cyclohexyl-isopropylamine | phenoxy | $-N(CH_3)_2$ | Melting point 125–126° C. |
| 6.304 | N-methyl pyrrolidine | $-OH$ | $-NH_2$ | Melting point 207–208-C. |
| 6.305 | N-methyl thiomorpholine | $-OH$ | $-NH_2$ | Melting point 178–180° C. |
| 6.306 | 3-ethyl-N-methyl piperidine | $-OH$ | $-NH_2$ | Melting point 176–177° C. |

TABLE 6-continued

Compounds of the formula II

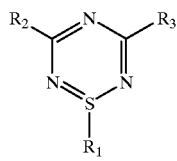

(II)

| Comp. No. | $R_1$ | $R_3$ | $R_2$ | Physical data |
|---|---|---|---|---|
| 6.307 | (N-methyl tetrahydropyridine) | —OH | —$NH_2$ | Melting point 170–171° C. |
| 6.308 | (N-methyl dihydropyrrole) | —OH | —$NH_2$ | Melting point 203–204° C. |
| 6.309 | (N-methyl decahydroisoquinoline) | —OH | —$NH_2$ | Melting point 187–188° C. |
| 6.310 | —N(CH₃)—C₆H₁₀—CH(CH₃)₂ | (phenylthio) | —N(CH₃)₂ | Resin; analysis: $C_{19}H_{29}N_5S$ calc. found [%] [%] N 17.88 17.86 S 16.38 16.36 |
| 6.311 | (N-methyl methoxy-benzazepine) | $C_6F_5O$— | —$NH_2$ | |
| 6.312 | (N-methyl benzoxazepine) | $C_6F_5O$— | —$NH_2$ | Melting point 150–151° C. |
| 6.313 | (N-methyl 4-phenyl-4-cyanopiperidine) | $C_6F_5O$— | —$NH_2$ | Melting point 191–192° C. |
| 6.314 | (N-methyl decahydrobenzazepine) | $C_6F_5O$— | —$NH_2$ | |

TABLE 6-continued
Compounds of the formula II
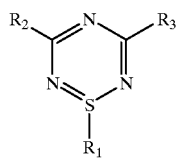
| Comp. No. | R₁ | R₃ | R₂ | Physical data |
|---|---|---|---|---|
| 6.315 | | $C_6F_5O-$ | $-NH_2$ | |
| 6.316 | ![structure](N-methyl morpholine-fused) | $C_6F_5O-$ | $-NH_2$ | |
| 6.317 | ![structure](N,N'-dimethyl piperazine-fused) | $C_6F_5O-$ | $-NH_2$ | |
| 6.318 | ![structure](N-methyl, C-methyl azabicyclic) | $C_6F_5O-$ | $-NH_2$ | |
| 6.319 | ![structure](N-methyl, gem-dimethyl azabicyclic) | $C_6F_5O-$ | $-NH_2$ | |
| 6.320 | $-N$(CH₂)₁₀ | ![tetrafluoro methoxyphenyl] | $-NH_2$ | Melting point 168–169° C. |

TABLE 6-continued

Compounds of the formula II

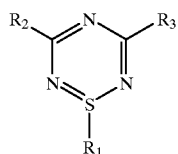

(II)

| Comp. No. | R₁ | R₃ | R₂ | Physical data |
|---|---|---|---|---|
| 6.321 | —N⟨(CH₂)₇⟩ | 2,3,5,6-tetrafluoro-4-methoxyphenyl | —NH₂ | Melting point 174–175° C. (Decomposition) |
| 6.322 | N-methyl-2,3,4,5-tetrahydro-1H-2-benzazepin-2-yl | $C_6F_5O-$ | —NH₂ | Melting point 171–172° C. |
| 6.323 | N-methyl-trans-decahydro-benzazepinyl | $C_6F_5O-$ | —NH₂ | |
| 6.324 | N-methyl-perhydroacridinyl | $C_6F_5O-$ | —NH₂ | Melting point 138–139° C. |
| 6.325 | 1,3,3,5,5-pentamethylhexahydroazepinyl | $C_6F_5O-$ | —NH₂ | Melting point 134–135° C. |
| 6.326 | 1,4,4-trimethylhexahydroazepinyl | $C_6F_5O-$ | —NH₂ | Melting point 122–123° C. |
| 6.327 | N-methyl-2,3,4,5-tetrahydro-1H-naphth[2,3-c]azepinyl | $C_6F_5O-$ | —NH₂ | |

TABLE 6-continued
Compounds of the formula II
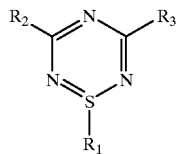
(II)
| Comp. No. | R₁ | R₃ | R₂ | Physical data |
|---|---|---|---|---|
| 6.328 | 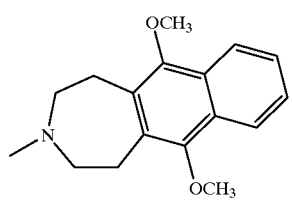 | $C_6F_5O-$ | $-NH_2$ | |
| 6.329 | 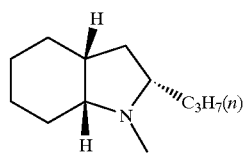 | $C_6F_5O-$ | $-NH_2$ | |
| 6.330 | 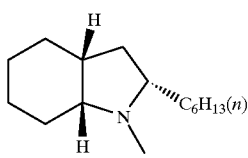 | $C_6F_5O-$ | $-NH_2$ | |
| 6.331 | 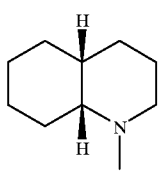 | 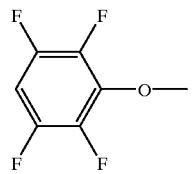 | $-NH_2$ | Melting point 179–180° C. |
| 6.332 | 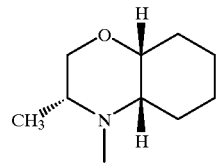 | $C_6F_5O-$ | $-NH_2$ | Melting point 166–167° C. |
| 6.333 | 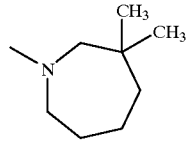 | $C_6F_5O-$ | $-NH_2$ | Melting point 173–174° C. |
| 6.334 | —NH-Adamant-1-yl | $C_6F_5O-$ | $-NH_2$ | |
| 6.335 | —NH-Adamant-2-yl | $C_6F_5O-$ | $-NH_2$ | |

Example H20

Preparation of 3-amino-5-chloro-1-(3-hexyloxy)thiatriazine

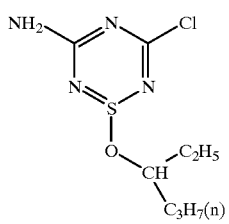

(Compound No. 7.203)

13.6 g of a 22% methylmagnesium chloride solution in THF (0.040 mol) are added to a solution of 4.1 g of 3-hexanol (0.040 mol) in 40 ml of absolute tetrahydrofuran (THF) at a temperature of −70° to −60° C., under a nitrogen atmosphere and with vigorous stirring. After thawing to 20° C., the solution is added dropwise to a solution, cooled to −65° C., of 8.2 g of 1,3,5-trichlorothiatriazine (0.040 mol) in 50 ml of absolute THF, while stirring vigorously. After warming to 0° C., the resulting colourless solution is treated with ammonia, while stirring vigorously. After the intermediate (3,5-dichloro-1-(3-hexyloxy)thiatriazine) has reacted further, 1 l of water is added to the reaction mixture. The resulting suspension is filtered with suction and the residue is rinsed with water and dissolved in methylene chloride, and the solution is dried over sodium sulfate. After the solvent has been evaporated off, the residue is stirred with pentane and the desired product is isolated as white crystals of melting point 144° C. by filtration with suction.

The compounds listed in the following Table 7 can be prepared analogously to Example H20.

TABLE 7

Compounds of the formula VIII

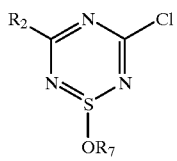

(VIII)

| Comp. No. | Process | R$_7$ | R$_2$ | Physical data |
|---|---|---|---|---|
| 7.1 | | —CH$_2$CH$_2$Cl | —NH$_2$ | |
| 7.2 | | —CH$_2$CH$_2$C$_6$H$_5$ | —N(CH$_3$)C$_4$H$_9$(n) | |
| 7.3 | | —CH(CH$_3$)$_2$ | —NH$_2$ | |
| 7.4 | | —CH$_2$CH$_2$Cl | —N(CH$_3$)$_2$ | |
| 7.5 | | —CH$_2$—(2,3-dichlorophenyl) | —NH$_2$ | |
| 7.6 | | —(cyclohexyl with methyl) | —NH$_2$ | |
| 7.7 | | —(cyclohexenyl with COOC$_2$H$_5$ and methyl) | —NH$_2$ | |
| 7.8 | | —CH$_2$CH$_2$C$_6$H$_5$ | —(bornyl-NH—) | |
| 7.9 | | —(1-methylcyclohexyl with CH$_3$) | —NH$_2$ | |

TABLE 7-continued

Compounds of the formula VIII (VIII)

| Comp. No. | Process | R₇ | R₂ | Physical data |
|---|---|---|---|---|
| 7.10 | | *decahydronaphthalenyl with methyl* | —NH₂ | |
| 7.11 | | —CH₂CH₂Cl | —NHC(CH₃)₃ | |
| 7.12 | | *indanyl* | —NH₂ | |
| 7.13 | | —CH₂CH₂Cl | —N(morpholino) | |
| 7.14 | | —CH(4-OCH₃-C₆H₄)(4-Cl-C₆H₄) | —NH₂ | |
| 7.15 | | *3,3,5-trimethylcyclohexyl (with CH₃ wedge)* | —NH₂ | |
| 7.16 | | *3-methylcyclopentyl-1-CN* | —NH₂ | |
| 7.17 | | —CH(CH₃)CH₂OCH₃ | —NH₂ | |
| 7.18 | | *4-methylcyclohexyl* | —NH₂ | |

TABLE 7-continued
Compounds of the formula VIII
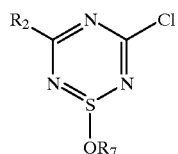
(VIII)
| Comp. No. | Process | R₇ | R₂ | Physical data |
|---|---|---|---|---|
| 7.19 | | (2-isobutylcyclohexyl) CH₂CH(CH₃)₂ | —NH₂ | |
| 7.20 | | —CH₂CH₂Cl | piperidin-1-yl | |
| 7.21 | | (1R,3R,4S)-menthyl, CH₃/CH₃—CH/CH₃ (+) | —NH₂ | |
| 7.22 | | PhCH(CH₃)— | —NH₂ | |
| 7.23 | | —CH₂CH=CH₂ | —NH₂ | |
| 7.24 | | 2-tert-butylcyclohexyl, C(CH₃)₃ | —NH₂ | |
| 7.25 | | —CH₂Ph | —NH-cyclopentyl | |
| 7.26 | | —(CH₂)₆CH₃ | —NH₂ | |
| 7.27 | | 2-isocyanocyclohexyl, NC | —NH₂ | |
| 7.28 | | 2-methylcyclopentyl | —NH₂ | |

TABLE 7-continued
Compounds of the formula VIII
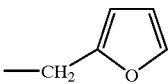
(VIII)
| Comp. No. | Process | R₇ | R₂ | Physical data |
|---|---|---|---|---|
| 7.29 | | 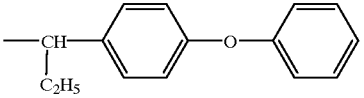 —CH₂- (furan) | —NH₂ | |
| 7.30 | | —CH₂CH₂NO₂ | —NH₂ | |
| 7.31 | | —CH₂C₆F₅ | —NH₂ | |
| 7.32 | | 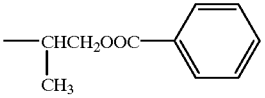 —CH(C₂H₅)-C₆H₄-O-C₆H₅ | —NH₂ | |
| 7.33 | | 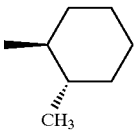 —CH(CH₃)CH₂OOC-C₆H₅ | —NH₂ | |
| 7.34 | | —CH₃ | —NHCH₂CH₂CH₃ | |
| 7.35 | | 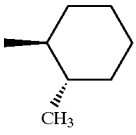 cyclohexyl-CH₃ (Diastereomer 1) | —NH₂ | |
| 7.36 | | 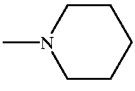 cyclohexyl-CH₃ (Diastereomer 2) | —NH₂ | |
| 7.37 | | —CH₂CH₂Cl | piperidinyl | |
| 7.38 | | 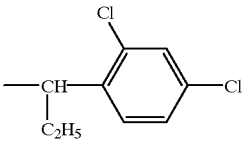 —CH(C₂H₅)-2,4-Cl₂-C₆H₃ | —NH₂ | |
| 7.39 | | —CH₃ | —N(CH₃)₂ | |
| 7.40 | |  4,4-dimethylcyclohexyl | —NH₂ | |

TABLE 7-continued
Compounds of the formula VIII
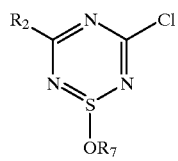
(VIII)
| Comp. No. | Process | R₇ | R₂ | Physical data |
|---|---|---|---|---|
| 7.41 | | —CH₂-(3-pyridyl) | —NH₂ | |
| 7.42 | | cyclohept-2-enyl | —NH₂ | |
| 7.43 | | 1,2,3,4-tetrahydronaphthalen-2-yl | —NH₂ | |
| 7.44 | | trans-4-(2-methylbutan-2-yl)cyclohexyl | —NH₂ | |
| 7.45 | | —CH₂CH₂Cl | —NHCH₂CH₂CH₃ | |
| 7.46 | | 1-methyl-4,5,6,7-tetrahydroindol-7-yl | —NH₂ | |
| 7.47 | | —CH₂-(1-methylindol-3-yl) | —NH₂ | |
| 7.48 | | 2-methylcyclopentyl-N=CH— | —NH₂ | |
| 7.49 | | tetrahydrothiopyran-3-yl | —NH₂ | |
| 7.50 | | —CH₂CH₂COOC₂H₅ | —NH₂ | |

TABLE 7-continued

Compounds of the formula VIII (VIII)

| Comp. No. | Process | R₇ | R₂ | Physical data |
|---|---|---|---|---|
| 7.51 | | *cis*-2-chlorocyclohexyl | —NH₂ | |
| 7.52 | | —CH₂C≡CH | —NH₂ | |
| 7.53 | | —CH₂-(2-thienyl) | —NH₂ | |
| 7.54 | | 1-tetralinyl | —NH₂ | |
| 7.55 | | —CH₃ | —NH₂ | |
| 7.56 | | —CH₂CH₂-phenyl | —NH₂ | |
| 7.57 | | *cis*-2-chlorocyclooctyl | —NH₂ | |
| 7.58 | | *cis*-2-chlorocyclooctyl | —NHCH₃ | |
| 7.59 | | 3-methyloxetanyl | —NH₂ | |
| 7.60 | | —CH₂-(2-chloro-6-nitrophenyl) | —NH₂ | |
| 7.61 | | —CH₂CH₂CCl₃ | —NH₂ | |

TABLE 7-continued

Compounds of the formula VIII (VIII)

[Structure: 1,2,4,6-thiatriazine ring with R_2 at 3-position, Cl at 5-position, and OR_7 on S]

| Comp. No. | Process | R_7 | R_2 | Physical data |
|---|---|---|---|---|
| 7.62 | | [2-naphthyl-CH(CH_3)–] | —NH_2 | |
| 7.63 | | [3,3,5-trimethylcyclohexyl] | —NH_2 | |
| 7.64 | | [1-naphthyl-CH(CH_3)–] | —NH_2 | |
| 7.65 | | [3,5,5-trimethylcyclohex-1-en-1-yl with CH_3] | —NH_2 | |
| 7.66 | | [2-methyl-1,1-dimethoxycyclohexyl] | —NH_2 | |
| 7.67 | | —CH_2-adamantyl | —NH_2 | |
| 7.68 | | [cis/trans-3,5,5-trimethylcyclohexyl] | —NH_2 | |

TABLE 7-continued
Compounds of the formula VIII
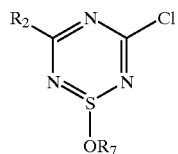
(VIII)
| Comp. No. | Process | R₇ | R₂ | Physical data |
|---|---|---|---|---|
| 7.69 | | (2,4,4-trimethylcyclohexyl) | —NH₂ | |
| 7.70 | | (+)-bornyl | —NH₂ | |
| 7.71 | | (guaiazulenyl-CH₂—) | —NH₂ | |
| 7.72 | | (indan-2-yl) | —NH₂ | |
| 7.73 | | —CH₂-(tetrahydrofuran-2-yl) | —NH₂ | |
| 7.74 | | (2-chloro-cyclooctyl, methyl) | 3-ethylpiperidin-1-yl | |
| 7.75 | | (2-trifluoromethyl-cyclohexyl) | —NH₂ | |
| 7.76 | | —CH₂CH₂OCH₃ | —NH₂ | |

TABLE 7-continued
Compounds of the formula VIII
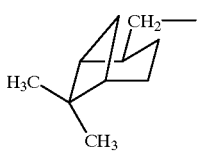
(VIII)
| Comp. No. | Process | R₇ | R₂ | Physical data |
|---|---|---|---|---|
| 7.77 | | 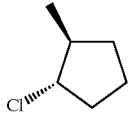 | —NHC$_4$H$_9$(n) | |
| 7.78 | | 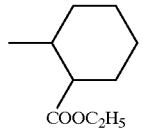 | —NH$_2$ | |
| 7.79 | | 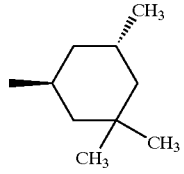 | —NH$_2$ | |
| 7.80 | | 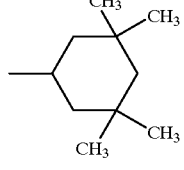 | —NH$_2$ | |
| 7.81 | | 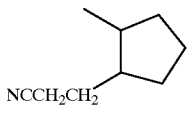 | —NH$_2$ | |
| 7.82 | | —CH$_2$CH$_2$F | —NH$_2$ | |
| 7.83 | | 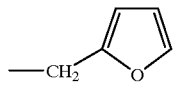 | —NH$_2$ | |
| 7.84 | | —(CH$_2$)$_7$CH$_3$ | —NHCH$_3$ | |
| 7.85 | |  | —NH$_2$ | |
| 7.86 | | —C$_2$H$_5$ | —NH$_2$ | |
| 7.87 | | —CH(CH$_3$)C$_2$H$_5$ | —NH$_2$ | |
| 7.88 | | —C(CH$_3$)$_3$ | —NH$_2$ | |

TABLE 7-continued

Compounds of the formula VIII (VIII)

| Comp. No. | Process | R₇ | R₂ | Physical data |
|---|---|---|---|---|
| 7.89 | | (3-methylcyclohexyl with CN) | —NH₂ | |
| 7.90 | | (methyl, chloro-substituted cyclodecyl) | —NH₂ | |
| 7.91 | | —CH₃ | —NHC(CH₃)₃ | |
| 7.92 | | (4-methyltetrahydropyranyl) | —NH₂ | |
| 7.93 | | (2-methylcyclopentyl-cyclopentyl) | —NH₂ | |
| 7.94 | | (methylnorbornyl) | —NH₂ | |
| 7.95 | | (methyl, NCCH₂CH₂-substituted cyclodecyl) | —NH₂ | |
| 7.96 | | (1,3,5-trimethylcyclohexyl) | —NH₂ | |

TABLE 7-continued

Compounds of the formula VIII (VIII)

[Structure: 1,2,4,6-thiatriazine ring with R₂, Cl, and OR₇ substituents]

| Comp. No. | Process | R₇ | R₂ | Physical data |
|---|---|---|---|---|
| 7.97 | | —CH₂—C₆H₅ | —NHCH(CH₃)CH₂OCH₃ | |
| 7.98 | | —CH(C₆H₅)CH₂Cl | —NH₂ | |
| 7.99 | | cyclooctyl with CH₂CH₂CN substituent | —NH₂ | |
| 7.100 | | cyclohexyl with CF₃ substituent | —NH₂ | |
| 7.101 | | —C₂H₅ | —NH₂ | |
| 7.102 | | cyclohexyl with two CH₃ groups | —NH₂ | |
| 7.103 | | trans-cyclohexyl with C(CH₃)₃ | —NH₂ | |
| 7.104 | | —CH₂-(2,6-difluorophenyl) | —NH₂ | |
| 7.105 | | —CH(C₆H₅)-(4-chlorophenyl) | —NH₂ | |
| 7.106 | | —CH₂-(4-biphenyl) | —NH₂ | |

TABLE 7-continued
Compounds of the formula VIII
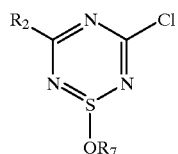
(VIII)
| Comp. No. | Process | R₇ | R₂ | Physical data |
|---|---|---|---|---|
| 7.107 | | —CH₂—(tetrahydropyran-2-yl) | —NH₂ | |
| 7.108 | | 2-(2-cyanoethyl)cyclohexyl | —NH₂ | |
| 7.109 | | —CH(CH₃)—phenyl | —NHCH₃ | |
| 7.110 | | —CH₂—(2-fluorophenyl) | —NH₂ | |
| 7.111 | | 3-(tetrahydrofuranyl) | —NH₂ | |
| 7.112 | | trans-3-methylcyclohexyl | —NH₂ | |
| 7.113 | | 3-cyclohexenyl | —NH₂ | |
| 7.114 | | —CH(CH₃)—(4-chlorophenyl)—C(CH₃)₂—(1,2,4-triazol-1-yl) | —NH₂ | |

TABLE 7-continued

Compounds of the formula VIII

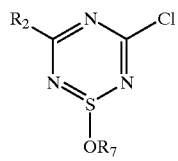

(VIII)

| Comp. No. | Process | R$_7$ | R$_2$ | Physical data |
|---|---|---|---|---|
| 7.115 | | (methylcyclooctyl) | —NH$_2$ | |
| 7.116 | | (3,5,5-trimethylcyclohexyl) | —NH$_2$ | |
| 7.117 | | (1-ethynyl-1-methylcyclohexyl) | —NH$_2$ | |
| 7.118 | | (4-(2-methylbutan-2-yl)cyclohexyl) with C(CH$_3$)$_2$C$_2$H$_5$ | —NH$_2$ | |
| 7.119 | | (2-chlorocyclopentyl) | —NHC$_2$H$_5$ | |
| 7.120 | | (1,1-dichloro-2-methyl-4-(prop-1-en-2-yl)cyclohexyl) | —NH$_2$ | |
| 7.121 | | (1-chloro-1-methyl-4-(prop-1-en-2-yl)cyclohexyl) | —NH$_2$ | |
| 7.122 | | (1,3-dioxan-5-yl) | —NH$_2$ | |
| 7.123 | | —(CH$_2$)$_4$CH$_3$ | —NH$_2$ | |

TABLE 7-continued

Compounds of the formula VIII

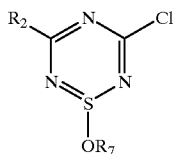

(VIII)

| Comp. No. | Process | R₇ | R₂ | Physical data |
|---|---|---|---|---|
| 7.124 | | ![norbornene-CH2] | —NH₂ | |
| 7.125 | | —CH₂CH₂SC₂H₅ | —NH₂ | |
| 7.126 | | —CH₂CH₂Si(CH₃)₃ | —NH₂ | |
| 7.127 | | —(CH₂)₉CH₃ | —NH₂ | |
| 7.128 | | ![trans-cyclohexyl-CH(CH₃)₂] | —NH₂ | |
| 7.129 | | ![cyclohexyl with Cl and 2x COOCH₃] | —NH₂ | |
| 7.130 | | ![cyclohexyl with Cl and 2x COOCH₃] | —NH₂ | |
| 7.131 | | ![chroman-4-yl] | —NH₂ | |
| 7.132 | | —(CH₂)₂(CF₂)₃CF₃ | —NH₂ | |
| 7.133 | | ![cycloheptyl-NCCH₂] | —NH₂ | |
| 7.134 | | —CH₂CH(C₆H₅)₂ | —NH₂ | |
| 7.135 | | —CH₂—C₆H₅ | —NH₂ | |
| 7.136 | | ![cyclohexyl-CCl₃] | —NH₂ | |

TABLE 7-continued

Compounds of the formula VIII

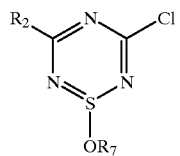
(VIII)

| Comp. No. | Process | R₇ | R₂ | Physical data |
|---|---|---|---|---|
| 7.137 | | CH₂CH₂COOC₂H₅ (on methylcyclohexyl) | —NH₂ | |
| 7.138 | | —CH₂CH₂Cl | —NHCH₂CH₂CH₃ | |
| 7.139 | | 3,5-dimethylcyclohexyl | —NHC₄H₉(n) | |
| 7.140 | | pinanyl-CH₂CH₂— | —NH₂ | |
| 7.141 | | 1-ethyl-3-methylpiperidinyl | —NH₂ | |
| 7.142 | | —CH₂CH₂Cl | —NHCH(CH₃)₂ | |
| 7.143 | | —CH₂CH₂Cl | —N(C₂H₅)₂ | |
| 7.144 | | 2,3-dimethylcyclohexyl | —NH₂ | |
| 7.145 | | 5-methoxy-1,8-dimethyltetrahydronaphthyl | —NH₂ | |
| 7.146 | | 2-methylcycloheptyl with NCCH₂CH₂ | —NH₂ | |

TABLE 7-continued

Compounds of the formula VIII (VIII)

| Comp. No. | Process | R$_7$ | R$_2$ | Physical data |
|---|---|---|---|---|
| 7.147 | | —CH$_2$CH$_2$Cl | —NHCH$_2$C$_6$H$_5$ | |
| 7.148 | | [bicyclic structure with three CH$_3$ groups] | —NH$_2$ | |
| 7.149 | | [methylcyclohexyl-cyclohexyl structure] | —NH$_2$ | |
| 7.150 | | [norbornyl structure with three CH$_3$ groups] | —NH$_2$ | |
| 7.151 | | [(CH$_3$)$_3$C-cyclohexenyl-CH$_3$ structure] | —NH$_2$ | |
| 7.152 | | [hexahydrobenzofuranone structure with CH$_3$] | —NH$_2$ | |
| 7.153 | | [methylcyclohexyl-CH$_2$CN structure] | —NH$_2$ | |
| 7.154 | | —CHCH$_2$Cl<br>\|<br>C$_2$H$_5$ | —NH$_2$ | |
| 7.155 | | —CHCH$_2$Cl<br>\|<br>C$_6$H$_5$ | —NH$_2$ | |

TABLE 7-continued
Compounds of the formula VIII
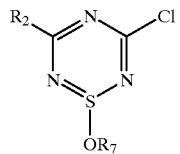
(VIII)
| Comp. No. | Process | $R_7$ | $R_2$ | Physical data |
|---|---|---|---|---|
| 7.156 | | (ethylnorbornyl) | —$NH_2$ | |
| 7.157 | | —CH(CH$_3$)CH$_2$Cl | —$NH_2$ | |
| 7.158 | | 2-chlorocyclohexyl | —$NH_2$ | |
| 7.159 | | 2-(n-propoxy)cyclohexyl (trans) | —$NH_2$ | |
| 7.160 | | 2-(methylthio)cycloheptyl (trans) | —$NH_2$ | |
| 7.161 | | 1-ethoxy-2-methylindanyl | —$NH_2$ | |
| 7.162 | | 2-methoxycyclopentyl (trans) | —$NH_2$ | |
| 7.163 | | 2-(n-propylthio)cyclooctyl (trans) | —$NH_2$ | |
| 7.164 | | 2,2-dimethyl-tetrahydroindanyl | —$NH_2$ | |

TABLE 7-continued
Compounds of the formula VIII
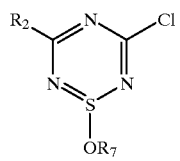
(VIII)
| Comp. No. | Process | $R_7$ | $R_2$ | Physical data |
|---|---|---|---|---|
| 7.165 | | (2,2-disubstituted bicyclic with $C_3H_7(n)$) | —$NH_2$ | |
| 7.166 | | (bicyclic with $C_2H_5$) | —$NH_2$ | |
| 7.167 | | (cyclopentene with $CH_3$, $CH_3$, $CH_3$) | —$NH_2$ | |
| 7.168 | | (tetrahydronaphthalene with $CH_3$) | —$NH_2$ | |
| 7.169 | | (bicyclohexyl) | —$NH_2$ | |
| 7.170 | | (cyclohexyl with $C_2H_5$, $C_2H_5$, $C_2H_5$) | —$NH_2$ | |
| 7.171 | | (cyclohexyl with $CH_3$, $CH_3$, $CH_3$, $CH_3$) | —$NH_2$ | |
| 7.172 | | (cyclohexyl with $C_4H_9(n)$) | —$NH_2$ | |

TABLE 7-continued

Compounds of the formula VIII $$\text{(VIII)}$$

| Comp. No. | Process | R₇ | R₂ | Physical data |
|---|---|---|---|---|
| 7.173 | | 4-methyl-2,2,3-trimethylcyclohexyl | —NH₂ | |
| 7.174 | | 4-(trimethylsilyl)cyclohexyl | —NH₂ | |
| 7.175 | | 4-(isopropylmethyl)cyclohexyl | —NH₂ | |
| 7.176 | | 4-(trifluoromethyl)cyclohexyl | —NH₂ | |
| 7.177 | | 2-(methylthio)cyclohexyl | —NH₂ | |
| 7.178 | | 2-benzylcyclohexyl | —NH₂ | |
| 7.179 | | 2-isopropylcyclohexyl | —NH₂ | |
| 7.180 | | 2-ethylcyclopentyl | —NH₂ | |
| 7.181 | | 2,2-dimethylcyclopentyl | —NH₂ | |

TABLE 7-continued

Compounds of the formula VIII $$\text{(VIII)}$$

| Comp. No. | Process | R$_7$ | R$_2$ | Physical data |
|---|---|---|---|---|
| 7.182 | | 1,1-dimethyl-3-methylcyclopentyl | —NH$_2$ | |
| 7.183 | | 2-methyl-4,4-dimethylcyclopentyl | —NH$_2$ | |
| 7.184 | | 2-(n-C$_6$H$_{13}$)cyclopentyl | —NH$_2$ | |
| 7.185 | | 3-(C(CH$_3$)$_2$C$_2$H$_5$)cyclopentyl | —NH$_2$ | |
| 7.186 | | 2,2,5,5-tetramethylcyclopentyl | —NH$_2$ | |
| 7.187 | | 2,2,4,4-tetramethylcyclopentyl | —NH$_2$ | |
| 7.188 | | —(CH$_2$)$_3$Si(CH$_3$)$_3$ | —NH$_2$ | |
| 7.189 | | trans-4-tert-butylcyclohexyl | —NH$_2$ | |
| 7.190 | b$_4$ | trans-4-methylcyclohexyl | —NH$_2$ | Melting point 144° C. (Decomposition) |

TABLE 7-continued

Compounds of the formula VIII

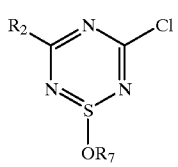

(VIII)

| Comp. No. | Process | $R_7$ | $R_2$ | Physical data |
|---|---|---|---|---|
| 7.191 | | —CH₂CH₂—N(C(=O)C(CH₃)=C(CH₃)C(=O)) (2,3-dimethylmaleimid-N-yl-ethyl) | —NH₂ | |
| 7.192 | | —CH₂-(2,6-dinitrophenyl) | —NH₂ | |
| 7.193 | | —CH₂Si(CH₃)₃ | —NH₂ | |
| 7.194 | | trans-4-tert-butylcyclohexyl | —NHC₂H₅ | |
| 7.195 | | cis-4-tert-butylcyclohexyl | —NHCH₃ | |
| 7.196 | | trans-2-(2-cyanoethyl)cyclopentyl | —NH₂ | |
| 7.197 | | cis-2-(2-cyanoethyl)cyclopentyl | —NH₂ | |
| 7.198 | | cis-4-methylcyclohexyl | —NH₂ | |
| 7.199 | | trans-4-methylcyclohexyl | —NH₂ | |
| 7.200 | | —CH(Si(CH₃)₃)—CH=CH₂ | —NH₂ | |
| 7.201 | | —CH(CH₃)—Si(CH₃)₃ | —NH₂ | |
| 7.202 | | —CH(CH₃)COOCH₃ | —NH₂ | |

TABLE 7-continued

Compounds of the formula VIII (VIII)

| Comp. No. | Process | R₇ | R₂ | Physical data |
|---|---|---|---|---|
| 7.203 | b₄ | —CH(C₂H₅)(C₃H₇(n)) | —NH₂ | Melting point 144° C. |
| 7.204 | | —CH₂CH₂S-cyclohexyl | —NH₂ | |
| 7.205 | b₄ | —CH[CH₂CH(CH₃)₂]₂ | —NH₂ | ¹H-NMR (CDCl₃, ppm): 6.3 (broad s, 1H); 5,4 (broad s, 1H); 4.25–4.35 (m, 1H); 1.9–1.3(m, 6H); 1.0–0.83(m, 12H) |
| 7.206 | | trans-4-methylcyclohexyl | —NH₂ | |
| 7.207 | | decahydronaphthalenyl | —NH₂ | |
| 7.208 | | decahydronaphthalenyl | —NH₂ | |
| 7.209 | | decahydronaphthalenyl | —NH₂ | |
| 7.210 | | —CH(CH₃)-(3-methylphenyl) | —NH₂ | |
| 7.211 | | 1,4-dioxaspiro[4.5]decyl | —NH₂ | |

TABLE 7-continued
Compounds of the formula VIII
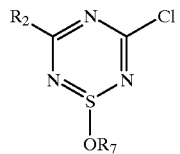
(VIII)
| Comp. No. | Process | R₇ | R₂ | Physical data |
|---|---|---|---|---|
| 7.212 | | (norbornenyl, H down) | —NH₂ | |
| 7.213 | | (norbornenyl, H) | —NH₂ | |
| 7.214 | | (norbornenyl-CH₂—, H) | —NH₂ | |
| 7.215 | | (pinanyl with CH₃, CH₃, CH₃) | —NH₂ | |
| 7.216 | | (pinanyl with CH₃, CH₃, CH₃) | —NH₂ | |
| 7.217 | | (pinenyl with CH₃, CH₃, CH₃) | —NH₂ | |
| 7.218 | | (trans-CF₃-cyclohexyl) | —NH₂ | |
| 7.219 | | (CF₃-cyclohexyl, Diastereomer 1) | —NH₂ | |

TABLE 7-continued
Compounds of the formula VIII
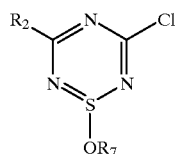
(VIII)
| Comp. No. | Process | R₇ | R₂ | Physical data |
|---|---|---|---|---|
| 7.220 | | —CH₂—C(CH₃)(CH₂CH₂CN)₂ | —NH₂ | |
| 7.221 | | (1,2-cis-cyanocyclopentyl) | —NH₂ | |
| 7.222 | | (1,2-trans-cyanocyclopentyl) | —NH₂ | |
| 7.223 | | —CH(CH₃)—[2-NO₂, 4-F, 5-OCHF₂-phenyl] | —NH₂ | |
| 7.224 | | —CH(C₂H₅)—[4-phenoxyphenyl] | —NH₂ | |
| 7.225 | | —CH(CH₃)—CH₂—[2-OCH₃-phenyl] | —NH₂ | |
| 7.226 | | —CH₂—CH(C₃H₇(n))—[2,4-Cl₂-phenyl] | —NH₂ | |
| 7.227 | | —CH<(CH₂)₉> (cycloundecyl) | —NH₂ | |

TABLE 7-continued
Compounds of the formula VIII
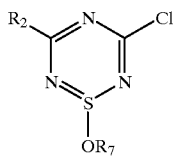
(VIII)
| Comp. No. | Process | R₇ | R₂ | Physical data |
|---|---|---|---|---|
| 7.228 | | —CH⟨(CH₂)₆⟩ | —NH₂ | |
| 7.229 | | —CH⟨(CH₂)₁₁⟩ | —NH₂ | |
| 7.230 | | —CH₂—C₆H₄(m-CF₃) | —NH₂ | |
| 7.231 | | —CH₂CH₂C₆F₅ | —NH₂ | |
| 7.232 | | —CH₂—cyclohexyl | —NH₂ | |
| 7.233 | | decahydronaphthyl (with CN), stereochem. | —NH₂ | |
| 7.234 | | decahydronaphthyl (with CN), stereochem. | —NH₂ | |
| 7.235 | | 4-C(CH₃)₃-cyclohexyl | —NH₂ | |

Example H21

Preparation of 3,5-dichloro-1-(octahydroindol-1-yl) thiatriazine (Compound No. 8.80)

A mixture of 3.1 g of octahydroindol (0.025 mol) and 2.5 g of triethylamine (0.025 mol) is added dropwise to a solution of 5.1 g of 1,3,5-trichlorothiatriazine (0.025 mol) in 65 ml of diethyl ether at a temperature of −70° to −60° C., under a nitrogen atmosphere and with vigorous stirring. After the reaction mixture has thawed, water is added and the organic phase is washed with water, sodium bicarbonate solution and brine, dried over sodium sulfate and evaporated. After crystallization from pentane, crystals of the desired compound of melting point 90–92° C. are isolated.

The compounds listed in the following Table 8 can be prepared analogously to Example H21.

TABLE 8

Compounds of the the formula IX (IX)

| Comp. No. | $R_1$ | Physical data |
|---|---|---|
| 8.1 | —NHCH$_2$CH$_2$CH$_3$ | |
| 8.2 | (structure) | |
| 8.3 | (structure) | |
| 8.4 | —N(CH$_3$)(CH$_2$)$_6$CH$_3$ | |
| 8.5 | (2,6-dimethylmorpholinyl) | |
| 8.6 | (octahydroindolyl) | |
| 8.7 | —N(CH$_3$)C$_6$H$_{11}$(c) | |
| 8.8 | (2,6-dimethylmorpholinyl) | |
| 8.9 | (4-trifluoromethylpiperidinyl) | |
| 8.10 | (tetrahydroisoquinolinyl) | |
| 8.11 | (3-ethylpiperidinyl) | |
| 8.12 | (decahydroquinolinyl) | |

TABLE 8-continued
Compounds of the the formula IX
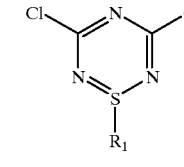
(IX)
| Comp. No. | R₁ | Physical data |
|---|---|---|
| 8.13 | 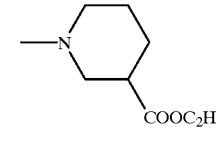 | |
| 8.14 | 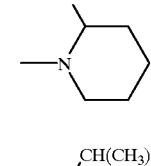 | |
| 8.15 | —N(CH₂CH₂CN)₂ | |
| 8.16 | —NHC₆H₁₁(c) | |
| 8.17 | —N(n-C₃H₇)₂ | |
| 8.18 | 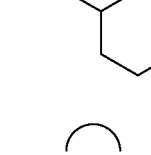 | |
| 8.19 | 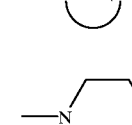 | |
| 8.20 | 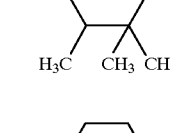 | |
| 8.21 | 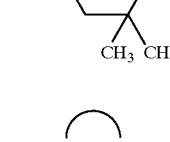 | |
| 8.22 | 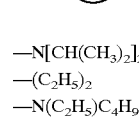 | |
| 8.23 | 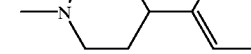 | |
TABLE 8-continued
Compounds of the the formula IX
(IX)
| Comp. No. | R₁ | Physical data |
|---|---|---|
| 8.24 | piperidine-3-COOC₂H₅ | |
| 8.25 | 2-ethylpiperidine | |
| 8.26 | N(CH(CH₃)₂)(cyclohexyl) | |
| 8.27 | N-(CH₂)₉ ring | |
| 8.28 | 2,3,3-trimethylpiperidine | |
| 8.29 | 3,3-dimethylpiperidine | |
| 8.30 | N-(CH₂)₆ ring | |
| 8.31 | —N[CH(CH₃)₂]₂ | |
| 8.32 | —(C₂H₅)₂ | |
| 8.33 | —N(C₂H₅)C₄H₉(n) | |
| 8.34 | 4-phenylpiperidine | |

TABLE 8-continued
Compounds of the formula IX
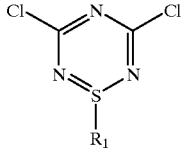
(IX)
| Comp. No. | R₁ | Physical data |
|---|---|---|
| 8.35 | 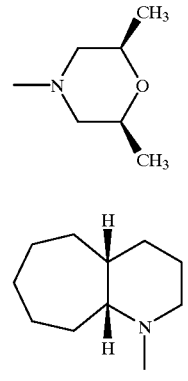 | |
| 8.36 | 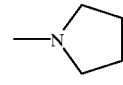 | |
| 8.37 | —N(CH₃)₂ | |
| 8.38 | 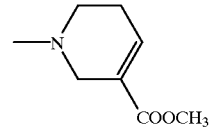 | |
| 8.39 | 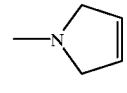 | |
| 8.40 | 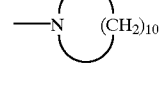 | |
| 8.41 | 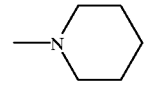 | |
| 8.42 | —N(C₂H₅)₂ | |
| 8.43 | 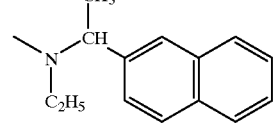 | (not isolated) |
| 8.44 |  | |
TABLE 8-continued
Compounds of the formula IX
(IX)
| Comp. No. | R₁ | Physical data |
|---|---|---|
| 8.45 | 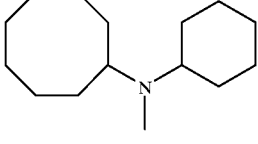 | |
| 8.46 | 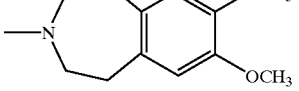 | |
| 8.47 | 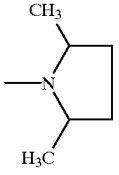 | |
| 8.48 | 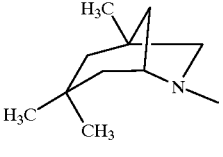 | |
| 8.49 | 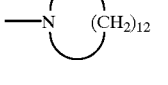 | |
| 8.50 | —NHCH₃ | |
| 8.51 | 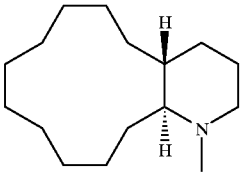 | |
| 8.52 | | |
| 8.53 | —NH(CH₂)₃CF₃ | |
| 8.54 | | |

TABLE 8-continued

Compounds of the formula IX (IX)

| Comp. No. | R₁ | Physical data |
|---|---|---|
| 8.55 | —N(CH₃)(CH₂-phenyl) | |
| 8.56 | dibenzazepine-N-yl | |
| 8.57 | 2,3,4,5-tetrahydro-1H-benzo[c]azepin-2-yl | |
| 8.58 | 4-phenylpiperazin-1-yl | |
| 8.59 | 3-cyano-4-methoxy-1,2,3,6-tetrahydropyridin-1-yl | |
| 8.60 | quinuclidin-3-yl (N-linked) | |
| 8.61 | 2-methyl-decahydroisoquinolin-2-yl | |
| 8.62 | —N(CH₃)(CH₂COOC₂H₅) | |
| 8.63 | 9-chloro-2,3,4,5-tetrahydro-1H-benzo[c]azepin-2-yl | |
| 8.64 | 1,2,3,4-tetrahydroisoquinolin-2-yl | |
| 8.65 | —N(CH₂-cyclohexyl)(CH(CH₃)₂) | |
| 8.66 | 3,5,5-trimethyl-azepan-1-yl | |
| 8.67 | azacyclotridecan-1-yl [—N(CH₂)₁₁—] | |
| 8.68 | decahydroquinolin-1-yl (N-methyl) | |
| 8.69 | —N(C₄H₉(n))₂ | |
| 8.70 | trans-decahydroisoquinolin-2-yl | |
| 8.71 | 1-azabicyclo[2.2.2]oct-3-yl derivative | |

TABLE 8-continued

Compounds of the formula IX (IX)

| Comp. No. | R₁ | Physical data |
|---|---|---|
| 8.72 | [2,3,4,5-tetrahydro-1H-benzo[d]azepine with OCH₃, N-methyl] | |
| 8.73 | [decahydrocycloocta[b]pyridine, N-methyl] | |
| 8.74 | [norbornenyl-CH₂N(CH₃)₃, H] | |
| 8.75 | —N(aziridine) | |
| 8.76 | [6,7-dimethoxy-1,2,3,4-tetrahydroisoquinoline, N-methyl] | |
| 8.77 | [hexahydrobenzo[h]quinoline, N-methyl] | |
| 8.78 | [8-chloro-2,3,4,5-tetrahydro-1H-benzo[d]azepine, N-methyl] | |
| 8.79 | [octahydroindole, N-methyl] | |
| 8.80 | [decahydroquinoline, N-methyl] | Melting point 90–92° C. |
| 8.81 | [2-methoxypyrrolidine (S), N-methyl] | |
| 8.82 | [2,3,4,4a,9,9a-hexahydro-1H-indeno[2,1-b]pyridine, N-methyl] | |
| 8.83 | —N(CH₃)₂ | |
| 8.84 | [3-(diethylcarbamoyl)piperidine, N-methyl, CON(C₂H₅)₂] | |
| 8.85 | [azetidine, N-methyl] | |
| 8.86 | [2,3-dihydro-1H-inden-1-yl-N(CH₂C₆H₅)methyl] | |
| 8.87 | [7-methoxy-2,3,4,5-tetrahydro-1H-benzo[d]azepine, N-methyl, OCH₃] | |
| 8.88 | [4-oxopiperidine, N-methyl] | |

TABLE 8-continued
Compounds of the the formula IX
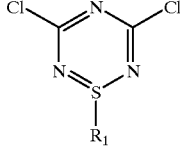
(IX)
| Comp. No. | R₁ | Physical data |
|---|---|---|
| 8.89 | 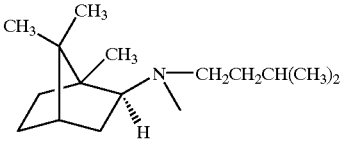 | |
| 8.90 | 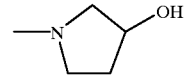 | |
| 8.91 | 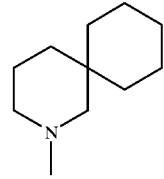 | |
| 8.92 | 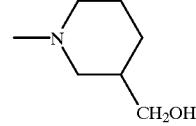 | |
| 8.93 | 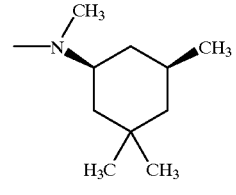 | |
| 8.94 | 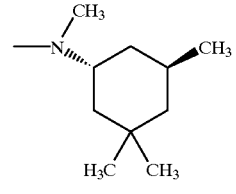 | |
| 8.95 | 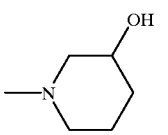 | |
TABLE 8-continued
Compounds of the the formula IX
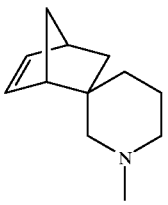
(IX)
| Comp. No. | R₁ | Physical data |
|---|---|---|
| 8.96 | 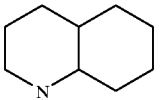 | |
| 8.97 | 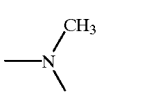 | |
| 8.98 | 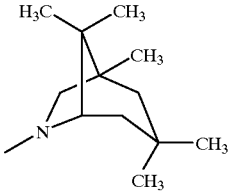 | |
| 8.99 | 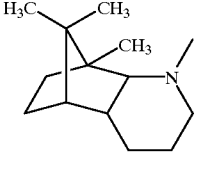 | |
| 8.100 | 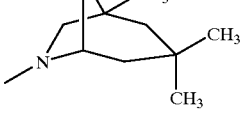 | |
| 8.101 | 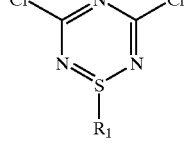 | |
| 8.102 | 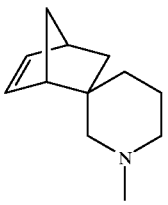 | |
| 8.103 | —N(C₄H₉(n))₂ | |

TABLE 8-continued

Compounds of the formula IX

| Comp. No. | R₁ | Physical data |
|---|---|---|
| 8.104 | (octahydrobenzoxazine, N-substituted) | |
| 8.105 | (octahydroindole, 2-methyl, N-substituted) | |
| 8.106 | (camphor-derived N(CH₃)(CH₂C₆H₅), H) | |
| 8.107 | (decahydroquinoline, 4a-CH₃, N-methyl) | |
| 8.108 | –N(CH₂CH(CH₃)₂)-(3,3,5-trimethylcyclohexyl) | |
| 8.109 | –NH-(3,3,5-trimethylcyclohexyl) | |
| 8.110 | –N(CH(CH₃)₂)-(3,5-dimethyl-3-methylcyclohexyl) | |
| 8.111 | –N(CH₃)CH₂-(6-chloropyridin-3-yl) | |
| 8.112 | (1,2,3,4-tetrahydroisoquinoline, N-methyl) | |
| 8.113 | (2-methylpiperidine, N-methyl) | |
| 8.114 | (decahydroquinoline, 4a-CH₃, N-methyl) | |
| 8.115 | –NHC₃H₇(n) | |
| 8.116 | (N-methyl azabicyclo) | |
| 8.117 | (octahydrobenzothiazine, N-methyl) | |
| 8.118 | –N(CH₃)CH₂C₆H₅ | |
| 8.119 | (camphor-derived N(C₂H₅), H) | |

TABLE 8-continued
Compounds of the the formula IX
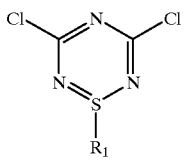
(IX)
| Comp. No. | R₁ | Physical data |
|---|---|---|
| 8.120 | 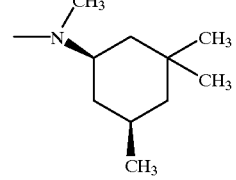 | |
| 8.121 | 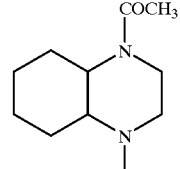 | |
| 8.122 | 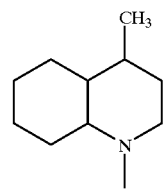 | |
| 8.123 | —NH—C₄H₉(n) | |
| 8.124 | 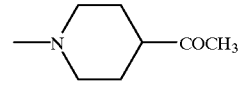 | |
| 8.125 | 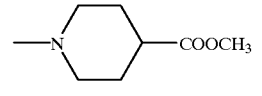 | |
| 8.126 | 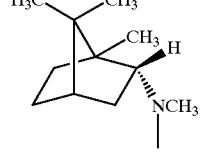 | |
| 8.127 | 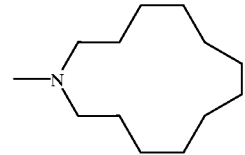 | |
| 8.128 | 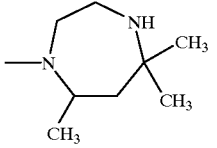 | |
| 8.129 | 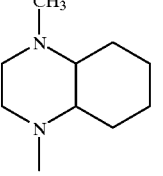 | |
| 8.130 | 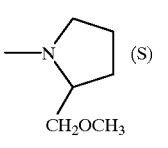 (S) | |
| 8.131 | 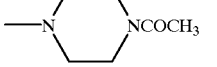 | |
| 8.132 | 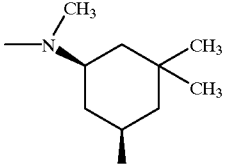 | |
| 8.133 | 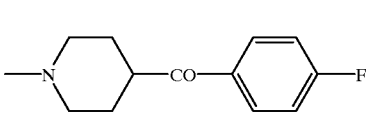 | |
| 8.134 | 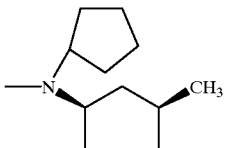 | |
| 8.135 | 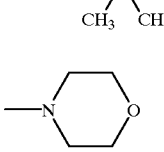 | |

TABLE 8-continued
Compounds of the the formula IX
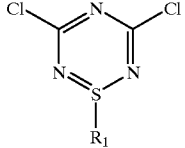
(IX)
| Comp. No. | R₁ | Physical data |
|---|---|---|
| 8.136 | 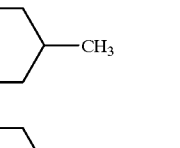 | |
| 8.137 | 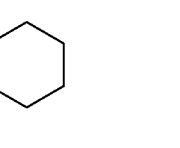 | |
| 8.138 |  | |
| 8.139 | —N[CH(CH₃)₂]₂ | |
| 8.140 | 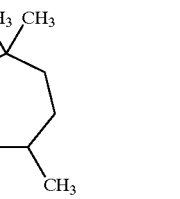 | |
| 8.141 | 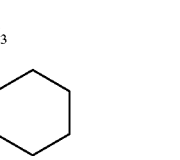 | |
| 8.141 | 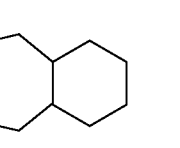 | |
| 8.143 | 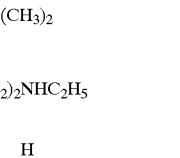 | |
| 8.144 | 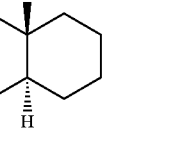 | |
TABLE 8-continued
Compounds of the the formula IX
(IX)
| Comp. No. | R₁ | Physical data |
|---|---|---|
| 8.145 | 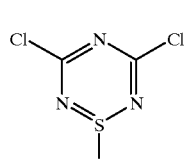 | |
| 8.146 | 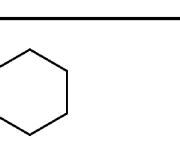 | |
| 8.147 | 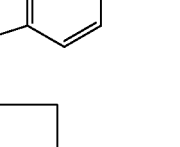 | |
| 8.148 | 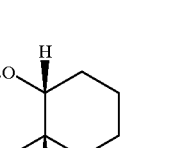 | |
| 8.149 | 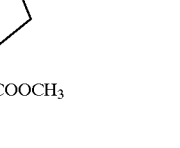 | |
| 8.150 | 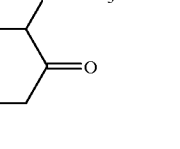 | |
| 8.151 | 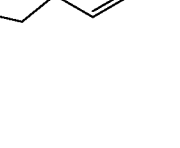 | |

TABLE 8-continued
Compounds of the the formula IX
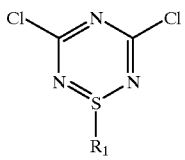
| Comp. No. | R₁ | Physical data |
|---|---|---|
| 8.152 | 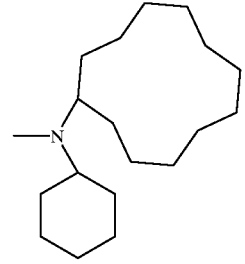 | |
| 8.153 | 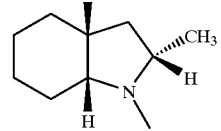 | |
| 8.154 | 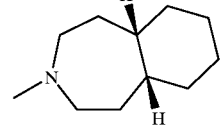 | |
| 8.155 | 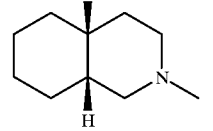 | |
| 8.156 | 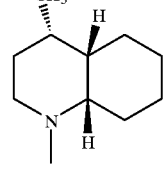 | |
| 8.157 | 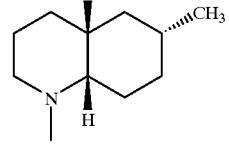 | |
| 8.158 | 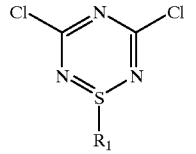 | (not isolated) |
| 8.159 | 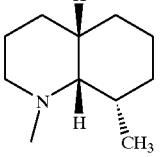 | |
| 8.160 | 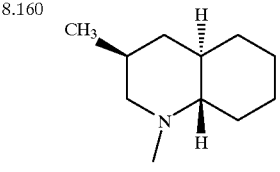 | |
| 8.161 | 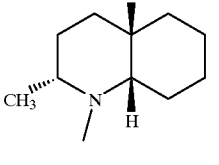 | |
| 8.162 | 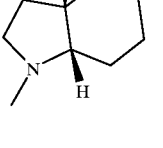 | |
| 8.163 | 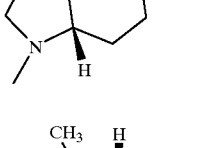 | |
| 8.164 | 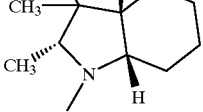 | |

TABLE 8-continued
Compounds of the the formula IX
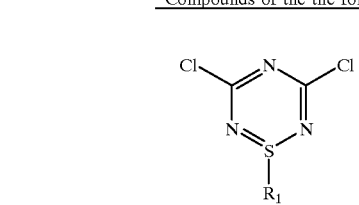
(IX)
| Comp. No. | R$_1$ | Physical data |
|---|---|---|
| 8.165 | 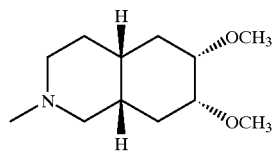 | |
| 8.166 | 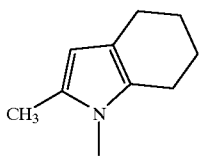 | |
| 8.167 | 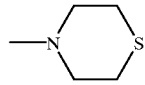 | |
| 8.168 | 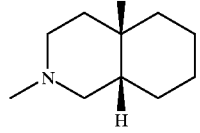 | |
| 8.169 | 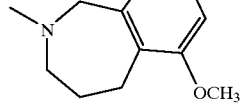 | |
| 8.170 | 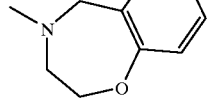 | |
| 8.171 |  | |
| 8.172 | 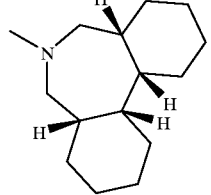 | |
| 8.173 | 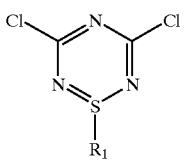 | |
| 8.174 | 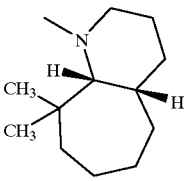 | |
| 8.175 | 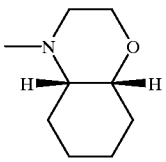 | |
| 8.176 | 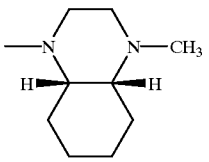 | |
| 8.177 | 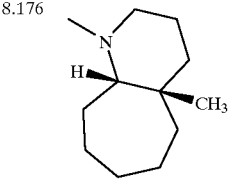 | |
| 8.178 | 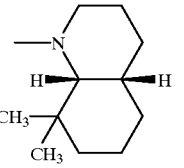 | |
| 8.179 | 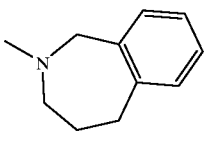 | |

TABLE 8-continued

Compounds of the the formula IX

| Comp. No. | R₁ | Physical data |
|---|---|---|
| 8.180 | (trans-fused decahydroacridine with N-methyl, 4 H stereo) | |
| 8.181 | N-methyl azepane with gem-dimethyl groups | |
| 8.182 | N-methyl azepane with gem-dimethyl | |
| 8.183 | N-methyl tetrahydrobenzazepine fused to naphthalene | |
| 8.184 | N-methyl tetrahydrobenzazepine with two OCH₃ groups on naphthalene | |
| 8.185 | octahydroindole, N-methyl, with C₃H₇(n) | |
| 8.186 | octahydroindole, N-methyl, with C₆H₁₃(n) | |

TABLE 8-continued

Compounds of the the formula IX

| Comp. No. | R₁ | Physical data |
|---|---|---|
| 8.187 | N-methyl decahydroquinoline | |
| 8.188 | octahydrobenzoxazine, N-methyl, with CH₃ | |

Example H22

Preparation of 3-amino-5-chloro-1-(piperidin-1-yl)thiatriazine (Compound No. 9.46)

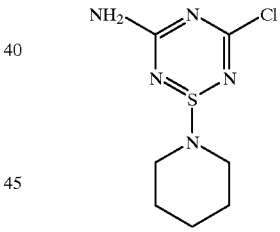

15.6 ml of a 1.6 molar n-butyllithium solution in hexane (0.025 mol) are added to a solution of 2.13 g of piperidine (0.025 mol) in 10 ml of absolute tetrahydrofuran at a temperature of −70° to −60° C., under a nitrogen atmosphere and with vigorous stirring. After thawing to 20° C., the resulting white suspension is added dropwise in portions to a solution, cooled to −60° C., of 5.11 g of 1,3,5-trichlorothiatriazine (0.025 mol) in 50 ml of absolute tetrahydrofuran, while stirring vigorously. After warming to −10° C. the reaction mixture is treated with ammonia (gas) with vigorous stirring. After all the intermediate has been used up, water and ethyl acetate are added to the reaction mixture. The organic phase is washed with water and brine, dried over sodium sulfate and evaporated. The residue is stirred with a diethyl ether/pentane mixture and filtered off with suction. The desired compound is isolated as yellowish crystals of melting point 118–120° C. (decomposition).

Example H23

Preparation of 3-amino-5-chloro-1-(octahydroindol-1-yl)thiatriazine

(Compound No. 9.93)

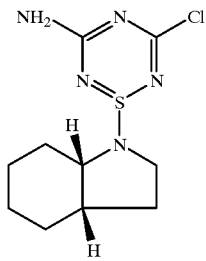

10.2 g of a 30% ammonia solution in water (0.180 mol) are added to a solution of 3.7 g of 3,5dichloro-1-(octahydroindol-1-yl)thiatriazine (0.0126 mol) in 120 ml of tetrahydrofuran at 20° C. and the mixture is stirred vigorously for 3 hours. After evaporation of the organic solvent, the resulting suspension is filtered off with suction and the residue is washed with water and then with diethyl ether and dried. The desired compound is isolated as slightly yellowish crystals of melting point 115° C. (decomposition).

The compounds listed in the following Table 9 can be prepared analogously to Examples H22 and H23.

TABLE 9

Compounds of the formula X

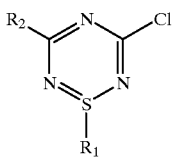

(X)

| Comp. No. | $R_1$ | $R_2$ | Physical data |
|---|---|---|---|
| 9.1 | —NHCH$_2$CH$_2$CH$_3$ | —NH$_2$ | |
| 9.2 | ![tetrahydropyridinyl] | —N(CH$_3$)$_2$ | |
| 9.3 | ![N-methyl decahydroquinolinyl] | —NH$_2$ | |
| 9.4 | —N(CH$_3$)(CH$_2$)$_6$CH$_3$ | —NH$_2$ | |
| 9.5 | ![2,6-dimethylmorpholinyl] | —NH$_2$ | |
| 9.6 | ![octahydroindolizinyl] (Diastereomer 1) | —NH$_2$ | |

TABLE 9-continued
Compounds of the formula X
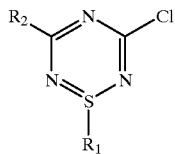
(X)
| Comp. No. | R₁ | R₂ | Physical data |
|---|---|---|---|
| 9.7 | —N(CH₃)(C₆H₁₁(c)) | —NH₂ | |
| 9.8 | 2,6-dimethylmorpholin-4-yl | —NH₂ | |
| 9.9 | 4-(CF₃)-piperidin-1-yl | —NH₂ | |
| 9.10 | cis-octahydro-1H-pyrrolizin-1-yl (Diastereomer 2) | —NH₂ | |
| 9.11 | 1,2,3,4-tetrahydroisoquinolin-2-yl | —NH₂ | |
| 9.12 | 3-ethyl-piperidin-1-yl | —NH₂ | |
| 9.13 | decahydroquinolin-1-yl | —NH₂ | |
| 9.14 | 4-methylpiperazin-1-yl | —NH₂ | |
| 9.15 | —N(CH₃)((CH₂)₃CH₃) | —NH₂ | |
| 9.16 | —N(CH₂CH₂CN)₂ | —NH₂ | |

TABLE 9-continued
Compounds of the formula X
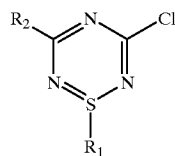
(X)
| Comp. No. | $R_1$ | $R_2$ | Physical data |
|---|---|---|---|
| 9.17 | —NHC$_6$H$_{11}$(c) | —NH$_2$ | |
| 9.18 | —N(CH$_3$)CH(CH$_3$)$_2$ | —NH$_2$ | |
| 9.19 | —N(n-C$_3$H$_7$)$_2$ | —NH$_2$ | |
| 9.20 | N(cycloheptyl)(cyclopentyl) with methyl | —NH$_2$ | |
| 9.21 | 3,5-dimethylpiperidin-1-yl | —NH$_2$ | |
| 9.22 | octahydroindol-1-yl | —NH$_2$ | |
| 9.23 | —N(CH$_2$)$_7$ (azacyclooctyl) | —NH$_2$ | |
| 9.24 | octahydroquinolin-1-yl (cis, H,H) | —NH$_2$ | |
| 9.25 | 2-(ethoxycarbonyl)piperidin-1-yl | —NH$_2$ | |
| 9.26 | 3-(ethoxycarbonyl)piperidin-1-yl | —NH$_2$ | |

TABLE 9-continued
Compounds of the formula X
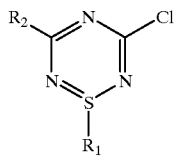
(X)
| Comp. No. | $R_1$ | $R_2$ | Physical data |
|---|---|---|---|
| 9.27 | [2-ethyl-piperidin-1-yl] | —$NH_2$ | |
| 9.28 | [N-cyclohexyl-N-isopropyl-amino] | —$NH_2$ | |
| 9.29 | [azecan-1-yl, (CH$_2$)$_9$] | —$NH_2$ | |
| 9.30 | [2,2,3-trimethyl-piperidin-1-yl] | —$NH_2$ | |
| 9.31 | [3,3-dimethyl-piperidin-1-yl] | —$NH_2$ | |
| 9.32 | [azepan-1-yl, (CH$_2$)$_6$] | —$NH_2$ | |
| 9.33 | —N[CH(CH$_3$)$_2$]$_2$ | —$NH_2$ | |
| 9.34 | —N(C$_2$H$_5$)C$_4$H$_9$(n) | —NHCH$_3$ | |
| 9.35 | [4-phenyl-piperidin-1-yl] | —$NH_2$ | |
| 9.36 | [2,6-dimethyl-morpholin-4-yl] | —$NH_2$ | |

TABLE 9-continued

Compounds of the formula X

(X)

| Comp. No. | $R_1$ | $R_2$ | Physical data |
|---|---|---|---|
| 9.37 | (octahydro-1H-1-methyl-cycloheptapyridine structure) | —$NH_2$ | |
| 9.38 | (pyrrolidinyl) | —$NHCH(CH_3)_3$ | |
| 9.39 | (tetrahydropyridinyl-COOCH$_3$) | —$NH_2$ | |
| 9.40 | (pyrrolinyl) | —$NH_2$ | |
| 9.41 | —$N(n-C_3H_7)_2$ | —$NH_2$ | |
| 9.42 | —N⟨(CH$_2$)$_{10}$⟩ | —$NH_2$ | |
| 9.43 | —$N(CH_3)_2$ | —$NH_2$ | |
| 9.44 | —$N(CH_3)_2$ | —$N(CH_3)_2$ | |
| 9.45 | —$N(C_2H_5)_2$ | —$NH_2$ | |
| 9.46 | (piperidinyl) | —$NH_2$ | Melting point 118–120° C. (Decomposition) |
| 9.47 | —$NHCH_2CH_2CH_3$ | —$NHCH_2CH_2CH_3$ | |
| 9.48 | —N(CH$_3$)(C$_2$H$_5$)—CH(CH$_3$)-(2-naphthyl) (Diastereomer 1) | —$NH_2$ | |

TABLE 9-continued

Compounds of the formula X

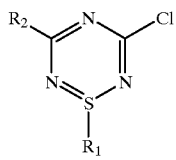

(X)

| Comp. No. | $R_1$ | $R_2$ | Physical data |
|---|---|---|---|
| 9.49 | ―N(CH₃)(C₂H₅)―CH(CH₃)―(2-naphthyl) (Diastereomer 2) | ―NH₂ | |
| 9.50 | ―N(azepane) | ―NH₂ | |
| 9.51 | ―N(CH₂)₈― (cyclic) | ―NH₂ | |
| 9.52 | ―N(CH₃)(cyclooctyl)(cyclohexyl) | ―NH₂ | |
| 9.53 | ―N(7,8-dimethoxy-2,3,4,5-tetrahydro-1H-benzo[c]azepin-3-yl) | ―NH₂ | |
| 9.54 | ―N(2,5-dimethylpyrrolidin-1-yl) | ―NH₂ | |
| 9.55 | ―N(CH₃)₂ | ―N(C₂H₅)₂ | |
| 9.56 | ―NHCH₃ | ―NHCH₃ | |
| 9.57 | ―N(C₂H₅)₂ | ―N(C₂H₅)₂ | |
| 9.58 | ―N(1,3,3-trimethyl-6-azabicyclic) | ―NH₂ | |
| 9.59 | ―N(CH₂)₁₂― (cyclic) | ―NH₂ | |

TABLE 9-continued

Compounds of the formula X (X)

| Comp. No. | R₁ | R₂ | Physical data |
|---|---|---|---|
| 9.60 | —N(CH₃)₂ | —NHCH(CH₃)₂ | |
| 9.61 | —NH(CH₂)₃CF₃ | —NH₂ | |
| 9.62 | [structure: decahydro-cyclooctaquinoline with N-methyl] | —NH₂ | |
| 9.63 | [structure: N-methyl-N-benzyl amine] | —NH₂ | |
| 9.64 | [structure: dibenzazepine with N] | —NH₂ | |
| 9.65 | [structure: 2,3,4,5-tetrahydro-1H-benzo[c]azepine] | —NH₂ | |
| 9.66 | [structure: 4-phenylpiperazine] | —NH₂ | |
| 9.67 | —N(CH₃)₂ | —NHC₃H₇(n) | |
| 9.68 | [structure: N-methyl-tetrahydropyridine with CN and OCH₃] | —NH₂ | |
| 9.69 | —N(CH₃)₂ | —NHC₂H₅ | |
| 9.70 | [structure: N-methyl azabicyclic] | —NH₂ | |

TABLE 9-continued

Compounds of the formula X

(X)

| Comp. No. | $R_1$ | $R_2$ | Physical data |
|---|---|---|---|
| 9.71 | (1-methyl-decahydroisoquinolin-2-yl) | —$NH_2$ | |
| 9.72 | —N(CH$_3$)CH$_2$COOC$_2$H$_5$ | —$NH_2$ | |
| 9.73 | (9-chloro-2,3,4,5-tetrahydro-1H-2-benzazepin-2-yl, N-methyl) | —$NH_2$ | |
| 9.74 | (2-methyl-1,2,3,4-tetrahydroisoquinolin-2-yl) | —$NH_2$ | |
| 9.75 | —N(CH$_3$)$_2$ | —NHCH$_3$ | |
| 9.76 | —N(CH$_2$-cyclohexyl)(CH(CH$_3$)$_2$) | —N(CH$_3$)$_2$ | |
| 9.77 | (3,5,5-trimethylazepan-1-yl) (Diastereomer 1) | —$NH_2$ | |
| 9.78 | (3,5,5-trimethylazepan-1-yl) (Diastereomer 2) | —$NH_2$ | |
| 9.79 | —N(CH$_2$)$_{11}$ (azacyclododecan-1-yl) | —$NH_2$ | |

TABLE 9-continued
Compounds of the formula X
| Comp. No. | $R_1$ | $R_2$ | Physical data |
|---|---|---|---|
| 9.80 | ![structure] | —$NH_2$ | |
| 9.81 | —$N(C_4H_9(n))_2$ | —$NH_2$ | |
| 9.82 | ![structure] | —$NH_2$ | |
| 9.83 | ![structure] | —$NH_2$ | |
| 9.84 | ![structure] | —$NH_2$ | |
| 9.85 | ![structure] | —$NH_2$ | |
| 9.86 | ![structure] | —$NH_2$ | |
| 9.87 | ![structure] | —$NH_2$ | |
| 9.88 | ![structure] | —$NH_2$ | |
| 9.89 | ![structure] | —$NH_2$ | |

TABLE 9-continued

Compounds of the formula X

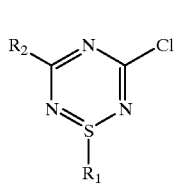

(X)

| Comp. No. | R₁ | R₂ | Physical data |
|---|---|---|---|
| 9.90 | (N-methyl tetrahydroquinoline fused to benzene) | —NH₂ | |
| 9.91 | (N-methyl chloro-benzazepine) | —NH₂ | |
| 9.92 | (N-methyl octahydroindole, cis) | —NH₂ | |
| 9.93 | (N-methyl octahydroindole, trans) | —NH₂ | Melting point 115° C. (Decomposition) |
| 9.94 | (N-methyl octahydroindole) | —NHCH₃ | |
| 9.95 | (N-methyl-2-methoxy pyrrolidine) | —NH₂ | |
| 9.96 | (N-methyl tetrahydro-β-carboline-like) | —NH₂ | |

TABLE 9-continued

Compounds of the formula X (X)

| Comp. No. | R₁ | R₂ | Physical data |
|---|---|---|---|
| 9.97 | *N-piperidinyl with CON(C₂H₅)₂ substituent* | —NH₂ | |
| 9.98 | *N-azetidinyl* | —NH₂ | |
| 9.99 | *N(CH₂C₆H₅)-indanyl* | —NH₂ | |
| 9.100 | *methoxy-benzazepinyl* | —NH₂ | |
| 9.101 | *4-oxo-piperidinyl* | —NH₂ | |
| 9.102 | *N(CH₃,CH₃,CH₃-bornyl)-CH₂CH₂CH(CH₃)₂* | —NH₂ | |
| 9.103 | *decahydroquinolinyl* | —NH₂ | |
| 9.104 | *3-hydroxy-pyrrolidinyl* | —NH₂ | |
| 9.105 | *spiro[5.5]azaundecane* | —NH₂ | |

TABLE 9-continued
Compounds of the formula X
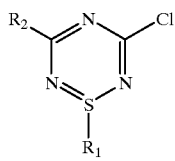
(X)
| Comp. No. | $R_1$ | $R_2$ | Physical data |
|---|---|---|---|
| 9.106 | —N(piperidine-3-yl-CH₂OH) | —NH₂ | |
| 9.107 | —N(C₂H₅)(3,5-dimethyl-5-methylcyclohexyl) | —NH₂ | |
| 9.108 | —N(CH₃)(3,5-dimethyl-5-methylcyclohexyl) | —NH₂ | |
| 9.109 | —N(3-hydroxypiperidinyl) | —NH₂ | |
| 9.110 | norbornene-spiro-N-methylpiperidine | —NH₂ | |
| 9.111 | N-methyl-octahydroindole | —NH₂ | |
| 9.112 | —N(CH₃)(CH₂CH₂CN) | —NH₂ | |

TABLE 9-continued

Compounds of the formula X

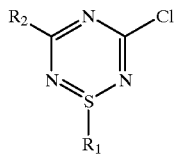

(X)

| Comp. No. | R₁ | R₂ | Physical data |
|---|---|---|---|
| 9.113 | (2,6,6-trimethyl-N-methyl bicyclic amine structure) | —NH₂ | |
| 9.114 | (gem-dimethyl methyl-octahydroquinoline structure) | —NH₂ | |
| 9.115 | (N-methyl-6,6-dimethyl bicyclic amine, Diastereomer 1) | —NH₂ | |
| 9.116 | (N-methyl-6,6-dimethyl bicyclic amine, Diastereomer 2) | —NH₂ | |
| 9.117 | —N(C₄H₉(n))₂ | —N(CH₃)₂ | |
| 9.118 | (N-methyl octahydrobenzo[b][1,4]oxazine) | —NH₂ | |
| 9.119 | (N-methyl-2-methyl octahydroindole) | —NH₂ | |
| 9.120 | (bornyl-N(CH₃)(CH₂C₆H₅)) | —NH₂ | |

TABLE 9-continued
Compounds of the formula X
| Comp. No. | R₁ | R₂ | Physical data |
|---|---|---|---|
| 9.121 | (4a-methyl-N-methyl-decahydroquinolin-8a-yl) | —NH₂ | |
| 9.122 | —N(CH₃)₂ | —NHC₄H₉(n) | |
| 9.123 | N(CH₂CH(CH₃)₂)-(3,3,5-trimethylcyclohexyl) | —NH₂ | |
| 9.124 | —NH-(3,3,5-trimethylcyclohexyl) | —NH₂ | |
| 9.125 | N(CH(CH₃)₂)-(3,3,5-trimethylcyclohexyl) | —NH₂ | |
| 9.126 | N(CH₃)(CH₂-(6-chloropyridin-3-yl)) | —NH₂ | |
| 9.127 | N-methyl-1,2,3,4-tetrahydroisoquinolin-2-yl | —NH₂ | |
| 9.128 | 1,2-dimethylpiperidin-1-yl | —NH₂ | |

TABLE 9-continued
Compounds of the formula X
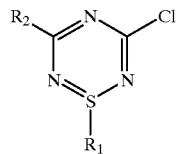
(X)
| Comp. No. | $R_1$ | $R_2$ | Physical data |
|---|---|---|---|
| 9.129 | (1-methyl-8a-methyl-decahydroquinolin-yl) | —$NH_2$ | |
| 9.130 | —$NHC_3H_7(n)$ | —$NH_2$ | |
| 9.131 | (1-methyl-azabicyclo[2.2.2]octyl) | —$NH_2$ | |
| 9.132 | (4-methyl-octahydro-benzothiazinyl) | —$NH_2$ | |
| 9.133 | —N(CH$_3$)CH$_2$C$_6$H$_5$ | —$NH_2$ | |
| 9.134 | (bornyl-N(CH$_3$)C$_2$H$_5$) | —$NH_2$ | |
| 9.135 | (3,3,5-trimethylcyclohexyl-N(CH$_3$)—) | —$NH_2$ | |
| 9.136 | (1-acetyl-4-methyl-decahydroquinoxalinyl) | —$NH_2$ | |

TABLE 9-continued

Compounds of the formula X

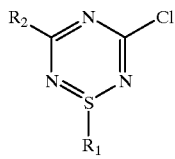

(X)

| Comp. No. | R₁ | R₂ | Physical data |
|---|---|---|---|
| 9.137 | ![structure: N-methyl decahydroquinoline with CH₃] | —NH₂ | |
| 9.138 | —NH—C₄H₉(n) | —NH₂ | |
| 9.139 | ![structure: N-piperidinyl-COCH₃] | —NH₂ | |
| 9.140 | —N(C₂H₅)₂ | —NHCH₃ | |
| 9.141 | ![structure: bornyl-N(CH₃) with H₃C, CH₃, CH₃, H, NCH₃] | —NH₂ | |
| 9.142 | ![structure: azacycloalkane ring] | —NH₂ | |
| 9.143 | —N(C₂H₅)₂ | —N(CH₃)₂ | |
| 9.144 | ![structure: diazepane with NH, CH₃, CH₃, CH₃] | —NH₂ | |
| 9.145 | ![structure: N,N'-dimethyl decahydroquinoxaline] | —NH₂ | |

TABLE 9-continued

Compounds of the formula X

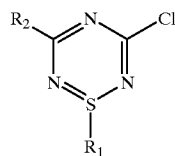

(X)

| Comp. No. | $R_1$ | $R_2$ | Physical data |
|---|---|---|---|
| 9.146 | (1-methyl-pyrrolidin-2-yl)-CHOCH$_3$ | —NH$_2$ | |
| 9.147 | 4-acetylpiperazin-1-yl (—N⟩N—COCH$_3$) | —N(C$_2$H$_5$)$_2$ | |
| 9.148 | N-methyl-3,3,5-trimethylcyclohexylamino | —NH$_2$ | |
| 9.149 | 4-(4-fluorobenzoyl)piperidin-1-yl | —NH$_2$ | |
| 9.150 | N-cyclopentyl-3,3,5-trimethylcyclohexylamino | —NH$_2$ | |
| 9.151 | 4-(methoxycarbonyl)piperidin-1-yl | —NH$_2$ | |
| 9.152 | morpholin-4-yl | —N(CH$_3$)$_2$ | |
| 9.153 | 4-methylpiperidin-1-yl | —NH$_2$ | |
| 9.154 | thiomorpholin-4-yl | —NH$_2$ | |

TABLE 9-continued

Compounds of the formula X $$\text{(X)}$$

| Comp. No. | R$_1$ | R$_2$ | Physical data |
|---|---|---|---|
| 9.155 | (N-methyl octahydrobenzoxazine) | —NH$_2$ | |
| 9.156 | —N[CH(CH$_3$)$_2$]$_2$ | —NH$_2$ | |
| 9.157 | (3,3,6-trimethyl-1-methylazepane) | —NH$_2$ | |
| 9.158 | —N(CH$_3$)(cyclohexyl) | —NHCH$_3$ | |
| 9.159 | (N-methyl octahydrobenzazepine) | —NH$_2$ | |
| 9.160 | —N(CH(CH$_3$)$_2$)((CH$_2$)$_2$NHC$_2$H$_5$) | —NH$_2$ | |
| 9.161 | (trans-N-methyl decahydroisoquinoline) | —NH$_2$ | |
| 9.162 | (N-methyl octahydrobenzothiazine) | —NH$_2$ | |
| 9.163 | —N(CH$_3$)$_2$ | —N(C$_3$H$_7$(n))$_2$ | |
| 9.164 | (2,3-dihydrobenzothiophen-2-yl) | —NH$_2$ | |

TABLE 9-continued

Compounds of the formula X (X)

| Comp. No. | R₁ | R₂ | Physical data |
|---|---|---|---|
| 9.165 | (dicyclopentyl-N-methyl) | —N(CH₃)₂ | |
| 9.166 | —N(CH₃)₂ | —NHC₄H₉(n) | |
| 9.167 | (3-methyl-octahydrobenzoxazine) | —NH₂ | |
| 9.168 | (1-methyl-2-methoxycarbonylpyrrolidinyl) | —NH₂ | |
| 9.169 | (1-methyl-3-methoxycarbonyl-4-oxopiperidinyl) | —NH₂ | |
| 9.170 | (9-chloro-2,3,4,5-tetrahydro-1H-benzazepine) | —NH₂ | |
| 9.171 | (N-cyclohexyl-N-cyclononyl-methyl) | —NH₂ | |

TABLE 9-continued
Compounds of the formula X
(X)
| Comp. No. | $R_1$ | $R_2$ | Physical data |
|---|---|---|---|
| 9.172 | (2-methyl-1-methyl-octahydroindole) | —$NH_2$ | |
| 9.173 | (2-methyl-decahydrobenzazepine) | —$NH_2$ | |
| 9.174 | (2-methyl-decahydroisoquinoline) | —$NH_2$ | |
| 9.175 | (4-methyl-1-methyl-decahydroquinoline) (Diastereomer 1) | —$NH_2$ | |
| 9.176 | (4-methyl-1-methyl-decahydroquinoline) (Diastereomer 2) | —$NH_2$ | |
| 9.177 | (7-methyl-1-methyl-decahydroquinoline) (Diastereomer 1) | —$NH_2$ | |

TABLE 9-continued
Compounds of the formula X
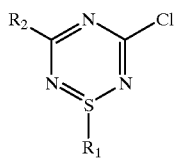
(X)
| Comp. No. | R$_1$ | R$_2$ | Physical data |
|---|---|---|---|
| 9.178 | (Diastereomer 2) | —NH$_2$ | |
| 9.179 | (Diastereomer 1 and 2) | —NH$_2$ | |
| 9.180 | (Diastereomer 1) | —NH$_2$ | |
| 9.181 | (Diastereomer 2) | —NH$_2$ | |
| 9.182 | (Diastereomer 1) | —NH$_2$ | |
| 9.183 | (Diastereomer 2) | —NH$_2$ | |

TABLE 9-continued
Compounds of the formula X
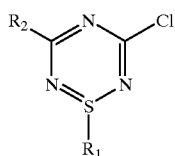
(X)
| Comp. No. | R₁ | R₂ | Physical data |
|---|---|---|---|
| 9.184 | ![structure] (Diastereomer mixture) | —NH₂ | |
| 9.185 | ![structure] (Diastereomer 1) | —NH₂ | |
| 9.186 | ![structure] (Diastereomer 2) | —NH₂ | |
| 9.187 | ![structure] (Diastereomer 1) | —NH₂ | |
| 9.188 | ![structure] (Diastereomer 2) | —NH₂ | |
| 9.189 | ![structure] (Diastereomer mixture) | —NH₂ | |

TABLE 9-continued

Compounds of the formula X $$R_2 \text{—ring—} Cl \quad (X)$$

(1,2,4,6-thiatriazine with R₂ and Cl on carbons, R₁ on S)

| Comp. No. | R₁ | R₂ | Physical data |
|---|---|---|---|
| 9.190 | *N-methyl-decahydroisoquinoline with two OCH₃ groups (Diastereomer mixture)* | —NH₂ | |
| 9.191 | *2-methyl-1-methyl-4,5,6,7-tetrahydroindole* | —NH₂ | |
| 9.192 | *azacyclo-N-(CH₂)₈* | —NH₂ | |
| 9.193 | *N-methyl-N-cyclohexyl-CH(CH₃)₂* | —N(CH₃)₂ | |
| 9.194 | *pyrrolidinyl* | —NH₂ | |
| 9.195 | *thiomorpholinyl* | —NH₂ | |
| 9.196 | *1,2,3,6-tetrahydropyridinyl* | —NH₂ | |
| 9.197 | *N-methyl-decahydroisoquinoline* | —NH₂ | |
| 9.198 | *N-methyl-benzazepine with OCH₃* | —NH₂ | |

TABLE 9-continued
Compounds of the formula X
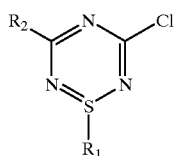
(X)
| Comp. No. | $R_1$ | $R_2$ | Physical data |
|---|---|---|---|
| 9.199 | | —$NH_2$ | |
| 9.200 | | —$NH_2$ | |
| 9.201 | | —$NH_2$ | |
| 9.202 | | —$NH_2$ | |
| 9.203 | | —$NH_2$ | |
| 9.204 | | —$NH_2$ | |
| 9.205 | | —$NH_2$ | |

TABLE 9-continued
Compounds of the formula X
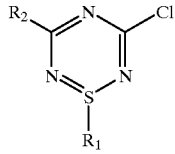
(X)
| Comp. No. | R₁ | R₂ | Physical data |
|---|---|---|---|
| 9.206 | 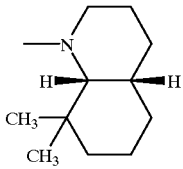 | —NH₂ | |
| 9.207 | 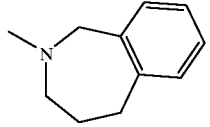 | —NH₂ | |
| 9.208 | 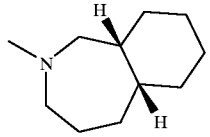 | —NH₂ | |
| 9.209 | 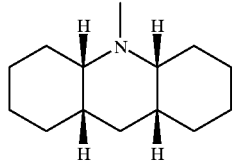 | —NH₂ | |
| 9.210 | 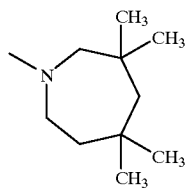 | —NH₂ | |
| 9.211 | 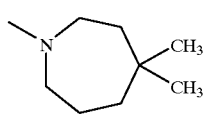 | —NH₂ | |
| 9.212 | 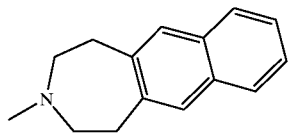 | —NH₂ | |

TABLE 9-continued

Compounds of the formula X

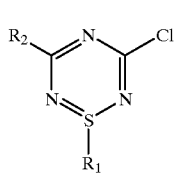

(X)

| Comp. No. | R₁ | R₂ | Physical data |
|---|---|---|---|
| 9.213 | 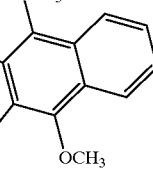 | —NH₂ | |
| 9.214 | 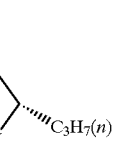 | —NH₂ | |
| 9.215 |  | —NH₂ | |
| 9.216 | 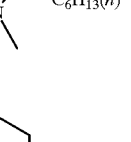 | —NH₂ | |
| 9.217 | 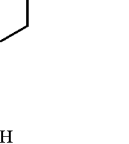 | —NH₂ | |

Formulation examples for active compounds of the formula I (%=percent by weight)

| F1. Emulsion concentrates | a) | b) | c) | d) |
|---|---|---|---|---|
| Active compound according to Tables 4–6 | 5% | 10% | 25% | 50% |
| Calcium dodecylbenzenesulfonate | 6% | 8% | 6% | 8% |
| Castor oil polyglycol ether (36 mol of EO) | 4% | — | 4% | 4% |
| Octylphenol polyglycol ether (7–8 mol of EO) | — | 4% | — | 2% |
| Cyclohexanone | — | — | 10% | 20% |
| Aromatic hydrocarbon mixture C₉–C₁₂ | 85% | 78% | 55% | 16% |

Emulsions of any desired concentration can be prepared from such concentrates by dilution with water.

F2. Solutions

|  | a) | b) | c) | d) |
|---|---|---|---|---|
| Active compound according to Tables 4–6 | 5% | 10% | 50% | 90% |
| 1-Methoxy-3-(3-methoxypropoxy)propane | — | 20% | 20% | — |
| Polyethylene glycol molecular weight 400 | 20% | 10% | — | — |
| N-Methyl-2-pyrrolidone | — | — | 30% | 10% |
| Aromatic hydrocarbon mixture $C_9$–$C_{12}$ | 75% | 60% | — | — |

The solutions are suitable for use in the form of tiny drops.

F3. Wettable powders

|  | a) | b) | c) | d) |
|---|---|---|---|---|
| Active compound according to Tables 4–6 | 5% | 25% | 50% | 80% |
| Sodium lignin sulfonate | 4% | — | 3% | — |
| Sodium lauryl sulfate | 2% | 3% | — | 4% |
| Sodium diisobutyl-naphthaline sulfonate | — | 6% | 5% | 6% |
| Octylphenol polyglycol ether (7–8 Mol EO) | — | 1% | 2% | — |
| Highly disperse silicic acid | 1% | 3% | 5% | 10% |
| Kaolin | 88% | 62% | 35% | — |

The active compound is mixed thoroughly with the additives and the mixture is ground thoroughly in a suitable mill. Wettable powders which can be diluted with water to give suspensions of any desired concentration are obtained.

F4. Coated granules

|  | a) | b) | c) |
|---|---|---|---|
| Active compound according to Tables 4–6 | 0.1% | 5% | 15% |
| Highly disperse silicic acid | 0.9% | 2% | 2% |
| Inorganic carrier (ø0.1–1 mm), for example $CaCO_3$ or $SiO_2$ | 99.0% | 93% | 83% |

The active compound is dissolved in methylene chloride, the solution is sprayed onto the carrier and the solvent is then evaporated off in vacuo.

F5. Coated granules

|  | a) | b) | c) |
|---|---|---|---|
| Active compound according to Tables 4–6 | 0.1% | 5% | 15% |
| Polyethylene glycol molecular weight 200 | 1.0% | 2% | 3% |
| Highly disperse silicic acid | 0.9% | 1% | 2% |
| Inorganic carrier (ø0.1–1 mm), for example $CaCO_3$ or $SiO_2$ | 98.0% | 92% | 80% |

The finely ground active compound is applied uniformly to the carrier, which has been moistened with polyethylene glycol, in a mixer. Dust-free coated granules are obtained in this manner.

F6. Extruded granules

|  | a) | b) | c) | d) |
|---|---|---|---|---|
| Active compound according to Tables 4–6 | 0.1% | 3% | 5% | 15% |
| Sodium lignin sulfonate | 1.5% | 2% | 3% | 4% |
| Carboxymethyl cellulose | 1.4% | 2% | 2% | 2% |
| Kaolin | 97.0% | 93% | 90% | 79% |

The active compound is mixed with the additives and the mixture is ground and moistened with water. This mixture is extruded and the extrudate is then dried in a stream of air.

F7. Dusts

|  | a) | b) | c) |
|---|---|---|---|
| Active compound according to Tables 4–6 | 0.1% | 1% | 5% |
| Talc | 39.9% | 49% | 35% |
| Kaolin | 60.0% | 50% | 60% |

Ready-to-use dusts are obtained by mixing the active compound with the carriers and grinding the mixture on a suitable mill.

F8. Suspension concentrates

|  | a) | b) | c) | d) |
|---|---|---|---|---|
| Active compound according to Tables 4–6 | 3% | 10% | 25% | 50% |
| Ethylene glycol | 5% | 5% | 5% | 5% |
| Nonylphenol polyglycol ether (15 mol of EO) | — | 1% | 2% | — |
| Sodium lignin sulfonate | 3% | 3% | 4% | 5% |
| Carboxymethyl cellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active compound is mixed intimately with the additives. A suspension concentrate from which suspensions of any desired concentration can be prepared by dilution with water is thus obtained.

BIOLOGICAL EXAMPLES

Example B1

Herbicidal Action Before Emergence of the Plants (Pre-emergent Action)

Monocotyledon and dicotyledon test plants are sown in standard soil in plastic pots. Immediately after sowing, the test substances are sprayed on (500 l of water/ha) in an aqueous suspension prepared from a 25% wettable powder (Example F3, b)), corresponding to a dosage of 2000 g of active substance/ha. The test plants are then grown under optimum conditions in a greenhouse. After a test period of 3 weeks, the test is evaluated with a ratings scale of nine levels (1=complete damage, 9=no action). Ratings of 1 to 4 (in particular 1 to 3) mean a good to very good herbicidal action.

Test plants: Avena, Setaria, Sinapis, Stellaria

In this test, the compounds of the formula I according to the examples in Tables 4, 5 and 6 show a potent herbicidal action.

Table B1 gives examples of the good herbicidal activity of the compounds of the formula I:

TABLE B1

Pre-emergent action

| Compound No. | Avena | Setaria | Sinapis | Stellaria |
|---|---|---|---|---|
| 5.52 | 4 | 2 | 1 | 1 |
| 5.78 | 3 | 2 | 2 | 1 |
| 5.86 | 5 | 3 | 1 | 1 |
| 5.120 | 4 | 2 | 1 | 1 |
| 5.127 | 4 | 2 | 1 | 1 |
| 5.131 | 4 | 2 | 1 | 1 |
| 5.146 | 4 | 1 | 1 | 1 |
| 5.176 | 4 | 2 | 1 | 1 |
| 5.317 | 4 | 2 | 2 | 1 |
| 5.321 | 3 | 1 | 1 | 1 |
| 5.326 | 4 | 4 | 1 | 1 |
| 5.327 | 4 | 3 | 2 | 1 |
| 5.329 | 2 | 1 | 1 | 1 |
| 5.332 | 3 | 1 | 1 | 1 |
| 6.10 | 4 | 4 | 1 | 1 |
| 6.27 | 4 | 3 | 2 | 1 |
| 6.30 | 3 | 2 | 1 | 1 |
| 6.34 | 3 | 1 | 1 | 1 |
| 6.37 | 3 | 2 | 1 | 1 |
| 6.42 | 4 | 2 | 1 | 1 |
| 6.53 | 3 | 3 | 1 | 1 |
| 6.63 | 4 | 3 | 1 | 1 |
| 6.77 | 4 | 3 | 1 | 1 |
| 6.89 | 2 | 2 | 1 | 1 |
| 6.92 | 4 | 1 | 1 | 1 |
| 6.93 | 2 | 1 | 1 | 1 |
| 6.124 | 3 | 1 | 1 | 1 |
| 6.129 | 4 | 4 | 1 | 1 |
| 6.135 | 3 | 3 | 1 | 1 |
| 6.140 | 4 | 3 | 2 | 1 |
| 6.145 | 4 | 2 | 1 | 1 |
| 6.153 | 4 | 3 | 1 | 1 |
| 6.154 | 4 | 1 | 1 | 1 |
| 6.170 | 3 | 4 | 4 | 1 |
| 6.173 | 4 | 3 | 1 | 1 |
| 6.185 | 4 | 4 | 1 | 1 |
| 6.192 | 2 | 1 | 1 | 1 |
| 6.194 | 7 | 5 | 2 | 2 |
| 6.200 | 4 | 1 | 1 | 1 |
| 6.229 | 3 | 2 | 1 | 1 |
| 6.257 | 3 | 2 | 1 | 1 |
| 6.282 | 4 | 2 | 1 | 1 |
| 6.285 | 5 | 2 | 1 | 1 |
| 6.292 | 5 | 1 | 1 | 1 |
| 6.295 | 3 | 1 | 1 | 1 |
| 6.296 | 4 | 2 | 1 | 1 |
| 6.298 | 3 | 2 | 1 | 1 |
| 6.302 | 3 | 2 | 1 | 1 |
| 6.331 | 4 | 2 | 1 | 1 |

The same results are obtained when the compounds of the formula I are formulated according to Examples F1, F2 and F4 to F8.

Example B2

Post-emergent Herbicidal Action (Contact Herbicide)

Monocotyledon and dicotyledon test plants are grown in plastic pots with standard soil in a greenhouse and, in the 4- to 6-leaf stage, are sprayed with an aqueous suspension of the test substances of the formula 1, prepared from a 25% wettable power (Example F3, b)), corresponding to a dosage of 2000 g of active substance/ha (500 l of water/ha). The test plants are then grown further in the greenhouse under optimum conditions. After a test period of about 18 days, the test is evaluated with a ratings scale of 9 levels (1=complete damage, 9=no action). Ratings of 1 to 4 (in particular 1 to 3) mean a good to very good herbicidal action.

Test plants: Sinapis, Stellaria

In this test also, the compounds of the formula I according to the examples in Tables 4, 5 and 6 show a good herbicidal action.

Table B2 gives examples of the good herbicidal activity of the compounds of the formula I:

TABLE B2

Post-emergent action

| Compound No. | Sinapis | Stellaria |
|---|---|---|
| 5.52 | 2 | 2 |
| 5.59 | 1 | 3 |
| 5.78 | 2 | 3 |
| 5.85 | 3 | 3 |
| 5.120 | 2 | 3 |
| 5.127 | 2 | 3 |
| 5.131 | 1 | 3 |
| 5.141 | 2 | 4 |
| 5.154 | 2 | 4 |
| 5.176 | 2 | 2 |
| 5.316 | 2 | 4 |
| 5.317 | 2 | 4 |
| 5.318 | 2 | 4 |
| 5.321 | 2 | 2 |
| 5.326 | 2 | 4 |
| 5.329 | 1 | 5 |
| 5.332 | 1 | 2 |
| 5.337 | 1 | 5 |
| 6.6 | 2 | 4 |
| 6.7 | 2 | 3 |
| 6.17 | 3 | 4 |
| 6.21 | 2 | 4 |
| 6.23 | 2 | 4 |
| 6.27 | 2 | 3 |
| 6.30 | 2 | 3 |
| 6.34 | 2 | 2 |
| 6.37 | 3 | 2 |
| 6.42 | 2 | 2 |
| 6.57 | 2 | 4 |
| 6.81 | 2 | 3 |
| 6.89 | 2 | 3 |
| 6.90 | 2 | 4 |
| 6.92 | 1 | 1 |
| 6.93 | 1 | 1 |
| 6.102 | 2 | 3 |
| 6.120 | 2 | 4 |
| 6.124 | 2 | 3 |
| 6.129 | 2 | 3 |
| 6.135 | 3 | 3 |
| 6.140 | 2 | 3 |
| 6.145 | 3 | 3 |
| 6.153 | 1 | 2 |
| 6.154 | 1 | 1 |
| 6.164 | 1 | 3 |
| 6.168 | 2 | 3 |
| 6.170 | 2 | 3 |
| 6.173 | 2 | 3 |
| 6.177 | 2 | 2 |
| 6.181 | 2 | 3 |
| 6.185 | 1 | 1 |
| 6.192 | 2 | 4 |
| 6.194 | 2 | 4 |
| 6.200 | 2 | 2 |
| 6.229 | 2 | 3 |
| 6.247 | 3 | 4 |
| 6.249 | 1 | 2 |
| 6.257 | 2 | 2 |
| 6.282 | 1 | 5 |
| 6.283 | 1 | 4 |
| 6.285 | 2 | 3 |
| 6.292 | 2 | 3 |
| 6.295 | 1 | 3 |

TABLE B2-continued

Post-emergent action

| Compound No. | Test plants | |
|---|---|---|
| | Sinapis | Stellaria |
| 6.296 | 2 | 4 |
| 6.298 | 1 | 4 |
| 6.302 | 2 | 3 |
| 6.331 | 1 | 2 |
| 6.320 | 2 | 3 |

The same results are obtained when the compounds of the formula I are formulated according to Examples F1, F2 and F4 to F8.

What is claimed is:

1. A compound of the formula I

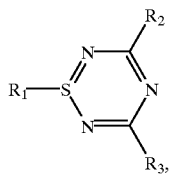

(I)

in which $R_1$ is a group —$OR_7$, —$NR_{90}R_{91}$ or $R_1$ is

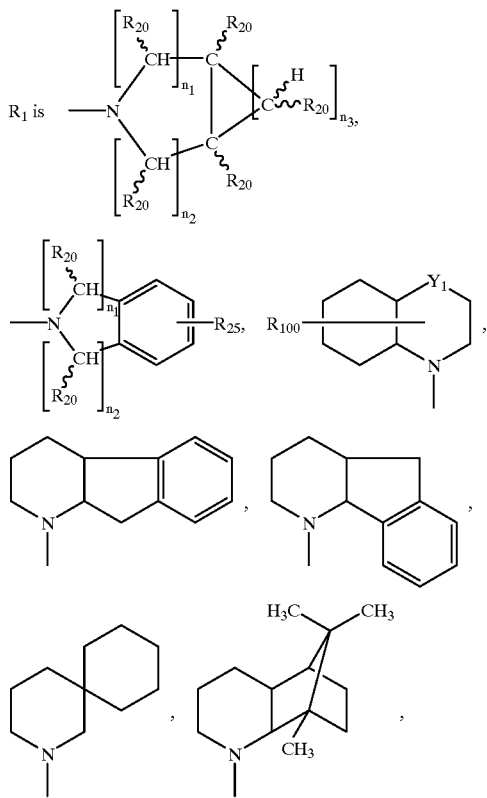

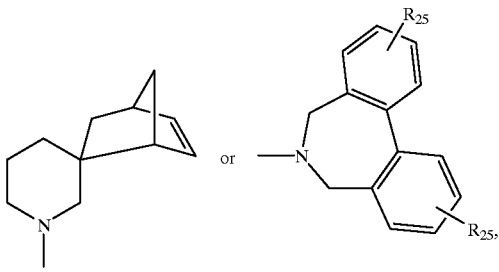

in which the radicals $R_{20}$ independently of one another are hydrogen, $C_1$–$C_4$alkyl or $C_1$–$C_3$alkoxy;

$R_{25}$ is hydrogen, chlorine, methyl or methoxy;

$R_{100}$ is hydrogen or $C_1$–$C_3$alkyl;

$Y_1$ is —O—, —S— or —$NR_{30}$;

$R_{30}$ is hydrogen, methyl, $C_1$–$C_3$alkylcarbonyl or ($C_1$–$C_3$alkyl)$_2$NCO;

$n_1$ is 1, 2, 3, 4 or 5;

$n_2$ is 0, 1 or 2; and $n_3$ is a number from 3 to 10;

$R_7$ is $C_1$–$C_{16}$alkyl, $C_1$–$C_{16}$alkyl substituted by up to 9 halogens, up to 3 $NO_2$, CN, $C_1$–$C_5$alkoxy, $C_1$–$C_5$alkylthio, $C_3$–$C_8$cycloalkoxy, $C_3$–$C_8$cycloalkylthio, $C_1$–$C_3$trialkylsilyl, $C_3$–$C_{10}$alkenyloxy, $C_3$–$C_5$alkynyloxy, $C_1$–$C_5$alkylcarbonyloxy, $C_1$–$C_3$alkoxycarbonyl, $C_1$–$C_3$alkylcarbonyl, $C_5$–$C_7$cycloalkenyl or $C_5$–$C_7$cycloalkenyl substituted up to 3 times by $C_1$–$C_4$alkyl, or $R_7$ is $C_1$–$C_{16}$alkyl substituted once by $C_3$–$C_8$cycloalkyl, $C_6$–$C_{12}$bicycloalkyl, $C_6$–$C_{12}$chlorobicycloalkyl, $C_6$–$C_{12}$bicycloalkenyl or adamantyl, or $R_7$ is $C_1$–$C_{16}$alkyl substituted once by up to 5 times substituted or unsubstituted aryl, aryloxy, arylmethyleneoxy, arylcarbonyl, arylcarbonyloxy or a heterocyclic ring of the formula

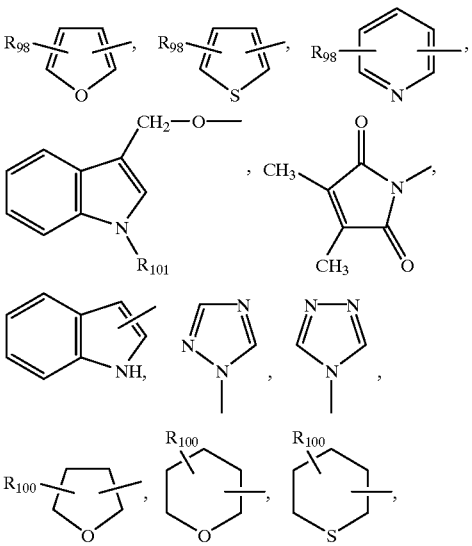

-continued

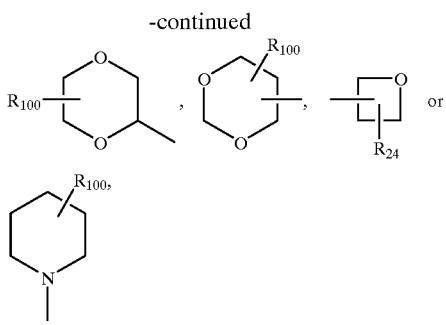

in which $R_{98}$ is hydrogen, fluorine, chlorine, bromine, CN, $C_1$–$C_3$alkoxy, $C_1$–$C_3$alkoxycarbonyl, $C_1$–$C_3$alkoxy-$C_1$–$C_3$alkyl, $C_1$- or $C_2$halogenoalkyl, $C_1$-$C_5$alkyl, $NO_2$, $C_3$–$C_5$alkenyl, cyclopropyl or $C_1$- or $C_2$halogenoalkoxy; $R_{100}$ is as defined above;

$R_{24}$ is hydrogen or methyl; and $R_{101}$ is $C_1$–$C_4$alkyl, $C_1$–$C_4$alkylcarbonyl or $C_1$–$C_3$-alkoxycarbonyl, or $R_7$ is $C_3$–$C_{15}$alkenyl, $C_3$–$C_{15}$alkenyl substituted by up to 9 halogens, up to 3 $C_1$–$C_3$alkoxy, $C_3$–$C_8$cycloalkyl, $C_1$–$C_3$trialkylsilyl or up to 5 times substituted or unsubstituted aryl or aryloxy, or $R_7$ is $C_3$–$C_5$alkynyl, $C_3$–$C_{12}$cycloalkyl, $C_3$–$C_{12}$cycloalkyl substituted by up to 9 halogens, up to 3 CN, $C_1$–$C_3$trialkylsilyl, =O, $C_1$–$C_6$alkyl, cyano-$C_1$–$C_5$alkyl, $C_1$–$C_5$alkyl-CONH—$C_1$–$C_5$alkyl, phenyl-CONH—$C_1$–$C_5$alkyl, $C_1$–$C_5$chloroalkyl, $C_1$–$C_3$alkoxy, $C_1$–$C_3$alkylthio, $C_1$–$C_3$alkoxycarbonyl, $C_1$–$C_3$alkoxycarbonyl-$C_1$–$C_5$alkyl, $C_5$–$C_7$cycloalkyl, $C_2$–$C_4$alkenyl, $C_2$–$C_4$alkynyl, benzyl or $C_1$–$C_3$halogenoalkyl, or $R_7$ is $C_5$–$C_7$cycloalkenyl, $C_5$–$C_7$cycloalkenyl substituted up to 3 times by $C_1$–$C_3$alkyl, or $R_7$ is $C_6$–$C_{12}$bicycloalkyl, $C_6$–$C_{12}$bicycloalkyl substituted up to 3 times by $C_1$–$C_3$alkyl, cyano or halogen, $C_6$–$C_{12}$bicycloalkenyl or $C_6$–$C_{12}$bicycloalkenyl substituted up to 3 times by $C_1$–$C_3$alkyl, or $R_7$ is a substituted or unsubstituted non-aromatic heterocyclic ring of the formula

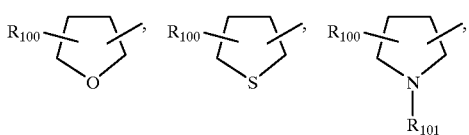

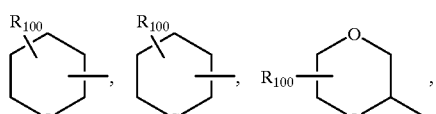

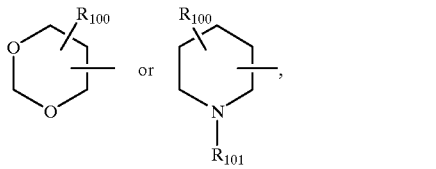

in which $R_{100}$ and $R_{101}$ are as defined above, or an alicyclic ring system;

$R_{90}$ and $R_{91}$ independently of one another are hydrogen, $C_1$–$C_{12}$alkyl, $C_1$–$C_{12}$alkyl substituted by up to 3 halogens, $NO_2$, CN, hydroxyl, $C_1$–$C_3$alkoxy, $C_1$–$C_3$alkoxycarbonyl, $C_1$–$C_3$trialkylsilyl, $C_1$–$C_6$alkylamino, di($C_1$–$C_6$alkyl)amino, $C_3$–$C_7$cycloalkyl,

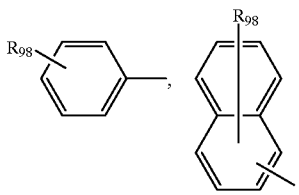

or a heterocyclic ring of the formula

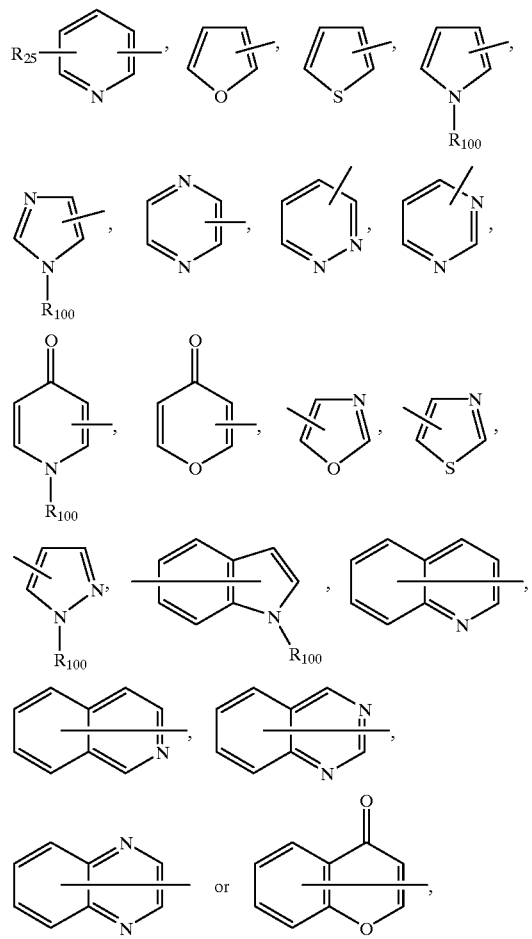

in which $R_{25}$ and $R_{100}$ are as defined above, or $C_3$–$C_{10}$alkenyl, $C_3$–$C_{10}$alkynyl, $C_6$–$C_{12}$bicycloalkyl, $C_6$–$C_{12}$bicycloalkenyl, $C_3$–$C_{12}$cycloalkyl, $C_3$–$C_{12}$cycloalkyl substituted up to 4 times by $C_1$–$C_4$alkyl, $C_5$–$C_7$cycloalkenyl or $C_5$–$C_7$cycloalkenyl substituted up to 4 times by $C_1$–$C_4$alkyl, with the proviso that $R_{90}$ and $R_{91}$ are not simultaneously hydrogen; or $R_{90}$ and $R_{91}$, together with the nitrogen atom to which they are bonded, form a saturated heterocyclic ring which contains 2–12 carbon atoms and can contain, as further heteroatoms, a nitrogen, an oxygen or a sulfur atom and can be substituted up to 3 times by $C_1$–$C_4$alkyl, $C_1$- or $C_2$halogenoalkyl, $C_1$- or $C_2$hydroxyalkyl, methoxy-$C_1$–$C_4$alkyl, halogen, hydroxyl, CN, $C_1$–$C_4$alkoxy, $C_1$–$C_4$alkylcarbonyl, $C_1$- or $C_2$halogenoalkyl,

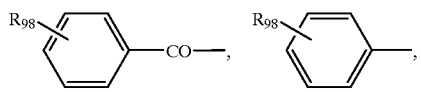

$C_1$–$C_3$alkoxycarbonyl, $(C_1$–$C_3$alkyl$)_2$NCO, di($C_1$–$C_4$alkyl)amino or =O and can additionally be bridged by 1 or 2

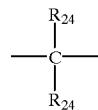

groups and onto which 1 or 2 further carbocyclic, heterocyclic or aromatic rings can be fused, or $R_{90}$ and $R_{91}$, together with the nitrogen atom to which they are bonded, form a mono- or diunsaturated heterocyclic ring which contains 5–7 carbon atoms and is substituted up to 3 times or unsubstituted by $C_1$–$C_4$alkyl, $C_1$- or $C_2$halogenoalkyl, halogen, hydroxyl, CN, amino, $C_1$–$C_4$alkylamino, di($C_1$–$C_4$alkyl)amino, phenyl, $C_1$–$C_4$alkoxy or $C_1$–$C_3$alkoxycarbonyl and additionally bridged by 1 or 2

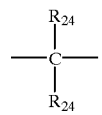

groups and onto which 1 or 2 further carbocyclic, heterocyclic or aromatic rings can be fused;

the radicals $R_{24}$ independently of one another are hydrogen or methyl;

$R_{98}$ is hydrogen, fluorine, chlorine, bromine, CN, $C_1$–$C_3$alkoxy, $C_1$–$C_3$alkoxycarbonyl, $C_1$–$C_3$alkoxy-$C_1$–$C_3$alkyl, $C_1$- or $C_2$halogenoalkyl, $C_1$–$C_5$alkyl, $NO_2$, $C_3$–$C_5$alkenyl, cyclopropyl or $C_1$- or $C_2$halogenoalkoxy;

$R_2$ is halogen, $C_1$–$C_{10}$alkoxy, $C_1$–$C_{10}$alkoxy substituted up to 3 times by halogens, CN, $NO_2$, $C_1$–$C_6$alkoxy, $C_1$–$C_6$alkylthio, $C_3$–$C_6$alkenyloxy, $C_1$–$C_6$alkoxycarbonyl, heterocyclyl of the formula

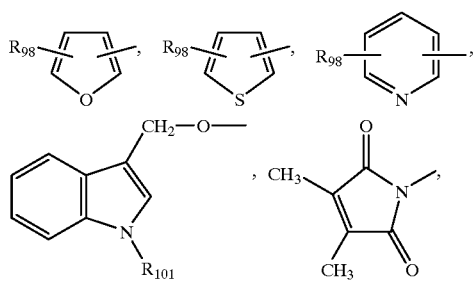

-continued

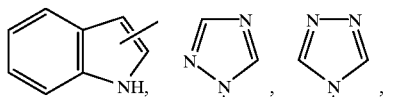

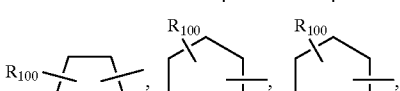

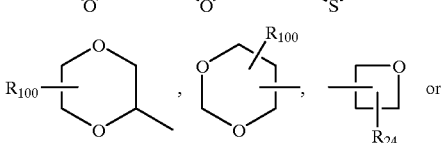

in which $R_{24}$, $R_{98}$, $R_{100}$ and $R_{101}$ are as defined above, or substituted up to 5 times or unsubstituted aryl or aryloxy, $C_3$–$C_{10}$alkenyloxy, $C_3$–$C_{10}$alkenyloxy substituted up to 3 times by halogens, CN, $NO_2$, $C_1$–$C_6$alkoxy, $C_3$–$C_6$alkenyloxy, $C_1$–$C_6$alkoxycarbonyl or substituted up to 5 times or unsubstituted aryl or aryloxy, $C_1$–$C_{10}$alkylthio, $C_1$–$C_{10}$alkylthio substituted up to 3 times by halogens, CN, $NO_2$, $C_1$–$C_6$alkoxy, $C_3$–$C_6$alkenyloxy, $C_1$–$C_6$alkoxycarbonyl or substituted up to 5 times or unsubstituted aryl or aryloxy, $C_3$–$C_{10}$alkenylthio or $C_3$–$C_{10}$alkenylthio substituted up to 3 times by halogens, CN, $NO_2$, $C_1$–$C_6$alkoxy, $C_3$–$C_6$alkenyloxy, $C_1$–$C_6$alkoxycarbonyl or substituted up to 5 times or unsubstituted aryl or aryloxy, or $R_2$ is $C_3$–$C_5$alkynyloxy, $C_3$–$C_5$alkynylthio, $C_3$–$C_8$cycloalkyl-X—, $C_6$–$C_{12}$bicycloalkyl-X—, heterocylyl-X—, alicyclyl-X—, aryl-X—, phthalidyl-X—, biphenyl-X— or heteroaryl-X—;

X is —O—, —S—, —SO— or —$SO_2$—, or $R_2$ is a group $R_{88}R_{89}N$—,

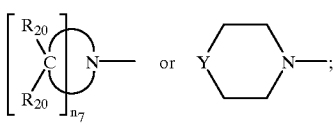

$R_{88}$ and $R_{89}$ independently of one another are hydrogen, $C_1$–$C_6$alkyl, $C_1$–$C_6$alkyl substituted up to 3 times by halogens, CN, $C_1$–$C_3$alkoxy or

$C_3$–$C_{12}$cycloalkyl, $C_3$–$C_{10}$alkenyl, $C_3$–$C_{10}$alkynyl, $C_6$–$C_{12}$bicycloalkyl or $C_6$–$C_{12}$bicycloalkyl substituted up to 3 times by $C_1$–$C_3$alkyl;- the radicals $R_{20}$ independently of one another are hydrogen or $C_1$–$C_4$alkyl;
$n_7$ is 4 or 5;
Y is —O—, —S—, —NH— or —$NR_{101}$—;
$R_{98}$ and $R_{101}$ are as defined above;
$R_3$ is halogen, hydroxyl, $C_1$–$C_{10}$alkoxy, $C_1$–$C_{10}$alkoxy substituted up to 3 times by halogens, CN, $NO_2$, $C_1$–$C_6$alkoxy, $C_1$–$C_6$alkylthio, $C_3$–$C_6$alkenyloxy, $C_1$–$C_6$alkoxycarbonyl, heterocyclyl of the formula

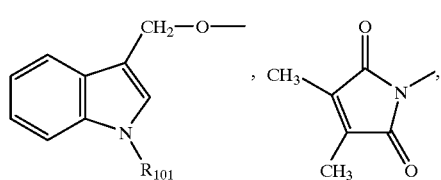

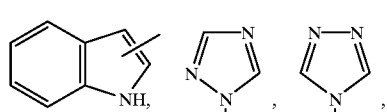

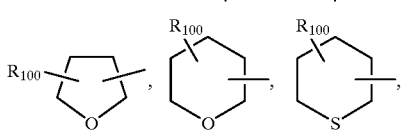

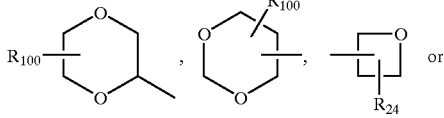

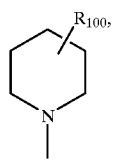

in which $R_{24}$, $R_{98}$, $R_{100}$ and $R_{101}$ are as defined above, or substituted up to 5 times or unsubstituted aryl or aryloxy, $C_3$–$C_{10}$alkenyloxy, $C_3$–$C_{10}$alkenyloxy substituted up to 3 times by halogens, CN, $NO_2$, $C_1$–$C_6$alkoxy, $C_3$–$C_6$alkenyloxy, $C_1$–$C_6$alkoxycarbonyl or substituted up to 5 times or unsubstituted aryl or aryloxy, $C_1$–$C_{10}$alkylthio, $C_1$–$C_{10}$alkylthio substituted up to 3 times by halogens, CN, $NO_2$, $C_1$–$C_6$alkoxy, $C_3$–$C_6$alkenyloxy, $C_1$–$C_6$alkoxycarbonyl or substituted up to 5 times or unsubstituted aryl or aryloxy, $C_3$–$C_{10}$alkenylthio or $C_3$–$C_{10}$alkenylthio substituted up to 3 times by halogens, CN, $NO_2$, $C_1$–$C_6$alkoxy, $C_3$–$C_6$alkenyloxy, $C_1$–$C_6$alkoxycarbonyl or substituted up to 5 times or unsubstituted aryl or aryloxy, or
$R_3$ is $C_3$–$C_5$alkynyloxy, $C_3$–$C_5$alkynylthio, $C_3$–$C_8$cycloalkyl-X—, $C_6$–$C_{12}$bicycloalkyl-X—, heterocyclyl-X—, alicyclyl-X—, aryl-X—, phthalidyl-X—, biphenyl-X— or heteroaryl-X—; and X is as defined above,
and stereoisomers of the compounds of the formula I, excluding the compounds of formulae $I_1$ to $I_7$:

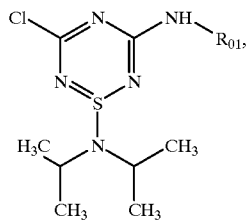
($I_1$)

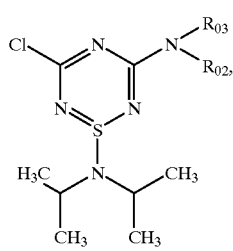
($I_2$)

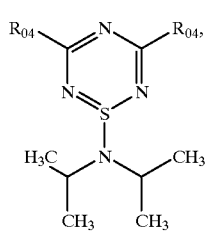
($I_3$)

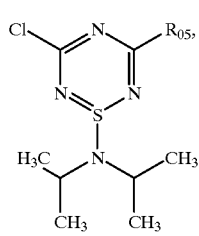
($I_4$)

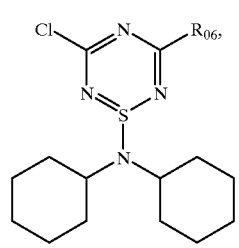
($I_5$)

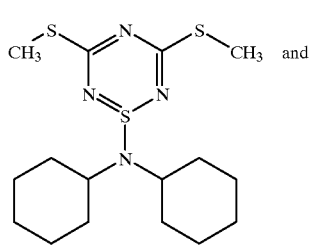
($I_6$)

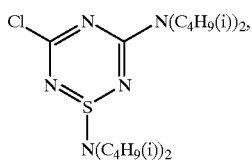
(I₇)

wherein R₀₁ is hydrogen, methyl, ethyl, n-propyl, i-butyl, tert-butyl, allyl, cyclohexyl or benzyl; R₀₂ is ethyl, benzyl or i-butyl and R₀₃ is ethyl, cyclohexyl, benzyl or i-butyl, or R₀₂ and R₀₃, together with the nitrogen atom to which they are bonded, form a piperidine ring;

R₀₄ is chlorine, methylthio, ethylthio, i-propylthio, n-butylthio, i-butylthio, phenylthio or benzylthio;

R₀₅ is ethoxy, methylthio, ethylthio or phenylthio; and

R₀₆ is chlorine or cyclohexylamino.

2. A compound according to claim 1, in which

R₁ is a group —OR₇, —NR₉₀R₉₁ or

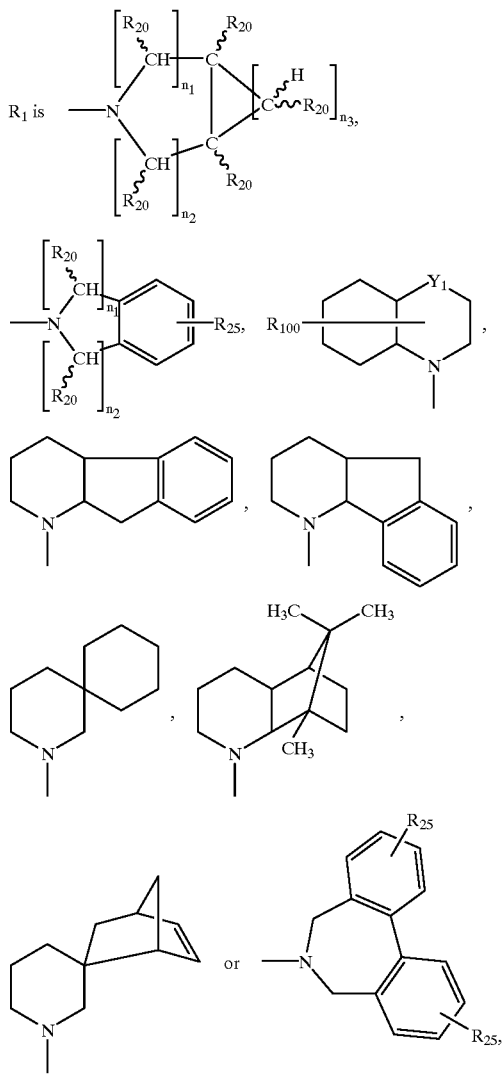

in which the radicals R₂₀ independently of one another are hydrogen, $C_1$–$C_4$alkyl or $C_1$–$C_3$alkoxy;

R₂₅ is hydrogen, chlorine, methyl or methoxy;

R₁₀₀ is hydrogen or $C_1$–$C_3$alkyl;

Y₁ is —O—, —S— or —NR₃₀;

R₃₀ is hydrogen, methyl, $C_1$–$C_3$alkylcarbonyl or ($C_1$–$C_3$alkyl)₂NCO;

n₁ is 1, 2, 3, 4 or 5;

n₂ is 0, 1 or 2; and n₃ is a number from 3 to 10;

R₇ is $C_1$–$C_{16}$alkyl, $C_1$–$C_{16}$alkyl substituted by halogen, NO₂, CN, $C_1$–$C_5$alkoxy, $C_1$–$C_5$alkylthio, $C_3$–$C_8$cycloalkoxy, $C_1$–$C_3$trialkylsilyl, $C_3$–$C_{10}$alkenyloxy, $C_3$–$C_5$alkynyloxy, $C_1$–$C_5$alkylcarbonyloxy, $C_1$–$C_3$alkoxycarbonyl, $C_1$–$C_3$alkylcarbonyl, $C_5$–$C_7$cycloalkenyl or $C_5$–$C_7$cycloalkenyl substituted by $C_1$–$C_4$alkyl, or R₇ is $C_1$–$C_{16}$alkyl substituted by $C_3$–$C_8$cycloalkyl, $C_6$–$C_{12}$bicycloalkyl, $C_6$–$C_{12}$chlorobicycloalkyl, $C_6$–$C_{12}$bicycloalkenyl or adamantyl, or R₇ is $C_1$–$C_{16}$alkyl substituted by substituted or unsubstituted aryl, aryloxy, arylmethylenoxy, arylcarbonyl, arylcarbonyloxy or a heterocyclic ring of the formula

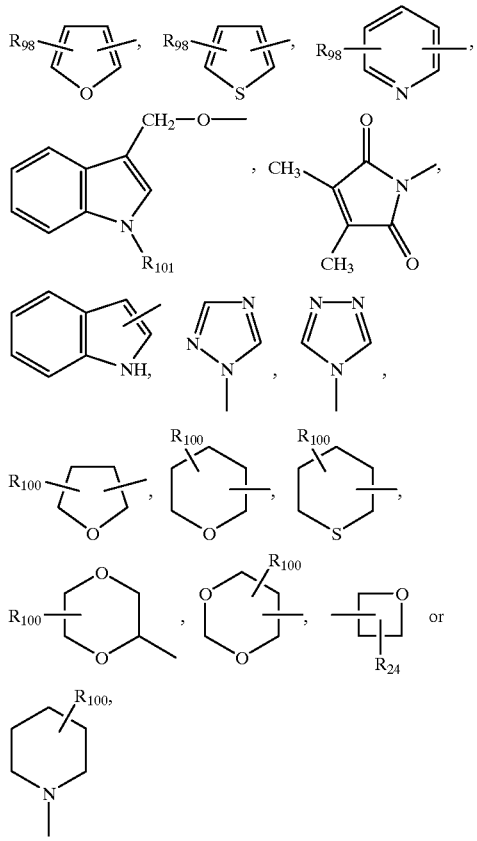

in which R₂₄, R₉₈, R₁₀₀ and R₁₀₁ are as defined in claim 1, or

R₇ is $C_3$–$C_{15}$alkenyl, $C_3$–$C_{15}$alkenyl substituted by halogen, $C_1$–$C_3$alkoxy, $C_3$–$C_8$cycloalkyl or substituted or unsubstituted aryl or aryloxy, or R₇ is $C_3$–$C_5$alkynyl, $C_3$–$C_{12}$cycloalkyl, $C_3$–$C_{12}$cycloalkyl substituted by halogen, CN, $C_1$–$C_3$-trialkylsilyl, =O, $C_1$–$C_6$alkyl, cyano-$C_1$–$C_5$alkyl, $C_1$–$C_5$alkyl-CONH—$C_1$–$C_5$alkyl, phenyl-CONH—$C_1$–$C_5$alkyl, $C_1$–$C_5$chloroalkyl, $C_1$–$C_3$alkoxy, $C_1$–$C_3$alkylthio, $C_1$–$C_3$alkoxycarbonyl, $C_1$–$C_3$alkoxycarbonyl-$C_1$–$C_5$alkyl, $C_5$–$C_7$cycloalkyl, $C_2$–$C_4$alkenyl, $C_2$–$C_4$alkynyl, benzyl or $C_1$–$C_3$halogenoalkyl, or $R_7$ is $C_5$–$C_7$cycloalkenyl, $C_5$–$C_7$cycloalkenyl substituted by $C_1$–$C_3$alkyl, or $R_7$ is $C_6$–$C_{12}$bicycloalkyl, $C_6$–$C_{12}$bicycloalkyl substituted by $C_1$–$C_3$alkyl or halogen, $C_6$–$C_{12}$bicycloalkenyl, $C_6$–$C_{12}$bicycloalkenyl substituted by $C_1$–$C_3$alkyl, or $R_7$ is a substituted or unsubstituted nonaromatic heterocyclic ring of the formula

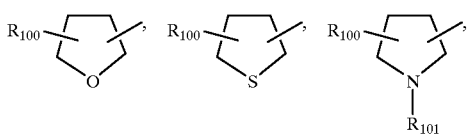

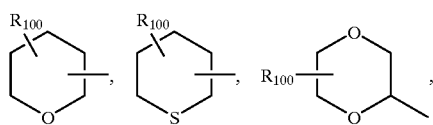

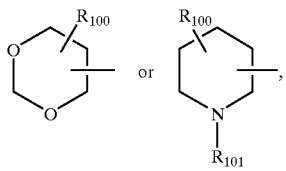

in which $R_{100}$ and $R_{101}$ are as defined above, or an alicyclic ring system;

$R_{90}$ and $R_{91}$ independently of one another are hydrogen, $C_1$–$C_{12}$alkyl, $C_1$–$C_{12}$alkyl substituted by halogen, $NO_2$, CN, hydroxyl, $C_1$–$C_3$alkoxy, $C_1$–$C_3$trialkylsilyl, $C_1$–$C_6$alkylamino, di($C_1$–$C_6$alkyl)amino, $C_3$–$C_7$cycloalkyl,

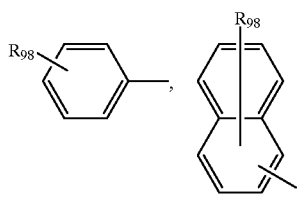

or a heterocyclic ring of the formula

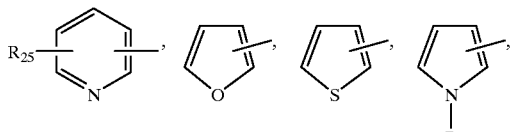

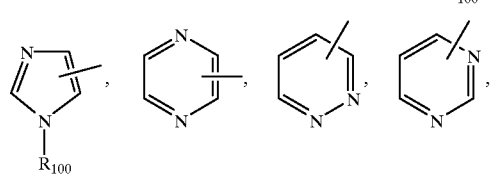

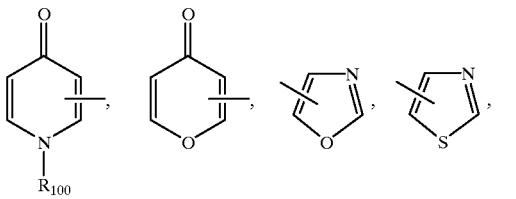

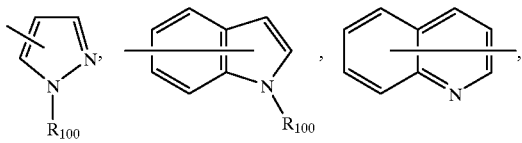

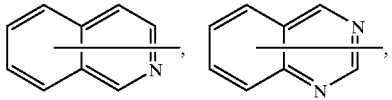

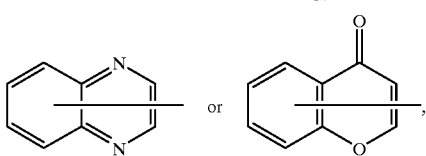

in which $R_{25}$ and $R_{100}$ are as defined above, or $R_{90}$ and $R_{91}$ independently of one another are $C_3$–$C_{10}$alkenyl, $C_3$–$C_{10}$alkynyl, $C_6$–$C_{12}$bicycloalkyl, $C_6$–$C_{12}$bicycloalkenyl, $C_3$–$C_{12}$cycloalkyl, $C_3$–$C_{12}$cycloalkyl substituted by $C_1$–$C_4$alkyl, $C_5$–$C_7$cycloalkenyl or $C_5$–$C_7$cycloalkenyl substituted by $C_1$–$C_4$alkyl, with the proviso that $R_{90}$ and $R_{91}$ are not simultaneously hydrogen; or $R_{90}$ and $R_{91}$, together with the nitrogen atom to which they are bonded, form a saturated heterocyclic ring which contains 2–12 carbon atoms and can contain, as further heteroatoms, a nitrogen, an oxygen or a sulfur atom and can be substituted by $C_1$–$C_4$alkyl, $C_1$- or $C_2$-halogenoalkyl, methoxy-$C_1$–$C_4$alkyl, halogen, hydroxyl, CN, $C_1$–$C_4$alkoxy, $C_1$–$C_4$alkylcarbonyl, $C_1$- or $C_2$halogenoalkyl,

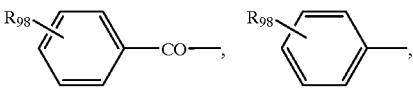

$C_1$–$C_3$alkoxycarbonyl, $(C_1$–$C_3$alkyl$)_2$NCO, di($C_1$–$C_4$alkyl)amino or =O and can additionally be bridged by 1 or 2

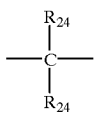

groups and onto which 1 or 2 further carbocyclic, heterocyclic or aromatic rings can be fused, or $R_{90}$ and $R_{91}$, together with the nitrogen atom to which they are bonded, form a monounsaturated heterocyclic ring which contains 5–7 carbon atoms and is substituted or unsubstituted by $C_1$–$C_4$alkyl, $C_1$- or $C_2$halogenoalkyl, halogen, hydroxyl, CN, amino, $C_1$–$C_4$alkylamino, di($C_1$–$C_4$alkyl)amino, phenyl, $C_1$–$C_4$alkoxy or $C_1$–$C_3$alkoxycarbonyl and is additionally bridged by 1 or 2

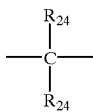

groups and onto which 1 or 2 further carbocyclic, heterocyclic or aromatic rings can be fused;
the radicals $R_{24}$ independently of one another are hydrogen or methyl;
$R_{98}$ is hydrogen, fluorine, chlorine, bromine, CN, $C_1$–$C_3$alkoxy, $C_1$–$C_3$alkoxycarbonyl, $C_1$–$C_3$-alkoxy-$C_1$–$C_3$alkyl, $C_1$- or $C_2$halogenoalkyl, $C_1$–$C_5$alkyl, $NO_2$, $C_3$–$C_5$alkenyl, cyclopropyl or $C_1$- or $C_2$halogenoalkoxy;
$R_2$ is halogen, $C_1$–$C_{10}$alkoxy, $C_1$–$C_{10}$alkoxy substituted by halogen, CN, $NO_2$, $C_1$–$C_6$alkoxy, $C_1$–$C_6$alkylthio, $C_3$–$C_6$alkenyloxy, $C_1$–$C_6$alkoxycarbonyl, heterocyclyl of the formula

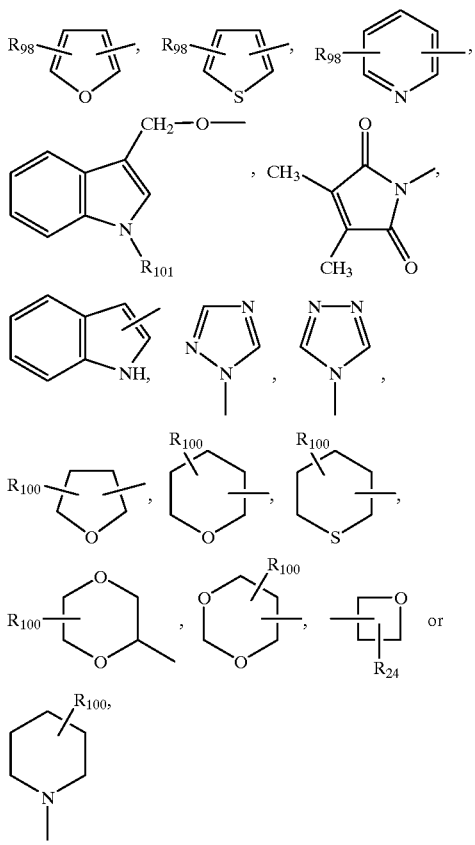

in which $R_{24}$, $R_{98}$, $R_{100}$ and $R_{101}$ are as defined above, or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylthio, $C_1$–$C_{10}$alkylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenylthio or $C_3$–$C_{10}$alkenylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, or $R_2$ is $C_3$–$C_5$alkynyloxy, $C_3$–$C_5$alkynylthio, $C_3$–$C_8$oycloalkyl-X—, $C_6$–$C_{12}$bicycloalkyl-X—, heterocyclyl-X—, alicyclyl-X—, aryl-X—, phthalidyl-X—, biphenyl-X— or heteroaryl-X—;
X is —O—, —S—, —SO— or —SO$_2$—, or
$R_2$ is a group $R_{88}R_{89}N$—,

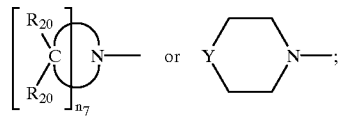

$R_{88}$ and $R_{89}$ independently of one another are hydrogen, $C_1$–$C_6$alkyl, $C_1$–$C_6$alkyl substituted by halogen, CN, $C_1$–$C_3$alkoxy or

$C_3$–$C_{12}$cycloalkyl, $C_3$–$C_{10}$alkenyl, $C_3$–$C_{10}$alkynyl, $C_6$–$C_{12}$bicycloalkyl or $C_6$–$C_{12}$bicycloalkyl substituted by $C_1$–$C_3$alkyl;
the radicals $R_{20}$ independently of one another are hydrogen or $C_1$–$C_4$alkyl;
$n_7$ is 4 or 5;
Y is —O—, —S—, —NH— or —NR$_{101}$—;
$R_{101}$ is $C_1$–$C_4$alkyl, $C_1$–$C_4$alkylcarbonyl or $C_1$–$C_3$alkoxycarbonyl and
$R_{98}$ is as defined above; and
$R_3$ is halogen, $C_1$–$C_{10}$alkoxy, $C_1$–$C_{10}$alkoxy substituted by halogen, CN, $NO_2$, $C_1$–$C_6$alkoxy, $C_1$–$C_6$alkylthio, $C_3$–$C_6$alkenyloxy, $C_1$–$C_6$alkoxycarbonyl, heterocyclyl of the formula

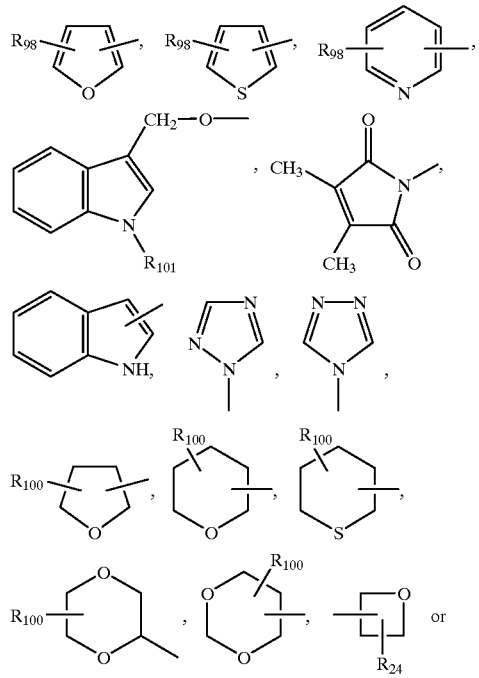

-continued

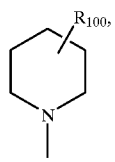

in which $R_{24}$, $R_{98}$, $R_{100}$ and $R_{101}$ are as defined above, or substituted or unsubstituted aryl or aryloxy, $C_3-C_{10}$alkenyloxy, $C_3-C_{10}$alkenyloxy substituted by halogen, CN, $NO_2$, $C_1-C_6$alkoxy, $C_3-C_6$alkenyloxy, $C_1-C_6$alkoxycarbonyl or substituted or unsubstituted aryl or aryloxy, $C_1-C_{10}$alkylthio, $C_1-C_{10}$alkylthio substituted by halogen, CN, $NO_2$, $C_1-C_6$alkoxy, $C_3-C_6$alkenyloxy, $C_1-C_6$alkoxycarbonyl or substituted or unsubstituted aryl or aryloxy, $C_3-C_{10}$alkenylthio or $C_3-C_{10}$alkenylthio substituted by halogen, CN, $NO_2$, $C_1-C_6$alkoxy, $C_3-C_6$alkenyloxy, $C_1-C_6$alkoxycarbonyl or substituted or unsubstituted aryl or aryloxy, or $R_3$ is $C_3-C_5$alkynyloxy, $C_3-C_5$alkynylthio, $C_3-C_8$cycloalkyl-X—, $C_6-C_{12}$bicycloalkyl-X—, heterocyclyl-X—, alicyclyl-X—, aryl-X—, phthalidyl-X—, biphenyl-X— or heteroaryl-X—; and X is as defined above.

3. A compound according to claim 2, in which

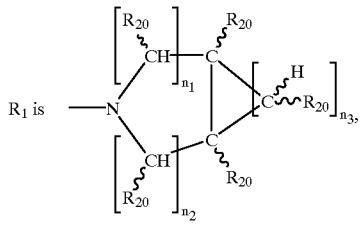

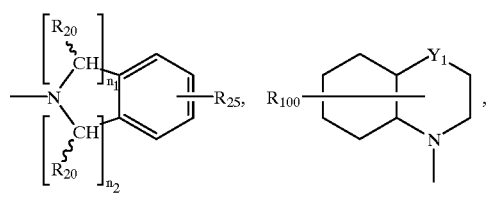

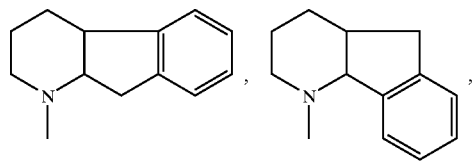

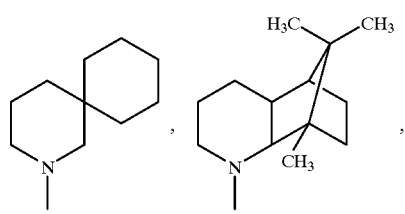

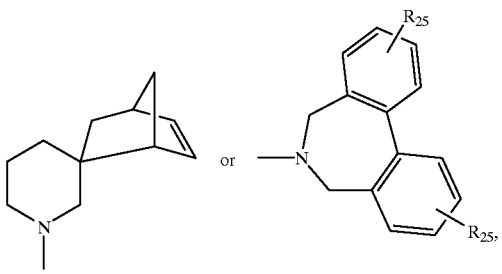

in which the radicals $R_{20}$ independently of one another are hydrogen or $C_1-C_4$alkyl;
$R_{25}$ is hydrogen, chlorine, methyl or methoxy;
$R_{100}$ is hydrogen or $C_1-C_3$alkyl;
$Y_1$ is —O—, —S— or —$NR_{30}$;
$R_{30}$ is hydrogen, methyl, $C_1-C_3$alkylcarbonyl or $(C_1-C_3$alkyl$)_2$NCO;
$n_1$ is 1, 2, 3, 4 or 5;
$n_2$ is 0, 1 or 2; and
$n_3$ is a number from 3 to 10.

4. A compound according to claim 2, in which
$R_1$ is the group —$OR_7$; and
$R_2$ and $R_3$ independently of one another are chlorine, $C_1-C_{10}$alkoxy, $C_1-C_{10}$alkoxy substituted by halogen, CN, $NO_2$, $C_1-C_6$alkoxy, $C_1-C_6$alkylthio, $C_3-C_6$alkenyloxy, $C_1-C_6$alkoxycarbonyl, heterocyclyl of the formula

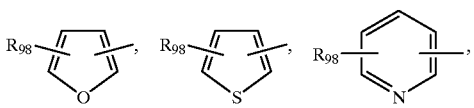

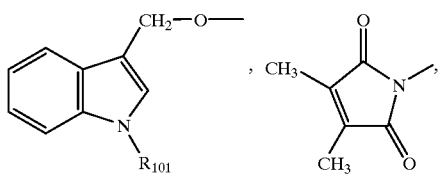

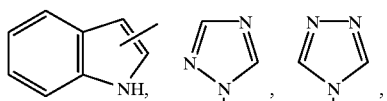

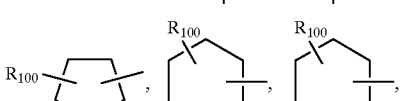

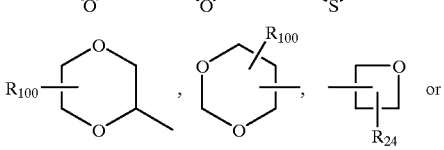

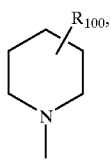

601 in which $R_{24}$, $R_{98}$, $R_{100}$ and $R_{101}$ are as defined above, or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylthio, $C_1$–$C_{10}$alkylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenylthio or $C_3$–$C_{10}$alkenylthio substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, or $R_2$ and $R_3$ independently of one another are $C_3$–$C_5$alkynyloxy, $C_3$–$C_5$alkynylthio, $C_3$–$C_8$cycloalkyl-X—, $C_6$–$C_{12}$bicycloalkyl-X—, heterocyclyl-X—, alicyclyl-X—, aryl-X—, phthalidyl-X—, biphenyl-X— or heteroaryl-X—.

5. A compound according to claim 2, in which $R_1$ is the group —$OR_7$;

$R_2$ is a group $R_{88}R_{89}N$—,

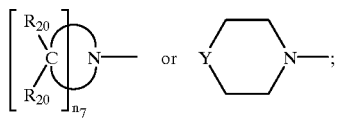

and $R_3$ is aryl-X—, phthalidyl-X—, biphenyl-X—, or heteroaryl-X—.

6. A compound according to claim 2, in which $R_1$ is a group —$NR_{90}R_{91}$ or

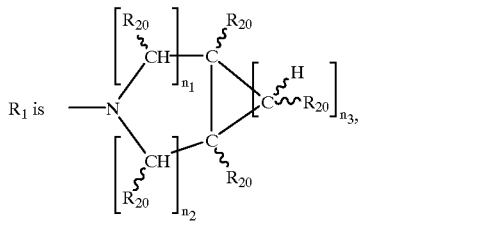

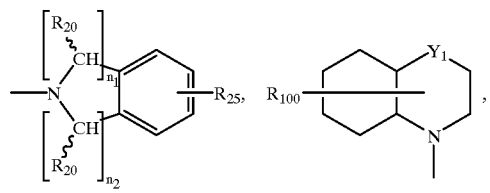

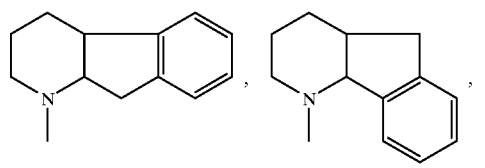

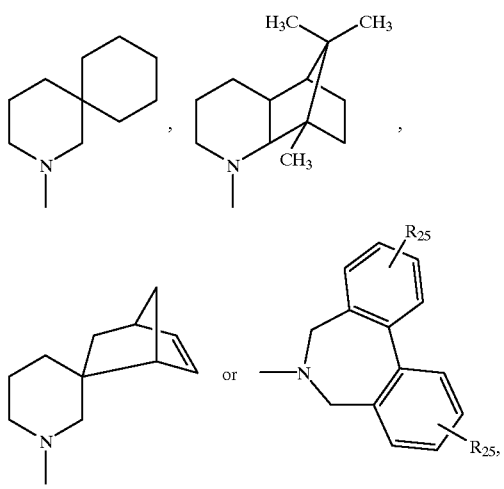

in which the radicals $R_{20}$, $R_{25}$, $R_{100}$, $Y_1$, $R_{30}$, $n_1$, $n_2$ and $n_3$ are as defined in claim 2; $R_2$ is a group $R_{88}R_{89}N$—,

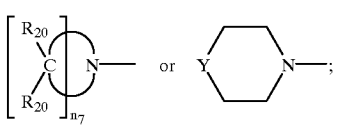

and $R_3$ is aryl-X—, phthalidyl-X—, biphenyl-X- or heteroaryl-X—.

7. A compound according to claim 5, in which
$R_1$ is a group —$OR_7$;
$R_7$ $C_1$–$C_{16}$alkyl, $C_1$–$C_{16}$alkyl substituted by halogen, $NO_2$, CN, $C_1$–$C_5$alkoxy, $C_1$–$C_5$alkylthio, $C_1$–$C_8$cycloalkoxy, $C_1$–$C_3$trialkylsilyl, $C_3$–$C_{10}$alkenyloxy, $C_3$–$C_5$alkynyloxy, $C_1$–$C_5$alkylcarbonyloxy, $C_1$–$C_3$alkoxycarbonyl, $C_1$–$C_3$alkylcarbonyl, $C_5$–$C_7$cycloalkenyl or $C_5$–$C_7$cycloalkenyl substituted by $C_1$–$C_4$alkyl, or $R_7$ is $C_1$–$C_{16}$alkyl substituted by $C_6$–$C_{12}$bicycloalkyl, $C_6$–$C_{12}$chlorobicycloalkyl, $C_6$–$C_{12}$bicycloalkenyl or adamantyl, or $R_7$ is $C_1$–$C_{16}$alkyl substituted by

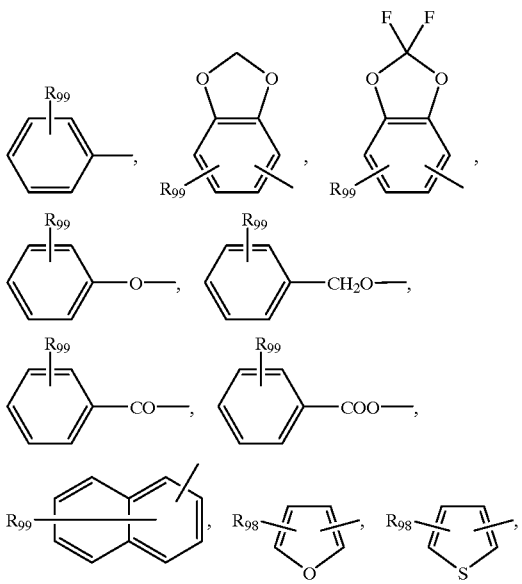

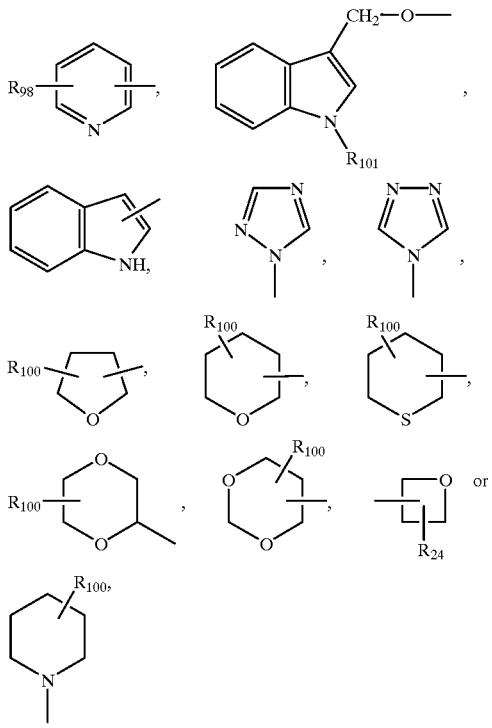

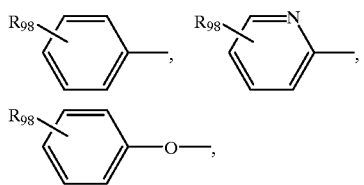

in which $R_{24}$ is hydrogen or methyl;

$R_{98}$ is hydrogen, fluorine, chlorine, bromine, CN, $C_1$–$C_3$alkoxy, $C_1$–$C_3$alkoxycarbonyl, $C_1$–$C_3$alkoxy-$C_1$–$C_3$alkyl, $C_1$- or $C_2$halogenoalkyl, $C_1$–$C_5$alkyl, $NO_2$, $C_3$–$C_5$alkenyl, cyclopropyl or $C_1$- or $C_2$halogenoalkoxy;

$R_{99}$ is hydrogen, halogen, $NO_2$, CN, $C_1$–$C_5$alkyl, $C_1$–$C_6$alkoxy, $C_1$–$C_6$alkenyloxycarbonyl, $C_1$–$C_3$alkylthio,

$C_1$–$C_6$alkoxycarbonyl, $NH_2$, $C_1$–$C_3$alkyl-CONH, di($C_1$–$C_6$alkyl)amino or $C_1$–$C_6$alkylamino;

$R_{100}$ is hydrogen or $C_1$–$C_3$alkyl; and $R_{101}$ is $C_1$–$C_4$alkyl, $C_1$–$C_4$alkylcarbonyl or $C_1$–$C_3$alkoxycarbonyl; or $R_7$ is $C_3$–$C_{12}$cycloalkyl, $C_3$–$C_{12}$cycloalkyl substituted by halogen, CN, $C_1$–$C_3$trialkylsilyl, =O, $C_1$–$C_6$alkyl, cyano-$C_1$–$C_5$alkyl, $C_1$–$C_5$alkyl-CONH—$C_1$–$C_5$alkyl, phenyl-CONH—$C_1$–$C_5$alkyl, $C_1$–$C_5$chloroalkyl, $C_1$–$C_3$alkoxy, $C_1$–$C_3$alkylthio, $C_1$–$C_3$alkoxycarbonyl, $C_1$–$C_3$alkoxycarbonyl-$C_1$–$C_5$alkyl, $C_5$–$C_7$cycloalkyl, $C_2$–$C_4$alkenyl, $C_2$–$C_4$alkynyl, benzyl or $C_1$–$C_3$halogenoalkyl, $C_5$–$C_7$cycloalkenyl or $C_5$–$C_7$cycloalkenyl substituted by $C_1$–$C_3$alkyl, or $R_7$ is $C_6$–$C_{12}$bicycloalkyl, $C_6$–$C_{12}$bicycloalkyl substituted by $C_1$–$C_3$alkyl or halogen, $C_6$–$C_{12}$bicycloalkenyl or $C_6$–$C_{12}$bicycloalkenyl substituted by $C_1$–$C_3$alkyl, or $R_7$ is a substituted or unsubstituted non-aromatic heterocyclic ring of the formula

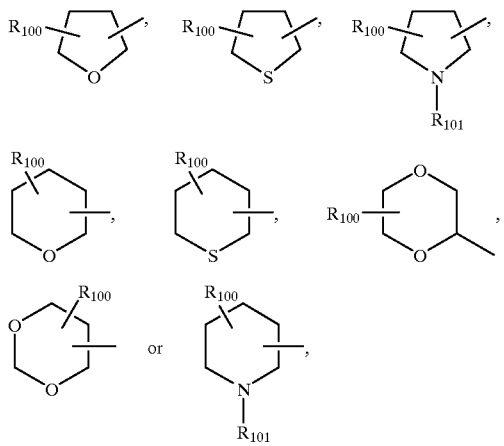

in which $R_{100}$ is hydrogen or $C_1$–$C_3$alkyl; and $R_{101}$ is $C_1$–$C_4$alkyl, $C_1$–$C_4$alkylcarbonyl or $C_1$–$C_3$alkoxycarbonyl, or $R_7$ is an alicyclic ring system;

$R_2$ is a group $R_{88}R_{89}N$—;

$R_{88}$ and $R_{89}$ independently of one another are hydrogen, $C_1$–$C_6$alkyl, $C_1$–$C_6$alkyl substituted by halogen, CN, $C_1$–$C_3$alkoxy or

$C_3$–$C_{12}$cycloalkyl, $C_3$–$C_{10}$alkenyl, $C_3$–$C_{10}$alkynyl, $C_6$–$C_{12}$bicycloalkyl or $C_6$–$C_{12}$bicycloalkyl substituted by $C_1$–$C_3$alkyl; and $R_3$ is aryl-X—, phthalidyl-X—, biphenyl-X— or heteroaryl-X—.

8. A compound according to claim 7, in which $R_7$ is $C_3$–$C_{12}$cycloalkyl, $C_3$–$C_{12}$cycloalkyl substituted by halogen, CN, $C_1$–$C_6$alkyl, cyano-$C_1$–$C_5$alkyl, $C_1$–$C_3$alkoxy or $C_1$–$C_3$halogenoalkyl, or $R_7$ $C_5$–$C_7$cycloalkenyl or $C_5$–$C_7$cycloalkenyl substituted by methyl, or $R_7$ is $C_6$–$C_{12}$bicycloalkyl, $C_6$–$C_{12}$bicycloalkyl substituted by methyl, or chlorine, $C_6$–$C_{12}$bicycloalkenyl or $C_6$–$C_{12}$bicycloalkenyl substituted by methyl, or $R_7$ is 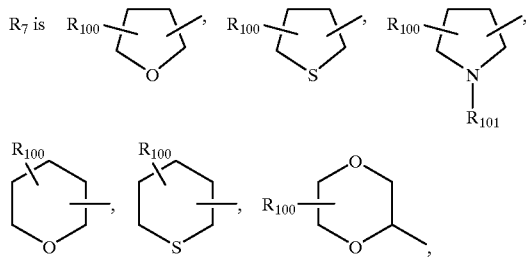

-continued

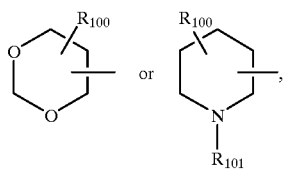

$R_{100}$ and $R_{101}$ are as defined in claim 7; or $R_7$ is 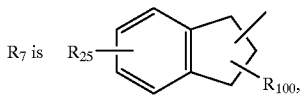

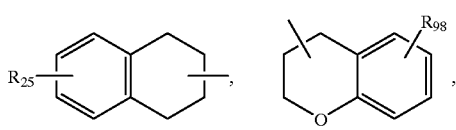

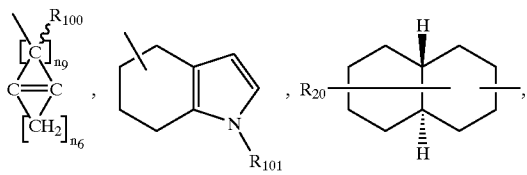

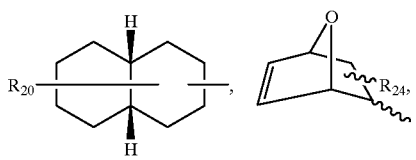

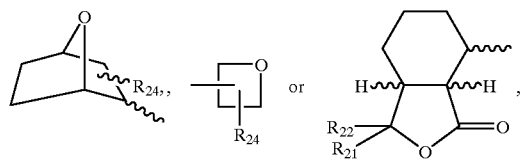

in which $R_{20}$ is hydrogen or $C_1$–$C_4$alkyl;

$R_{21}$ and $R_{22}$ independently of one another are hydrogen or $C_1$–$C_4$alkyl;

$R_{24}$ is hydrogen or methyl;

$R_{25}$ is hydrogen, chlorine, methyl or methoxy;

$R_{98}$ is hydrogen, fluorine, chlorine, bromine, CN, $C_1$–$C_3$alkoxy, $C_1$–$C_3$alkoxycarbonyl, $C_1$–$C_3$alkoxy-$C_1$–$C_3$alkyl, $C_1$- or $C_2$halogenoalkyl, $C_1$–$C_5$alkyl, $NO_2$, $C_3$–$C_5$alkenyl, cyclopropyl or $C_1$- or $C_2$-halogenoalkoxy;

$n_6$ is 3, 4, 5 or 6;

$n_9$ is 3 or 4; and $R_{100}$ and $R_{101}$ are as defined above;

$R_2$ is a group $R_{88}R_{89}N$—;

$R_{88}$ and $R_{89}$ independently of one another are hydrogen or $C_1$–$C_6$alkyl; and $R_3$ is 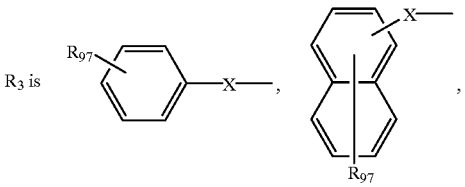

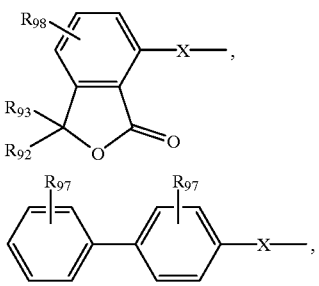

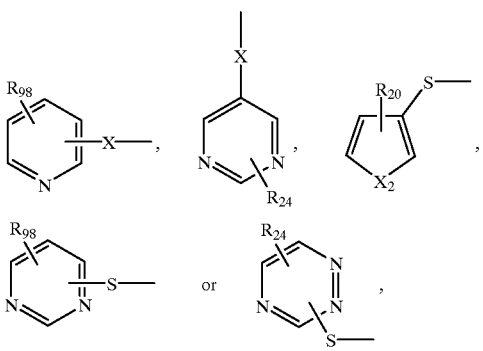

in which X is —O— or —S—;

$X_2$ is —O—, —S— or —$NR_{100}$—;

$R_{20}$, $R_{24}$ and $R_{100}$ are as defined above;

$R_{92}$ is hydrogen or $C_1$–$C_4$alkyl;

$R_{93}$ is hydrogen, $C_1$–$C_4$alkyl, hydroxyl, $C_1$–$C_4$alkoxy or $C_1$–$C_4$alkylthio;

$R_{97}$ is hydrogen, halogen, $NO_2$, CN, $C_3$–$C_6$cycloalkoxy, $C_1$–$C_{10}$alkyl, $C_1$–$C_{10}$alkyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenyl, $C_3$–$C_{10}$alkenyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkoxy, $C_1$–$C_{10}$alkoxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylcarbonyl, $C_1$–$C_{10}$alkylcarbonyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkoxycarbonyl, $C_1$–$C_{10}$alkoxycarbonyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylcarbonyloxy or $C_1$–$C_{10}$alkylcarbonyloxy substituted by halogen, CN, $NO_2$, $C_1$–$C_6$-alkoxy, $C_3$–$C_6$alkenyloxy, $C_1$–$C_6$alkoxycarbonyl or substituted or unsubstituted aryl or aryloxy, or $R_{97}$ is CHO, $C_3$–$C_8$cycloalkyl, $C_1$–$C_4$alkylthio, $C_3$- or $C_4$alkenylthio, $(R_{94})_2N$—, $(R_{95})_2N$—CO—, aryl, aryloxy, arylcarbonyl or aryloxycarbonyl, or a group

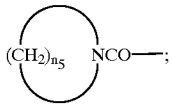

the radicals $R_{94}$ independently of one another are hydrogen, $C_1$–$C_{10}$alkyl, $C_3$–$C_8$cycloalkyl, $C_1$–$C_{10}$alkylcarbonyl or substituted or unsubstituted arylcarbonyl; the radicals $R_{95}$ independently of one another are hydrogen, $C_1$–$C_5$alkyl or $C_3$–$C_8$cycloalkyl;

$n_5$ is a number from 5 to 12; and $R_{98}$ is as defined above.

9. A compound according to claim 8, in which X and $X_2$ are —O—.

10. A compound according to claim 6, in which $R_1$ is a group —$NR_{90}R_{91}$ or

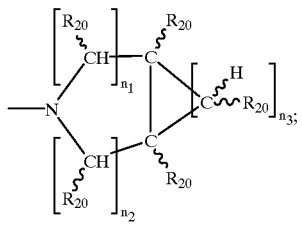

$R_{90}$ and $R_{91}$ independently of one another are $C_1$–$C_{12}$alkyl, $C_1$–$C_{12}$alkyl substituted by halogen, CN or $C_1$–$C_3$alkoxy, $C_6$–$C_{12}$bicycloalkyl, $C_6$–$C_{12}$bicycloalkenyl, $C_3$–$C_{12}$cycloalkyl, $C_3$–$C_{12}$cycloalkyl substituted by $C_1$–$C_4$alkyl, $C_5$–$C_7$cycloalkenyl or $C_5$–$C_7$cycloalkenyl substituted by $C_1$–$C_4$alkyl;

the radicals $R_{20}$ independently of one another are hydrogen or $C_1$–$C_4$alkyl;

$n_1$ is 1, 2, 3, 4 or 5;

$n_2$ is 0, 1 or 2; and $n_3$ is a number from 3 to 10;

$R_2$ is a group $R_{88}R_{89}N$—;

$R_{88}$ and $R_{89}$ independently of one another are hydrogen or $C_1$–$C_6$alkyl and

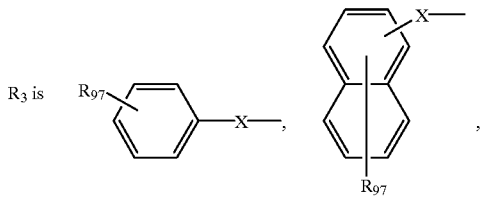

$R_3$ is

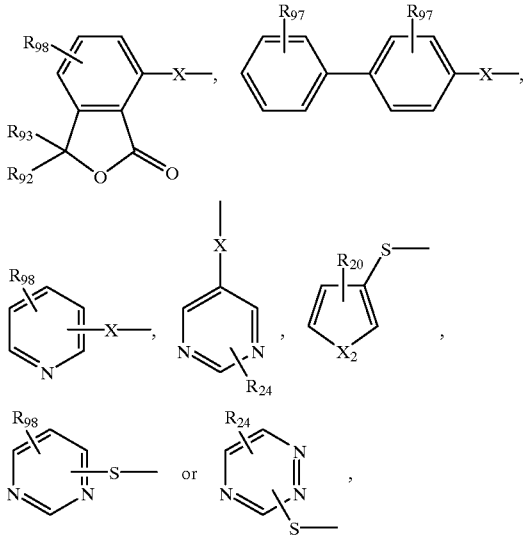

in which X is —O—, —S—, —SO— or —$SO_2$—;

$X_2$ is —O—, —S— or —$NR_{100}$—;

$R_{100}$ is hydrogen or $C_1$–$C_3$alkyl;

$R_{20}$ is as defined above;

$R_{24}$ is hydrogen or methyl;

$R_{92}$ is hydrogen or $C_1$–$C_4$alkyl;

$R_{93}$ is hydrogen, $C_1$–$C_4$alkyl, $C_1$–$C_4$alkoxy or $C_1$–$C_4$alkylthio;

$R_{97}$ is hydrogen, halogen, $NO_2$, CN, $C_3$–$C_6$cycloalkoxy, $C_1$–$C_{10}$alkyl, $C_1$–$C_{10}$alkyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenyl, $C_3$–$C_{10}$alkenyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkoxy, $C_1$–$C_{10}$alkoxy substituted by halogen, CN, $NO_2$, $C_1$–$C_6$alkoxy, $C_3$–$C_6$-alkenyloxy, $C_1$–$C_6$alkoxycarbonyl or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylcarbonyl, $C_1$–$C_{10}$alkylcarbonyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkoxycarbonyl, $C_1$–$C_{10}$alkoxycarbonyl substituted by halogen, CN, $NO_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylcarbonyloxy or $C_1$–$C_{10}$alkylcarbonyloxy substituted by halogen, CN, $NO_2$, $C_1$–$C_6$-alkoxy, $C_3$–$C_6$alkenyloxy, $C_1$–$C_6$alkoxycarbonyl or substituted or unsubstituted aryl or aryloxy, or $R_{97}$ is CHO, $C_3$–$C_8$cycloalkyl, $C_1$–$C_4$alkylthio, $C_3$- or $C_4$alkenylthio, $(R_{94})_2N$—, $(R_{95})_2N$—CO—, aryl, aryloxy, arylcarbonyl or aryloxycarbonyl, or a group

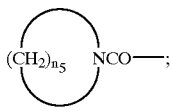

the radicals $R_{94}$ independently of one another are hydrogen, $C_1$–$C_{10}$alkyl, $C_3$–$C_8$cycloalkyl, $C_1$–$C_{10}$alkylcarbonyl or substituted or unsubstituted arylcarbonyl;

the radicals $R_{95}$ independently of one another are hydrogen, $C_1$–$C_5$alkyl or $C_3$–$C_8$cycloalkyl;

$n_5$ is a number from 5 to 12; and $R_{98}$ is hydrogen, fluorine, chlorine, bromine, CN, $C_1$–$C_3$alkoxy, $C_1$–$C_3$alkoxycarbonyl, $C_1$–$C_3$-alkoxy-$C_1$–$C_3$alkyl, $C_1$- or $C_2$halogenoalkyl, $C_1$–$C_5$alkyl, $NO_2$, $C_3$–$C_5$alkenyl, cyclopropyl or $C_1$- or $C_2$halogenoalkoxy.

11. A compound according to claim 10, in which $R_1$ is a group —$NR_{90}R_{91}$ or

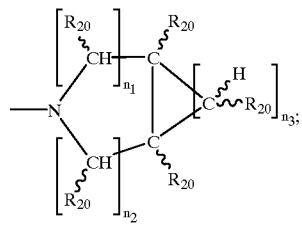

$R_{90}$ and $R_{91}$ independently of one another are $C_1$–$C_{12}$alkyl, $C_1$–$C_{12}$alkyl substituted by halogen, CN or $C_1$–$C_3$alkoxy, $C_3$–$C_8$cycloalkyl, $C_3$–$C_8$cycloalkyl substituted by methyl, $C_5$–$C_7$cycloalkenyl or $C_5$–$C_7$cycloalkenyl substituted by methyl;

the radicals $R_{20}$ independently of one another are hydrogen or methyl;

$n_1$ is 2, 3 or 4;

$n_2$ is 0 or 1; and $n_3$ is 3, 4 or 5;

$R_2$ is a group $R_{88}R_{89}N$—;

$R_{88}$ and $R_{89}$ independently of one another are hydrogen or $C_1$–$C_3$alkyl; and $R_3$ is 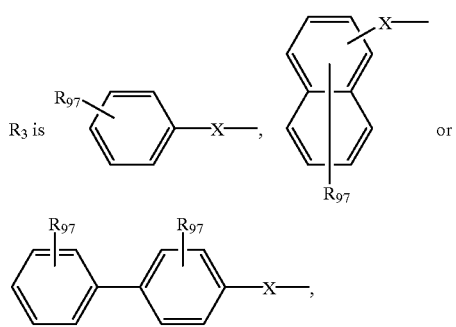

in which X is —O— or —S—;

$R_{97}$ is hydrogen, halogen, $NO_2$, CN, $C_1$–$C_{10}$alkyl, $C_1$–$C_{10}$alkyl substituted by halogen, CN, $NO_2$, $C_1$–$C_6$alkoxy or substituted or unsubstituted aryl or aryloxy, $C_3$–$C_{10}$alkenyl, $C_3$–$C_{10}$alkenyl substituted by halogen, CN, $NO_2$, $C_1$–$C_6$alkoxy or substituted or unsubstituted aryl or aryloxy, $C_1$–$C_{10}$alkoxy, $C_1$–$C_{10}$alkoxy substituted by halogen, CN, $NO_2$, $C_1$–$C_6$alkoxy or substituted or unsubstituted aryl or aryloxy, $C_3$–$C_{10}$alkenyloxy, $C_3$–$C_{10}$alkenyloxy substituted by halogen, CN, $NO_2$, $C_1$–$C_6$alkoxy or substituted or unsubstituted aryl or aryloxy, $C_1$–$C_{10}$alkoxycarbonyl, $C_1$–$C_{10}$alkoxycarbonyl substituted by halogen, CN, $NO_2$, $C_1$–$C_6$alkoxy or substituted or unsubstituted aryl or aryloxy, $C_1$–$C_{10}$alkylcarbonyloxy or $C_1$–$C_{10}$alkylcarbonyloxy substituted by halogen, CN, $NO_2$, $C_1$–$C_6$alkoxy or substituted or unsubstituted aryl or aryloxy, or $R_{97}$ is $(R_{94})_2N$—, $(R_{95})_2N$—CO—, aryl, aryloxy, arylcarbonyl or aryloxycarbonyl;

the radicals $R_{94}$ independently of one another are hydrogen, $C_1$–$C_4$alkyl, $C_3$–$C_8$cycloalkyl, $C_1$–$C_5$alkylcarbonyl or substituted or unsubstituted arylcarbonyl; and the radicals $R_{95}$ independently of one another are hydrogen, $C_1$–$C_3$alkyl or $C_3$–$C_6$cycloalkyl.

12. A compound according to claim 2, selected from the group consisting of:

3-amino-5-pentafluorophenoxy-1-(trans-3,3,5-trimethylcyclohexanolyl)thiatriazine;

3-amino-5-pentafluorophenoxy-1-[(N-cis-3,3,5-trimethylcyclohexyl)methylamino]thiatriazine;

3-amino-5-pentafluorophenoxy-1-octamethyleneimino-thiatriazine;

3-amino-5-pentafluorophenoxy-1-decahydroquinolyl-thiatriazine;

3-amino-5-pentafluorophenoxy-1-tetrahydroisoquinolyl-thiatriazine; and the compound of the formula

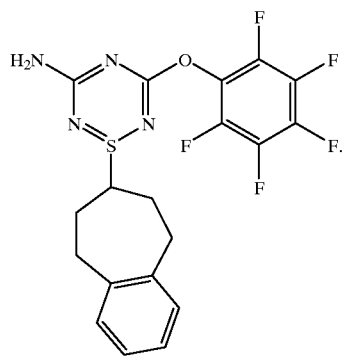

13. A process for the preparation of a compound according to claim 1, in which $R_1$ is the group —$OR_7$; $R_2$ and $R_3$ independently of one another are halogen, $C_1$–$C_{10}$alkoxy, $C_1$–$C_{10}$alkoxy substituted by halogen, CN, $NO_2$, $C_1$–$C_6$alkoxy, $C_1$–$C_6$alkylthio, $C_3$–$C_6$alkenyloxy, $C_1$–$C_6$alkoxycarbonyl, heterocyclyl of the formula

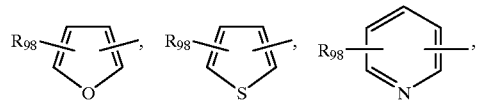

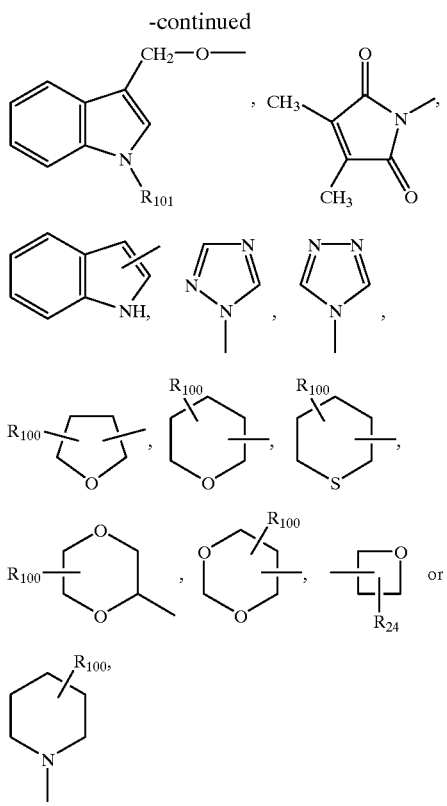

in which $R_{24}$, $R_{98}$, $R_{100}$ and $R_{101}$ are as defined in claim 1, or substituted or unsubstituted aryl or aryloxy, $C_3$–$C_{10}$alkenyloxy, $C_3$–$C_{10}$alkenyloxy substituted by halogen, CN, NO$_2$, $C_1$–$C_6$alkoxy, $C_3$–$C_6$alkenyloxy, $C_1$–$C_6$alkoxycarbonyl or substituted or unsubstituted aryl or aryloxy, $C_1$–$C_{10}$alkylthio, $C_1$–$C_{10}$alkylthio substituted by halogen, CN, NO$_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_{10}$alkenylthio or $C_3$–$C_{10}$alkenylthio substituted by halogen, CN, NO$_2$, $C_1$–$C_6$alkoxy, $C_3$–$C_6$alkenyloxy, $C_1$–$C_6$alkoxycarbonyl or substituted or unsubstituted aryl or aryloxy, or $R_2$ and $R_3$ independently of one another are $C_3$–$C_5$alkynyloxy, $C_3$–$C_5$alkynylthio, $C_3$–$C_8$cycloalkyl-X—, $C_6$–$C_{12}$bicycloalkyl-X—, heterocyclyl-X—, alicyclyl-X—, aryl-X—, phthalidyl-X—, biphenyl-X— or heteroaryl-X—, and X is as defined in claim 1, which comprises a procedure in which a$_1$) 1,3,5-trichlorothiatriazine is converted with an alcohol of the formula XVII $$R_7\text{—OH} \qquad (XVII),$$

in which $R_7$ is as defined in claim 1 if appropriate in the presence of an equimolar amount of base and an inert organic solvent, into the compound of the formula VII

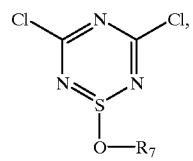

(VII)

in which $R_7$ is as defined, and this compound is then either b$_1$) reacted with a compound of the formula XXIII $$R_{14}\text{—}X_1\text{H} \qquad (XXIII),$$

in which $R_{14}$ is $C_1$–$C_{10}$alkyl, $C_1$–$C_{10}$alkyl substituted by halogen, CN, NO$_2$, $C_1$–$C_6$alkoxy, $C_1$–$C_6$alkylthio, $C_3$–$C_6$alkenyloxy, $C_1$–$C_6$alkoxycarbonyl, heterocyclyl of the formula

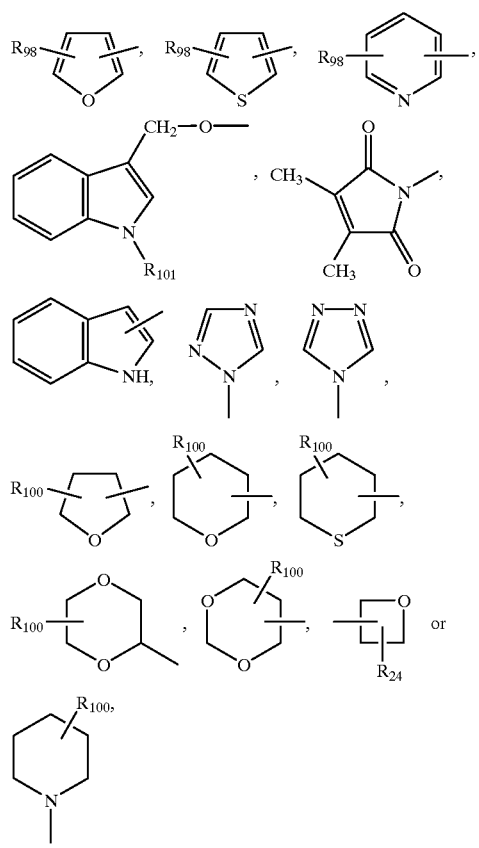

in which $R_{24}$, $R_{98}$, $R_{100}$ and $R_{101}$ are as defined in claim 1, or substituted or unsubstituted aryl or aryloxy, $C_3$–$C_{10}$alkenyl or $C_3$–$C_{10}$alkenyl substituted by halogen, CN, NO$_2$, $C_1$–$C_6$alkoxy, $C_3$–$C_6$alkenyloxy, $C_1$–$C_6$alkoxycarbonyl or substituted or unsubstituted aryl or aryloxy, $C_3$–$C_5$alkynyl, $C_3$–$C_8$cycloalkyl, $C_6$–$C_{12}$bicycloalkyl, heterocyclyl of the formula

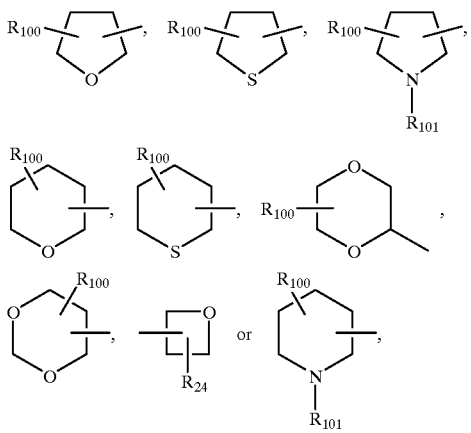

in which $R_{24}$, $R_{100}$ and $R_{101}$ are as defined above, or alicyclyl, and $X_1$ is oxygen or sulfur, in the presence of an equimolar amount of base and an inert organic solvent, or b$_2$) converted with a compound of the formula XVI

$$R_{12}-X_1H \qquad (XVI),$$

in which $R_{12}$ is an aryl, phthalidyl, biphenyl or heteroaryl radical; and $X_1$ is oxygen or sulfur, in the presence of an equimolar amount of base and an aprotic solvent, into the compound of the formula VI

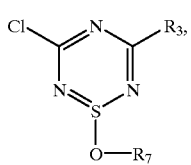
$$(VI)$$

in which $R_3$ is $-X_1-R_{12}$, and this compound is either c$_2$) reacted with the compound of the formula XXIII

$$R_{14}-X_1H \qquad (XXIII),$$

in which $R_{14}$ and $X_1$ are as defined above, in the presence of an equimolar amount of base and an inert organic solvent, or c$_3$) converted with the compound of the formula XVI

$$R_{12}-X_1H \qquad (XVI),$$

in which $R_{12}$ and $X_1$ are as defined above, in the presence of an equimolar amount of base and an aprotic solvent, into the compound of the formula V

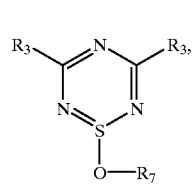
$$(V)$$

in which $R_3$ is $-X_1-R_{12}$ and $R_7$, $X_1$ and $R_{12}$ are as defined above, and this compound is then d$_3$) reacted with the compound of the formula XXIII

$$R_{14}-X_1H \qquad (XXIII),$$

in which $R_{14}$ and $X_1$ are as defined, in the presence of an equimolar amount of base and in an inert organic solvent, or the compound of the formula VII b$_3$) is converted with 2 mol of compound of the formula XVI

$$R_{12}-X_1H \qquad (XVI),$$

in which $R_{12}$ and $X_1$ are as defined, in the presence of an equimolar amount of base and in an aprotic organic solvent, into the compound of the formula V, and this compound is then reacted in a manner analogous to that described under d$_3$), or a$_2$) 1,3,5-trichlorothiatriazine is converted with a $C_6-C_{12}$bicycloalkyl epoxide, a $C_6-C_{12}$bicycloalkyl epoxide substituted by $C_1-C_3$alkyl or an epoxide of the formula XVIII or XIX

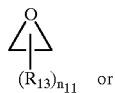
$$(XVIII)$$

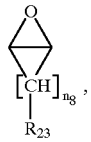
$$(XIX)$$

in which the radicals $R_{13}$ independently of one another are hydrogen, $C_3-C_8$alkenyl, $C_1-C_{14}$alkyl, $C_1-C_{14}$alkyl substituted by halogen, $NO_2$, CN, $C_1-C_5$alkoxy, aryloxy or $C_1-C_3$alkoxycarbonyl;

the radicals $R_{23}$ independently of one another are hydrogen or $C_1-C_6$alkyl;

$n_8$ is a number from 3–10; and $n_{11}$ is 1 or 2, in an inert organic solvent, into the compound of the formula VII in which $R_7$ is $C_2-C_{16}$-β-chloroalkyl, $C_2-C_{16}$-β-chloroalkyl substituted by halogen, $NO_2$, CN, $C_1-C_5$alkoxy, aryloxy or $C_1-C_3$alkoxycarbonyl, $C_5-C_{12}$-β-chlorocycloalkyl or $C_5-C_{12}$-β-chlorocycloalkyl substituted by $C_1-C_6$alkyl, and this compound is reacted further in a manner analogous to that described under b$_1$); b$_2$) and c$_2$); b$_2$), c$_3$) and d$_3$); or b$_3$) and d$_3$), or a₃) 1,3,5-trichlorothiatriazine is reacted with an alcohol of the formula XVII $R_7$—OH  (XVII), in which $R_7$ is $C_1$–$C_{10}$alkyl, $C_1$–$C_{10}$alkyl substituted by halogen, CN, $NO_2$, $C_1$–$C_5$alkoxy, $C_1$–$C_5$alkylthio, $C_3$–$C_6$alkenyloxy, $C_1$–$C_3$alkoxycarbonyl, heterocyclyl of the formula

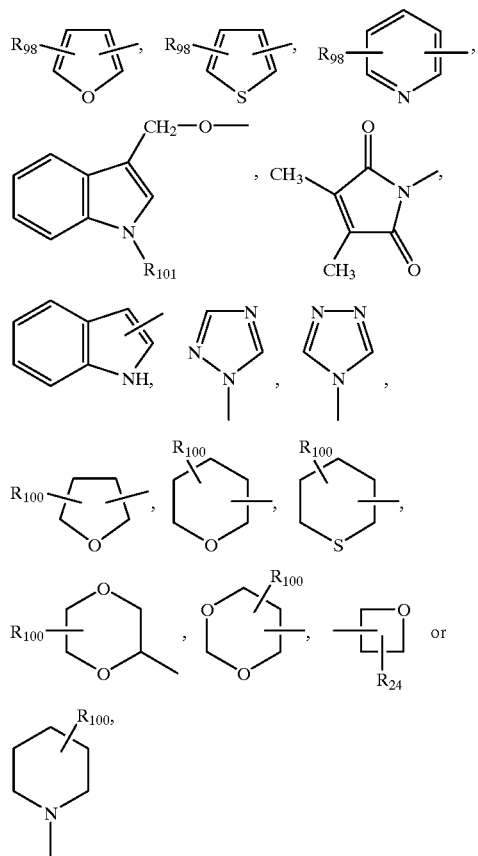

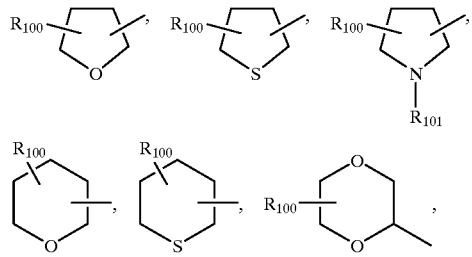

in which $R_{24}$, $R_{98}$, $R_{100}$ and $R_{101}$ are as defined in claim 1, or substituted or unsubstituted aryl or aryloxy, $C_3$–$C_{10}$alkenyl, $C_3$–$C_{10}$alkenyl substituted by halogen, $C_1$–$C_3$alkoxy or substituted or unsubstituted aryl or aryloxy, $C_3$–$C_5$alkynyl, $C_3$–$C_8$cycloalkyl, $C_6$–$C_{12}$bicycloalkyl, a heterocyclic ring of the formula

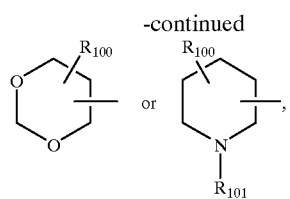

in which $R_{100}$ and $R_{101}$ are as defined above, or alicyclyl,
if appropriate in an inert solvent in the presence of an eqimolar amount of base.

14. A process for the preparation of a compound according to claim 1, in which $R_1$ is the group —$OR_7$;
$R_2$ is a group $R_{88}R_{89}N$—,

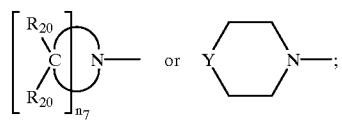

and $R_3$ is aryl-X—, phthalidyl-X—, biphenyl-X— or heteroaryl-X—, which comprises a procedure in which c₄) a compound of the formula VI

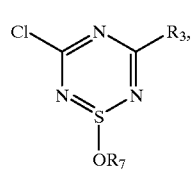 (VI)

in which $R_7$ is as defined in claim 1 and
$R_3$ is as defined above,
is reacted with an amine of the formula XIII, XIV or XV $R_{88}R_{89}NH$ (XIII),

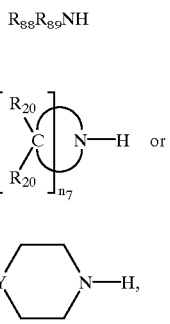 (XIV)

(XV)

in which $R_{20}$, $R_{88}$, $R_{89}$, Y and $n_7$ are as defined in claim 1,
if appropriate in a solvent; or
c₃) the compound of the formula VI is first converted with a compound of the formula XVI $R_{12}$—$X_1$H (XVI), in which $R_{12}$ is an aryl, phthalidyl, biphenyl or heteroaryl radical, and
$X_1$ is oxygen or sulfur, in the presence of an equimolar amount of base and in an aprotic organic solvent, into the compound of the formula V

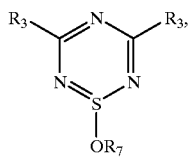 (V)

in which $R_3$ is —$X_1$—$R_{12}$ and
$R_7$, $R_{12}$ and $X_1$ are as defined, and $d_4$) this is then reacted with an amine of the formula XIII, XIV or XV in a manner analogous to that described under $C_4$); or in which $a_4$) 1,3,5-trichlorothiatriazine is converted with an alcoholate of the formula $XVII_1$

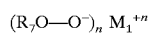 ($XVII_1$), in which $R_7$ is as defined in claim 1;
$M_1^{+n}$ is an alkali metal or alkaline earth metal ion or a metal ion of the first or second sub-group of the Periodic Table; and
n is 1, 2, 3 or 4,
in the presence of an inert organic solvent, into the compound of the formula VII

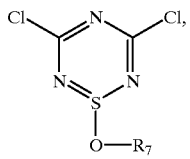 (VII)

in which $R_7$ is as defined, and
$b_4$) this is reacted with an amine of the formula XIII, XIV or XV

 (XIII),

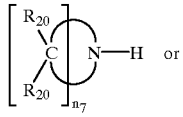 (XIV)

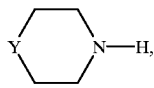 (XV)

in which $R_{20}$, $R_{88}$, $R_{89}$, Y and $n_7$ are as defined in claim 1,
if appropriate in a solvent, to give the compound of the formula VIII

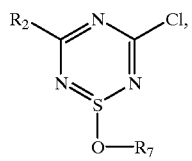 (VIII)

in which $R_2$ and $R_7$ are as defined, and
$c_5$) this is then reacted with a compound of the formula XVI

 (XVI), in which $R_{12}$ is an aryl, phthalidyl, biphenyl or heteroaryl radical; and
$X_1$ is oxygen or sulfur,
in a solvent in the presence of a tertiary amine and, if appropriate, another base.

15. A process for the preparation of a compound according to claim 1, in which $R_1$ is a group —$NR_{90}R_{91}$ or $R_1$ is

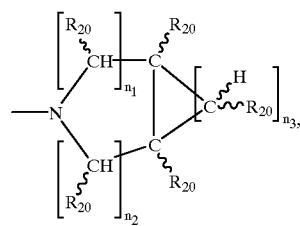

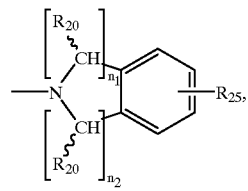

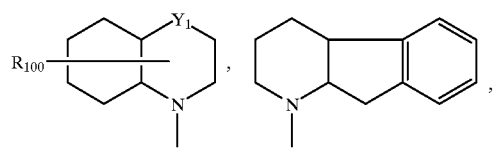

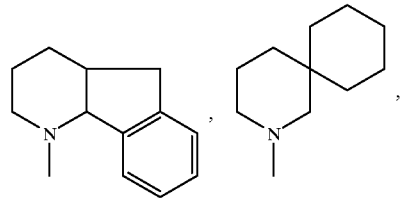

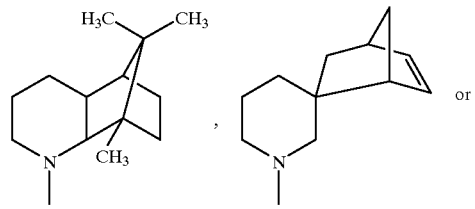 or

-continued

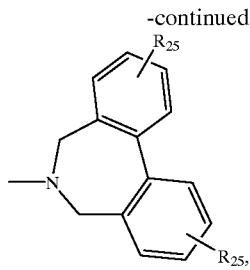

in which the radicals $R_{20}$ independently of one another are hydrogen, $C_1$–$C_4$alkyl or $C_1$–$C_3$alkoxy;
$R_{25}$ is hydrogen, chlorine, methyl or methoxy;
$R_{100}$ is hydrogen or $C_1$–$C_3$alkyl;
$Y_1$ is —O—, —S— or —$NR_{30}$;
$R_{30}$ is hydrogen, methyl, $C_1$–$C_3$alkylcarbonyl or $(C_1$–$C_3$alkyl$)_2$NCO;
$n_1$ is 1, 2, 3, 4 or 5;
$n_2$ is 0, 1 or 2; and
$n_3$ is a number from 3 to 10;
$R_2$ is a group $R_{88}R_{89}N$—,

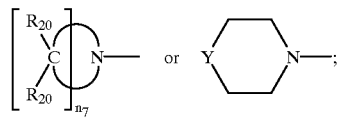

and
$R_3$ is aryl-X—, phthalidyl-X—, biphenyl-X— or heteroaryl-X—,
which comprises a procedure in which
e) a compound of the formula III

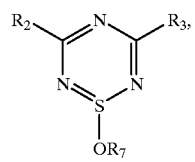

in which $R_7$ is as defined in claim 1 and
$R_2$ and $R_3$ are as defined,
is reacted with an amine of the formula XI or XII $R_{90}R_{91}NH$ or (XI)

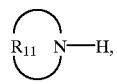 (XII)

in which $R_{90}$ and $R_{91}$ are as defined in claim 1 and
$R_{11}$ is a cyclic radical onto which 1 or 2 further carbocyclic, heterocyclic or aromatic rings can be fused and which can contain further heteroatoms, if appropriate in a solvent; or in which
$a_5$) 1,3,5-trichlorothiatriazine is converted with an amine of the formula XI or XII $R_{90}R_{91}NH$ or (XI)

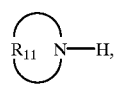 (XII)

in which $R_{90}$ and $R_{91}$ are as defined in claim 1 and
$R_{11}$ is a cyclic radical onto which 1 or 2 carbocyclic, heterocyclic or aromatic rings can be fused and which can contain further heteroatoms,
or with an amide of the formula $XI_1$ or $XII_1$ $(R_{90}R_{91}N^-)_nM_2^{+n}$ or $(XI_1)$

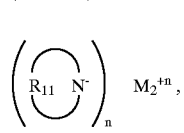 $(XII_1)$ in which $R_{90}$, $R_{91}$ and $R_{11}$ are as defined;
$M_2^{+n}$ is an alkali metal or alkaline earth metal ion or a metal ion of the first or second sub-group of the Periodic Table; and
n is 1, 2, 3 or 4,
in the presence of an inert organic solvent and if appropriate a base, into the compound of the formula IX

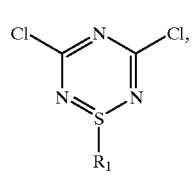 (IX)

in which $R_1$ is as defined, and
$b_5$) this is reacted with an amine of the formula XIII, XIV or XV $R_{88}R_{89}NH$ (XIII),

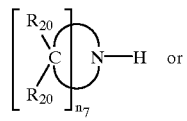 (XIV)

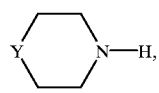 (XV)

in which $R_{20}$, $R_{88}$, $R_{89}$, Y and $n_7$ are as defined in claim 1,
if appropriate in a solvent, to give the compound of the formula X

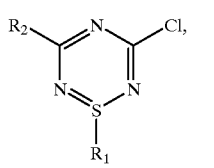
(X)

in which $R_1$ and $R_2$ are as defined, and $c_6$) this is then reacted with a compound of the formula XVI $$R_{12}-X_1H \qquad (XVI),$$

in which $R_{12}$ is an aryl, phthalidyl, biphenyl or heteroaryl radical; and $X_1$ is oxygen or sulfur, in a solvent in the presence of a tertiary amine and a further equivalent amount of base.

16. A process for the preparation of a compound according to claim 1, in which $R_1$ is a group —$OR_7$;

$R_2$ is a group $R_{88}R_{89}N$—,

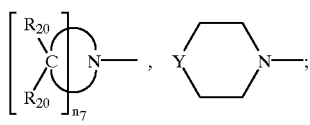

aryl-X—, phthalidyl-X—, biphenyl-X— or heteroaryl-X—; and $R_3$ is aryl-X—, phthalidyl-X—, biphenyl-X— or heteroaryl-X—, which comprises a procedure in which a compound of the formula I, in which $R_1$ is a group —$OR_7$, in which $R_7$ is other than in the end product; and $R_2$ and $R_3$ are as defined, is reacted with an alcohol of the formula XVII $$R_7\text{—OH} \qquad (XVII),$$

in which $R_7$ is other than in the starting substance of the formula I, in the presence of an inert organic solvent and a catalytic or equimolar amount of base.

17. A compound of the formula VII

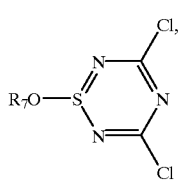
(VII)

in which $R_7$ is as defined in claim 1.

18. A compound of the formula VI

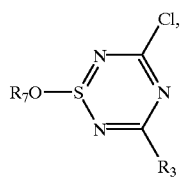
(VI)

in which $R_7$ is as defined in claim 1, $R_3$ is aryl-X—, phthalidyl-X—, biphenyl-X— or heteroaryl-X—, and X is as defined in claim 1.

19. A compound of the formula V

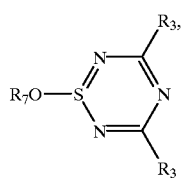
(V)

in which $R_7$ is as defined in claim 1, $R_3$ is aryl-X—, phthalidyl-X—, biphenyl-X— or heteroaryl-X—, and X is as defined in claim 1.

20. A compound of the formula VIII

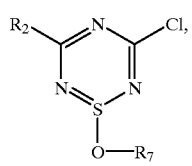
(VIII)

in which $R_2$ is a group $R_{88}R_{89}N$—,

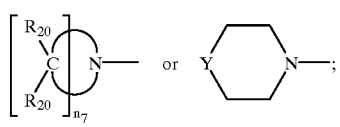

and $R_7$, $R_{20}$, $R_{88}$, $R_{89}$, Y and $n_7$ are as defined in claim 1.

21. A compound of the formula IX

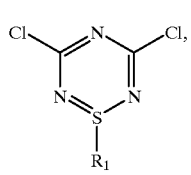
(IX)

in which $R_1$ is a group $R_{90}R_{91}N$— or

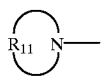

$R_{90}$ and $R_{91}$ are as defined in claim 1; and
$R_{11}$ is a cyclic radical onto which 1 or 2 carbocyclic, heterocyclic or aromatic rings can be fused and which can contain further heteroatoms, excluding the compounds

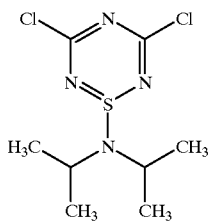 and 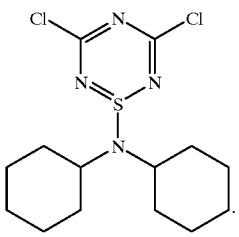.

22. A compound of the formula X

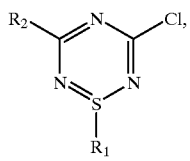 (X)

in which $R_1$ is a group $R_{90}R_{91}N$— or

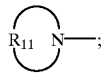;

and
$R_2$ is a group $R_{88}R_{89}N$—,

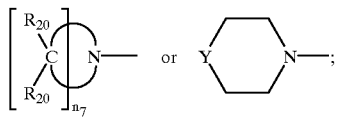

and
$R_{20}$, $R_{88}$, $R_{89}$, $R_{90}$, $R_{91}$, Y and $n_7$ are as defined in claim 1; and
$R_{11}$ is a cyclic radical onto which 1 or 2 carbocyclic, heterocyclic or aromatic rings can be fused and which can contain further heteroatoms, excluding the compounds

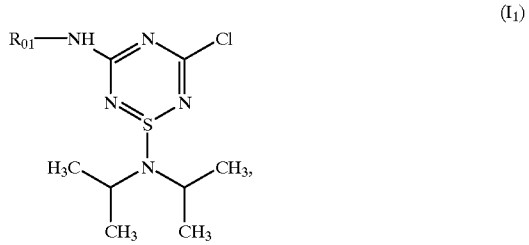 (I$_1$)

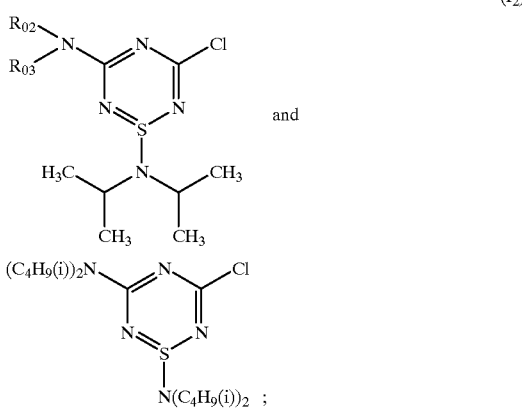 (I$_2$) and wherein $R_{01}$ is hydrogen, methyl, ethyl, n-propyl, i-butyl, tert-butyl, allyl, cyclohexyl or benzyl; $R_{02}$ is ethyl or i-butyl, $R_{03}$ is cyclohexyl or i-butyl; and $R_{02}$ and $R_{03}$ together with the nitrogen atom to which they are bonded, form a piperidine ring.

23. A herbicidal or plant growth-inhibiting composition, which comprises a compound according to claim 1, in a herbicidal or plant growth-inhibiting effective amount, and an inert carrier.

24. The composition according to claim 23, in which the compound comprises between 0.1% and 95% of the composition.

25. A method of controlling undesirable plant growth, which comprises applying to the plants, in a herbicidally effective amount, the compound according to claim 1 to the plants or their environment.

26. The method according to claim 25, wherein an amount of between 0.001 and 4 kg of the compound per hectare is applied to the plants.

27. A method of inhibiting plant growth, which comprises applying a compound according to claim 1 in an effective inhibiting amount to the plants or their environment.

* * * * *